(12) United States Patent
Haque et al.

(10) Patent No.: US 7,812,037 B2
(45) Date of Patent: Oct. 12, 2010

(54) DUAL ANTIPLATELET/ANTICOAGULANT PYRIDOXINE ANALOGS

(75) Inventors: Wasimul Haque, Edmonton (CA); James Diakur, Winnipeg (CA); Vinh Pham, Winnipeg (CA); Atiq Rehman, Winnipeg (CA); Tara Whitney, San Diego, CA (US); Mohammed Omar, Winnipeg (CA); Seng Yi, Winnipeg (CA); A. Qasim Khan, Winnipeg (CA)

(73) Assignee: Medicure International, Inc., St. James (BB)

( * ) Notice: Subject to any disclaimer, the term of this patent is extended or adjusted under 35 U.S.C. 154(b) by 1289 days.

(21) Appl. No.: 11/262,509

(22) Filed: Oct. 28, 2005

(65) Prior Publication Data

US 2006/0094761 A1 May 4, 2006

Related U.S. Application Data

(60) Provisional application No. 60/622,627, filed on Oct. 28, 2004.

(51) Int. Cl.
*A61K 31/4425* (2006.01)
*C07D 213/65* (2006.01)

(52) U.S. Cl. .................. 514/351; 514/349; 514/352; 514/357; 546/297; 546/300; 546/304; 546/307; 546/332

(58) Field of Classification Search ................ 546/297, 546/300, 304, 307, 332; 514/349, 351, 352, 514/357
See application file for complete search history.

(56) References Cited

U.S. PATENT DOCUMENTS

| | | | |
|---|---|---|---|
| 3,206,463 A | 9/1965 | Baetz | |
| 3,227,724 A | 1/1966 | Firestone et al. | |
| 3,282,778 A | 11/1966 | Lobel | |
| 3,632,806 A | 1/1972 | Ichizo et al. | |
| 3,910,921 A | 10/1975 | Esanu | |
| 3,987,177 A | 10/1976 | Giudicelli et al. | |
| 4,012,377 A | 3/1977 | Claisse et al. | |
| 4,032,534 A | 6/1977 | Chodkiewicz | |
| 4,036,844 A | 7/1977 | Thorne et al. | |
| 4,053,607 A | 10/1977 | Thorne et al. | |
| 4,137,316 A | 1/1979 | Esanu | |
| 4,167,562 A | 9/1979 | Evers | |
| 4,237,118 A | 12/1980 | Howard | |
| 4,361,570 A | 11/1982 | Fici | |
| 4,369,172 A | 1/1983 | Schor et al. | |
| 4,374,841 A | 2/1983 | Descamps et al. | |
| 4,515,771 A | 5/1985 | Fine | |
| 4,567,179 A | 1/1986 | Lombardino | |
| 4,569,938 A | 2/1986 | Esanu | |
| 4,569,939 A | 2/1986 | Esanu | |
| 4,581,363 A | 4/1986 | Esanu | |
| 4,605,741 A | 8/1986 | Zagnoli et al. | |
| 4,696,920 A | 9/1987 | Bentzen et al. | |
| 4,730,042 A | 3/1988 | Hege et al. | |
| 4,735,950 A | 4/1988 | Esanu | |
| 4,735,956 A | 4/1988 | Baldwin et al. | |
| 4,837,239 A | 6/1989 | Benjamin et al. | |
| 4,843,071 A | 6/1989 | Hohenwarter | |
| 4,898,879 A | 2/1990 | Madsen et al. | |
| 4,962,121 A | 10/1990 | Hamberger et al. | |
| 5,001,115 A | 3/1991 | Sloan | |
| 5,053,396 A | 10/1991 | Blass | |
| 5,118,505 A | 6/1992 | Költringer | |
| 5,130,311 A | 7/1992 | Guillaumet et al. | |
| 5,130,324 A | 7/1992 | Ulrich et al. | |
| 5,132,115 A | 7/1992 | Wolter et al. | |
| 5,155,116 A | 10/1992 | Guillaumet et al. | |
| 5,210,083 A | 5/1993 | Pfirrmann | |
| 5,213,813 A | 5/1993 | Kornecki et al. | |
| 5,254,557 A | 10/1993 | Buckle et al. | |
| 5,254,572 A | 10/1993 | Serfontein | |
| 5,272,165 A | 12/1993 | Ulrich et al. | |
| 5,278,154 A | 1/1994 | Lacoste et al. | |
| 5,288,716 A | 2/1994 | Speck | |
| 5,326,757 A | 7/1994 | Demopoulos | |
| 5,328,453 A | 7/1994 | Sibalis | |
| 5,372,999 A | 12/1994 | Schneider et al. | |
| 5,385,937 A | 1/1995 | Stamler et al. | |
| 5,420,112 A | 5/1995 | Lewis et al. | |
| 5,441,972 A | 8/1995 | Ogata et al. | |
| 5,504,090 A | 4/1996 | Neely | |
| 5,563,126 A | 10/1996 | Allen et al. | |
| 5,569,459 A | 10/1996 | Shlyankevich | |

(Continued)

FOREIGN PATENT DOCUMENTS

BE 831350 1/1976

(Continued)

OTHER PUBLICATIONS

"B Vitamins May Cut Heart Disease Risk", *Harvard Health Letter*, 1 page (1998).

(Continued)

*Primary Examiner*—Patricia L Morris
(74) *Attorney, Agent, or Firm*—Merchant & Gould P.C.; Brian R. Dorn

(57) ABSTRACT

Compounds with antiplatelet aggregation and anticoagulant characteristics for the treatment of cardiovascular, cerebrovascular, and cardiovascular related diseases and symptoms, are described. The methods are directed to administering pharmaceutical compositions comprising aryl sulfonic pyridoxine and/or substituted pyridoxine analogs.

22 Claims, No Drawings

U.S. PATENT DOCUMENTS

| | | |
|---|---|---|
| 5,569,648 A | 10/1996 | Lewis et al. |
| 5,594,004 A | 1/1997 | Katano et al. |
| 5,631,271 A | 5/1997 | Serfontein |
| 5,633,228 A | 5/1997 | Lewis et al. |
| 5,648,335 A | 7/1997 | Lewis et al. |
| 5,728,684 A | 3/1998 | Cheng et al. |
| 5,733,884 A | 3/1998 | Barbul et al. |
| 5,733,916 A | 3/1998 | Neely |
| 5,770,215 A | 6/1998 | Moshyedi |
| 5,795,873 A | 8/1998 | Allen |
| 5,804,163 A | 9/1998 | Gibby et al. |
| 5,804,594 A | 9/1998 | Murad |
| 5,833,998 A | 11/1998 | Biedermann et al. |
| 5,834,446 A | 11/1998 | Dow et al. |
| 5,840,685 A | 11/1998 | Fujii et al. |
| 5,847,008 A | 12/1998 | Doebber et al. |
| 5,858,017 A | 1/1999 | Demopulos et al. |
| 5,859,051 A | 1/1999 | Adams et al. |
| 5,874,420 A | 2/1999 | Pelleg |
| 5,874,443 A | 2/1999 | Kiely et al. |
| 5,888,514 A | 3/1999 | Weisman |
| 5,944,020 A | 8/1999 | Markov et al. |
| 6,043,259 A | 3/2000 | Dhalla et al. |
| 6,051,587 A | 4/2000 | Dakashinamurti et al. |
| 6,066,659 A | 5/2000 | Speck |
| 6,121,249 A | 9/2000 | Weissman et al. |
| 6,274,170 B1 | 8/2001 | Heibel et al. |
| 6,323,188 B1 | 11/2001 | Weissman |
| 6,339,085 B1 | 1/2002 | Haque |
| 6,358,960 B1 | 3/2002 | Senokuchi et al. |
| 6,417,204 B1 | 7/2002 | Haque |
| 6,489,345 B1 | 12/2002 | Sethi |
| 6,544,547 B2 | 4/2003 | Hageman |
| 6,548,519 B1 | 4/2003 | Haque |
| 6,586,414 B2 | 7/2003 | Haque et al. |
| 6,605,612 B2 | 8/2003 | Haque |
| 6,667,315 B2 | 12/2003 | Haque |
| 6,677,356 B1 | 1/2004 | Sethi et al. |
| 6,780,997 B2 | 8/2004 | Haque |
| 6,861,439 B2 | 3/2005 | Haque et al. |
| 6,867,215 B2 | 3/2005 | Haque |
| 6,890,943 B2 | 5/2005 | Haque |
| 6,897,228 B2 | 5/2005 | Haque |
| 7,105,673 B2 | 9/2006 | Haque |
| 7,115,625 B2 | 10/2006 | Sethi et al. |
| 7,115,626 B2 | 10/2006 | Sethi et al. |
| 7,125,889 B2 | 10/2006 | Sethi et al. |
| 7,132,430 B2 | 11/2006 | Sethi et al. |
| 7,144,892 B2 | 12/2006 | Sethi et al. |
| 7,148,233 B2 | 12/2006 | Sethi et al. |
| 7,230,009 B2 | 6/2007 | Haque et al. |
| 2003/0114424 A1 | 6/2003 | Haque et al. |
| 2004/0121988 A1 | 6/2004 | Haque et al. |
| 2004/0171588 A1 | 9/2004 | Haque |
| 2004/0186077 A1 | 9/2004 | Diakur et al. |
| 2004/0235907 A1 | 11/2004 | Sethi |
| 2005/0107443 A1 | 5/2005 | Haque |
| 2006/0019929 A1 | 1/2006 | Friesen |
| 2006/0035864 A1 | 2/2006 | Friesen |
| 2006/0094748 A1 | 5/2006 | Haque et al. |
| 2006/0094749 A1 | 5/2006 | Haque et al. |
| 2006/0148763 A1 | 7/2006 | Friesen et al. |
| 2006/0241083 A1 | 10/2006 | Diakur et al. |
| 2007/0032456 A1 | 2/2007 | Friesen |
| 2007/0060549 A1 | 3/2007 | Friesen |
| 2007/0142270 A1 | 6/2007 | Haque et al. |
| 2007/0149485 A1 | 6/2007 | Friesen |
| 2007/0167411 A1 | 7/2007 | Reimer |
| 2007/0243249 A1 | 10/2007 | Friesen et al. |
| 2007/0249562 A1 | 10/2007 | Friesen |

FOREIGN PATENT DOCUMENTS

| | | |
|---|---|---|
| BE | 863754 | 5/1978 |
| CA | 933 522 | 9/1973 |
| CH | 561 183 | 4/1975 |
| DE | 24 61 742 A | 7/1976 |
| DE | 37 05 549 A1 | 9/1988 |
| DE | 43 44 751 A1 | 6/1995 |
| EP | 0 121 036 A1 | 10/1984 |
| EP | 0 144 051 A2 | 6/1985 |
| EP | 0 270 026 A2 | 6/1988 |
| EP | 0 416 248 A2 | 3/1991 |
| EP | 0 891 719 A1 | 1/1999 |
| FR | 5552 M | 12/1967 |
| FR | 5801 M | 3/1968 |
| FR | 6453 M | 12/1968 |
| FR | 2101010 | 3/1972 |
| FR | 2255883 | 7/1975 |
| FR | 2428640 | 1/1980 |
| GB | 1 013 939 | 12/1965 |
| GB | 1 201 014 | 8/1970 |
| GB | 1 248 324 | 2/1972 |
| GB | 1 297 080 | 11/1972 |
| GB | 1 360 536 | 7/1974 |
| GB | 1 493 993 | 12/1977 |
| GB | 1 597 428 | 9/1981 |
| GB | 2 254 556 A | 10/1992 |
| JP | 48-21959 | 7/1973 |
| JP | 54-17130 | 2/1979 |
| JP | 10-158244 | 6/1998 |
| JP | 2000-26295 | 1/2000 |
| WO | WO 83/00085 | 1/1983 |
| WO | WO 91/19500 | 12/1991 |
| WO | WO 94/18965 | 9/1994 |
| WO | WO 97/30047 | 8/1997 |
| WO | WO 98/28310 | 7/1998 |
| WO | WO 02/34711 | 5/2002 |
| WO | WO 2005/060975 | 7/2005 |
| WO | WO 2005/070889 | 8/2005 |
| WO | WO 2006/005173 | 1/2006 |
| WO | WO 2006/026868 | 3/2006 |
| WO | WO 2006/056079 | 6/2006 |
| WO | WO 2006/058411 | 6/2006 |
| WO | WO 2006/102748 | 10/2006 |
| WO | WO 2006/136004 | 12/2006 |

OTHER PUBLICATIONS

Arbuzov, S., "Pharmacologocial Properties of the Products of the Condensation of Phenamine with Some Metabolites", *Farmakol. Toksikol*, vol. 31, No. 3, pp. 373-376 (Abstract only) (1968).

Arbuzov., S., "Synthesis and Pharmacological Investigation of Some New Compounds Related Structurally to Some Natural Metabolites", *Conf. Hug. Ther. Invest. Pharmacol., Soc. Pharmacol. Hung.*, 489-502 (1966) (Abstract only).

Aybak, M. et al., "Effect of Oral Pyridoxine Hydrochloride Supplementation on Arterial Blood Pressure in Patients with Essential Hypertension", *Drug Res.*, vol. 45, No. 12, pp. 1271-1273 (1995).

Baliga, B. et al., "Hyperhomocysteinemia in Type 2 Diabetes Mellitus: Cardiovascular Risk Factors and Effect of Treatment with Folic Acid and Pyridoxine", *Endocrine Practice*, vol. 6, No. 6, pp. 435-441 (Nov./Dec. 2000).

Barrett, S., "Homocysteine: A Cardiovascular Risk Factor Worth Considering", http://www.quackwatch.com/03HealthPromotion/homocysteine.html, 2 pages (© 1997).

Bennett, R. et al., "Vitamin $B_6$-Phosphonic Acids", *Journal of Medicinal and Pharmaceutical Chemistry*, vol. 1, No. 3, pp. 213-221 (1959).

Berger, A.R. et al., "Dose response, coasting, and differential fiber vulnerability in human toxic neuropathy: A prospective study of pyridoxine neurotoxicity", *Neurology*, vol. 42, No. 7, pp. 1367-1370 (Jul. 1992).

Bernstein, A., "Vitamin B$_6$ in Clinical Neurology", *Annals of New York Academy of Sciences*, vol. 585, pp. 250-260 (1990).
Bertrand et al. "Double-Blind Study of the Safety of Clopidogrel With and Without a Loading Dose in Combination With Aspirin Compared with Ticlopidine in Combination With Aspirin after Coronary Stenting", *Circulation*, 102: 624-629 (Aug. 8, 2000).
Bhagavan et al., "Effect of Postweanling Pyridoxine Deficiency on Growth and Concentration of the Coenzyme Pyridoxal-5'-phosphate in Heart, Kidneys, Lungs, and Adrenals in Rats", *Pediat. Res.*, vol. 10, pp. 730-732 (1976).
Bode, W. et al., "Pyridoxal-5'-Phosphate and Pyridoxal Biokinetics in Male Wistar Rats Fed Graded Levels of Vitamin B-6", *J. Nutr.*, vol. 121, No. 11, pp. 1738-1745 (Nov. 1991).
Brass, "Thrombin and platelet activation," *Chest*, 124: 18S-25S (2003).
Buffon et al., "Widespread coronary inflammation in unstable angina," *N. Engl. J. Med.*, 347: 5-12 (2002).
Bundgaard, Design and Application of Prodrugs in A Textbook of Drug Design and Development (Krogsgaard-Larson & Bundgaard, eds., Hardwood Academic Publishers, Reading, United Kingdom (1991).
Califf et al., "Myonecrosis after revascularization procedures", J. Am. Coll. Cardiol. 31: 241-251 (1998).
Chasan-Taber, L. et al., "A Prospective Study of Folate and Vitamin B$_6$ and Risk of Myocardial Infarction in US Physicians", *Journal of the American College of Nutrition*, vol. 15, No. 2, pp. 136-143 (Apr. 1996).
Chen et al., "Thrombin receptor activation," *J. Biol. Chem.*, 269: 16041-16045 (1994).
Cho, Y. et al., "In Vivo Evidence for a Vitamin B-6 Requirement in Carnitine Synthesis", *J. Nutr.*, vol. 120, pp. 258-265 (1990).
Chung et al., "Mechanisms of action of proteinase-activated receptor agonists on human platelets," *Br. J. Pharmacol.*, 135: 1123-1132 (2002).
Ebadi et al., "Convulsant Activity of Pyridoxal Sulphate and Phosphonoethyl Pyridoxal: Antagonism by GABA and its Synthetic Analogues", *Neuropharmacology*, vol. 22, No. 7, pp. 865-873 (1983).
Ellis et al., "Prevention of Myocardial Infarction by Vitamin B$_6$", *Res. Commun. Molec. Pathol. Pharmacol.*, vol. 89, No. 2, pp. 208-220 (Aug. 1995).
Esmon, "Role of coagulation inhibitors in inflammation," *Thromb. Haemost.*, 86: 51-56 (2001).
ESPRIT investigators, "Novel dosing regimen of eptifibatide in planned coronary stent implantation (ESPRIT): a randomised, placebo-controlled trial", Lancet 356: 2037-2044 (2000).
Fitzgerald, "Vascular biology of thrombosis," *Neurology*, 57: S1-S4 (2001).
Folsom et al., "Clinical Investigation and Reports: Prospective Study of Coronary Heart Disease Incidence in Relation to Fasting Total Homocysteine, Related Genetic Polymorphisms, and B Vitamins: The Atherosclerosis Risk in Communities (ARIC) Study", *Circulation*, vol. 98, pp. 204-210 (Jul. 21, 1998).
Fonda, "Interaction of Pyridoxal Analogues with Glutamate Apodecarboxylase and Aspartate Apoaminotransferase", *The Journal of Biological Chemistry*, vol. 246, No. 7, pp. 2230-2240 (Apr. 10, 1971).
Gilchrist et al. "Pharmacodynamics and Pharmacokinetics of Higher-Dose, Double Bolus Eptifibatide in Percutaneous Coronary Intervention" Circulation 104: 406-411 (Jul. 24, 2001).
Gundermann et al., "Oligomere von 5-Amino-8-vinylphthalazin-1,4(2H,3H)-dion", *Liebigs Ann. Chem.*, vol. 1979, No. 8, pp. 1657-1664 (Aug. 1979).
Harada et al., "Studies on Vitamin B$_6$. (IV) Behavior of Pyridoxal Acylates in the Body After Parenteral Administration", *Vitamins Journal of the Vitamin Society of Japan*, vol. 45, No. 2, pp. 69-75 (Feb. 1972).
Harrington et al. "A possible mechanism for the inhibition of blood platelet aggregation by pyridoxal-5'-phosphate" Biochemical Society Transactions 24: 76S (1996).
Hathcock, "Vitamins and minerals: efficacy and safety", *Am J Clin Nutr*, vol. 66, pp. 427-437 (1997).

Hayakawa et al., "The In Vitro and In Vivo Inhibition of Protein Glycosylation and Diabetic Vascular Basement Membrane Thickening by Pyridoxal-5'-Phosphate", *J. Nutr. Sci. Vitaminol.*, vol. 37, pp. 149-159 (1991).
Heemskerk et al., "Platelet activation and blood coagulation," *Thromb. Haemost.*, 88: 186-193 (2002).
Hoover et al., "Ultrastructural Lesions of Pyridoxine Toxicity in Beagle Dogs", *Vet. Pathol.*, vol. 18, pp. 769-777 (1981).
Kambayashi et al. " Cilostazol as a Unique Antithrombotic Agent", *Current Pharmaceutical Design*, 9:2289-2302 (2003).
Karnalitsky, "Comparative Biochemical Characteristic of B$_6$-Vitamin Deficiency Caused by Alimentary Insufficiency of Pyridoxine and Isonicotinylhydrazide", *BOΠPOCbI*, vol. 3, pp. 44-46 (1971).
Kim et al., "Synthesis and Structure-Activity Relationships of Pyridoxal-6-arylazo-5'-phosphate and Phosphonate Derivatives as P2 Receptor Antagonists", *Drug Development Research*, vol. 45, pp. 52-66 (1998).
Kok et al., "Low Vitamin B$_6$ Status in Patients with Acute Myocardial Infarction", *Am. J. Cardiol.*, vol. 63, pp. 513-516 (Mar. 1, 1989).
Korytnyk et al., Schiff Bases of Pyridoxal: Their Structure and the Stabilization of their Ring-Chain Tautomeric Forms by Acylation, Tetrahedron, 26 (23), 5415-25 (1970).
Korytnyk et al., "Synthesis and Antagonist Properties of Pyridoxal Analogs Modified in the 5 Position", *J. Am. Chem. Soc.*, vol. 10, pp. 345-350 (May 1967).
Korytnyk, "Pyridoxine Chemistry. VI. Homologs of Pyridoxol and of 5-Pyridoxic Acid", *J. Am. Chem .Soc.*, vol. 8, pp. 112-115 (Jan. 1965).
Korytnyk et al., "Selective Modifications of the $^4$-Position of Pyridoxol. I. Extension and branching of the 4-side Chain", *Dept. of Exp. Therapeutics*, Roswell Park Memorial Institute, Buffalo, New York, vol. 13, pp. 187-191 (Mar. 1970).
Krinke et al., "Pyridoxine Megavitaminosis: An Analysis of the Early Changes Induced with Massive Doses of Vitamin B$_6$ in Rat Primary Sensory Neurons", *J. Neuropathol. Exp. Neurol.*, vol. 44, No. 7, pp. 117-129 (Mar. 1985).
Kubyshkin et al., "Comparative characteristics of the arrhythmic syndrome and the possibility for its coenzyme correction in dilated and hypertrophic cardiomyopathy", *Ter. Arkh.* 61(9): 82-85 (1989).
Kunapuli et al., "Platelet purinergic receptors," *Curr. Opin. Pharmacol.*, 3: 175-180 (2003).
Lal et al., "Calcium channels in vitamin B$_6$ deficiency-induced hypertension", *Journal of Hypertension*, vol. 11, No. 12, pp. 1357-1362 (Dec. 1993).
Lal et al., "Hypotensive action of 5-HT receptor agonists in the vitamin B$_6$-deficient hypertensive rat", *Eur. J. Pharmacol.*, vol. 234, Nos. 2/3, pp. 183-189 (Apr. 1993).
Lal et al., "The effect of vitamin B$_6$ on the systolic blood pressure of rats in various animal models of hypertension", *Journal of Hypertension*, vol. 14, No. 3, pp. 355-363 (Mar. 1996).
Levy et al., "Pyridoxine Deficiency in Congestive Heart Failure", *P.S.E.B.M.*, vol. 101, pp. 617-621 (1959).
Manore et al., "Changes in Plasma Pyridoxal Phosphate (PLP) In Diabetic (D), Hypertensive (HTN) and Hypertensive-diabetic (HTN-D) Men Fed A Constant Vitamin B-6 (B6) Diet", *FASEB J*, Abstract 1254 (1991).
Markov et al, "Hemodynamic, electrocardiographic, and metabolic effects of fructose diphosphate on acute myocardial ischemia", *American Heart Journal*, vol. 100, No. 5, pp. 639-646 (Nov. 1980).
Medicure brochure, "Pyridoxine as a Template for the Design of Novel Anti-Platelet Agents," 1 page (Date Unknown).
Mendelsohn et al., "Hemodynamic and Clinical Effects of Oral Levodopa in Children With Congestive Heart Failure", *JACC*, vol. 30, No. 1, pp. 237-242 (Jul. 1997).
Merrill, Jr. et al., "Diseases associated with defects in vitamin B$_6$ metabolism or utilization", *Ann. Rev. Nutr.*, vol. 7, pp. 137-156 (1987).
Miura et al., "Reactions of Phosphonate Analogs of Pyridoxal Phosphate with Apo-aspartate Aminotransferase", *Archives of Biochemistry and Biophysics*, vol. 270, No. 2, pp. 526-540 (May 1, 1989).
Mulvaney et al., "Electrocardiographic changes in vitamin B$_6$ deficient rats", *Cardiovascular Research*, vol. 13, pp. 506-513 (1979).

Nair, et al., "Effect of Pyridoxine and Insulin Administration on Brain Glutamate Dehydrogenase Activity and Blood Glucose Control in Streptozotocin-Induced Diabetic Rats", *Biochimica et Biophysica Acta*, vol. 1381, pp. 351-354 (1998).

Nolan et al. "Effect of Pyridoxal-5'-phosphate on aggregation of platelets from stored human concentrates induced by arachidonic acid" Biochemical Society Transactions, 24:95S (1996).

Nystedt et al., "Molecular cloning of a potential proteinase activated receptor," *Proc. Natl. Acad. Sci. USA*, 91: 9208-9212 (1994).

Omenn et al., "Preventing Coronary Heart Disease", *Circulation*, vol. 97, pp. 421-424 (1998).

Onorato et al., "Pyridoxamine, an Inhibitor of Advanced Glycation Reactions, Also Inhibits Advanced Lipoxidation Reactions", *The Journal of Biological Chemistry*, vol. 275, No. 28, pp. 21177-21184 (Jul. 14, 2000).

Pasechnik, "Effect of Pyridoxine on the Blood Sugar Level Normally and During Experimental Hyperglycemia", *Vop. Pitan.*, vol. 30, No. 3, pp. 44-46 (Abstract only from Chemical Abstracts—Pharmacodynamics, vol. 75 No. 9, p. 293 (Aug. 30, 1971)).

Patrono, "Aspirin: New Cardiovascular Uses for an Old Drug," *The American Journal of Medicine*, vol. 110, pp. 62S-65S (Jan. 8, 2001).

Paulose et al., "Sympathetic Stimulation and Hypertension in the Pyridoxine-Deficient Adult Rat", *Hypertension*, vol. 11, No. 4, pp. 387-391 (Apr. 1988).

Pham et al., "Design and Synthesis of Novel Pyridoxine 5'-Phosphonates as Potential Antiischemic Agents", *Journal of Medicinal Chemistry*, 46(17):3680-3687 (2003).

Popma et al., "Antithrombotic Therapy in Patients Undergoing Coronary Angioplasty", *CHEST*, 114: 728S-741S (1998).

Rao et al., "Congenital disorders of platelet signal transduction," *Arterioscler. Thromb. Vasc. Biol.*, 20: 285-289 (2000).

Rao et al., "Failure of Pyridoxine to Improve Glucose Tolerance in Diabetics", *Journal of Clinical Endocrinology & Metabolism*, vol. 50, No. 1, pp. 198-200 (Jan. 1980).

Rauch et al., "Thrombus formation on atherosclerotic plaques: pathogenesis and clinical consequences," *Ann. Intern. Med.*, 134: 224-238 (2001).

Rimm et al., "Folate and Vitamin $B_6$ From Diet and Supplements in Relation to Risk of Coronary Heart Disease Among Women", *JAMA*, vol. 279, No. 5, pp. 359-364 (Feb. 4, 1998).

Sakuragi, T. et al., "The Synthesis of Long Chain Fatty Acid Derivatives of the Vitamin $B_6$ Group", *J. Am. Chem. Soc.*, vol. 78, pp. 839-842 (Feb. 20, 1956).

Sasaki, H. et al., "Effect of Pyridoxal Phosphate on the Carbohydrate and Lipid Metabolism of the Patient with Diabetes Mellitus", *Niigata Igakkai Zasshi*, vol. 85, No. 3, pp. 163-169 (1971). (Abstract provided in English).

Savage et al., "Mechanisms of platelet aggregation," *Curr. Opin. Hematol.*, 8: 270-276 (2001).

Sethi et al., "Differential changes in left and right ventricular adenylyl cyclase activities in congestive heart failure", *The American Physiological Society*, vol. 272, No. 2, Part 2 of Two Parts, pp. H884-H893 (Feb. 1997).

Sethi et al., "Inotropic Responses to Isoproterenol in Congestive Heart Failure Subsequent to Myocardial Infarction in Rats", *Journal of Cardiac Failure*, vol. 1, No. 5, pp. 391-399 (Dec. 1995).

Sexton, Abstract, 1 page, "Aspirin in cardiovascular disease," *Tenn. Med.*, vol. 94, No. 6, pp. 208-210, (Jun. 2001).

Sharis et al. "The Antiplatelet Effects of Ticlopidine and Clopidogrel", *Annals of Internal Medicine*, 129(5):394-405 (Sep. 1, 1988).

Stirtan et al., "Phosphonate and α-Fluorophosphonate Analogue Probes of the Ionization State of Pyridoxal 5'-Phosphate (PLP) in Glycogen Phosphorylase", *Biochemistry*, vol. 35, pp. 15057-15064 (1996).

Takuma et al., "Combination Therapy of Infantile Spasms With High-Dose Pyridoxal Phosphate and Low-Dose Corticotropin", *Journal of Child Neurology*, vol. 11, No. 1, pp. 35-40 (Jan. 1996).

Tanaka, T. et al., "Pyridoxine Derivatives", *Chemical Abstracts*, vol. 62, No. 12, 1 page (Jun. 7, 1965).

Tcheng "Perspectives on the Future of Platelet Glycoprotein IIb/IIIa Blockade Therapy" Texas Heart Institute Journal, 25(1):49-56 (1998).

Tomita, I. et al., "Synthesis of Vitamin $B_6$ Derivatives. II 3-Hydroxy-4-Hydroxymethyl-2-Methyl-5-Pyridine Acetic Acid and Related Substances", *J. Heterocyclic Chemistry.*, vol. 3, pp. 178-183 (Jun. 1966).

Trezise, D. et al., "$P_2$ purinoceptor antagonist properties of pyridoxal-5-phosphate", *Eur. J. Pharmacol.*, vol. 259, No. 3, pp. 295-300 (Jul. 11, 1994).

Tsutsui et al. "Effect of Cilostazol, a Novel Anti-Platelet Drug, on Restenosis After Percutaneous Transluminal Coronary Angioplasty" *Japan Circulation Journal*, 60: 207-215 (1996).

Vanderjagt et al., "Vitamin $B_6$ Status in a Healthy Elderly Population", *Annals New York Academy of Sciences*, pp. 562-564, (date unknown).

Verhoef et al., "A Common Mutation in the Methylenetetrahydrofolate Reductase Gene and Risk of Coronay Heart Disease: Results Among U.S. Men", *JACC*, Vo. 32, No. 2, pp. 353-359 (Aug. 1998).

Verhoef et al., "Homocysteine Metabolism and Risk of Myocardial Infarction: Relation with Vitamins $B_6$, $B_{12}$, and Folate", *Am. J. Epidemiol.*, vol. 143, No. 9, pp. 845-859 (May 1, 1996).

Vermaak et al., "Vitamin $B_6$ and coronary artery disease. Epidemiological observations and case studies", *Atherosclerosis*, vol. 63, pp. 235-238 (Feb. 1987).

Vidrio, "Interaction with Pyridoxal as a Possible Mechanism of Hydralazine Hypotension", *Journal of Cardiovascular Pharmacology*, vol. 15, pp. 150-156 (1990).

Viscontini et al., "Über einige Derivate des Pyridoxals", *Helvetica Chimica Acta*, vol. 34, No. 296, pp. 2438-2439 (1951).

Vu et al., "Molecular cloning of a function thrombin receptor reveals a novel proteolytic mechanism of receptor activation," *Cell*, 64: 1057-1068 (1991).

Weltermann et al. "Effects of pretreatment with clopidogrel on platelet and coagulation activation in patients undergoing elective coronary stenting" Thrombosis Research 112 (2003) p. 19-24.

Windebank, "Neurotoxicity of Pyridoxine Analogs Is Related to Coenzyme Structure", *Neurochemical Pathology*, vol. 3, pp. 159-167 (1985).

Wyk et al., "The In Vivo effect in humans of pyridoxal-5'-phosphate on platelet function and blood coagulation" Thrombosis Research 66: 657-668, (1992).

Yamagata, S. et al., "Therapeutic Effects of Pyridoxal Phosphate on Diabetic Neuropathy", *Bitamin*, vol. 35, No. 6, pp. 485-493 (1967). (Abstract provided in English).

Yan, S. et al., "A Role for Pyridoxal Phosphate in the Control of Dephosphorylation of Phosphorylase a", *The Journal of Biological Chemistry*, vol. 264, No. 17, pp. 8263-8269 (1979).

Yarat, A. et al., "Effect of vitamin B6 on lenses of diabetic rats", *Indian Journal of Experimental Biology*, vol. 36, pp. 1269-1272 (Dec. 1998).

Zempleni, J. et al., "The utilization of intravenously infused pyridoxine in humans", *Clinica Chimica Acta*, vol. 229, Nos. 1, 2, pp. 27-36 (Sep. 1994).

Zhang, W., et al., "Pyridoxine as a template for the design of antiplatelet agents," Bioorganic & Medicinal Chemistry Letters, 14: 4747-4750 (2004).

Diakur et al., "Pyridoxine as a template for the design of novel anti-platelet agents", Abstracts of Papers, 226th ACS National Meeting, New York, NY, United States, Sep. 7-11, 2003, MEDI-328, American Chemical Society, Washington, D.C. (English) (2003).

DUAL ANTIPLATELET/ANTICOAGULANT PYRIDOXINE ANALOGS

This application claims the benefit under 35 U.S.C. §119 (e) of U.S. Provisional Application No. 60/622,627, filed Oct. 28, 2004, the entire disclosure of which is hereby incorporated by reference.

FIELD OF THE INVENTION

This invention relates to pyridoxine analogs and methods of treating cardiovascular, cerebrovascular, and cardiovascular related diseases or symptoms by administering pharmaceutical compositions comprising pyridoxine analogs to inhibit coagulation and platelet aggregation.

BACKGROUND

Thrombosis, the development of blood clots within arterial vessels, is due to a complex mechanism involving the activation of both platelet aggregation and the coagulation protease cascade (*Ann. Intern Med.* (2001) 134: 224-38; *N. Engl. J. Med.* (2002) 347: 5-12; *Thromb. Haemost.* (2002) 86: 51-6). The pathways involved normally inhibit blood loss after vessel injury, but in thrombosis and related conditions, these reactions are inappropriately initiated and propagated.

On the molecular level, thrombosis is initiated by the release of mediators such as tissue factor (TF), von Willebrand Factor (vWF) (*J. Thromb. Haemost.* (2003) 1: 1602-12), and collagen from ruptured atherosclerotic plaques or from damaged blood vessels. Collagen and vWF bind to receptors on platelets and initiate their activation. Once activated, platelets release secretory granules containing ADP, ATP, and calcium (*Curr. Opin. Hematol.* (2001) 8: 270-6). Activated platelets also synthesize and release thromboxane. The released ADP and thromboxane bind to receptors on the platelets to further propagate platelet activation. Once platelets are activated they start aggregating to initiate clot formation.

TF and vWF also initiate the blood coagulation cascade, which consists of two separate pathways that converge on a common endpoint. Both pathways involve the serial activation of the serine protease clotting factors and ultimately lead to the activation of thrombin. Thrombin, once activated, cleaves fibrinogen to form fibrin. Thrombin, Factor Xa, and Factor VIIa can also activate platelets by cleaving the G protein-coupled protease-activated receptors PAR-1, PAR-3, and PAR-4 (*Chest* (2003) 124: 18S-25S). PAR-1, the prototype receptor, is activated following cleavage of its amino-terminal exodomain to produce a new amino-terminus (*Cell* (1991) 64: 1057-68). The new amino terminus then binds to the receptor to effect signaling (*J. Biol. Chem.* (1994) 269: 16041-45). PARs are therefore peptide receptors that contain their own ligand. PAR-2 is activated by trypsin and not by thrombin (*Proc. Natl. Acad. Sci. USA* (1994) 91: 9208-12).

Therefore, there is a need for compounds that inhibit the proteases of the blood and thus block platelet aggregation.

SUMMARY OF THE INVENTION

One embodiment of the invention includes pyridoxine analogs, particularly bis-amidine pyridoxine analogs, and methods of treatment using therapeutically effective amounts of the pyridoxines. Another embodiment of the invention includes substituted bis-amidine pyridoxine analogs, compositions containing substituted pyridoxine analogs, and methods of treatment using therapeutically effective amounts of substituted bis-amidine pyridoxine analogs. Compounds and compositions of the invention are both antiplatelet and anticoagulant, and thus can be used to treat cardiovascular, cerebrovascular, or related diseases and symptoms thereof.

The invention provides an embodiment of the formula I:

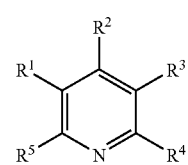

wherein
$R^1$ is $—(CR^7R^8)_m OH$, where m is an integer from 0 to 8, where $R^7$ is H, halo, alkyl, cycloalkyl, hydroxyl, O-alkyl, or O-alkyl-aryl-$R^6$, where $R^6$ is $—NO_2$, $—NH_2$, amidine, alkyl, cycloalkyl, $—CN$,

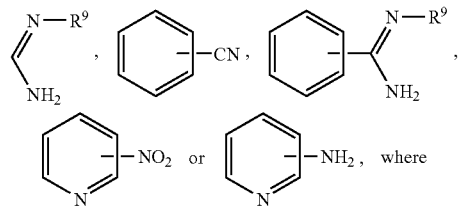

$R^9$ is H, OH, or O-alkyl, and where $R^8$ is H, halo, alkyl, cycloalkyl, hydroxyl, O-alkyl, or O-alkyl-aryl-$R^6$, where $R^6$ is as defined above;
$—(CR^7R^8)_m$O-alkyl, where m, $R^7$, and $R^8$ are as defined above;
$—(CR^7R^8)_m$O-aryl-$R^6$, where m, $R^6$, $R^7$, and $R^8$ are as defined above;
$(CR^7R^8)_m$O-alkyl-aryl-$R^6$, where m and $R^6$ are as defined above;
$—(CR^7R^8)_n$—NH-aryl-$R^6$, where n is an integer from 0 to 8, and where $R^6$, $R^7$ and $R^8$ are as defined above;
$—(CR^7R^8)_n$—NH—CO-aryl-$R^6$, where n, $R^6$, $R^7$ and $R^8$ are as defined above;
$—(CR^7R^8)_n$—NH-aryl-$R^6$, where n, $R^6$, $R^7$ and $R^8$ are as defined above;
$—(CR^7R^8)_n$—NH—CO-aryl-aryl-$R^6$ where n, $R^6$, $R^7$ and $R^8$ are as defined above;
$—$NH-aryl-$R^6$, where $R^6$ is as defined above;
$—(CR^7R^8)_n$—NH—CO-aryl-aryl-$R^6$, where n, $R^6$, $R^7$, and $R^8$ are as defined above; or
$—(CR^7R^8)_n$—CO—NH-aryl-aryl-$R^6$, where n, $R^6$, $R^7$, and $R^8$ are as defined above;
$R^2$ is hydroxyl;
  halo;
  alkyl;
  $—(CR^7R^8)_m$—X, where m, $R^7$ and $R^8$ are as defined above, and where X is H, OH, F, Cl, or Br;
  $—(CH_2)_n$COOH, where n is as defined above;
  $—(CR^7R^8)_m$COO$(CR^7R^8)_n$CH$_3$, where m, n, $R^7$, and $R^8$ are as defined above;
  $—(CR^7R^8)_m$NH$(CR^7R^8)_n$COOH, where m, n, $R^7$, and $R^8$ are as defined above;
  $—(CR^7R^8)_n$-aryl-$R^6$, where n, $R^6$, $R^7$, and $R^8$ are as defined above;

—(CR$^7$R$^8$)$_n$-aryl-aryl-R$^6$, where n, R$^6$, R$^7$, and R$^8$ are as defined above;

—(CR$^7$R$^8$)$_m$—CHF$_2$, where m, R$^7$, and R$^8$ are as defined as above;

—(CR$^7$R$^8$)$_n$—NH-aryl-R$^6$, where n, R$^6$, R$^7$, and R$^8$ are as defined above;

—(CR$^7$R$^8$)$_n$—NH—CO-aryl-R$^6$, where n, R$^6$, R$^7$, and R$^8$ are as defined above;

—(CR$^7$R$^8$)$_n$NH-aryl-R$^6$, where n, R$^6$, R$^7$, R$^8$ are as defined above;

—(CR$^7$R$^8$)—NH—CO-aryl-aryl-R$^6$, where n, R$^6$, R$^7$, and R$^8$ are as defined above;

NH-aryl-R$^6$, where R$^6$ is as defined above;

—(CR$^7$R$^8$)$_n$—NH—CO-aryl-aryl-R$^6$, where n, R$^6$, R$^7$, and R$^8$ are as defined above; or —(CR$^7$R$^8$)$_n$—NH—CO-aryl-aryl-R$^6$, where n, R$^6$, R$^7$, and R$^8$ are as defined above;

R$^3$ is —(CR$^7$R$^8$)$_m$OH, where m, R$^7$, and R$^8$ are as defined above;

—(CR$^7$R$^8$)$_n$O-alkyl, where m, R$^7$, and R$^8$ are as defined above;

—(CR$^7$R$^8$)$_n$—O-aryl-R$^6$, where m, R$^6$, R$^7$, and R$^8$ are as defined above;

—(CR$^7$R$^8$)$_m$O-alkyl-aryl-R$^6$, where m and R$^6$ are as defined above;

—(CR$^7$R$^8$)$_n$OH, where n, R$^6$, R$^7$, and R$^8$ are defined above;

—(CR$^7$R$^8$)$_n$—NH-aryl-R$^6$, where n, R$^6$, R$^7$, and R$^8$ as defined above;

—(CR$^7$R$^8$)$_n$—NH-aryl-R$^6$, where n, R$^6$, R$^7$ and R$^8$ are as defined above;

—(CR$^7$R$^8$)$_n$—NH—CO-aryl-R$^6$, where n, R$^6$, R$^7$, and R$^8$ are as defined above; or —(CR$^7$R$^8$)$_n$—NH—CO-aryl-R$^6$, where n, R$^6$, R$^7$, and R$^8$ are as defined above;

R$^4$ is H, aryl, cycloalkyl, arylalkyl, CHF$_2$, CHO, or R$^2$;

R$^5$ is H, aryl, cycloalkyl, arylalkyl, CHF$_2$, CHO, or R$^2$; and at least two of R$^1$, R$^2$, R$^3$, R$^4$, and R$^5$ have amidine groups; or a pharmaceutically acceptable salt thereof.

In another embodiment, the invention provides compounds of formula II:

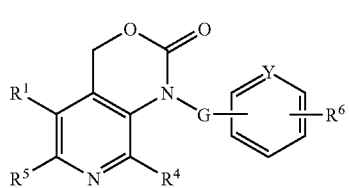

II wherein
R$^1$ is hydroxyl, O-alkyl, or

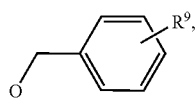

where R$^9$ is —NO$_2$, —NH$_2$, amidine, alkyl, cycloalkyl, —CN

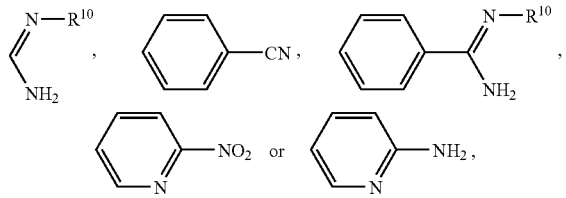

where R$^{10}$ is H, OH, or O-alkyl;

R$^4$ is H;
halo;
aryl;
cycloalkyl;
arylalkyl;
CHF$_2$;
CHO;
alkyl;

—(CR$^7$R$^8$)$_m$—X, where m is an integer from 0 to 8, where R$^7$ is H, F, alkyl, cycloalkyl, hydroxyl, O-alkyl, or O-alkyl-aryl-R$^6$, where R$^8$ is H, F, alkyl, cycloalkyl, hydroxyl, O-alkyl, or O-alkyl-aryl-R$^6$, where R$^6$ is as defined above, and where X is OH, F, or Br;

—(CH$_2$)$_n$COOH, where n is an integer from 0 to 8;

—(CR$^7$R$^8$)$_m$COO(CR$^7$R$^8$)$_n$CH$_3$, where m, n, R$^7$, and R$^8$ are as defined above;

—(CR$^7$R$^8$)$_m$NH(CR$^7$R$^8$)$_n$COOH, where m, n, R$^7$, and R$^8$ are as defined above;

—(CR$^7$R$^8$)$_n$-aryl-R$^6$, where n, R$^6$, R$^7$, and R$^8$ are as defined above;

—(CR$^7$R$^8$)$_n$-aryl-aryl-R$^6$, where n, R$^6$, R$^7$, and R$^8$ are as defined above;

—(CR$^7$R$^8$)$_n$—CHF$_2$, where n, R$^7$ and R$^8$ are defined as above;

—(CR$^7$R$^8$)$_n$—NH-aryl-R$^6$, where n, R$^6$, R$^7$, and R$^8$ are as defined above;

—(CR$^7$R$^8$)$_n$—NH-aryl-R$^6$, where n, R$^6$, R$^7$ and R$^8$ are as defined above;

—(CR$^7$R$^8$)$_n$—NH—CO-aryl-R$^6$, where n, R$^6$, R$^7$, and R$^8$ are as defined above;

—(CR$^7$R$^8$)$_n$—NH—CO-aryl-R$^6$, where n, R$^6$, R$^7$, and R$^8$ are as defined above;

—(CR$^7$R$^8$)$_n$—NH—CO-aryl-aryl-R$^6$, where n, R$^6$, R$^7$, and R$^8$ are as defined above;

NH-aryl-R$^6$, where R$^6$ is as defined above;

—(CR$^7$R$^8$)$_n$—NH—CO-aryl-aryl-R$^6$, where n, R$^6$, R$^7$, and R$^8$ are as defined above; or —(CR$^7$R$^8$)$_n$—NH—CO-aryl-aryl-R$^6$, where n, R$^6$, R$^7$, or R$^8$ are as defined above;

R$^5$ is H, aryl, cycloalkyl, arylalkyl, CHF$_2$, CHO, or R$^4$, where R$^4$ is a defined above;

G is C=O or (CR$^7$R$^8$)$_{n'}$, where n'=0, 1, 2 or 3, where R$^7$ and R$^8$ are as defined above;

Y is C—H, C—F, C—OCH$_3$, C—OCF$_3$, C—CF$_3$, or N; and at least two of R$^1$, R$^4$, R$^5$, and R$^9$ have amidine groups; or a pharmaceutically acceptable salt thereof.

DETAILED DESCRIPTION OF THE INVENTION

The invention provides an embodiment of the formula I:

<img src="formula-I" /> wherein
$R^1$ is —$(CR^7R^8)_m$OH, where m is an integer from 0 to 8, where $R^7$ is H, halo, alkyl, cycloalkyl, hydroxyl, O-alkyl, or O-alkyl-aryl-$R^6$, where $R^6$ is —$NO_2$, —$NH_2$, amidine, alkyl, cycloalkyl, —CN, <img src="substituent-groups" /> where $R^9$ is H, OH, or O-alkyl, and where $R^8$ is H, halo, alkyl, cycloalkyl, hydroxyl, O-alkyl, or O-alkyl-aryl-$R^6$, where $R^6$ is as defined above;
—$(CR^7R^8)_m$O-alkyl, where m, $R^7$, and $R^8$ are as defined above;
—$(C^7R^8)_m$O-aryl-$R^6$, where m, $R^6$, $R^7$, and $R^8$ are as defined above;
—$(CR^7R^8)_m$O-alkyl-aryl-$R^6$, where m and $R^6$ are as defined above;
—$(CR^7R^8)_n$—NH-aryl-$R^6$, where n is an integer from 0 to 8, and where $R^6$, $R^7$ and $R^8$ are as defined above;
—$(CR^7R^8)_n$—NH—CO-aryl-$R^6$, where n, $R^6$, $R^7$ and $R^8$ are as defined above;
—$(CR^7R^8)$—NH-aryl-aryl-$R^6$, where n, $R^6$, $R^7$ and $R^8$ are as defined above;
—$(CR^7R^8)_n$—NH—CO-aryl-aryl-$R^6$ where n, $R^6$, $R^7$ and $R^8$ are as defined above;
—NH-aryl-$R^6$, where $R^6$ is as defined above;
—$(CR^7R^8)_n$—NH—CO-aryl-aryl-$R^6$ where n, $R^6$, $R^7$ and $R^8$ are as defined above; or
—$(CR^7R^8)_n$—NH—CO-aryl-aryl-$R^6$ where n, $R^6$, $R^7$ and $R^8$ are as defined above;
$R^2$ is hydroxyl;
halo;
alkyl;
—$(CR^7R^8)_m$—X, where m, $R^7$ and $R^8$ are as defined above, and where X is H, OH, F, Cl, or Br;
—$(CH_2)_n$COOH, where n is as defined above;
—$(CR^7R^8)_m$COO$(CR^7R^8)_n$CH_3, where m, n, $R^7$, and $R^8$ are as defined above;
—$(CR^7R^8)_m$NH$(CR^7R^8)_n$COOH, where m, n, $R^7$, and $R^8$ are as defined above;
—$(CR^7R^8)_n$-aryl-$R^6$, where n, $R^6$, $R^7$, and $R^8$ are as defined above;
—$(CR^7R^8)_n$-aryl-aryl-$R^6$, where n, $R^6$, $R^7$, and $R^8$ are as defined above;
—$(CR^7R^8)_m$—$CHF_2$, where m, $R^7$, and $R^8$ are as defined as above;
—$(CR^7R^8)_n$—NH-aryl-$R^6$, where n, $R^6$, $R^7$, and $R^8$ are as defined above;
—$(CR^7R^8)_n$—NH—CO-aryl-$R^6$, where n, $R^6$, $R^7$, and $R^8$ are as defined above;
—$(CR^7R^8)_n$—NH-aryl-aryl-$R^6$, where n, $R^6$, $R^7$, and $R^8$ are as defined above;
—$(CR^7R^8)_n$—NH—CO-aryl-aryl-$R^6$, where n, $R^6$, $R^7$, and $R^8$ are as defined above;
NH-aryl-$R^6$, where $R^6$ is as defined above;
—$(CR^7R^8)_n$—NH—CO-aryl-aryl-$R^6$, where n, $R^6$, $R^7$, and $R^8$ are as defined above; or
—$(CR^7R^8)_n$—NH—CO-aryl-aryl-$R^6$, where n, $R^6$, $R^7$, and $R^8$ are as defined above;
$R^3$ is —$(CR^7R^8)_m$OH, where m, $R^7$, and $R^8$ are as defined above;
—$(CR^7R^8)_m$O-alkyl, where m, $R^7$, and $R^8$ are as defined above;
—$(CR^7R^8)_m$O-aryl-$R^6$, where m, $R^6$, $R^7$, and $R^8$ is as defined above;
—$(CR^7R^8)_m$O-alkyl-aryl-$R^6$, where $R^6$ is as defined above;
—$(CR^7R^8)_n$OH, where n, $R^6$, $R^7$, and $R^8$ are defined above;
—$(CR^7R^8)_n$—NH-aryl-$R^6$, where n, $R^6$, $R^7$, and $R^8$ are as defined above;
—$(CR^7R^8)_n$—NH—CO-aryl-$R^6$, where n, $R^6$, $R^7$, and $R^8$ are as defined above;
—$(CR^7R^8)_n$—NH-aryl-aryl-$R^6$, where n, $R^6$, $R^7$, and $R^8$ are as defined above;
—$(CR^7R^8)_n$—NH—CO-aryl-aryl-$R^6$, where n, $R^6$, $R^7$, and $R^8$ are as defined above;
—NH-aryl-$R^6$, where $R^6$ is as defined above;
—$(CR^7R^8)_n$—NH—CO-aryl-$R^6$, where n, $R^6$, $R^7$, and $R^8$ are as defined above; or
—$(CR^7R^8)_n$—NH—CO-aryl-$R^6$, where n, $R^6$, $R^7$, and $R^8$ are as defined above;
$R^4$ is H, aryl, cycloalkyl, arylalkyl, $CHF_2$, CHO, or $R^2$;
$R^5$ is H, aryl, cycloalkyl, arylalkyl, $CHF_2$, CHO, or $R^2$; and
at least two of $R^1$, $R^2$, $R^3$, $R^4$, and $R^5$ have amidine groups; or a pharmaceutically acceptable salt thereof.

In another embodiment, the invention provides compounds of formula II:

<img src="formula-II" /> wherein
$R^1$ is hydroxyl, O-alkyl, or

<img src="R1-substituent" /> where $R^9$ is $-NO_2$, $-NH_2$, amidine, alkyl, cycloalkyl, $-CN$

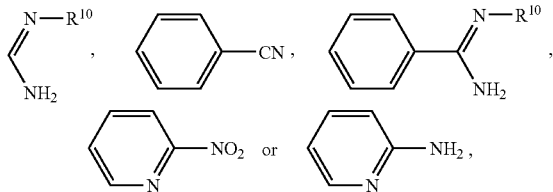

where $R^{10}$ is H, OH, or O-alkyl;

$R^4$ is H;

halo;

aryl;

cycloalkyl;

arylalkyl;

$CHF_2$;

CHO;

alkyl;

- $-(CR^7R^8)_m-X$, where m is an integer from 0 to 8, where $R^7$ is H, F, alkyl, cycloalkyl, hydroxyl, O-alkyl, or O-alkyl-aryl-$R^6$, where $R^8$ is H, F, alkyl, cycloalkyl, hydroxyl, O-alkyl, or O-alkyl-aryl-$R^6$, where $R^6$ is as defined above, and where X is OH, F, or Br;
- $-(CH_2)_n COOH$, where n is an integer from 0 to 8;
- $-(CR^7R^8)_m COO(CR^7R^8)_n CH_3$, where m, n, $R^7$, and $R^8$ are as defined above;
- $-(CR^7R^8)_m NH(CR^7R^8)_n COOH$, where m, n, $R^7$, and $R^8$ are as defined above;
- $-(CR^7R^8)_n$-aryl-$R^6$, where n, $R^6$, $R^7$, and $R^8$ are as defined above;
- $-(CR^7R^8)_n$-aryl-aryl-$R^6$, where n, $R^6$, $R^7$, and $R^8$ are as defined above;
- $-(CR^7R^8)_n-CHF_2$, where n, $R^7$ and $R^8$ are defined as above;
- $-(CR^7R^8)_n-NH$-aryl-$R^6$, where n, $R^6$, $R^7$, and $R^8$ are as defined above;
- $-(CR^7R^8)_n-NH-CO$-aryl-$R^6$, where n, $R^6$, $R^7$, and $R^8$ are as defined above;
- $-(CR^7R^8)_n-NH$-aryl-aryl-$R^6$, where n, $R^6$, $R^7$ and $R^8$ are as defined above;
- $-(CR^7R^8)_n-NH-CO$-aryl-aryl-$R^6$, where n, $R^6$, $R^7$, and $R^8$ are as defined above;

NH-aryl-$R^6$, where $R^6$ is as defined above;

- $-(CR^7R^8)_n-NH-CO$-aryl-aryl-$R^6$, where n, $R^6$, $R^7$, and $R^8$ are as defined above; or NH-aryl-$R^6$, where $R^6$ is as defined above;

$R^5$ is H, aryl, cycloalkyl, arylalkyl, $CHF_2$, CHO, or $R^4$, where $R^4$ is a defined above;

$R^5$ is H, aryl, cycloalkyl, arylalkyl, $CHF_2$, CHO, and $R^4$, where $R^4$ is a defined above;

G is C=O or $(CR^7R^8)_{n'}$, where n'=0, 1, 2 or 3, where $R^7$ and $R^8$ are as defined above;

Y is C—H, C—F, C—$OCH_3$, C—$OCF_3$, C—$CF_3$, or N; and at least two of $R^1$, $R^4$, $R^5$, and $R^6$ have amidine groups; or a pharmaceutically acceptable salt thereof.

The invention further provides an embodiment of the formula III:

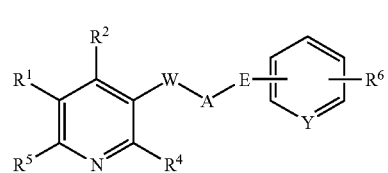

wherein $R^1$ is hydroxyl, O-alkyl, or

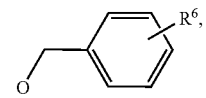

where $R^6$ is $-NO_2$, $-NH_2$, amidine, alkyl, cycloalkyl, $-CN$,

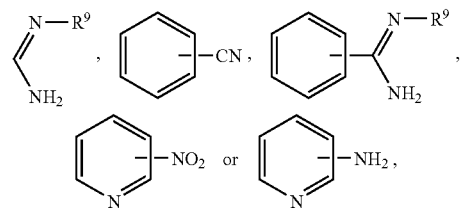

where $R^9$ is H, OH, or O-alkyl;

$R_2$ is $CH_2OH$;

$CH_2OCH_3$;

COOZ, where Z is H, $CH_3$, $CH_2CH_3$, or

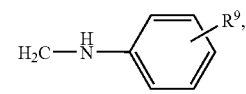

where $R^9$ is defined above;

$CH_2OBn$;

$CH_3$;

$CH_2F$;

$CHF_2$;

$CH_2-NH-(CH_2)_{m'}-COZ$, where m'=0, 1, 2, 3, 4, or 5, and where Z is as defined above; or $(CH_2)_{n'}-COZ$, where n'=1, 2 or 3, and where Z is as defined above;

A is O or NH;

W is C=O or $(CH_2)_{n'}$, where n' is as defined above;

E is C=O; $(CH_2)_{n'}$, where n' is as defined above; or $CHR^{10}$, where $R^{10}$ is $CH_2COZ$, where Z is as defined above;

Y is C—H, C—F, C—$OCH_3$, C—$OCF_3$, C—$CF_3$, or N;

$R^4$ is H;

halo;

aryl;

cycloalkyl;

arylalkyl;

CHF$_2$;

CHO;

alkyl;

—(CR$^7$R$^8$)$_m$—X, where m is an integer from 0 to 8, where R$^7$ is H, F, alkyl, cycloalkyl, hydroxyl, O-alkyl, or O-alkyl-aryl-R$^6$, R$^8$ is H, F, alkyl, cycloalkyl, hydroxyl, O-alkyl, or O-alkyl-aryl-R$^6$, where R$^6$ is as defined above, and where X is OH, F, or Br;

—(CH$_2$)$_n$COOH, where n is an integer from 0 to 8;

—(CR$^7$R$^8$)$_m$COO(CR$^7$R$^8$)$_n$CH$_3$, where m, n, R$^7$, and R$^8$ are as defined above;

—(CR$^7$R$^8$)$_m$NH(CR$^7$R$^8$)$_n$COOH, where m, n, R$^7$, and R$^8$ are as defined above;

—(CR$^7$R$^8$)$_n$-aryl-R$^6$, where n, R$^6$, R$^7$, and R$^8$ are as defined above;

—(CR$^7$R$^8$)$_n$-aryl-aryl-R$^6$, where n, R$^6$, R$^7$, and R$^8$ are as defined above;

—(CR$^7$R$^8$)$_n$—CHF$_2$, where n, R$^7$ and R$^8$ are defined as above;

—(CR$^7$R$^8$)$_n$—NH-aryl-R$^6$, where n, R$^6$, R$^7$, and R$^8$ are as defined above;

—(CR$^7$R$^8$)$_n$—NH—CO-aryl-R$^6$, where n, R$^6$, R$^7$, and R$^8$ are as defined above;

—(CR$^7$R$^8$)$_n$—NH-aryl-aryl-R$^6$, where n, R$^6$, R$^7$ and R$^8$ are as defined above;

—(CR$^7$R$^8$)—NH—CO-aryl-aryl-R$^6$, where n, R$^6$, R$^7$, and R$^8$ are as defined above;

NH-aryl-R$^6$ where R$^6$ is as defined above;

—(CR$^7$R$^8$)$_n$—NH—CO-aryl-aryl-R$^6$, where n, R$^6$, R$^7$, and R$^8$ are as defined above; or —(CR$^7$R$^8$)$_n$—CO—NH-aryl-aryl-R$^6$, where n, R$^6$, R$^7$, and R$^8$ are as defined above;

R$^5$ is H, aryl, cycloalkyl, arylalkyl, CHF$_2$, CHO, or R$^4$, where R$^4$ is as defined above; and at least two of R$^1$, R$^4$, R$^5$, and R$^9$ have amidine groups; or a pharmaceutically acceptable salt thereof.

In another embodiment, the invention provides compounds of formula IV:

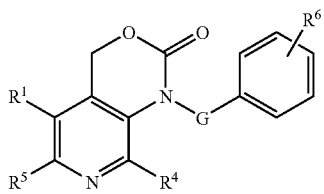

IV wherein

R$^1$ is hydroxyl, O-alkyl, or

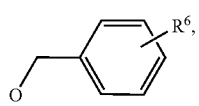

where R$^6$ is —NO$_2$, —NH$^2$, amidine, alkyl, cycloalkyl, —CN,

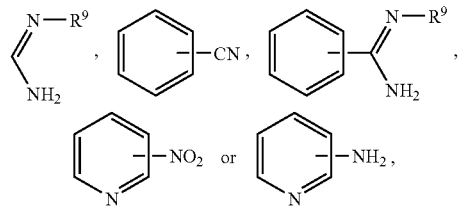

where R$^9$ is H, OH, or O-alkyl;

G is C=O or (CR$^7$R$^8$)$_{n'}$, where n'=0, 1, 2, or 3, where R$^7$ is H, halo, alkyl, cycloalkyl, hydroxyl, O-alkyl, or O-alkyl-aryl-R$^6$, where R$^8$ is H, F, alkyl, cycloalkyl, hydroxyl, O-alkyl, or O-alkyl-aryl-R$^6$, where R$^6$ is as defined above;

R$^4$ is H;

halo;

aryl;

cycloalkyl;

arylalkyl;

CHF$_2$;

CHO;

alkyl;

—(CR$^7$R$^8$)$_m$—X, where m is an integer from 0 to 8, where R$^7$ and R$^8$, and where X is OH, F, Cl, or Br;

—(CH$_2$)$_n$COOH, where n is an integer from 0 to 8;

—(CR$^7$R$^8$)$_m$COO(CR$^7$R$^8$)$_n$CH$_3$, where m, n, R$^7$, and R$^8$ are as defined above;

—(CR$^7$R$^8$)$_m$NH(CR$^7$R$^8$)$_n$COOH, where m, n, R$^7$, and R$^8$ are as defined above;

—(CR$^7$R$^8$)$_n$-aryl-R$^6$, where n, R$^6$, R$^7$, and R$^8$ are as defined above;

—(CR$^7$R$^8$)$_n$-aryl-aryl-R$^6$, where n, R$^6$, R$^7$, and R$^8$ are as defined above;

—(CR$^7$R$^8$)$_n$—CHF$_2$, where n, R$^7$ and R$^8$ are defined as above;

—(CR$^7$R$^8$)$_n$—NH-aryl-aryl-R$^6$, where n, R$^6$, R$^7$, and R$^8$ are as defined above;

—(CR$^7$R$^8$)$_n$—NH—CH-aryl-R$^6$, where n, R$^6$, R$^7$ and R$^8$ are as defined above;

—(CR$^7$R$^8$)$_n$—NH-aryl-aryl-R$^6$, where n, R$^6$, R$^7$, and R$^8$ are as defined above;

—(CR$^7$R$^8$)$_n$—NH—CO—NH-aryl-R$^6$, where n, R$^6$, R$^7$ and R$^8$ are as defined above;

NH-aryl-R$^6$, where R$^6$ is as defined above;

—(CR$^7$R$^8$)$_n$—CO—NH-aryl-aryl-R$^6$, where n, R$^6$, R$^7$, and R$^8$ are as defined above; or —(CR$^7$R$^8$)$_n$—CO—NH-aryl-aryl-R$^6$, where n, R$^6$, R$^7$, and R$^8$ are as defined above;

R$^5$ is H, aryl, cycloalkyl, arylalkyl, CHF$_2$, CHO, or R$^4$, where R$^4$ is as defined above; and at least two of R$^1$, R$^4$, R$^5$, and R$^6$ have amidine groups; or a pharmaceutically acceptable salt thereof.

The invention provides an embodiment of the formula V:

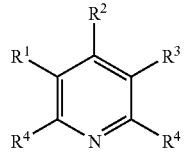

V wherein
$R^1$ is hydroxyl, O-alkyl, or O-alkyl-aryl-$R^5$, where $R^5$ is —CN, amidine, alkyl, or cycloalkyl;
$R^2$ is alkyl;
—$(CH_2)_m$—X, where m is an integer from 1 to 8 and X is OH or halo;
—$(CH_2)_n$COOH, where n is an integer from 0 to 8;
—$(CH_2)_n$COO$(CH_2)_n$CH$_3$, where n is as defined above;
—$(CH_2)_n$NH$(CH_2)_n$COOH, where n is as defined above;
—$(CH_2)_n$-aryl-$R^6$, where n is as defined above, and $R^6$ is —CN or amidine;
—$(CH_2)_n$-aryl-aryl-$R^6$, where n and $R^6$ are as defined above;
—$(CH_2)_m$—CHF$_2$, where m is defined as above;
—$(CH_2)_n$—NH-aryl-$R^6$, where n is as defined above and $R^6$ is as defined above;
—$(CH_2)_n$—NH—CO-aryl-$R^5$, where n and $R^5$ are as defined above;
—$(CH_2)_n$—NH-aryl-aryl-$R^6$, where n and $R^6$ are as defined above;
—$(CR_2)_n$—NH—CO-aryl-aryl-$R^7$, where n is as defined above and $R^7$ is —CN, —NO$_2$, NH$_2$ or amidine; or
—NH-aryl-$R^7$ where $R^7$ is as defined above;
$R^3$ is —$(CH_2)_m$OH, where m is as defined above;
—$(CH_2)_n$—NH-aryl-$R^6$, where n is as defined above and $R^6$ is as defined above;
—$(CH_2)_n$—NH—CO-aryl-$R^5$, where n and $R^5$ are as defined above;
—$(CH_2)_n$—NH-aryl-aryl-$R^6$, where n and $R^6$ are as defined above;
—$(CH_2)_n$—NH—CO-aryl-aryl-$R^7$, where n is as defined above and $R^7$ is —CN, —NO$_2$, NH$_2$, or amidine; or
—NH-aryl-$R^7$, where $R^7$ is as defined above;
$R^4$ is H, aryl, cycloalkyl, arylalkyl, CHF$_2$, CHO, or $R^2$, where $R^2$ is as defined above; and
at least two of $R^5$, $R^6$, and $R^7$ have amidine groups; or a pharmaceutically acceptable salt thereof.
In another embodiment, the invention provides compounds of formula VI:

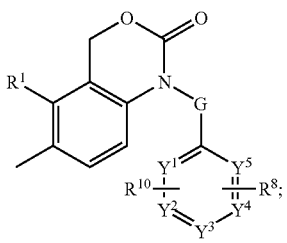

VI wherein
$R^1$ is hydroxyl, O-alkyl, or

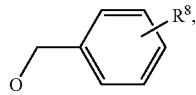

where $R^8$ is

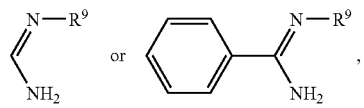

where $R^9$ is H, OH or O-alkyl;
G is C=O or $(CH_2)_{n'}$ where n=0, 1, 2 or 3;
$Y^1$, $Y^2$, $Y^3$, $Y^4$, and $Y^5$ are C—H and optionally one of $Y^1$-$Y^5$ is N; and
$R^{10}$ is H, F, —OCH$_3$, —OCF$_3$, or —CF$_3$;
or a pharmaceutically acceptable salt thereof.

DEFINITIONS

As used herein "alkyl" includes a saturated linear or branched hydrocarbon radical. In one embodiment, alkyl has from 1 to 8 carbon atoms. In another embodiment, alkyl has from 1 to 6 carbon atoms. In another embodiment, alkyl has from 1 to 4 carbon atoms, for example methyl, ethyl, propyl, isopropyl, butyl, and the like. The alkyl group may optionally be substituted with one or more substituents such as halo, for example, fluorine, chlorine, bromine, alkoxy groups having from 1 to 8 carbon atoms (e.g., methoxy or ethoxy), or amido groups having from 1 to 8 carbon atoms, such as acetamido. These substituents may themselves be substituted with one or more functional groups such as hydroxy groups, carboxy groups, acetoxy groups, or halogens.

As used herein "cycloalkyl" refers to a saturated hydrocarbon having from 3 to 8 carbon atoms, preferably 3 to 6 carbon atoms, such as, for example, cyclopropyl, cyclopentyl, cyclohexyl, and the like.

As used herein "aryl" means a mono- or poly-nuclear aromatic hydrocarbon radical. Examples of "aryl" groups include, but are not limited to aromatic hydrocarbons such as a phenyl group or a naphthyl group. The aromatic group may optionally be substituted with one or more substituents such as halo, for example, fluorine, chlorine, alkyl groups having from 1 to 8 carbon atoms (e.g., methyl or ethyl), alkoxy groups having from 1 to 8 carbon atoms (e.g., methoxy or ethoxy), alkoxyalkyl groups having from 1 to 8 carbon atoms and one or more oxygen atoms, or amido groups having from 1 to 8 carbon atoms, such as acetamido. These substituents may themselves be substituted with one or more functional groups such as hydroxy groups, carboxy groups, acetoxy groups, or halogens.

In one embodiment, aryl is a phenyl group or a naphthyl group that is either unsubstituted or substituted.

In another embodiment, aryl is a heteroaryl such as a five or six membered ring in which one or more of the carbon atoms of an aromatic hydrocarbon is substituted with a nitrogen, sulfur, or oxygen, or a combination thereof. Examples of a "heteroaryl" include, but are not limited to pyridine, pyrimidine, pyran, dioxin, oxazine, and oxathiazine. Likewise, the heteroaryl may optionally be substituted with functional groups such as hydroxy groups, carboxy groups, halogens, and amino groups.

As used herein, "amidine" means a group having the formula:

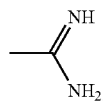

The invention also includes pharmaceutically acceptable salts of the compounds of the invention. The compounds of the invention are capable of forming both pharmaceutically acceptable acid addition and/or base salts. Pharmaceutically acceptable acid addition salts of the compounds of the invention include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and di-carboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine, etc. (see Berge et al., J. Pharmaceutical Science, 66: 1-19 (1977). The term "pharmaceutically acceptable salts" also includes any pharmaceutically acceptable base salt including, but not limited to, amine salts, trialkyl amine salts and the like. Such salts can be formed quite readily by those skilled in the art using standard techniques.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention. Base salts are formed with metals or amines, such as alkali and alkaline earth metals or organic amines. Examples of metals used as cations include, but are not limited to, sodium, potassium, magnesium, and calcium. Examples of suitable amines are N,N'-dibenzylethylenediamine, chloroprocaine, choline, diethanolamine, ethylenediamine, N-methylglucamine, and procaine.

Some of the compounds described herein contain one or more asymmetric centers and may thus give rise to enantiomers, diastereomers, and other stereoisomeric forms which may be defined in terms of absolute stereochemistry as (R)- or (S)-. The present invention is meant to include all such possible diastereomers and enantiomers as well as their racemic and optically pure forms. Optically active (R)- and (S)-isomers may be prepared using chiral synthons or chiral reagents, or resolved using conventional techniques. When the compounds described herein contain centers of geometric asymmetry, and unless specified otherwise, it is intended that the compounds include both E and Z geometric isomers. Likewise all tautomeric forms are intended to be included.

General Methods for Preparing Compounds of Formulae I to VI

Based on the numbering indicated in Formulae I, II and III, the following general methods outline the strategy for preparation of the various bis-amidines described herein. These methods describe modifications on the core pyridine ring of pyridoxine wherein an amidine or precursor or equivalent is installed at one of the positions $R^1$-$R^5$ (Formula 1), and a second amidine or precursor or equivalent is installed at one of the remaining ring positions. The compounds are generally prepared by combining an aldehyde, carboxylic acid, halide, or amine at a desired position with a complimentary aldehyde, carboxylic acid, halide, or amine group under conditions known to those skilled in the art, to produce an elaborated pyridine structure as shown in Schemes 1-4. The general methods for preparing the compounds of the formulae comprise of protecting the hydroxyl groups at $R_1$ and $R_2$ of pyridoxine with known blocking groups such as esters, ethers, cyclic acetals, cyclic ketals, etc. A thorough description of the application of such blocking groups is described in "Protective Groups in Organic Synthesis", Third Edition, T. W. Greene, P. G. M. Wuts, Wiley-Interscience (1999). Subsequent elaboration at $R^3$ can be achieved by generating an aldehyde, acid, halide, or amine functionality as shown in Schemes 1-4, and coupling with a suitable $R^6$-substituted aryl/biaryl agent. Substituent $R^6$ may be a nitro, amino, or cyano group that can be converted to an amidine by known chemical procedures.

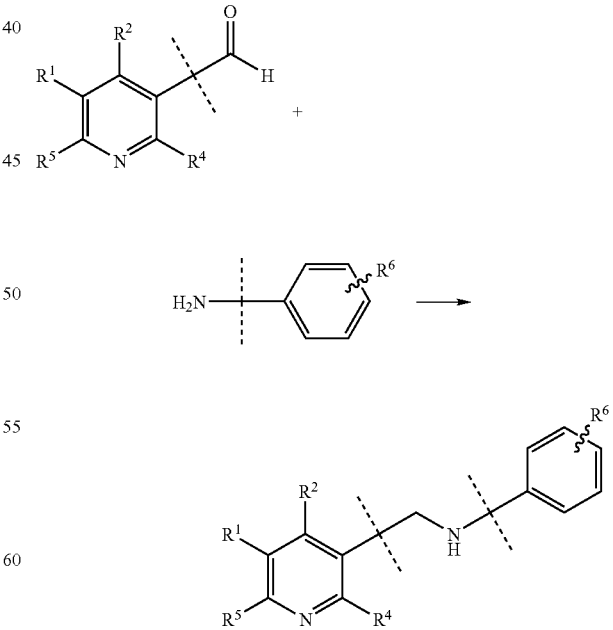

Where the dashed lines are $(CH_2)_n$, and n is an integer from 0 to 8. The aryl amine can also be a biaryl amine, and $R^6$ is as defined above.

Scheme 2 (where $R^3 = CO_2H$)

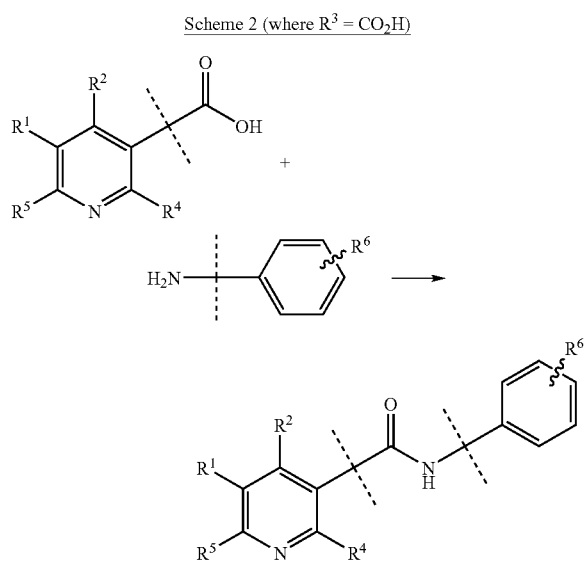

Where the dashed lines are $(CH_2)_n$, and n is an integer from 0 to 8. The aryl amine can also be a biaryl amine, and $R^6$ is as defined above.

Scheme 3 (where $R^3 = CH_2NH_2$)

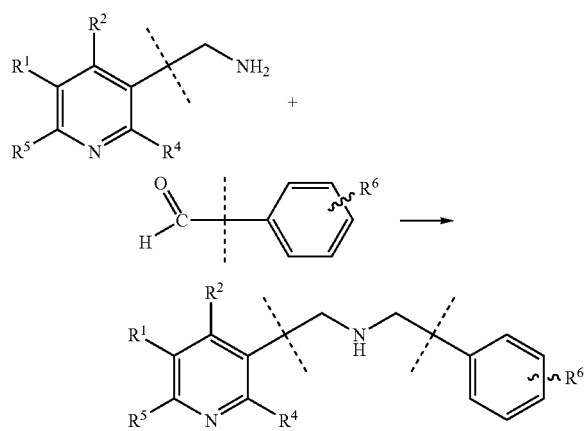

Where the dashed lines are $(CH_2)_n$, and n is an integer from 0 to 8. The aryl aldehyde can also be a biaryl aldehyde, and $R^6$ is as defined above.

Scheme 4 (where $R^3 = CH_2NH_2$)

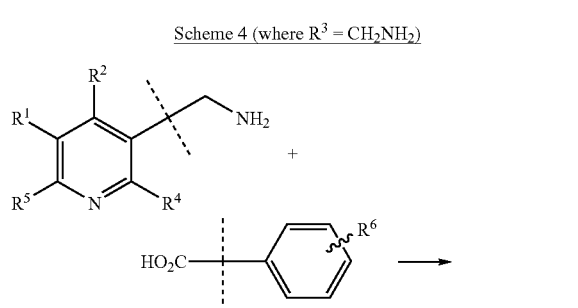

-continued

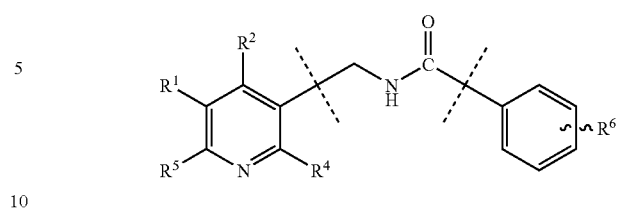

Where the dashed lines are $(CH_2)_n$, and n is an integer from 0 to 8. The aryl carboxylic acid can also be a biaryl carboxylic acid, and $R^6$ is as defined above. Assembly of the bis-amidine precursor then involves deprotection at $R^1$ and $R^2$, and subsequent O-alkylation at $R^1$ under conditions known to those skilled in the art, gives the bis-amidine and/or precursor as shown in Scheme 5.

Scheme 5 (where $R^1 = OH$)

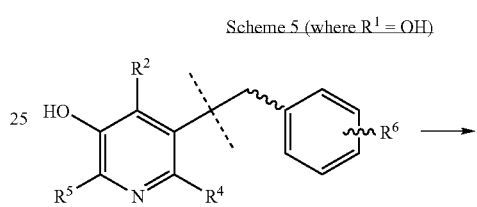

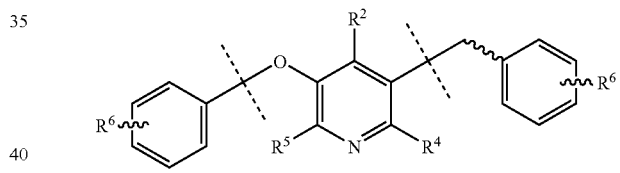

Where the dashed lines are $(CH_2)_n$, and n is an integer from 0 to 8. The initial amidine bearing substituent may be introduced at a position other than $R^3$. For example, protecting $R^1$ and $R^3$ with known blocking groups such as esters, ethers, cyclic acetals, cyclic ketals, etc., and elaborating $R^2$ through generating an aldehyde, acid, halide, or amine functionality and condensing with an appropriately functionalized amidine precursor bearing reagent under conditions known to those skilled in the art can be achieved as shown in Scheme 6. A second amidine carrying substituent can be introduced for example, as shown in Scheme 5 above if not already installed.

Scheme 6 (where $R^2$ is an aldehyde)

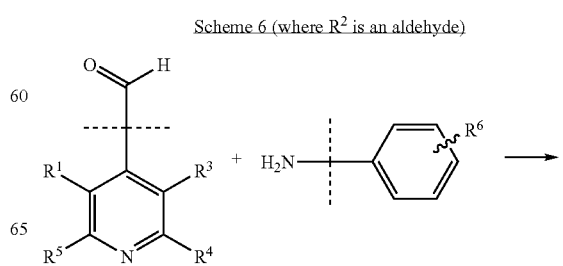

-continued

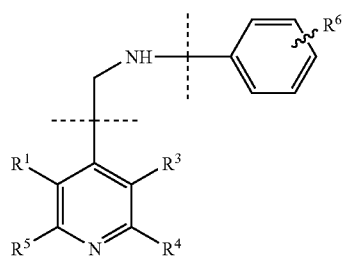

-continued

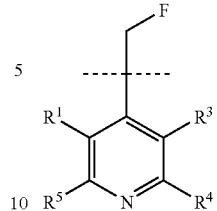

Where the dashed lines are $(CH_2)_n$, and n is an integer from 0 to 8. $R^7$ can represent an alkyl chain, branched or straight chain, and may include or terminate with a functional group.

Where the dashed lines are $(CH_2)_n$, and n is an integer from 0 to 8. Where $R^3$ is $CH_2OR'$ ($R'$ is a hydroxyl protecting group) or alternatively, $R^3$ is $(CH_2)_n$—Het-Ar—X, where n is an integer from 0 to 8, Ar—X is any aromatic terminating in a cyano, nitro, amidine, or amine and Het is O, NH, or NH flanked on either side with a carbonyl (C=O).

Other positions on the pyridoxine ring can also be substituted according to the aforementioned general schemes to provide a variety of bis-amidines on the pyridine ring of pyridoxine or one of its derivatives. Substitutions are not specific to the positions described above.

To provide further structural variations on the pyridine core of the pyridoxine bis-amidine series of compounds described herein, the starting material can include any commercially available pyridoxine derivative such as 4-deoxypyridoxine ($R^1$=OH, $R^2$=$CH_3$, $R^3$=$CH_2OH$, $R^4$=H, $R^5$=$CH_3$), and the methods described in the previous Schemes can be utilized to derive the novel bis-amidines from these starting materials as described herein. Other modifications at $R^2$ that lead to modified pyridoxine precursors suitable for the synthesis of novel bis-amidines are shown in Scheme 7. Note, fluorination is only one type of functional modification that can be carried out at position $R^2$ once the aldehyde is reduced.

The pyridine ring can be modified at $R^4$ by protecting the three hydroxyl groups of pyridoxine, then forming the N-oxide using reagents such as m-chlorobenzoic acid and carrying out aromatic nucleophilic substitutions using Grignard reagents or other methods known to those skilled in the art. A second approach to modification of this position is to employ the Diels Alder route to construct the pyridine ring of pyridoxine as shown in Scheme 8. The first step is to prepare diene A from the appropriate acyclic precursors, and secondly to form adduct C by reaction with appropriately functionalized dienophile B. The $R^{1'}$, $R^{2'}$ and $R^{3'}$ precursors can in turn, be converted to $R^1$, $R^2$ and $R^3$ under conditions known to those skilled in the art.

Scheme 8 (Modifications at $R^4$)

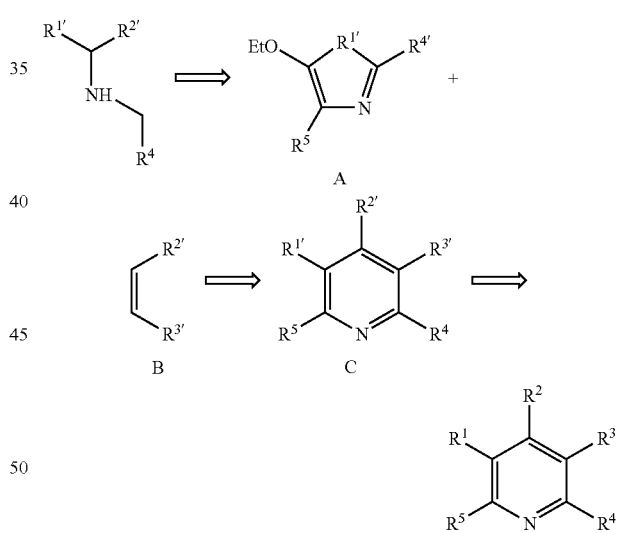

Scheme 7 (Modifications at $R^2$)

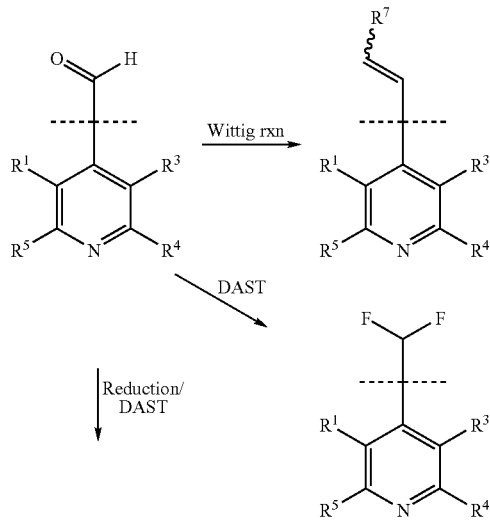

With the modification at $R^4$ now in hand, assembly of the bis-amidine can proceed as described in the previous schemes.

Modification at $R^5$ can be carried out conveniently after the bis-amidine precursor has been assembled as shown in Scheme 9. When $R^5$ is an alkyl group such as the methyl group and when pyridoxine is the starting material, preparation of the N-oxide, as mentioned earlier, and subsequent treatment with trifluoroacetic anhydride leads to oxidation at this position to a hydroxyl group. The hydroxyl functionality can be converted to many other functional groups (i.e. OH→F) under conditions known to those skilled in the art.

Scheme 9 (Modifications at $R^5$)

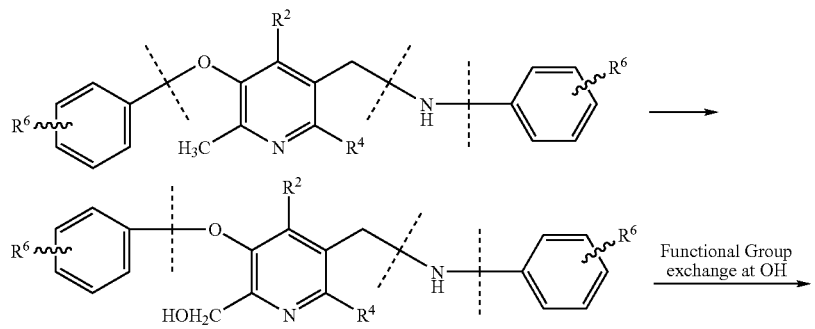

Where the dashed lines are $(CH_2)_n$, and n=0-8 and $R^6$ is as defined above. The above methods for preparing bis-amidines can also be applied to preparing blocked amidines that can behave as prodrugs. The term prodrug is used to describe compounds that are metabolized in the body to form compounds that are pharmacologically active. Simple examples of prodrugs of amidines are shown in Scheme 9.

Scheme 10 (Prodrugs)

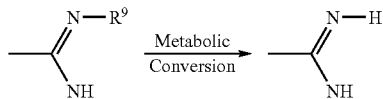

The methods described above pertain to preparing bis-amidines utilizing any of the positions $R^1$-$R^5$ of pyridoxine, and in addition, extending the functionality of any or all of the remaining positions.

Conditions to Be Treated

In one embodiment of the invention, compounds of the invention can be used to treat cardiovascular or related diseases. Cardiovascular or related diseases include, for example, cerebral ischemia, cerebral hemorrhage, ischemic stroke, hemorrhagic stroke, hypertension, myocardial infarction, ischemia reperfusion injury, myocardial ischemia, congestive heart failure, cardiac hypertrophy, thrombotic disorders related to coagulation enzymes and/or platelet adhesion, activation and aggregation. Cardiovascular or related diseases also include diseases that arise from thrombotic and prothrombotic states in which the coagulation cascade is activated such as, for example: arterial thrombosis, such as heart attack and stroke or peripheral arterial disease, such as intermittent claudication, or deep vein thrombosis, disseminated intravascular coagulopathy, and pulmonary embolism.

Pharmaceutical Compositions

Although it is possible for compounds of the invention to be administered alone in a unit dosage form, the compounds are typically administered in admixture with a carrier as a pharmaceutical composition to provide a unit dosage form. The invention provides pharmaceutical compositions containing at least one compound of the invention. A pharmaceutical composition comprises a pharmaceutically acceptable carrier in combination with a compound of the invention or a pharmaceutically acceptable salt of a compound of the invention.

A pharmaceutically acceptable carrier includes, but is not limited to, physiological saline, ringers, phosphate-buffered saline, and other carriers known in the art. Pharmaceutical compositions can also include additives such as, for example, stabilizers, antioxidants, colorants, excipients, binders, thickeners, dispersing agents, readsorpotion enhancers, buffers, surfactants, preservatives, emulsifiers, isotonizing agents, and diluents. Pharmaceutically acceptable carriers and additives are chosen such that side effects from the pharmaceutical compound are minimized and the performance of the compound is not canceled or inhibited to such an extent that treatment is ineffective.

Methods of preparing pharmaceutical compositions containing a pharmaceutically acceptable carrier in combination with a therapeutic compound of the invention or a pharmaceutically acceptable acid addition salt of a compound of the invention are known to those of skill in the art. All methods can include the step of bringing the compound of the invention in association with the carrier and additives. The formulations generally are prepared by uniformly and intimately bringing the compound of the invention into association with a liquid carrier or a finely divided solid carrier or both, and then, if necessary, shaping the product into the desired unit dosage forms.

For oral administration as a tablet or capsule, the compositions can be prepared according to techniques well known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or di-glycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Method of Treatment Using Compounds of the Invention

In another aspect of the invention, methods are provided for the treatment of cardiovascular or related diseases and symptoms thereof.

As used herein, the terms "treatment" and "treating" include inhibiting, alleviating, and healing cardiovascular or related diseases or symptoms thereof. Treatment can be carried out by administering a therapeutically effective amount of at least one compound of the invention. A "therapeutically effective amount" as used herein includes a prophylactic amount, for example an amount effective for alleviating or healing the above mentioned diseases or symptoms thereof.

A physician or veterinarian of ordinary skill readily determines a mammalian subject who is exhibiting symptoms of any one or more of the diseases described above. Regardless of the route of administration selected, a compound of the invention or a pharmaceutically acceptable acid addition salt of a compound of the invention can be formulated into pharmaceutically acceptable unit dosage forms by conventional methods known in the pharmaceutical art. An effective but nontoxic quantity of the compound is employed in treatment. The compounds can be administered in enteral unit dosage forms, such as, for example, tablets, sustained-release tablets, enteric coated tablets, capsules, sustained-release capsules, enteric coated capsules, pills, powders, granules, solutions, and the like. They can also be administered parenterally, such as, for example, subcutaneously, intramuscularly, intradermally, intramammarally, intravenously, and by other administrative methods known in the art.

The ordinarily skilled physician or veterinarian will readily determine and prescribe the therapeutically effective amount of the compound to treat the disease for which treatment is administered. In so proceeding, the physician or veterinarian could employ relatively low dosages at first, subsequently increasing the dose until a maximum response is obtained. Typically, the particular disease, the severity of the disease, the compound to be administered, the route of administration, and the characteristics of the mammal to be treated, for example, age, sex, and weight, are considered in determining the effective amount to administer. Administering a therapeutic amount of a compound of the invention for treating cardiovascular or related diseases or symptoms thereof, is in a range of about 0.1-100 mg/kg of a patient's body weight, more preferably in the range of about 0.5-50 mg/kg of a patient's body weight, per daily dose. The compound can be administered for periods of short and long duration. Although some individual situations can warrant to the contrary, short-term administration, for example, 30 days or less, of doses larger than 25 mg/kg of a patient's body weight is preferred to long-term administration. When long-term administration, for example, months or years, is required, the suggested dose usually does not exceed 25 mg/kg of a patient's body weight.

A therapeutically effective amount of a compound of the invention or a pharmaceutically acceptable addition salt of a compound of the invention for treating the above-identified diseases or symptoms thereof can be administered prior to, concurrently with, or after the onset of the disease or symptom. A compound of the invention can be administered concurrently. "Concurrent administration" and "concurrently administering" as used herein includes administering a compound of the invention and another therapeutic agent in admixture, such as, for example, in a pharmaceutical composition or in solution, or separately, such as, for example, separate pharmaceutical compositions or solutions administered consecutively, simultaneously, or at different times but not so distant in time such that the compound of the invention and the other therapeutic agent cannot interact and a lower dosage amount of the active ingredient cannot be administered.

In one embodiment of the invention, a method is provided for treating cardiovascular or related diseases comprising administering to a mammal a therapeutically effective amount of a compound of the invention or a pharmaceutically acceptable addition salt of a compound of the invention in a unit dosage form. The cardiovascular or related diseases that can be treated include cerebral ischemia, ischemia reperfusion injury, myocardial infarction, blood coagulation, or platelet aggregation. Preferably, the cardiovascular disease treated is ischemia reperfusion injury.

The compound of the invention can also be administered to treat cardiovascular diseases and other diseases that arise from thrombotic and prothrombotic states in which the coagulation cascade is activated, such as, for example, venous thrombosis, coagulation syndromes, deep vein thrombosis, disseminated intravascular coagulopathy, Kasabach-Merritt syndrome, pulmonary embolism, cerebral thrombosis, atrial fibrillation, cerebral embolism, myocardial infarction, stroke, thromboembolic complications of surgery (i.e., hip replacement, endarterectomy, introduction of artificial heart valves, vascular grafts, and mechanical organs), implantation or transplantation of organ, tissue, or cells, and peripheral arterial occlusion. A compound of the invention may also be useful in the treatment of complications of medications (i.e., oral contraceptives, hormone replacement, and heparin). A compound of the invention may also be useful in the treatment of adult respiratory distress syndrome, septic shock, septicemia, or inflammatory responses, such as edema and acute or chronic atherosclerosis, because thrombin has been shown to activate a large number of cells outside of the coagulation process, such as, for example, neutrophils, fibroblasts, endothelial cells, and smooth muscle cells. A compound of the invention may be useful in preventing thrombosis associated with artificial heart valves, stents, and ventricular enlargement including dilated cardiac myopathy and heart failure. A compound of the invention may be useful in treating thrombosis due to confinement (i.e. immobilization, hospitalization, bed rest etc.).

The method for treating cardiovascular or related diseases can further comprise concurrent administration of other therapeutic agents already known to be suitable for treating the above-identified diseases. For example, methods of the invention include concurrently administering a compound of the invention or a pharmaceutically acceptable acid addition salt of a compound of the invention in combination with a therapeutic cardiovascular compound to myocardial ischemia, ischemia reperfusion injury, or myocardial infarction. Preferably, the cardiovascular disease treated is ischemia reperfusion injury.

The compounds of the invention can also be used in combination with other therapeutic cardiovascular compounds that are generally used to treat cardiovascular or related diseases as well as symptoms thereof. A skilled physician or veterinarian readily determines a subject who is exhibiting symptoms of any one or more of the diseases described above and makes the determination about which compound is generally suitable for treating specific cardiovascular conditions and symptoms.

For example, myocardial ischemia can be treated by the administration of a compound of the invention or a pharmaceutically acceptable acid addition salt of a compound of the invention concurrently with another therapeutic agent. Other suitable therapeutic agents include, for example, a angiotensin converting enzyme inhibitor, an angiotensin II receptor antagonist, a calcium channel blocker, an antithrombolytic agent, a β-adrenergic receptor antagonist, a diuretic, an α-adrenergic receptor antagonist, or a mixture thereof.

Myocardial infarction can be treated by the administration of a compound of the invention or a pharmaceutically acceptable acid addition salt of a compound of the invention concurrently with another therapeutic agent. Other suitable therapeutic agents include, for example, a angiotensin converting enzyme inhibitor, a calcium channel blocker, an anti-thrombolytic agent, a β-adrenergic receptor antagonist, a diuretic, an α-adrenergic receptor antagonist, or a mixture thereof.

Blood clots in the arteries (arterial thrombosis) or veins (venous thrombosis) can be reduced or removed by the administration of a compound of the invention or a pharmaceutically acceptable acid addition salt of a compound of the invention concurrently with an anti-platelet agent such as clopidogrel, aspirin, dipyridamole, etc., glycoprotein IIb/IIIa inhibitor such as integrillin etc., or by anticoagulant such as UFH (unfractionated heparins) or LMWH (low molecular weight heparins) or by hirudin or argatroban etc.

Ischemia reperfusion injury can be treated by the administration of a compound of the invention or a pharmaceutically acceptable acid addition salt of a compound of the invention concurrently with another therapeutic agent. Other suitable therapeutic agents include, for example, an angiotensin converting enzyme inhibitor, an angiotensin II receptor antagonist, a calcium channel blocker, or a mixture thereof.

These compounds are also useful in preventing thrombosis and complications in patients genetically predisposed to arterial thrombosis or venous thrombosis (including activated protein C resistance, $FV_{leiden}$, Prothrombin 20210, elevated coagulation factors FVII, FVIII, FIX, FX, FXI, prothrombin, TAFI and fibrinogen), elevated levels of homocystine, and deficient levels of antithrombin, protein C, and protein S. The inventive compounds may be used for treating heparin-intolerant patients, including those with congenital and acquired antithrombin III deficiencies, heparin-induced thrombocytopenia, and those with high levels of polymorphonuclear granulocyte elastase.

The present compounds may also be used to inhibit blood coagulation in connection with the preparation, storage, fractionation, or use of whole blood. For example, the compounds may be used to maintain whole and fractionated blood in the fluid phase such as required for analytical and biological testing, e.g., for ex vivo platelet and other cell function studies, bioanalytical procedures, and quantitation of blood-containing components. The compounds may be used as anticoagulants in extracorpeal blood circuits, such as those necessary in dialysis and surgery (such as coronary artery bypass surgery); for maintaining blood vessel patency in patients undergoing transluminal coronary angioplasty, vascular surgery including bypass grafting, arterial reconstruction, atherectomy, vascular graft and stent patency, tumor cell metastasis, and organ, tissue, or cell implantation and transplantation.

The inventive compounds are also useful as anti-inflammatory agents, in treating chronic asthma, allergic rhinitis, inflammatory bowel disease, psoriasis, conjunctivitis, atopic dermatitis, pancreatis, rheumatoid arthritis, osteoarthritis, septic shock, and chronic inflammatory joint diseases, diseases of joint cartilage destruction, and/or vascular damage due to bacterial and/or viral infections. Additionally, the inventive compounds may be useful for treating diabetic retinopathy or motor neuron diseases such as amyotrophic lateral sclerosis, progressive muscular atrophy, and primary lateral sclerosis. Additionally, the inventive compounds may be useful for tissue remodeling diseases and for treating plaque instability and sequelli. In addition, these compounds may be useful for treating fibrotic diseases and conditions, for example, fibrosis, scleroderma, pulmonary fibrosis, liver cirrhosis, myocardial fibrosis, neurofibromas, and hypertrophic scars.

In addition, the compounds of the present invention are useful in treating cancer and preventing the prothrombotic complications of cancer. In view of their metastasis inhibition activity, the compounds are useful in treating tumor growth, as an adjunct to chemotherapy, and for treating diseases involving metastases including, but not limited to cancer, more particularly, cancer of the lung, prostate, colon, breast, ovaries, and bone. These compounds may also be useful in preventing angiogenesis.

The inventive compounds may also be used in combination with other antithrombotic or anticoagulant drugs such as thrombin inhibitors, platelet aggregation inhibitors such as aspirin, clopidogrel, ticlopidine or CS-747, warfarin, low molecular weight heparins (such as LOVENOX), AT-III binding pentasaccharides or heparin-derived oligosaccharides, GPIIb/GPIIIa blockers, PAI-I inhibitors such as XR-330 and T-686, inhibitors of α-2-antiplasmin such as anti-α-2-antiplasmin antibody and thromboxane receptor antagonists (such as ifetroban), prostacyclin mimetics, phosphodiesterase (PDE) inhibitors, such as dipyridamole or cilostazol, PDE inhibitors in combination with thromboxane receptor antagonists/thromboxane A synthetase inhibitors (such as picotamide), serotonin-2-receptor antagonists (such as ketanserin), fibrinogen receptor antagonists, hypolipidemic agents, such as HMG-CoA reductase inhibitors, e.g., pravastatin, simvastatin, atorvastatin, fluvastatin, cerivastatin, AZ4522, itavastatin (Nissan/Kowa), microsomal triglyceride transport protein inhibitors (such as disclosed in U.S. Pat. Nos. 5,739,135, 5,712,279 and 5,760,246), antihypertensive agents such as angiotensin-converting enzyme inhibitors (e.g., captopril, lisinopril or fosinopril); angiotensin-II receptor antagonists (e.g., irbesartan, losartan or valsartan), and/or ACE/NEP inhibitors (e.g., omapatrilat and gemopatrilat), β-blockers (such as propranolol, nadolol and carvedilol), PDE inhibitors in combination with aspirin, ifetroban, picotamide, ketanserin, or clopidogrel. The inventive compounds are also useful in combination with anti-arrhythmic agents such as for atrial fibrillation, for example, amiodarone or dofetilide.

The inventive compounds may also be useful in combination with other anticancer strategies and chemotherapies such as taxol and/or cisplatin.

The compounds may act synergistically with one or more of the above agents. For example, the inventive compounds may act synergistically with the above agents to prevent reocclusion following a successful thrombolytic therapy and/or reduce the time to reperfusion. Thus, reduced doses of thrombolytic agent(s) may be used, therefore minimizing potential hemorrhagic side effects.

Additionally, medical devices can be coated with the compounds of the invention or pharmaceutically acceptable acid salts of the compound alone or in mixture with other suitable therapeutic agents (e.g., an angiotensin converting enzyme inhibitor). Medical devices that can be coated with the compounds of the invention or pharmaceutically acceptable salts thereof alone or in mixture with other suitable therapeutic agents include, but are not limited to, intravascular stents and catheters. Intravascular stents are used to prevent blood vessel wall collapse. Drug-eluting stents are coated with a mixture of polymers and drug to prevent restenosis. Examples of drug-eluting stents are the CYPHER™ sirolimus-eluting stent (Cordis Corp., Miami, Fla.) and TAXUS™ paclitaxel-eluting stent (Boston Scientific Corp., Natick, Mass.).

This invention is further characterized by the following examples. These examples are not meant to limit the scope of the invention but are provided for exemplary purposes to more fully describe the invention. Variation within the scope of the invention will be apparent to those skilled in the art.

EXAMPLES

All reagents used were purchased from standard commercial sources, or synthesized by known literature methods. HPLC analysis was performed using a Water 996 PDA High performance Liquid chromatograph equipped with a Water 600 controller. Signals were detected with a photodiode array detector (set at max plot 254-400 nm). NMR spectra were recorded on a Bruker AM-300 instrument ($^{13}C$, $^{19}F$ and $^{31}P$ at 75.5, 282 and 121 MHz respectively) and were calibrated using residual nondeuterated solvent as the internal reference. All $^{19}F$ spectra are reported using hexafluorobenzene ($\delta$-162.9 ppm) as the external standard while $^{31}P$ spectra were collected using 85% $H_3PO_4$ ($\delta$0.0 ppm) as the external reference.

Example 1

Synthesis of 4-{[3-(4-Cyano-benzyloxy)-5-hydroxymethyl-2-methyl-pyridin-4-ylmethyl]-amino}-benzonitrile (2)

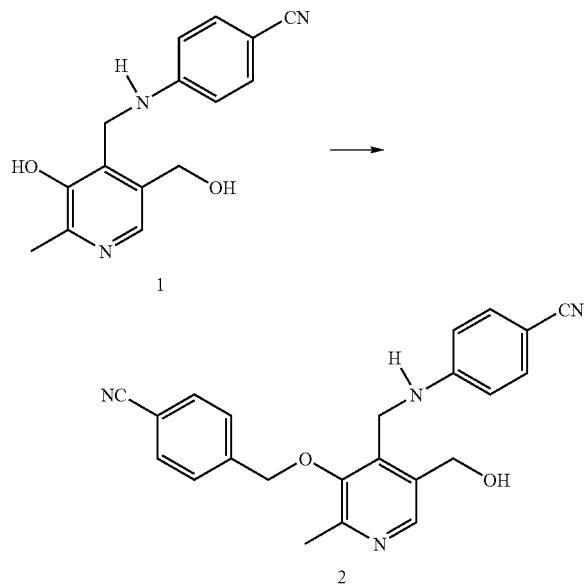

A mixture of 4-[(3-hydroxy-5-hydroxymethyl-2-methyl-pyridin-4-ylmethyl)-amino]-benzonitrile (1)* (404 mg, 1.5 mmol), α-bromo-p-tolunitrile (322 mg, 1.65 mmol), potassium carbonate (622 mg, 4.5 mmol) and DMF (10 mL) was stirred at room temperature under nitrogen atmosphere overnight. The reaction mixture was evaporated to dryness, and the crude product purified by column chromatography on silica gel using a gradient of dichloromethane:methyl alcohol (9:1) as eluant to give 4-{[3-(3-cyano-benzyloxy)-5-hydroxymethyl-2-methyl-pyridin-4-ylmethyl]-amino}-benzonitrile (2) (348 mg, 60% yield) as a colorless solid.

$^1$H-NMR (DMSO-d6): δ 8.32 (s, 1H), 7.83-7.74 (m, 3H), 7.56 (t, 1H), 7.44 (d, 2H), 6.76 (t, 1H), 6.69 (d, 2H), 5.32 (s, 1H), 4.95 (s, 2H), 4.59 (s, 2H), 4.31 (d, 2H), 2.47 (s, 3H).

*U.S. Pat. No. 6,417,204B1(2002)

Example 2

Synthesis of 4-{[3-(4-Carbamimidoyl-benzyloxy)-5-hydroxymethyl-2-methyl-pyridin-4-ylmethyl]-amino}-benzamidine (3)

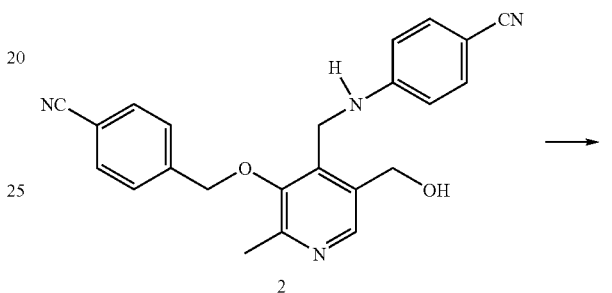

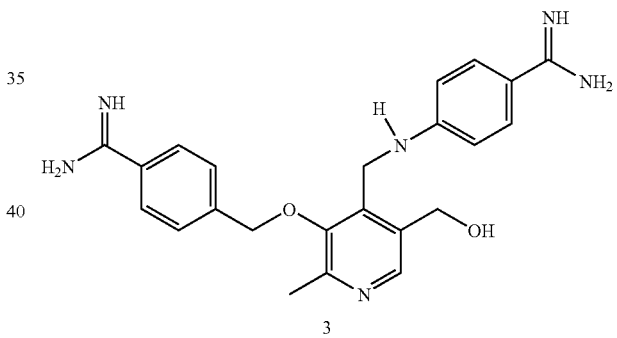

Hydrogen chloride gas was bubbled into a suspension of 4-{[3-(4-cyano-benzyloxy)-5-hydroxymethyl-2-methyl-pyridin-4-ylmethyl]-amino}-benzonitrile (2) (102 mg, 0.265 mmol) in absolute ethyl alcohol (100 mL) at room temperature for 30 minutes. The septum was replaced and the reaction mixture was stirred for overnight at room temperature. The reaction mixture was purged with nitrogen gas for 2 hours to remove excess hydrogen chloride and the solvent evaporated to give the crude imino ester as a solid. Ammonia in methyl alcohol (10 mL, 7M, 70 mmol) was then added to the crude amide ester and stirred overnight at room temperature. The solvent was evaporated and the product purified on a silica gel column using a mixture of water:methyl alcohol:chloroform (1:10:20) as eluant to give the corresponding 4-{[3-(4-carbamimidoyl-benzyloxy)-5-hydroxymethyl-2-methyl-pyridin-4-ylmethyl]-amino}-benzamidine (3) as a light yellow solid.

$^1$H-NMR (CD$_3$OD): δ 8.30 (s, 1H), 7.93 (t, 1H), 7.81 (d, 1H), 7.60-7.56 (m, 3H), 7.43 (t, 1H), 6.75 (d, 2H), 5.01 (s, 2H), 4.74 (s, 2H), 4.46 (s, 2H), 2.57 (s, 3H).

MS m/z (ES$^+$): 420.40 (M+H$^+$).

Example 3

Synthesis of 4'-{[5-(4-Cyano-benzyloxy)-4-hydroxymethyl-6-methyl-pyridin-3-ylmethyl]-amino}-biphenyl-4-carbonitrile (4)

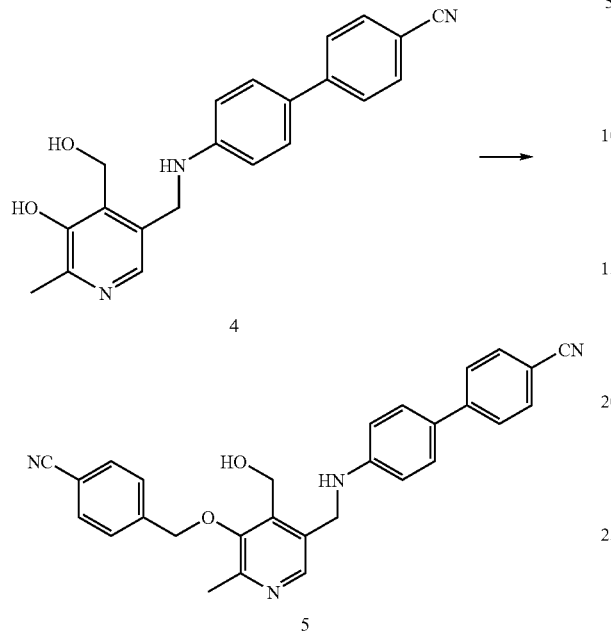

A mixture of 4'-[(5-hydroxy-4-hydroxymethyl-6-methyl-pyridin-3-ylmethyl)-amino]-biphenyl-4-carbonitrile (4) (691 mg, 2.0 mmol), α-bromo-p-tolunitrile (392 mg, 2.0 mmol), cesium carbonate (1303 mg, 4.0 mmol) and DMF (20 mL) was stirred at room temperature under nitrogen atmosphere overnight. The reaction mixture was evaporated to dryness, and the crude product purified by column chromatography on silica gel using a gradient of dichloromethane:methyl alcohol (20:1) as eluant to give product 4'-{[5-(4-cyano-benzyloxy)-4-hydroxymethyl-6-methyl-pyridin-3-ylmethyl]-amino}-biphenyl-4-carbonitrile (5) (513 mg, 56% yield).

$^1$H-NMR (DMSO-d6): δ 8.22 (s, 1H), 7.92 (d, 2H), 7.81-7.71 (m, 6H), 7.54 (d, 2H), 6.73 (d, 2H), 6.54 (t, 1H), 5.32 (t, 1H), 5.04 (s, 2H), 4.65 (d, 2H), 4.50 (d, 2H), 2.42 (s, 3H).

Example 4

Synthesis of 4'-{[5-(4-Carbamimidoyl-benzyloxy)-4-hydroxymethyl-6-methyl-pyridin-3-ylmethyl]-amino}-biphenyl-4-carboxamidine (6)

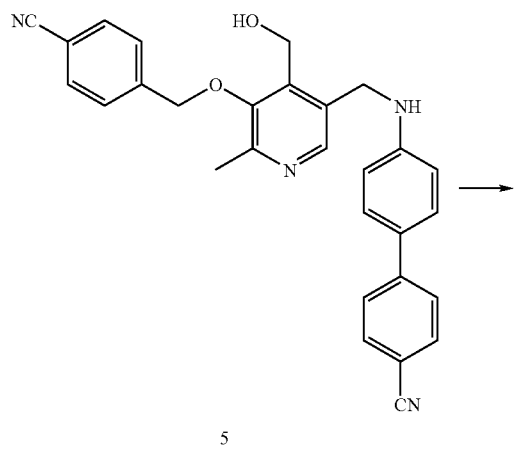

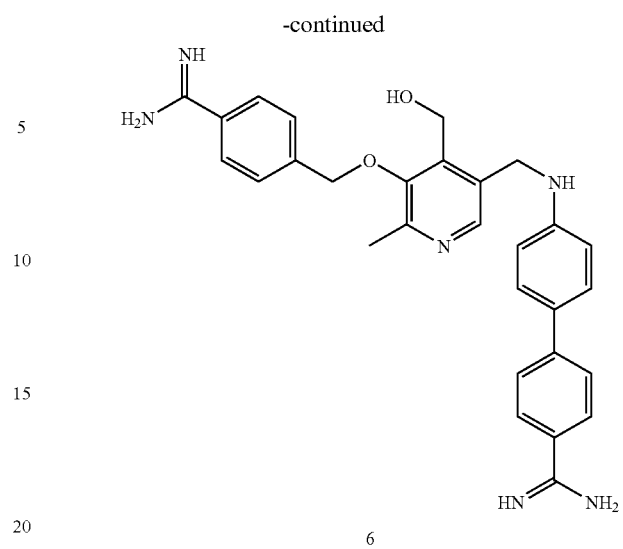

The conversion of bis-nitrile (5) to bis-amidine (6) was carried out as described in Example 2.

$^1$H-NMR (DMSO-d6): δ 7.97 (s, 1H), 7.69-7.43 (m, 8H), 7.32 (d, 2H), 6.50 (d, 2H), 6.34 (t, 1H), 5.17 (t, 1H), 4.81 (s, 2H), 4.43 (d, 2H), 4.26 (d, 2H), 2.17 (s, 3H).

MS m/z (ES$^+$): 495.48 (M+H$^+$).

Example 5

Synthesis of 4-{[5-(4-Cyano-benzyloxy)-4-hydroxymethyl-6-methyl-pyridin-3-ylmethyl]-amino}-benzonitrile (8)

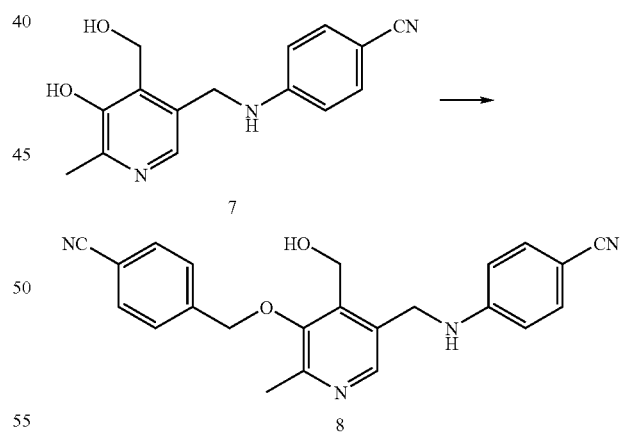

The coupling of 4-[(5-hydroxy-4-hydroxymethyl-6-methyl-pyridin-3-ylmethyl)-amino]-benzonitrile (805 mg, 3.0 mmol) (7) and α-bromo-p-tolunitrile (588 mg, 3.0 mmol), as described in Example 3, gave 4-{[5-(4-cyano-benzyloxy)-4-hydroxymethyl-6-methyl-pyridin-3-ylmethyl]-amino}-benzonitrile (8) (23 mg, 9% yield) as a colorless solid.

$^1$H-NMR (CDCl$_3$): δ 8.35 (s, 1H), 7.72 (d, 2H), 7.58 (d, 2H), 7.46 (d, 2H), 6.68 (d, 2H), 5.01 (s, 2H), 4.76 (s, 2H), 4.45 (s, 2H), 2.56 (s, 3H).

Example 6

Synthesis of 4-{4-Hydroxymethyl-2-methyl-5-[(4-carbamimidoyl-benzyloxy)-methyl]-pyridin-3-yloxymethyl}-benzamidine (9)

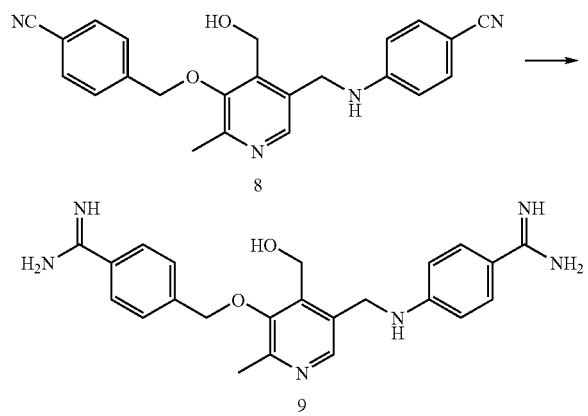

The conversion of bis-nitrile (8) to bis-amidine (9) was carried out as described in Example 2.

$^1$H-NMR (CD$_3$OD): δ 8.22 (s, 1H), 7.91 (d, 2H), 7.81 (d, 2H), 7.66 (d, 2H), 6.81 (d, 2H), 5.14 (s, 2H), 4.68 (s, 2H), 2.51 (s, 3H).

MS m/z (ES$^+$): 419.61 (M+H$^+$).

Example 7

Synthesis of 4-{[5-(4-Cyano-benzyloxy)-4-fluoromethyl-6-methyl-pyridin-3-ylmethyl]-amino}-benzonitrile (10)

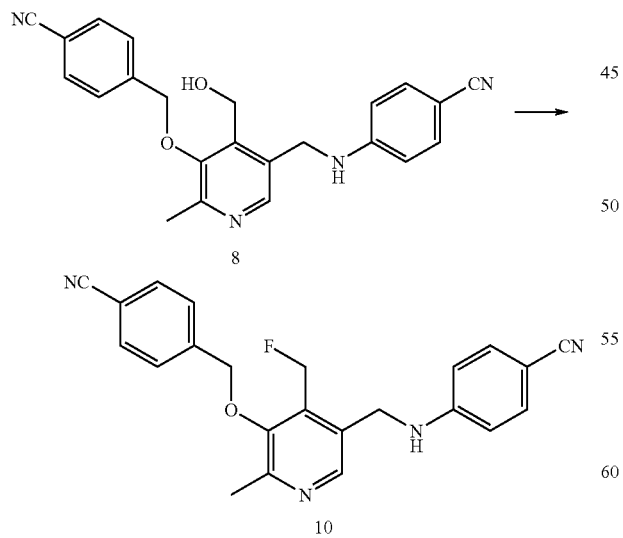

To a solution of 4-{[5-(4-cyano-benzyloxy)-4-hydroxymethyl-6-methyl-pyridin-3-ylmethyl]-amino}-benzonitrile (8) (1765 mg, 4.60 mmol) in dry dichloromethane (200 mL) was slowly added diethylaminosulfurtrifluoride (DAST) (741 mg, 4.6 mmol) in dry dichloromethane (50 mL) at −78° C. under nitrogen atmosphere. The reaction temperature was warmed to −40° C. and stirred for 30 minutes. The reaction mixture was then poured into a cold solution of saturated aqueous sodium bicarbonate, and the crude product was extracted with dichloromethane, washed with water, and dried over anhydrous magnesium sulfate. Evaporation of the solvent gave a crude residue, which was purified by column chromatography on silica gel using dichloromethane:hexane:methyl alcohol (15:10:1) as an eluant to give 4-{[5-(4-cyano-benzyloxy)-4-fluoromethyl-6-methyl-pyridin-3-ylmethyl]-amino}-benzonitrile (10) (650 mg, 37% yield) as a colorless solid.

$^1$H-NMR (CDCl$_3$): δ 8.39 (s, 1H), 6.74-7.61 (m, 8H), 5.52 (d, 2H), 4.97 (s, 2H), 4.48 (s, 2H), 2.57 (s, 3H).

$^{19}$F-NMR(CDCl$_3$): δ-211.35.

Example 8

Synthesis of 4-{4-Fluoromethyl-2-methyl-5-[(4-carbamimidoyl-benzyloxy)-methyl]-pyridin-3-yloxymethyl}-benzamidine (11)

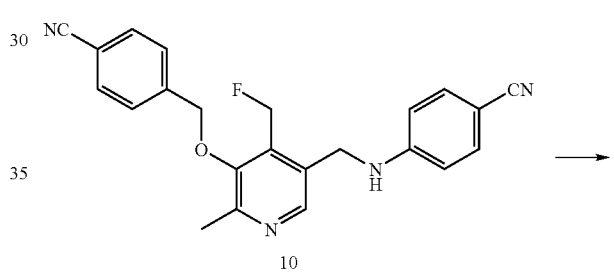

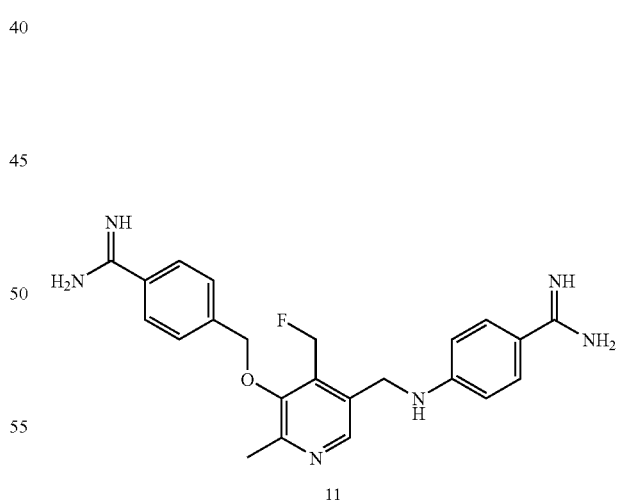

The conversion of bis-nitrile (10) to bis-amidine (11) was carried out as described in Example 2.

$^1$H-NMR (CD$_3$OD): δ 8.29 (s, 1H), 6.90-7.76 (m, 8H), 5.66 (d, 2H), 5.09 (s, 2H), 4.61 (s, 2H), 2.53 (s, 3H).

$^{19}$F-NMR (DMSO-d$_6$): δ-211.43.

Example 9

Synthesis of 4-(2,2,8-Trimethyl-4H-[1,3]dioxino[4,5-c]pyridin-5-ylmethoxy)-benzonitrile

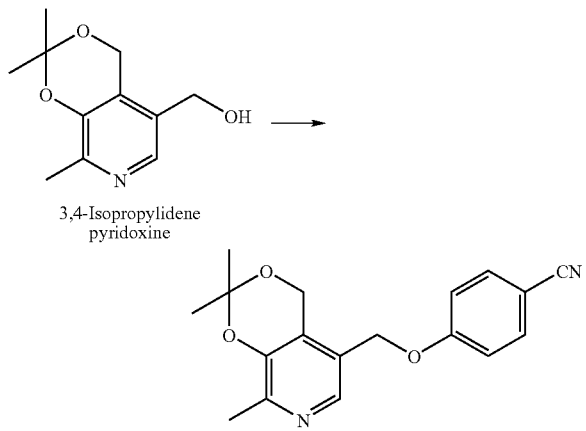

To a mixture of the 3,4-isopropylidene pyridoxine (2.30 g, 11 mmol), 4-hydroxybenzonitrile (1.19 g, 10 mmol) and triphenylphosphine (PPh$_3$) (2.9 g, 11 mmol) in 100 mL dry THF was added diethyl azodicarboxylate (DEAD) (1.9 g, 11 mmol). The reaction mixture was stirred at room temperature for 1.5 hours. The solvent was then removed under vacuum and the residue purified by column chromatography on silica gel to give 4-(2,2,8-trimethyl-4H-[1,3]dioxino[4,5-c]pyridin-5-ylmethoxy)-benzonitrile (12) as a light color solid in quantitive yield.

$^1$H-NMR (CDCl$_3$): δ 8.05 (s, 1H), 7.60 (d, 2H), 7.01 (d, 2H), 4.99 (s, 2H), 4.86 (s, 2H), 2.43 (s, 3H), 1.55 (s, 6H).

Example 10

Synthesis of 4-(5-Hydroxy-4-hydroxymethyl-6-methyl-pyridin-3-ylmethoxy)-benzonitrile

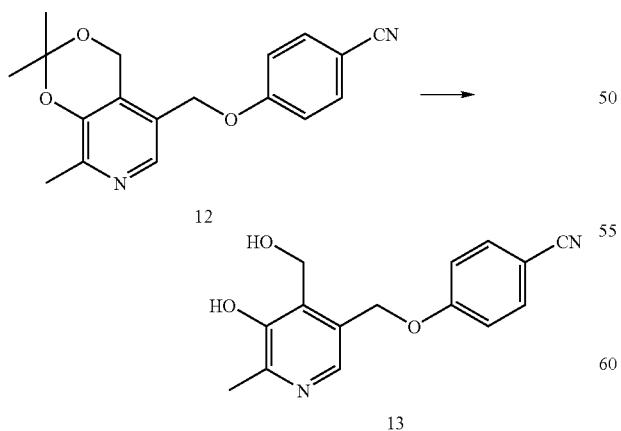

A solution of 4-(2,2,8-trimethyl-4H-[1,3]dioxino[4,5-c]pyridin-5-ylmethoxy)-benzonitrile (12) (3.10 g, 10 mmol) in THF (30 mL) was heated in a solution of 10% formic acid in water for 2 hours at 80° C. Upon evaporating the solvent, the crude product was washed with a mixture of ethyl acetate and hexane (1:2, 200 mL) to give 4-(5-hydroxy-4-hydroxymethyl-6-methyl-pyridin-3-ylmethoxy)-benzonitrile (13) (2.48 g, 92% yield).

$^1$H-NMR (DMSO-d6): δ 9.33 (br, 1H), 8.01 (s, 1H), 7.78 (dd, 2H), 7.19 (dd, 2H), 5.81 (br, 1H), 5.23 (s, 2H), 4.74 (s, 2H), 2.36 (s, 3H).

Example 11

Synthesis of 4-(5-(4-Cyano-benzyloxy)-4-hydroxymethyl-6-methyl-pyridin-3-ylmethoxy)-benzonitrile (14)

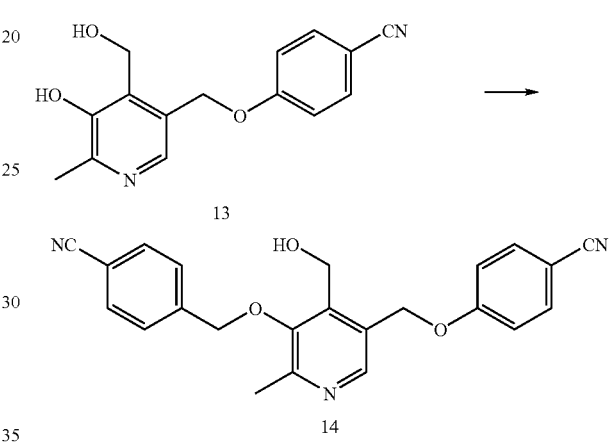

The coupling of 4-(5-hydroxy-4-hydroxymethyl-6-methyl-pyridin-3-ylmethoxy)-benzonitrile (13) (1.08 g, 4.0 mmol) and α-bromo-p-tolunitrile (0.9 g, 4.8 mmol), as described in Example, gave 4-(5-(4-cyano-benzyloxy)-4-hydroxymethyl-6-methyl-pyridin-3-ylmethoxy)-benzonitrile (14) (755 mg, 49% yield) as a colorless solid.

$^1$H-NMR (DMSO-d6): δ 8.36 (s, 1H), 7.91 (d, 2H), 7.80 (d, 2H), 7.72 (d, 2H), 7.22 (d, 2H), 5.37 (s, 2H), 5.32 (t, 1H), 5.04 (s, 2H), 4.62 (d, 2H), 2.46 (s, 3H).

Example 12

Synthesis of 4-(5-(4-Carbamimidoyl-benzyloxy)-4-hydroxymethyl-6-methyl-pyridin-3-ylmethoxy)-benzamidine (15)

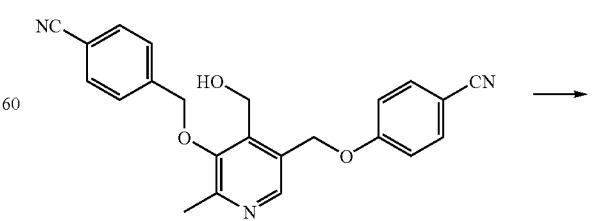

-continued

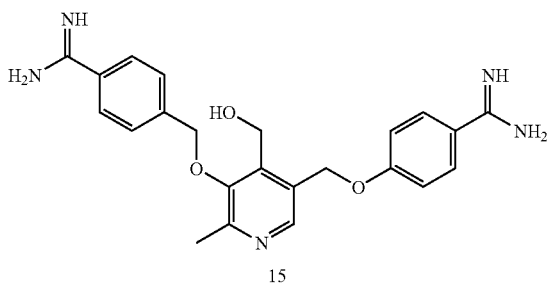

The conversion of bis-nitrile (14) to bis-amidine (15) was carried out as described in Example 2.

$^1$H-NMR (CD$_3$OD): δ 9.56-9.16 (m, 6H), 8.58 (s, 1H), 7.96-7.20 (m, 8H), 5.57 (s, 2H), 5.20 (s, 2H), 4.74 (s, 2H), 2.69 (s, 3H).

MS m/z (ES$^+$): 420.60 (M+H$^+$).

Example 13

Synthesis of 4-[4-Carbaldehyde-6-methyl-5-(4-cyano-benzyloxy)-pyridin-3-ylmethoxy]-benzonitrile (16)

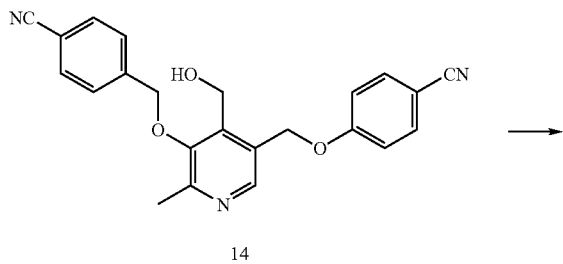

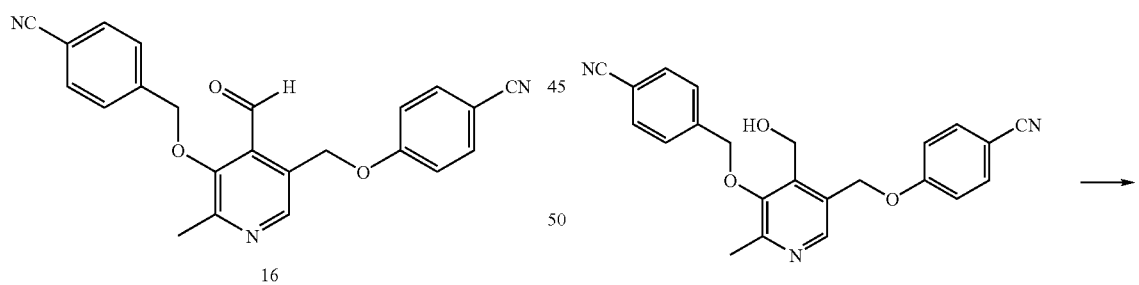

A solution of 4-(5-(4-cyano-benzyloxy)-4-hydroxymethyl-6-methyl-pyridin-3-ylmethoxy)-benzonitrile (14) (1.02 g, 2.65 mmol) and an excess amount of manganese (IV) dioxide in toluene (50 mL) was stirred at 90° C. for 5 hours. Excess manganese (IV) dioxide was filtered through a celite pad and washed with ethyl acetate. The filtrate was evaporated to give 4-[4-carbaldehyde-6-methyl-5-(4-cyano-benzyloxy)-pyridin-3-ylmethoxy]-benzonitrile (16) as a colorless solid (3.6 g, 65% yield).

$^1$H-NMR (CDCl$_3$): δ 10.48 (s, 1H), 8.72 (s, 1H), 7.075-7.04 (m, 8H), 5.41 (s, 2H), 5.08 (s, 2H), 2.65 (s, 3H).

Example 14

Synthesis of 4-[4-Carbaldehyde-6-methyl-5-(4-carbamimidoyl-benzyloxy)-pyridin-3-ylmethoxy]-benzamidine (17)

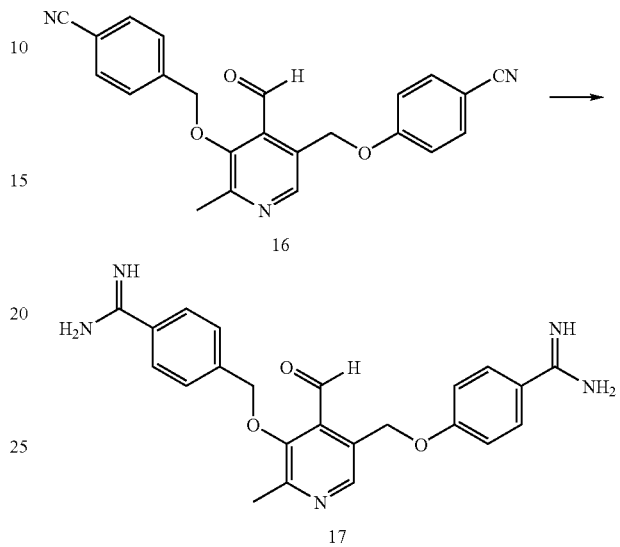

The conversion of bis-nitrile (16) to bis-amidine (17) was carried out as described in Example 2.

$^1$H NMR (DMSO-d$_6$): δ 10.46 (s, 1H), 9.39-9.16 (br, 6H), 8.59 (s, 1H), 7.90-7.21 (m, 8H), 5.49 (s, 2H), 5.21 (s, 2H), 2.56 (s, 3H)

Example 15

Synthesis of 4-[4-Fluoromethyl-6-methyl-5-(4-cyano-benzyloxy)-pyridin-3-ylmethoxy]-benzonitrile (18)

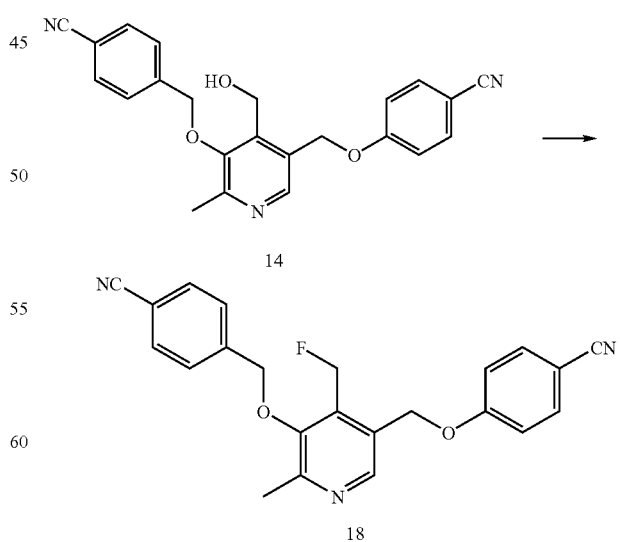

To a solution of 4-(5-(4-cyano-benzyloxy)-4-hydroxymethyl-6-methyl-pyridin-3-ylmethoxy)-benzonitrile (14) (600 mg, 1.6 mmol) in dry dichloromethane (20 mL) was slowly added DAST (251 mg, 1.6 mmol, in 50 mL dry dichloromethane) at −78° C. under nitrogen atmosphere. The reaction mixture was warmed to room temperature and stirred for 3 hours. The reaction mixture was then poured into a cold solution of saturated aqueous sodium bicarbonate, and the crude product extracted with dichloromethane, washed with water, dried over anhydrous magnesium sulfate. Evaporation of the solvent gave a crude residue, which was purified by column chromatography on silica gel using ethyl acetate:hexane:methyl alcohol (7:7:1) as an eluant to give 4-[4-fluoromethyl-6-methyl-5-(4-cyano-benzyloxy)-pyridin-3-ylmethoxy]-benzonitrile (18) (314 mg, 52% yield) as a colorless solid.

$^1$H-NMR (CDCl$_3$): δ 8.45 (s, 1H), 7.73-7.01 (m, 8H), 5.52 (d, 2H), 5.19 (s, 2H), 4.97 (s, 2H), 2.58 (s, 3H).

$^{19}$F-NMR (CDCl$_3$): δ-213.12.

Example 16

Synthesis of 4-[4-Fluoromethyl-6-methyl-5-(4-carbamimidoyl-benzyloxy)-pyridin-3-ylmethoxy]-benzamidine (19)

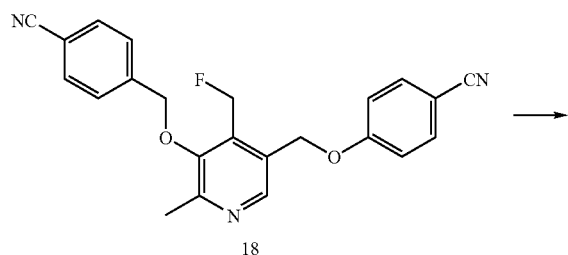

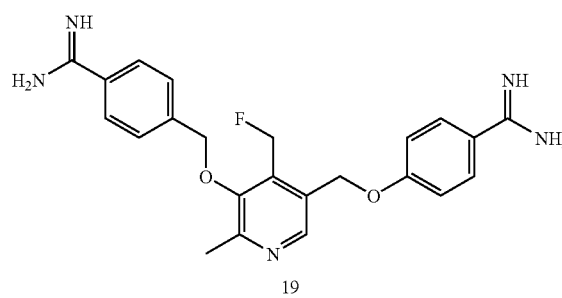

The conversion of bis-nitrile (18) to bis-amidine (19) was carried out as described in Example 2.

$^1$H-NMR (CD$_3$OD): δ 8.54 (s, 1H), 7.91-7.27 (m, 8H), 5.70 (d, 2H), 5.42 (s, 2H), 5.15 (s, 2H), 2.63 (s, 3H).

$^{19}$F-NMR (CD3OD): δ-216.86.

Example 17

Synthesis of 4-[4,4-Difluoromethyl-6-methyl-5-(4-cyano-benzyloxy)-pyridin-3-ylmethoxy]-benzonitrile (20)

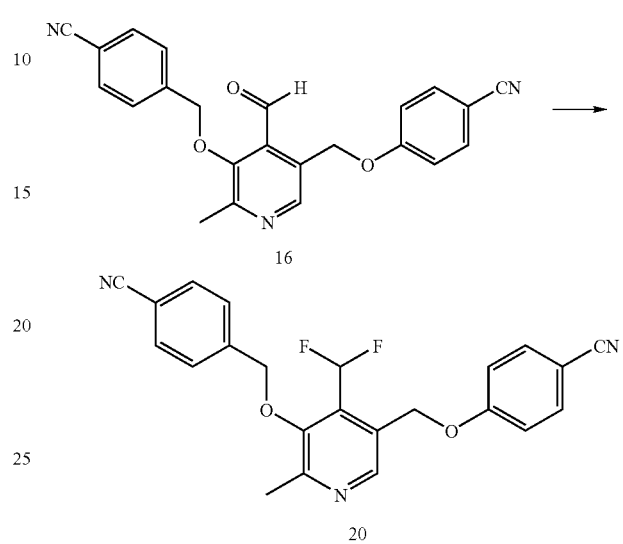

To a solution of 4-[4-carbaldehyde-6-methyl-5-(4-cyano-benzyloxy)-pyridin-3-ylmethoxy]-benzonitrile (16) (383 mg, 1.0 mmol) in dry dichloromethane (20 mL) was slowly added DAST (482 mg, 3.0 mmol) at −78° C. under nitrogen atmosphere. The reaction temperature was warmed to room temperature and stirred for 1 hour. The reaction mixture was then poured into cold water, and the crude product was extracted with dichloromethane, washed with water and dried over anhydrous magnesium sulfate. Evaporation of the solvent gave a crude residue which was purified by column chromatography on silica gel using dichloromethane:hexane:methyl alcohol (5:15:1) as an eluant to give 4-[4,4-difluoromethyl-6-methyl-5-(4-cyano-benzyloxy)-pyridin-3-ylmethoxy]-benzonitrile (20) (260 mg, 64% yield) as a colorless solid.

$^1$H-NMR (CDCl$_3$): δ 8.61 (s, 1H), 7.77-7.02 (m, 8H), 7.00 (t, 1H), 5.34 (s, 2H), 4.99 (s, 2H), 2.61 (s, 3H).

$^{19}$F-NMR (CDCl$_3$): δ-113.85 (s).

Example 18

Synthesis of 4-[4,4-Difluoromethyl-6-methyl-5-(4-carbamimidoyl-benzyloxy)-pyridin-3-ylmethoxy]-benzamidine (21)

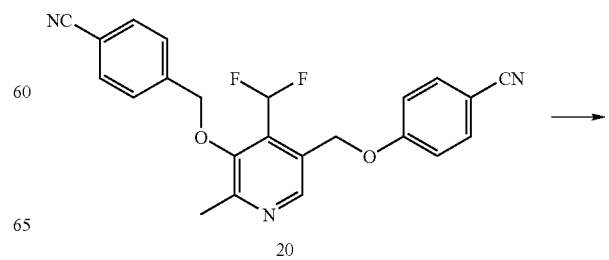

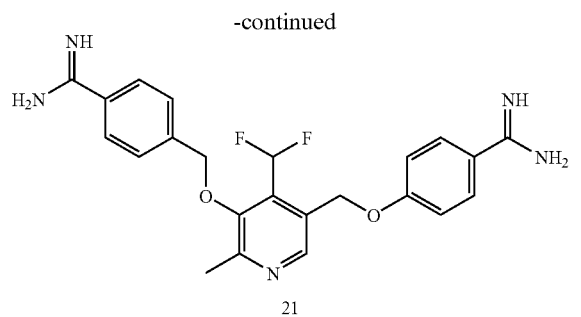

21

The conversion of bis-nitrile (20) to bis-amidine (21) was carried out as described in Example 2.

¹H-NMR (CD₃OD): δ 8.55 (s, 1H), 7.90-7.76 (m, 6H), 7.24 (dd, 2H), 7.20 (t, 1H), 5.44 (s, 2H), 5.15 (s, 2H), 2.60 (s, 3H).

¹⁹F-NMR (CD₃OD): δ-115.45 (s).

Example 19

Synthesis of 4-(5-Hydroxymethyl-2,4-dimethyl-pyridin-3-yloxymethyl)-benzonitrile (22) 4-Deoxypyridoxine 22

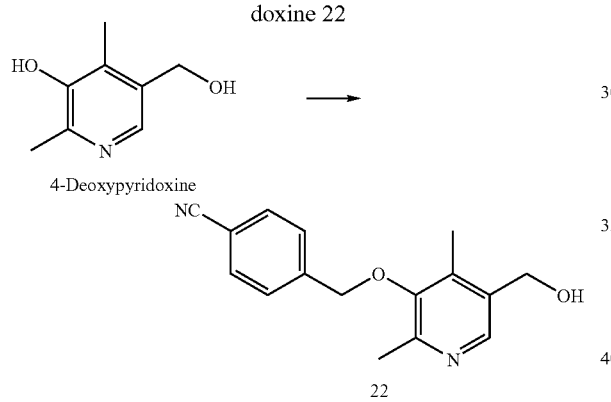

The coupling of 4-deoxypyridoxine hydrochloride (5.0 g, 0.026 mol) and α-bromo-p-tolunitrile (5.2 g, 0.026 mol), as described in Example 3, gave 4-(5-hydroxymethyl-2,4-dimethyl-pyridin-3-yloxymethyl)-benzonitrile (22) (5.6 g, 80% yield) as a colorless solid.

¹H-NMR: (CDCl₃): δ 8.24 (s, 1H), 7.73 (d, 2H), 7.59 (d, 2H), 4.88 (s, 2H), 4.71 (s, 2H), 2.52 (s, 3H), 2.33 (s, 3H).

Example 20

Synthesis of 4-(5-Formyl-2,4-dimethyl-pyridin-3-yloxymethyl)-benzonitrile (23)

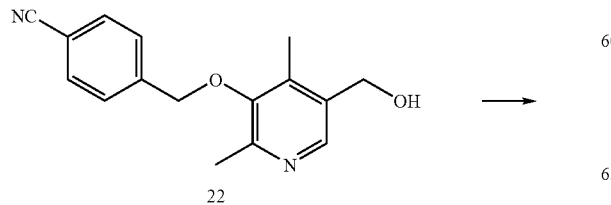

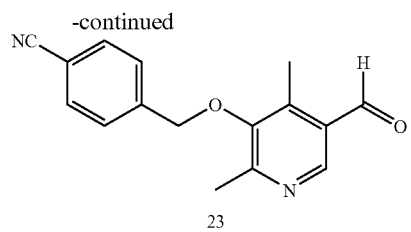

23

A solution of 4-(5-hydroxymethyl-2,4-dimethyl-pyridin-3-yloxymethyl)-benzonitrile (22) (5.6 g, 21 mmol) and manganese (IV) dioxide (9.1 g, 0.105 mol) in toluene (250 mL) was stirred at 60° C. for about 18 hours. Excess manganese (IV) dioxide was filtered through a celite pad and washed with ethyl acetate. The filtrate was evaporated to give 4-(5-formyl-2,4-dimethyl-pyridin-3-yloxymethyl)-benzonitrile (23) (3.6 g, 65% yield) as a colorless solid.

¹H-NMR (CDCl₃): δ 10.22 (s, 1H), 8.66 (s, 1H), 7.73 (d, 2H), 7.59 (d, 2H), 4.90 (s, 2H), 2.59 (s, 6H).

Example 21

Synthesis of 4'-{[5-(4-Cyano-benzyloxy)-4,6-dimethyl-pyridin-3-ylmethylene]-amino}-biphenyl-4-carbonitrile (24)

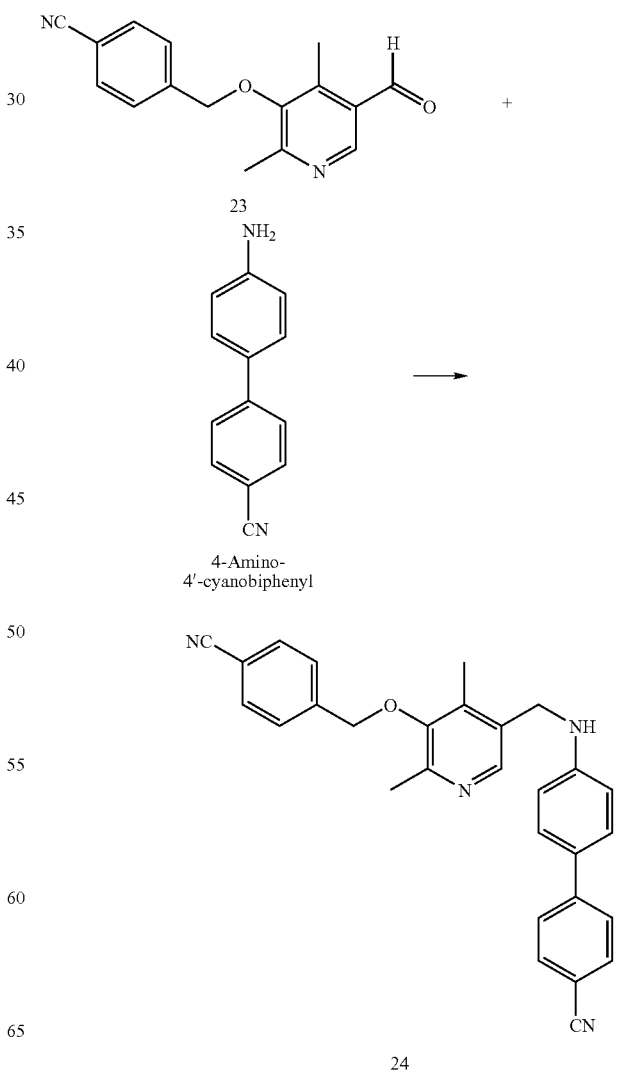

A mixture of 4-(5-formyl-2,4-dimethyl-pyridin-3-yloxymethyl)-benzonitrile (23) (0.40 g, 1.5 mmol), 4-amino-4'-cyanobiphenyl (0.35 g, 1.8 mmol) and p-toluenesulfonic acid monohydrate (0.08 g, 0.45 mmol) was heated at 100° C. in benzene (15 mL) under nitrogen atmosphere with a Dean-Stark condenser for 18 hours. The solvent mixture was then evaporated and the crude product dissolved in methyl alcohol (20 mL), and to the solution was added sodium borohydride (0.56 g, 15 mmol). The reaction mixture was stirred at room temperature for 2 hours, quenched with saturated aqueous sodium bicarbonate, extracted with ethyl acetate and then back washed with water. The combined organic layer was dried over anhydrous magnesium sulfate, filtered and evaporated to dryness. The crude product was purified by column chromatography on silica gel using a gradient mixture of ethyl acetate:hexane (0:1 to 1:1) as eluant to give 4'-{[5-(4-cyano-benzyloxy)-4,6-dimethyl-pyridin-3-ylmethyl]-amino}-biphenyl-4-carbonitrile (24) (266 mg, 40% overall yield for two steps).

$^1$H-NMR (CDCl$_3$): δ 8.27 (s, 1H), 7.72 (d, 2H), 7.62 (m, 6H), 7.48 (d, 2H), 6.74 (d, 2H), 4.90 (s, 2H), 4.33 (s, 2H), 2.53 (s, 3H), 2.31 (s, 3H).

Example 22

Synthesis of 4'-{[5-(4-Carbamimidoyl-benzyloxy)-4,6-dimethyl-pyridin-3-ylmethyl]-amino}-biphenyl-4-carboxamidine (25)

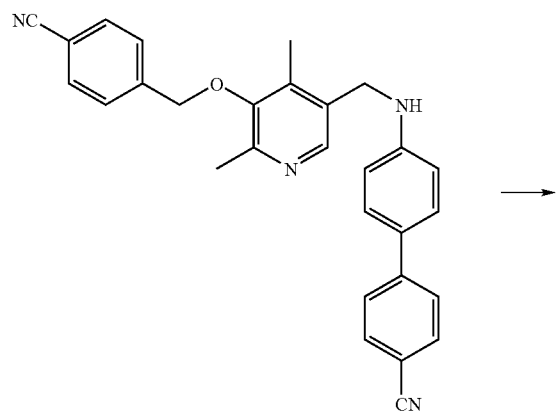

24

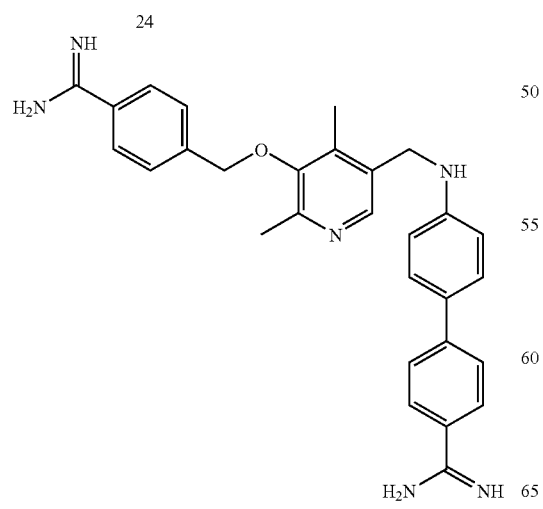

25

The conversion of bis-nitrile (24) to bis-amidine (25) was carried out as described in Example 2.

$^1$H-NMR (CD$_3$OD): δ 8.15 (s, 1H), 7.87 (d, 2H), 7.79 (m, 6H), 7.54 (d, 2H), 6.76 (d, 2H), 5.02 (s, 2H), 4.39 (s, 2H), 2.46 (s, 3H), 2.38 (s, 3H).

MS m/z (ES$^+$): 479.5 (M+H$^+$).

Example 23

Synthesis of 3-(5-Hydroxymethyl-2,4-dimethyl-pyridin-3-yloxymethyl)-benzonitrile (26)

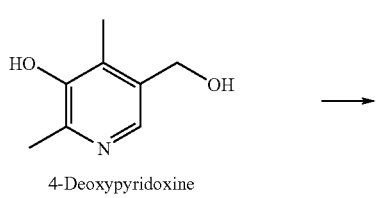

4-Deoxypyridoxine

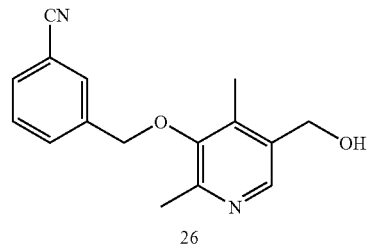

26

The coupling of 4-deoxypyridoxine hydrochloride (5.0 g, 0.026 mol) and α-bromo-m-tolunitrile (5.2 g, 0.026 mol), as described in Example 3, gave 3-(5-hydroxymethyl-2,4-dimethyl-pyridin-3-yloxymethyl)-benzonitrile (26) (3.7 g, 52% yield).

$^1$H-NMR (CDCl$_3$): δ 8.25 (s, 1H), 7.79 (s, 1H), 7.68 (t, 2H), 7.55 (dd, 1H), 4.85 (s, 2H), 4.72 (s, 2H), 2.53 (s, 3H), 2.33 (s, 3H).

Example 24

Synthesis of 3-(5-Formyl-2,4-dimethyl-pyridin-3-yloxymethyl)-benzonitrile (27)

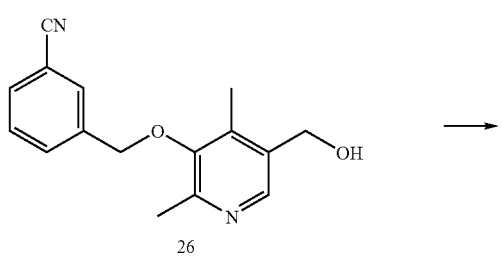

26

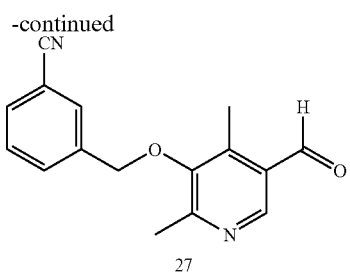

The oxidation of 3-(5-hydroxymethyl-2,4-dimethyl-pyridin-3-yloxymethyl)-benzonitrile (26) (3.68 g, 13.7 mmol) to 3-(5-formyl-2,4-dimethyl-pyridin-3-yloxymethyl)-benzonitrile (27) (3.1 g, 85% yield) was carried out as described in Example 20.

$^1$H-NMR (CDCl$_3$): δ 10.21 (s, 1H), 8.65 (s, 1H), 7.79 (s, 1H), 7.67 (s, 2H), 7.54 (t, 1H), 4.86 (s, 2H), 2.58 (s, 6H).

Example 25

Synthesis of 4'-{[5-(3-Cyano-benzyloxy)-4,6-dimethyl-pyridin-3-ylmethyl]-amino}-biphenyl-4-carbonitrile (28)

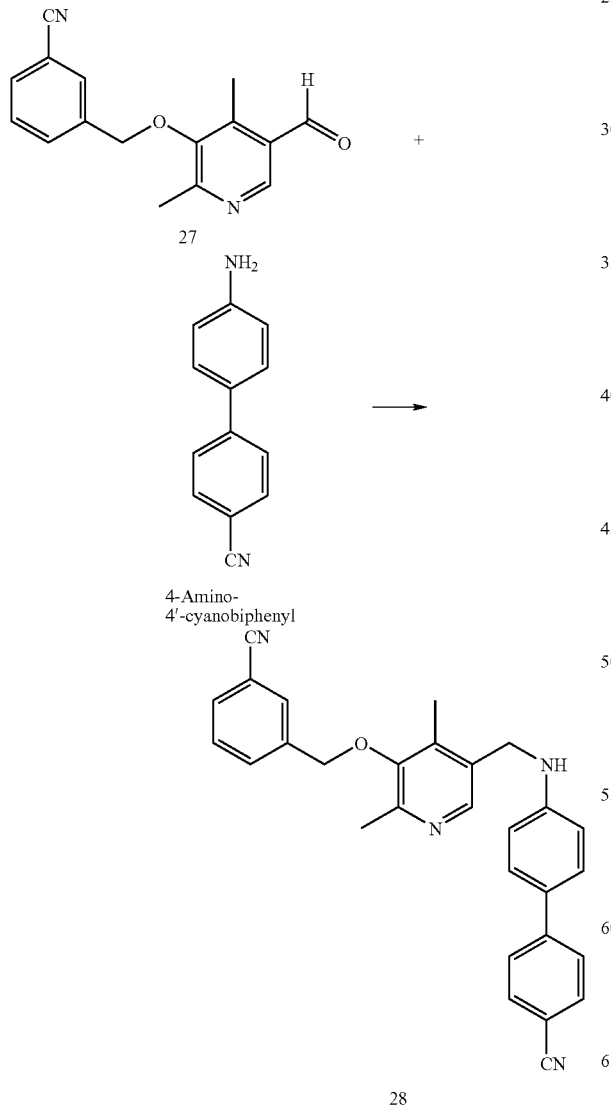

The reductive amination of 3-(5-formyl-2,4-dimethyl-pyridin-3-yloxymethyl)-benzonitrile (27) (10.0 g, 37.6 mmol) and 4-amino-4'-cyanobiphenyl (8.8 g, 45.1 mmol), as described in Example 21, gave 4'-{[5-(3-cyano-benzyloxy)-4,6-dimethyl-pyridin-3-ylmethyl]-amino}-biphenyl-4-carbonitrile (28) (5.0 g, 30% yield) as a colorless solid.

$^1$H-NMR (DMSO-d6): δ 8.14 (s, 1H), 7.97 (s, 1H), 7.86 (dd, 2H), 7.77 (dd, 4H), 7.65 (t, 1H), 7.54 (d, 2H), 6.71 (d, 2H), 6.50 (t, 1H), 4.89 (s, 2H), 4.28 (d, 2H), 2.40 (s, 3H), 2.27 (s, 3H).

Example 26

Synthesis of 4'-{[5-(3-Carbamimidoyl-benzyloxy)-4,6-dimethyl-pyridin-3-ylmethyl]-amino}-biphenyl-4-carboxamidine (29)

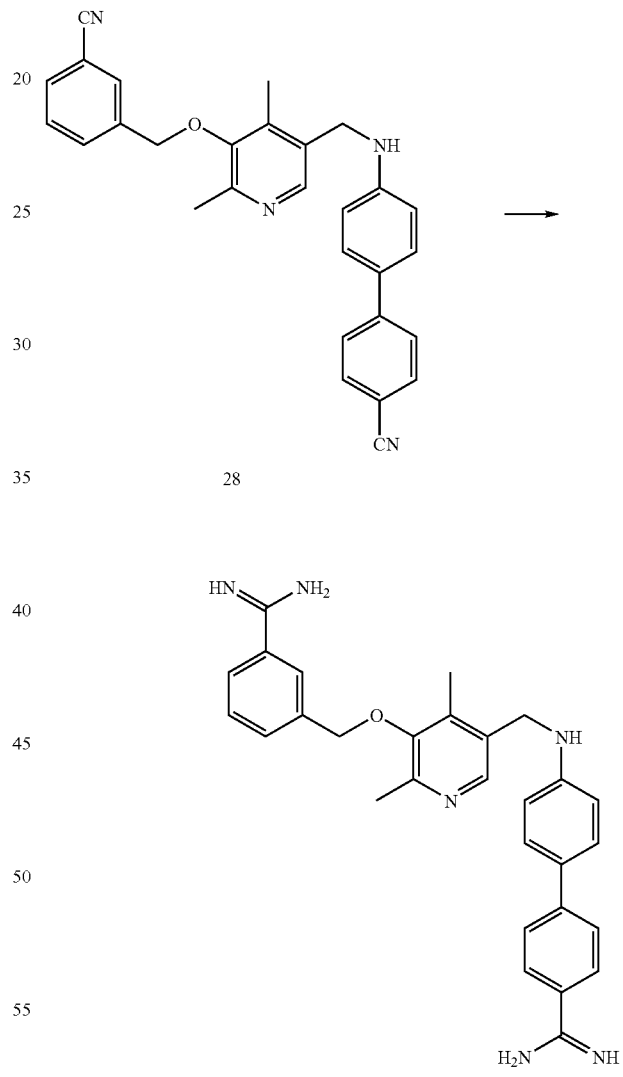

The conversion of bis-nitrile (28) to bis-amidine (29) was carried out as described in Example 2.

$^1$H-NMR (DMSO-d6): δ 9.55-9.00 (m, 6H), 8.16 (s, 1H), 7.99 (s, 1H), 7.84 (m, 6H), 7.69 (t, 1H), 7.59 (d, 2H), 6.74 (d, 2H), 6.55 (t, 1H), 4.91 (s, 2H), 4.31 (d, 2H), 2.44 (s, 3H), 2.32 (s, 3H).

MS m/z (ES$^+$): 479.56 (M+H$^+$).

Example 27

Synthesis of 4-{[5-(4-Cyano-benzyloxy)-4,6-dimethyl-pyridin-3-ylmethyl]-amino}-benzonitrile (30)

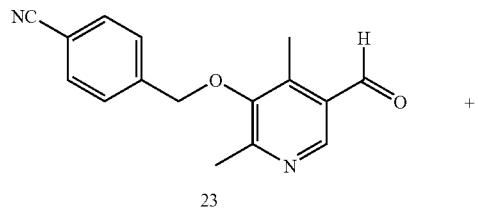

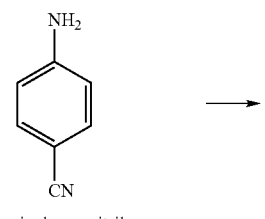

4-Aminobenzonitrile

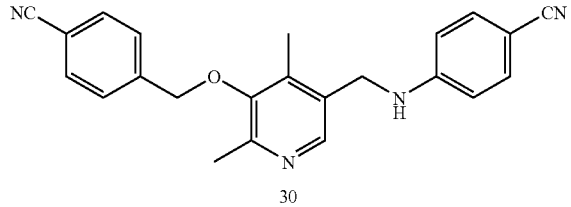

The reductive amination of 4-(5-formyl-2,4-dimethyl-pyridin-3-yloxymethyl)-benzonitrile (23) (2.3 g, 8.6 mmol) and 4-aminobenzonitrile (4.4 g, 37.2 mmol), as described in Example 21, gave 4-{[5-(4-cyano-benzyloxy)-4,6-dimethyl-pyridin-3-ylmethyl]-amino}-benzonitrile (30) (2.6 g, 82% yield) as a colorless solid.

$^1$H-NMR (CDCl$_3$) δ: 8.20 (s, 1H), 7.70 (d, 2H), 7.58 (d, 2H), 7.33 (d, 2H), 6.61 (d, 2H), 4.89 (s, 2H), 4.69 (bs, 1H), 4.31 (d, 2H), 2.51 (d, 3H), 2.29 (s, 3H).

Example 28

Synthesis of 4-{[5-(4-Carbamimidoyl-benzyloxy)-4,6-dimethyl-pyridin-3-ylmethyl]-amino}-benzamidine (31)

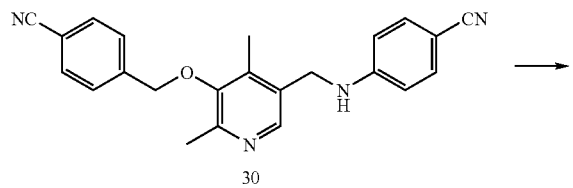

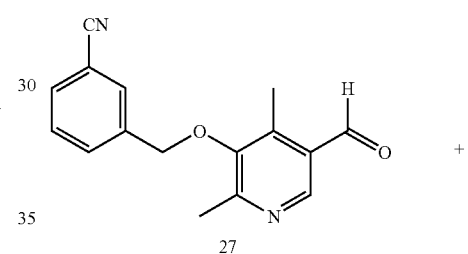

The conversion of bis-nitrile (30) to bis-amidine (31) was carried out as described in Example 2.

$^1$H-NMR (D$_2$O): δ 8.11 (s, 1H), 6.72 (d, 2H), 7.61 (d, 2H), 7.57 (d, 2H), 6.72 (d, 2H), 4.99 (s, 2H), 4.39 (s, 2H), 2.43 (s, 3H), 2.23 (s, 2H).

Example 29

Synthesis of 4-{[5-(3-Cyano-benzyloxy)-4,6-dimethyl-pyridin-3-ylmethyl]-amino}-benzonitrile (32)

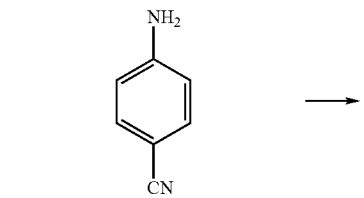

4-Aminobenzonitrile

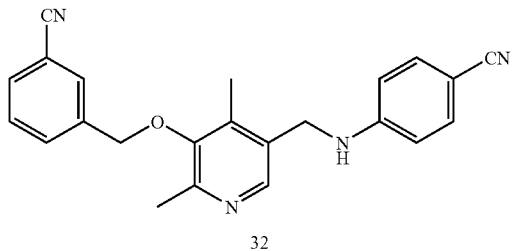

The reductive amination of 3-(5-formyl-2,4-dimethyl-pyridin-3-yloxymethyl)-benzonitrile (27) (7.0 g, 26.3 mmol) and 4-aminobenzonitrile (10.2 g, 86.3 mmol), as described in Example 21, gave 4-{[5-(3-cyano-benzyloxy)-4,6-dimethyl-pyridin-3-ylmethyl]-amino}-benzonitrile (32) (4.1 g, 68% yield) as a colorless solid.

$^1$H-NMR (CDCl$_3$): δ 8.20 (s, 1H), 7.70 (d, 2H), 7.58 (d, 2H), 7.33 (d, 2H), 6.61 (d, 2H), 4.89 (s, 2H), 4.69 (bs, 1H), 4.31 (d, 2H), 2.51 (d, 3H), 2.29 (s, 3H).

Example 30

Synthesis of 4-{[5-(3-Carbamimidoyl-benzyloxy)-4,6-dimethyl-pyridin-3-ylmethyl]-amino}-benzamidine (33)

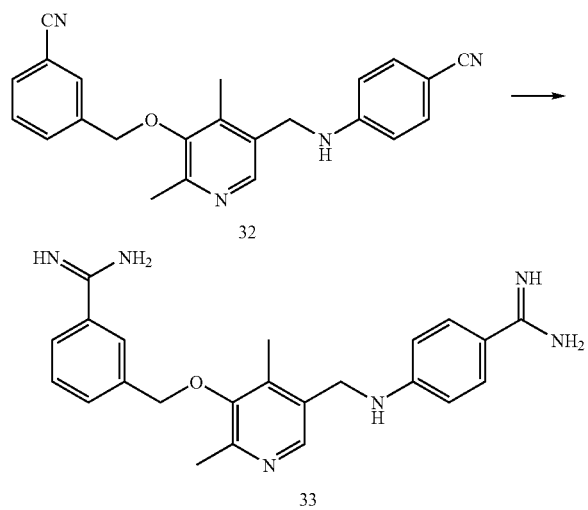

The conversion of bis-nitrile (32) to bis-amidine (33) was carried out as described in Example 2.

$^1$H-NMR (DMSO-d$_6$): δ 8.10 (s, 1H), 7.96 (s, 1H), 7.89 (s, 1H), 7.80 (s, 1H), 7.69-7.61 (s, 3H), 6.75 (d, 2H), 4.98 (s, 2H), 4.44 (s, 2H), 2.46 (s, 3H), 2.83 (s, 3H).

Example 31

Synthesis of 3-(3-Hydroxy-5-hydroxymethyl-2-methyl-pyridin-4-yl)-acrylic acid ethyl ester (34)

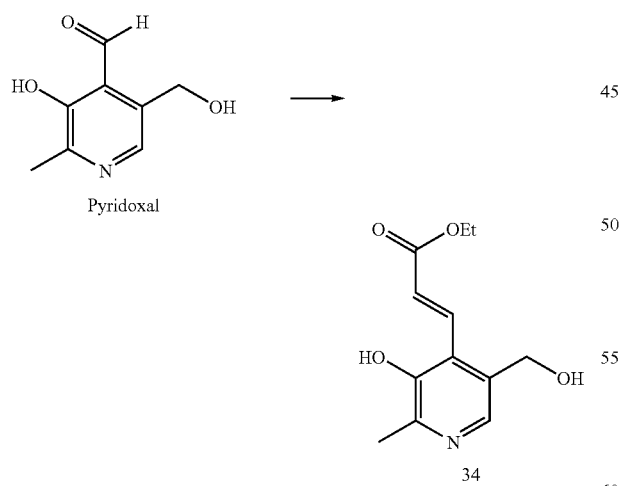

A clear solution of (carbethoxymethylene)triphenylphosphorane (22.3 g, 64.02 mmol) in THF was added to pyridoxal (13.01 g, 64.0 mmol) in THF at room temperature. The mixture was stirred for one hour, then triethylamine (10 mL) was added and the mixture was stirred until the solution turned to a yellow suspension. The solvent was evaporated, and the crude product purified by column chromatography on silica gel using a mixture of dichloromethane:methyl alcohol (20:1) as eluant to give 3-(3-hydroxy-5-hydroxymethyl-2-methyl-pyridin-4-yl)-acrylic acid ethyl ester (34) (15.2 g, quantitative yield) as a yellow solid.

$^1$H-NMR (CDCl$_3$): δ 8.00 (s, 1H), 7.80 (d, 1H), 6.80 (d, 1H), 4.69 (s, 2H), 4.26 (q, 2H), 2.49 (s, 3H), 1.33 (t, 3H).

Example 32

Synthesis of 3-(3-Hydroxy-5-hydroxymethyl-2-methyl-pyridin-4-yl)-propionic acid ethyl ester (35)

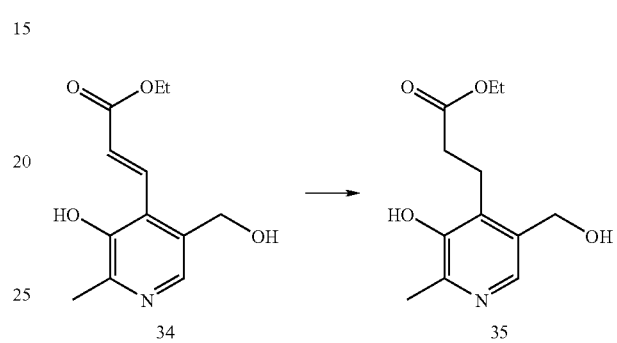

The 3-(3-hydroxy-5-hydroxymethyl-2-methyl-pyridin-4-yl)-acrylic acid ethyl ester (34) (15.2 g, 64 mmol) in ethyl acetate (250 mL) was hydrogenated in the presence of 10% palladium on carbon (8.0 g) at room temperature overnight. The product was filtered through a celite pad and evaporated. The crude product thus obtained was purified by column chromatography on silica gel using a gradient mixture of ethyl acetate:hexane:methyl alcohol (7:7:1 to 4:4:1) to give 3-(3-hydroxy-5-hydroxymethyl-2-methyl-pyridin-4-yl)-propionic acid ethyl ester (35) (11.1 g, 62% yield) as a colorless solid.

$^1$H-NMR (CDCl$_3$): δ 7.91 (s, 1H), 4.63 (s, 2H), 4.16 (q, 2H), 3.01 (t, 2H), 2.87 (t, 2H), 2.48 (s, 3H), 1.25 (t, 3H).

Example 33

Synthesis of 3-[3-(4-Cyano-benzyloxy)-5-hydroxymethyl-2-methyl-pyridin-4-yl]-propionic acid ethyl ester (36)

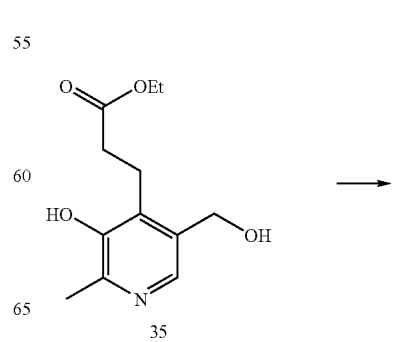

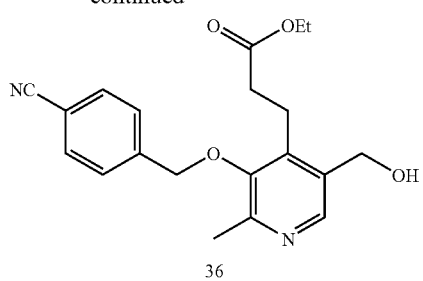

36

The coupling of 3-(3-hydroxy-5-hydroxymethyl-2-methyl-pyridin-4-yl)-propionic acid ethyl ester (35) (3.4 g, 14.2 mmol) and α-bromo-p-tolunitrile (4.2 g, 21.4 mmol), as described in Example 1, gave 3-[3-(4-cyano-benzyloxy)-5-hydroxymethyl-2-methyl-pyridin-4-yl]-propionic acid ethyl ester (36) (3.5 g, 70% yield).

$^1$H-NMR (CDCl$_3$): δ 8.39 (s, 1H), 7.74 (d, 2H), 7.59 (d, 2H), 4.95 (s, 2H), 4.77 (s, 2H), 4.10 (q, 2H), 3.02 (t, 2H), 2.66 (t, 2H), 2.61 (s, 3H), 1.21 (t, 3H).

Example 34

Synthesis of 3-[3-(4-Cyano-benzyloxy)-5-(4-cyano-phenoxymethyl)-2-methyl-pyridin-4-yl]-propionic acid ethyl ester (37)

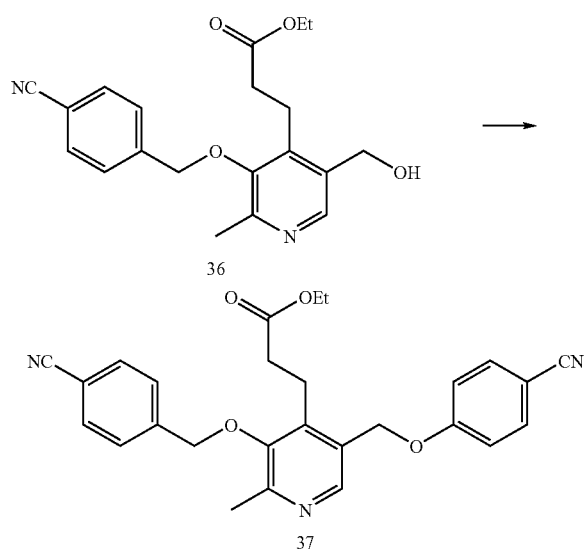

The coupling of 3-[3-(4-cyano-benzyloxy)-5-hydroxymethyl-2-methyl-pyridin-4-yl]-propionic acid ethyl ester (36) (3.5 g, 9.89 mmol) and 4-cyanophenol (1.2 g, 9.9 mmol), as described in Example 9, gave 3-[3-(4-cyano-benzyloxy)-5-(4-cyano-phenoxymethyl)-2-methyl-pyridin-4-yl]-propionic acid ethyl ester (37) (4.2 g, 91% yield).

$^1$H-NMR (CDCl$_3$): δ 8.33 (s, 1H). 7.73-7.56 (m, 6H), 7.03 (d, 2H), 5.12 (s, 2H), 4.95 (s, 2H), 4.04 (q, 2H), 2.92 (t, 2H), 2.59 (t, 2H), 2.56 (s, 3H), 1.16 (t, 3H).

Example 35

Synthesis of 3-[3-(4-Carbamimidoyl-benzyloxy)-5-(4-carbamimidoyl-phenoxymethyl)-2-methyl-pyridin-4-yl]-propionic acid ethyl ester (38)

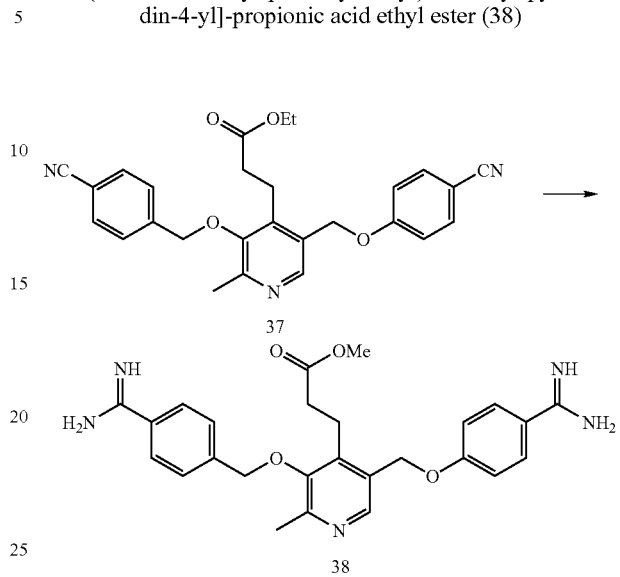

The conversion of bis-nitrile (37) to bis-amidine (38) was carried out as described in Example 2.

$^1$H NMR (DMSO): δ 9.39-9.01 (m, 6H), 8.45 (s, 1H), 7.90-7.84 (m, 4H), 7.75 (d, 2H), 7.28 (d, 2H), 5.33 (s, 2H), 5.07 (s, 2H), 3.54 (s, 3H), 3.02 (t, 2H), 2.61 (t, 2H), 2.52 (s, 3H).

Example 36

Synthesis of 3-[3-(4-Carbamimidoyl-benzyloxy)-5-(4-carbamimidoyl-phenoxymethyl)-2-methyl-pyridin-4-yl]-propionic acid (39)

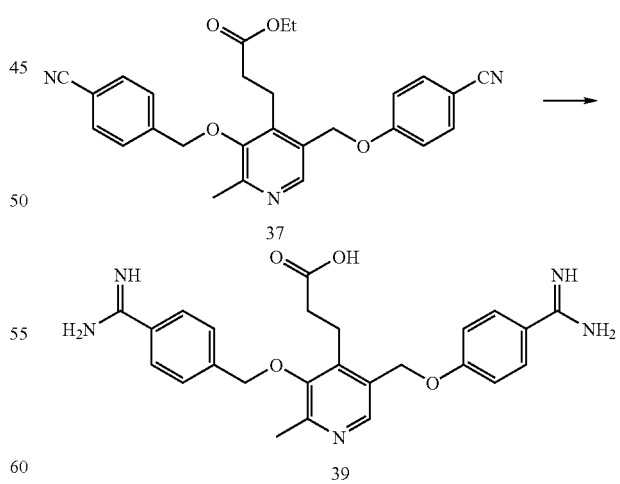

Hydrogen chloride gas was bubbled into a suspension of 3-[3-(4-cyano-benzyloxy)-5-(4-cyano-phenoxymethyl)-2-methyl-pyridin-4-yl]-propionic acid ethyl ester (37) (389 mg, 0.9 mmol) in absolute ethyl alcohol (10 mL) at 0° C. for 30 minutes. The septum was replaced and the reaction mixture was stirred overnight at room temperature. Hydrochloride gas was purged with nitrogen gas for about 2 hours and the solvent evaporated to give the crude imino ester as a solid. Ammonia in methyl alcohol (12 mL, 7M, 84 mmol) was added to the crude imino ester and stirred overnight at room temperature. The solvent was evaporated and the reaction mixture was treated with 1N hydrochloric acid (10 mL) until completion of reaction and evaporated to dryness. The crude product was purified by HPLC on a reverse phase column using a gradient mixture of 1% trifluoroacetic acid in water: methyl alcohol (1:0 to 0:1) as eluant to give the corresponding 3-[3-(4-carbamimidoyl-benzyloxy)-5-(4-carbamimidoyl-phenoxymethyl)-2-methyl-pyridin-4-yl]-propionic acid (39) as a colorless solid.

Example 37

Synthesis of 6-[(3-Hydroxy-5-hydroxymethyl-2-methyl-pyridin-4-ylmethyl)-amino]hexanoic acid (40)

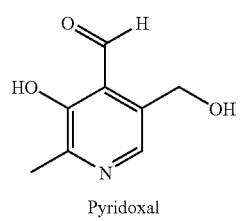

Pyridoxal

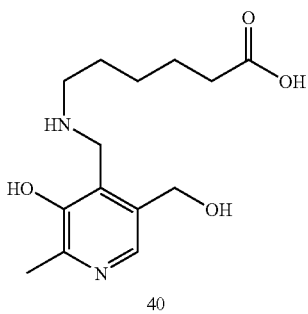

40

A mixture of pyridoxal (20.0 g, 98.5 mmol) and 6-aminocaproic acid (22.2 g, 169 mmol) was stirred in methyl alcohol (2 L) at room temperature for 12 hours. The solution was placed in an ice bath and sodium borohydride (5.7 g, 167 mmol) was added slowly. The resulting mixture was stirred for one hour at room temperature and then the solvent was evaporated to dryness. The crude product was purified by column chromatography on silica gel using a mixture of dichloromethane:methyl alcohol:30% ammonium hydroxide (5:5:1) to give 6-[(3-hydroxy-5-hydroxymethyl-2-methyl-pyridin-4-ylmethyl)-amino]hexanoic acid (40) (11.3 g, 41% yield) as colorless crystals.

$^1$H-NMR (CD$_3$OD): δ 7.74 (s, 1H), 4.40 (s, 2H), 3.96 (s, 2H), 2.52 (t, 2H), 2.26 (s, 1H), 2.19 (t, 1H), 1.46 (m, 4H), 1.30 (m, 2H).

Example 38

Synthesis of 6-[tert-Butoxycarbonyl-(3-hydroxy-5-hydroxymethyl-2-methyl-pyridin-4-ylmethyl)-amino]-hexanoic acid (41)

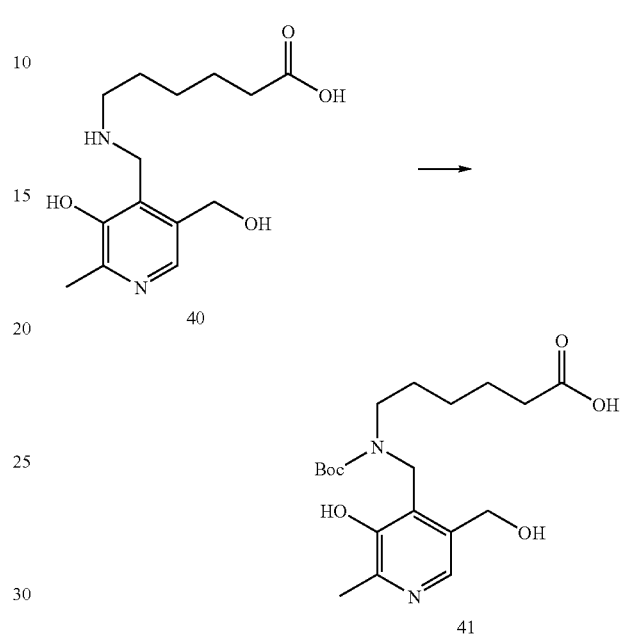

A mixture of 6-[(3-hydroxy-5-hydroxymethyl-2-methyl-pyridin-4-ylmethyl)-amino]hexanoic acid (40) (4.5 g, 15.9 mmol) and di-tert-butyldicarbonate (5.8 g, 26.6 mmol) was heated in a mixture of dioxane (50 mL) and methyl alcohol (200 mL) at 100° C. for 4 hours. The solvent was evaporated and the crude was purified by column chromatography on silica gel using a mixture of methyl alcohol:dichloromethane (1:20) as eluant to give 6-[tert-butoxycarbonyl-(3-hydroxy-5-hydroxymethyl-2-methyl-pyridin-4-ylmethyl)-amino]-hexanoic acid (41) (3.0 g, 49% yield).

$^1$H-NMR (DMSO-d$_6$): δ 7.75 (s, 1H), 4.97 (s, 1H), 4.32 (m, 4H), 2.84 (t, 2H), 2.16 (t, 2H), 1.94 (t, 3H), 1.20 (m, 11H), 0.96 (m, 4H).

Example 39

Synthesis of 6-[(3-Benzyloxy-5-hydroxymethyl-2-methyl-pyridin-4-ylmethyl)-tert-butoxycarbonyl-amino]-hexanoic acid benzyl ester (42)

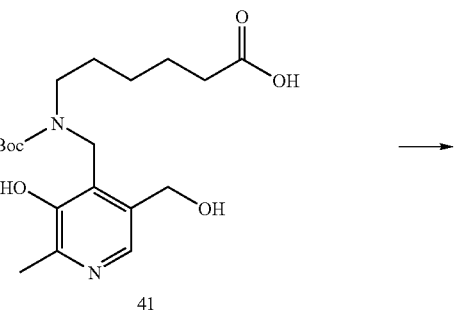

-continued

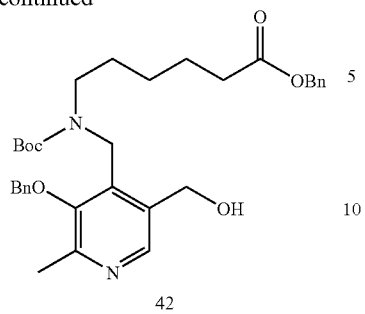

42

The coupling of 6-[tert-butoxycarbonyl-(3-hydroxy-5-hydroxymethyl-2-methyl-pyridin-4-ylmethyl)-amino]-hexanoic acid (41) (3.0 g, 7.8 mmol) and benzyl chloride (7.0 g, 55 mmol), as described in Example 3, gave 6-[(3-benzyloxy-5-hydroxymethyl-2-methyl-pyridin-4-ylmethyl)-tert-butoxycarbonyl-amino]-hexanoic acid benzyl ester (42) (3.2 g, 73% yield).

$^1$H-NMR (CDCl$_3$): δ 8.26 (s, 1H), 7.43-7.30 (m, 10H), 5.09 (s, 2H), 4.77 (s, 2H), 4.66 (s, 2H), 4.61 (s, 2H), 2.91 (t, 2H), 2.62 (s, 3H), 2.26 (t, 2H), 1.52 (m, 2H), 1.42 (m, 9H), 1.36 (m, 2H), 1.13 (m, 2H).

Example 40

Synthesis of 6-[(3-Benzyloxy-5-formyl-2-methyl-pyridin-4-ylmethyl)-tert-butoxycarbonyl-amino]-hexanoic acid benzyl ester (43)

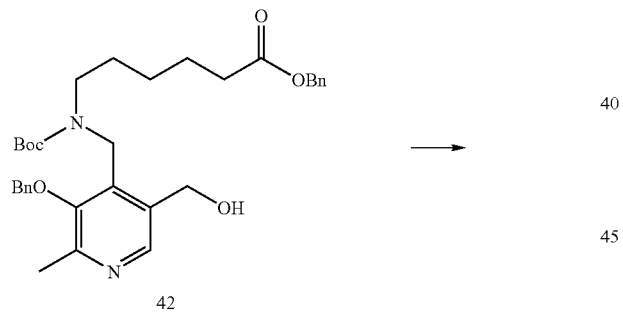

The oxidation of 6-[(3-benzyloxy-5-hydroxymethyl-2-methyl-pyridin-4-ylmethyl)-tert-butoxycarbonyl-amino]-hexanoic acid benzyl ester (42) (3.3 g, 5.8 mmol) to 6-[(3-benzyloxy-5-formyl-2-methyl-pyridin-4-ylmethyl)-tert-butoxycarbonyl-amino]-hexanoic acid benzyl ester (43) (3.2 g, 97% yield) was carried out as described in Example 20.

$^1$H-NMR (CDCl$_3$): δ 10.33 (s, 1H), 8.73 (s, 1H), 7.43-7.30 (m, 10H), 5.10 (s, 2H), 4.86 (s, 2H), 4.78 (s, 2H), 2.97 (t, 2H), 2.57 (s, 3H), 2.24 (t, 2H), 1.44 (m, 1H), 1.33 (m, 2H), 1.12 (m, 2H).

Example 41

Synthesis of 6-({3-Benzyloxy-5-[(4'-cyano-biphenyl-4-ylamino)-methyl]-2-methyl-pyridin-4-ylmethyl}-tert-butoxycarbonyl-amino)-hexanoic acid benzyl ester (44)

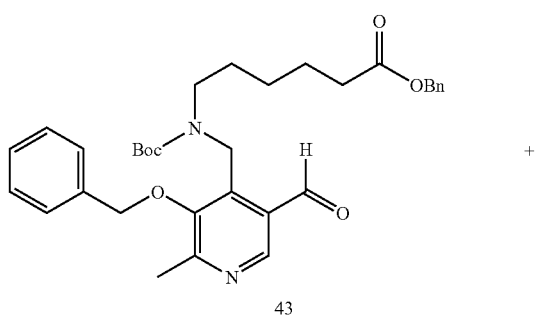

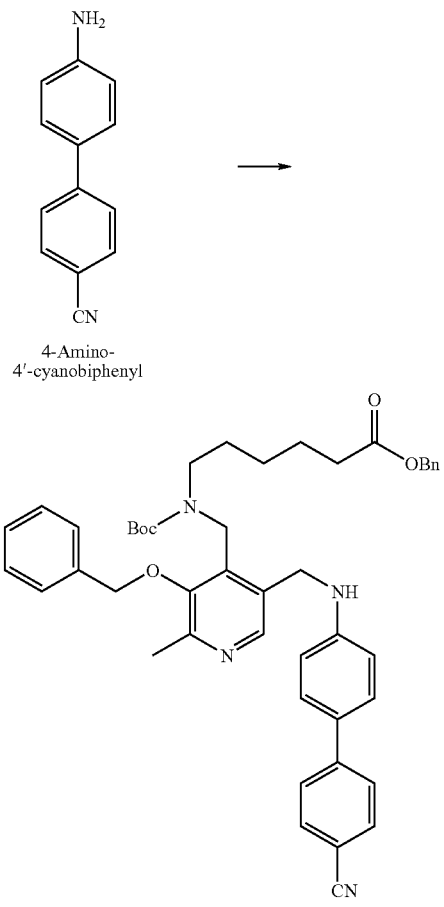

The reductive amination of 6-[(3-benzyloxy-5-formyl-2-methyl-pyridin-4-ylmethyl)-tert-butoxycarbonyl-amino]- hexanoic acid benzyl ester (2.2 g, 3.9 mmol) and 4-amino-4'-cyanobiphenyl (2.1 g, 10.8 mmol), as described in Example 21, gave 6-({3-benzyloxy-5-[(4'-cyano-biphenyl-4-ylamino)-methyl]-2-methyl-pyridin-4-ylmethyl}-tert-butoxycarbonyl-amino)-hexanoic acid benzyl ester (44) (2.4 g, 83% yield).

$^1$H-NMR (CDCl$_3$): δ 8.36 (s, 1H), 7.66-7.35 (m, 16H), 6.72 (d, 2H), 5.11 (s, 2H), 4.80 (s, 2H), 4.63 (s, 1H), 4.37 (s, 2H), 4.34 (s, 2H), 2.96 (t, 2H), 2.58 (s, 3H), 2.20 (t, 2H), 1.49 (m, 2H), 1.44 (m, 9H), 1.36 (m, 2H), 1.15 (m, 2H).

Example 42

Synthesis of 6-({3-Benzyloxy-5-[(4'-carbamimidoyl-biphenyl-4-ylamino)-methyl]-2-methyl-pyridin-4-ylmethyl}-amino)-hexanoic acid (45)

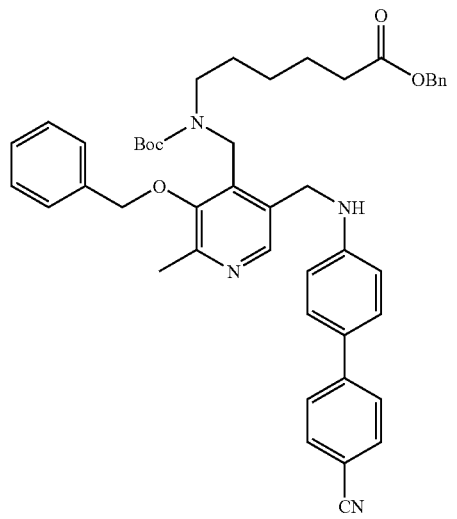

44

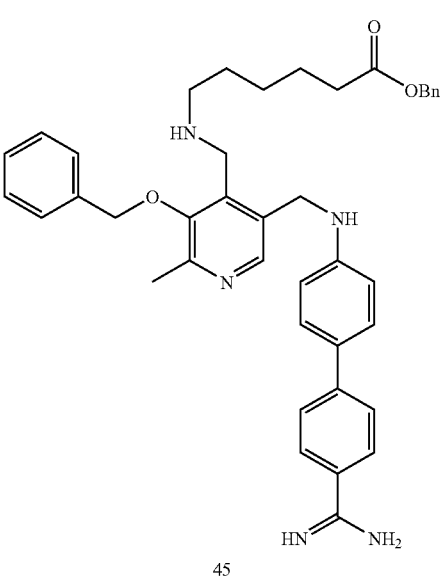

45

The conversion of nitrile (44) to amidine (45) was carried out as described in Example 2.

$^1$H-NMR (CD$_3$OD) δ: 8.29 (s, 1H), 7.87-7.24 (m, 16H), 6.88 (d, 2H), 5.49 (s, 2H), 5.00 (s, 2H), 4.60 (s, 2H), 4.47 (q, 2H), 2.65 (t, 2H), 2.56 (s, 3H), 2.19 (t, 2H), 1.45 (m, 4H), 1.20 (m, 5H).

Example 43

Synthesis of 6-({5-[(4'-Carbamimidoyl-biphenyl-4-ylamino)-methyl]-3-hydroxy-2-methyl-pyridin-4-ylmethyl}-amino)-hexanoic acid (46)

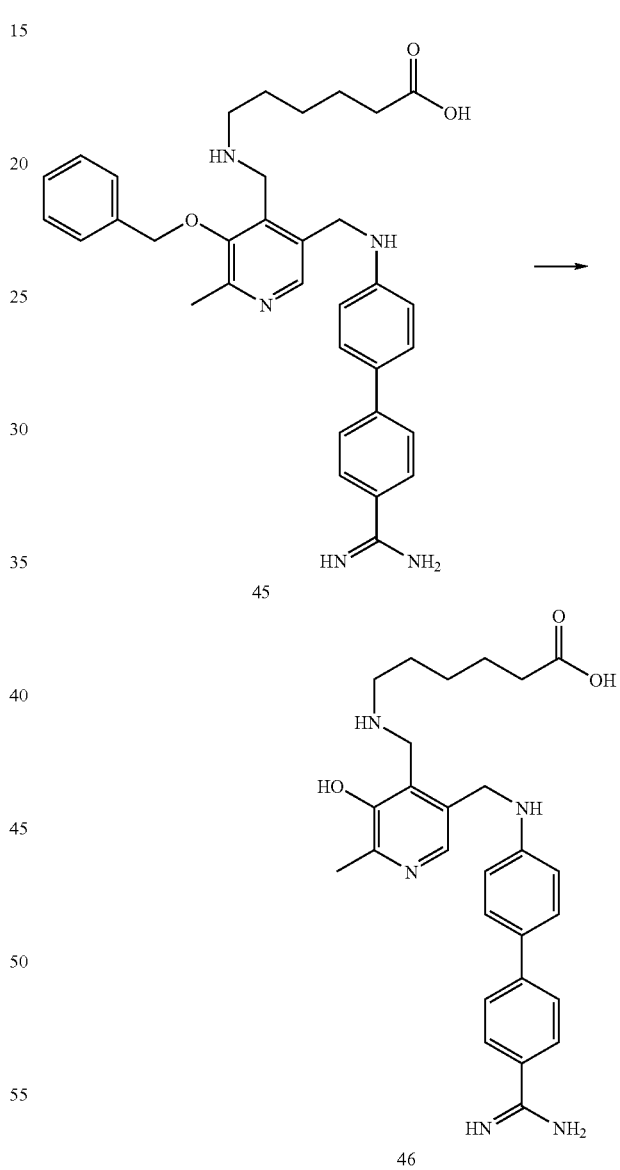

The debenzylation of 6-({3-benzyloxy-5-[(4'-carbamimidoyl-biphenyl-4-ylamino)-methyl]-2-methyl-pyridin-4-ylmethyl}-amino)-hexanoic acid (45) (250 mg, 0.44 mmol) was carried out in methyl alcohol (30 mL) using 10% palladium on carbon (0.5 g) with a pressure of 50 psi at room temperature for 2 hours. The product was filtered through a celite pad, and evaporated to give a crude product, which was purified by column chromatography on silica gel using a mixture of dichloromethane:methyl alcohol:30% ammonium hydroxide (10:5:1) to give 6-({5-[(4'-carbamimidoyl-biphenyl-4-ylamino)-methyl]-3-hydroxy-2-methyl-pyridin-4-yl-methyl}-amino)-hexanoic acid (46) (200 mg, 96% yield).

¹H-NMR (CD₃OD) δ: 7.82 (s, 1H), 7.72 (m, 4H), 7.59 (d, 2H), 6.84 (d, 2H), 4.41 (s, 2H), 4.35 (s, 2H), 2.88 (t, 2H), 2.48 (s, 3H), 2.06 (t, 2H), 1.47 (m, 7H), 1.27 (m, 2H), 1.11 (m, 2H).

Example 44

Synthesis of 6-({3-Benzyloxy-5-[(4-cyano-phenylamino)-methyl]-2-methyl-pyridin-4-ylmethyl}-tert-butoxycarbonyl-amino)-hexanoic acid benzyl ester (47)

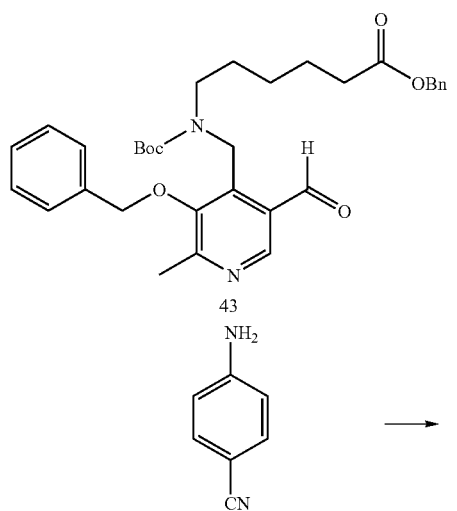

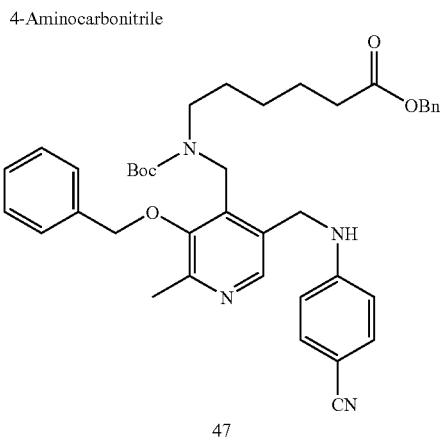

The reductive amination of 6-[(3-benzyloxy-5-formyl-2-methyl-pyridin-4-ylmethyl)-tert-butoxycarbonyl-amino]-hexanoic acid benzyl ester (43) (2.2 g, 3.9 mmol), 4-aminocarbonitrile (2.1 g, 17.8 mmol), as described in Example 21, gave 6-({3-Benzyloxy-5-[(4-cyano-phenylamino)-methyl]-2-methyl-pyridin-4-ylmethyl}-tert-butoxycarbonyl-amino)-hexanoic acid benzyl ester (47) (2.4 g, 93% yield).

¹H-NMR (CDCl₃): δ 8.30 (s, 1H), 7.40 (d, 2H), 7.36-7.30 (m, 10H), 6.55 (d, 2H), 5.11 (s, 2H), 4.80 (s, 2H), 4.78 (s, 1H), 4.56 (s, 2H), 4.36 (s, 2H), 4.34 (s, 2H), 2.93 (t, 2H), 2.60 (s, 3H), 2.20 (t, 2H), 1.47 (m, 2H), 1.44 (m, 9H), 1.34 (m, 2H), 1.13 (m, 2H).

Example 45

Synthesis of 6-({3-Benzyloxy-5-[(4-carbamimidoyl-phenylamino)-methyl]-2-methyl-pyridin-4-ylmethyl}-amino)-hexanoic acid, ethyl ester (48)

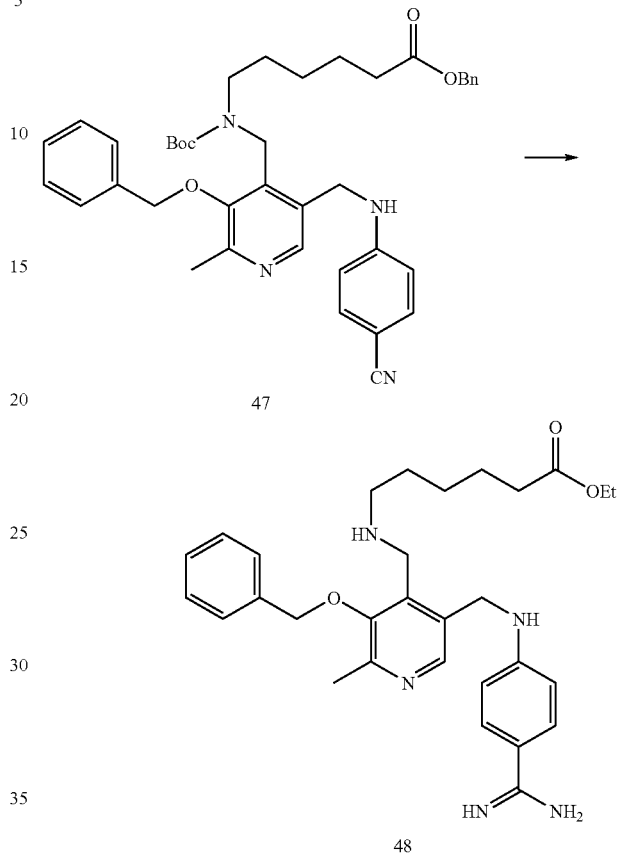

The conversion of nitrile (47) to amidine (48) was carried out as described in Example 2.

¹H-NMR (CD₃OD) δ: 8.26 (s, 1H), 7.67 (d, 2H), 7.52-7.36 (m, 5H), 6.86 (d, 2H), 5.05 (s, 2H), 4.56 (s, 2H), 4.10 (q, 2H), 3.96 (s, 2H), 2.72 (t, 2H), 2.58 (s, 3H), 2.28-2.21 (m, 2H), 1.51 (m, 4H), 1.30-1.20 (m, 2H), 1.23 (t, 3H).

Example 46

Synthesis of 6-({5-[(4-Carbamimidoyl-phenylamino)-methyl]-3-hydroxy-2-methyl-pyridin-4 ylmethyl}-amino)-hexanoic acid (49)

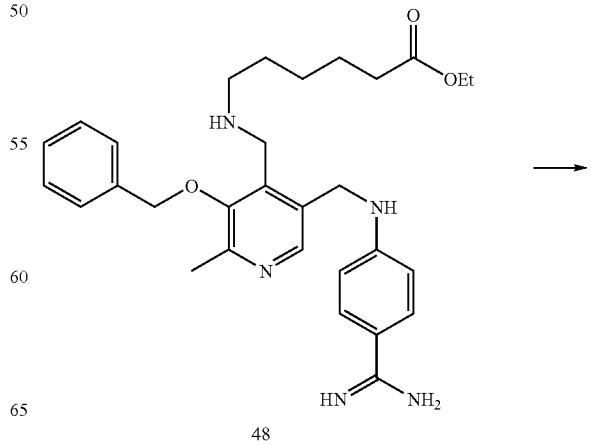

57
-continued

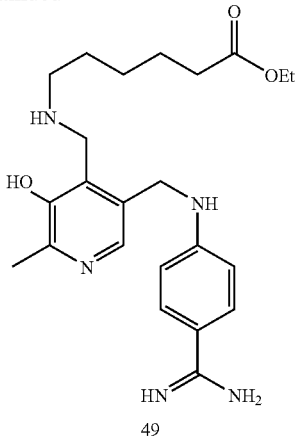

49

The debenzylation of 6-({3-Benzyloxy-5-[(4-carbamimidoyl-phenylamino)-methyl]-2-methyl-pyridin-4-ylmethyl}-amino)-hexanoic acid, ethyl ester (43) (100 mg, 0.2 mmol), as described in Example 43, gave 6-({5-[(4-carbamimidoyl-phenylamino)-methyl]-3-hydroxy-2-methyl-pyridin-4 ylmethyl}-amino)-hexanoic acid (49) (30 mg, 38% yield).

$^1$H-NMR (CD$_3$OD): δ 7.86 (s, 1H), 7.80 (d, 2H), 6.95 (d, 2H), 4.57 (s, 2H), 4.36 (s, 2H), 4.24 (q, 2H), 3.02 (t, 2H), 2.56 (s, 3H), 2.49-2.41 (m, 2H), 1.85-1.66 (m, 4H), 1.54 (m, 2H), 1.32 (t, 3H)

Example 47

Synthesis of 6-({3-Benzyloxy-5-[(4-carbamimidoyl-phenylamino)-methyl]-2-methyl-pyridin-4-ylmethyl}-amino)-hexanoic acid (50)

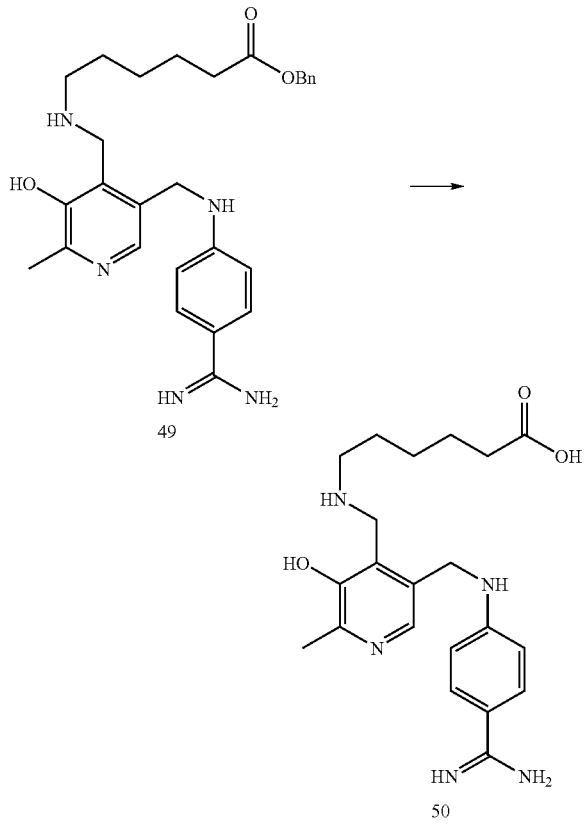

58

The hydrolysis of 6-({5-[(4-carbamimidoyl-phenylamino)-methyl]-3-hydroxy-2-methyl-pyridin-4 ylmethyl}-amino)-hexanoic acid (49) (100 mg, 0.2 mmol) was carried out in 6N hydrochloric acid for 2 hours. The solvent was then evaporated and the crude product purified by column chromatography on silica gel using a mixture of dichloromethane:methyl alcohol:30% ammonium hydroxide (5:3:1) as eluant to give 6-({3-benzyloxy-5-[(4-carbamimidoyl-phenylamino)-methyl]-2-methyl-pyridin-4-ylmethyl}-amino)-hexanoic acid (50).

$^1$H-NMR (D$_2$O): δ 7.63 (s, 1H), 7.59 (d, 2H), 6.79 (d, 2H), 4.32 (s, 2H), 4.23 (s, 2H), 2.82 (t, 2H), 2.31 (s, 3H), 2.07 (t, 2H), 1.57 (m, 2H), 1.42 (m, 2H), 1.23 (m, 2H).

Example 48

Synthesis of 6-{tert-Butoxycarbonyl-[3-(4-cyano-benzyloxy)-5-hydroxymethyl-2-methyl-pyridin-4-ylmethyl]-amino}-hexanoic acid (51)

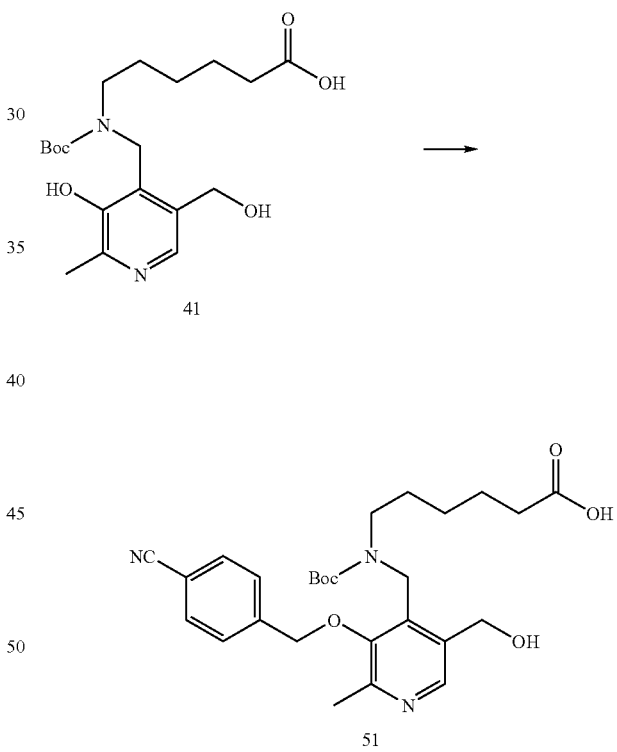

The coupling of 6-[tert-butoxycarbonyl-(3-hydroxy-5-hydroxymethyl-2-methyl-pyridin-4-ylmethyl)-amino]-hexanoic acid (44) (3.0 g, 8.0 mmol) and α-bromo-p-tolunitrile (10.0 g, 51.0 mmol), as described in Example 3, gave 6-{tert-butoxycarbonyl-[3-(4-cyano-benzyloxy)-5-hydroxymethyl-2-methyl-pyridin-4-ylmethyl]-amino}-hexanoic acid (51) (2.8 g, 70% yield).

$^1$H-NMR (CDCl$_3$): δ 8.25 (s, 1H), 7.71 (d, 2H), 7.56 (d, 2H), 4.84 (s, 2H), 4.64 (s, 2H), 4.62 (s, 2H), 2.97 (t, 2H), 2.52 (s, 3H), 2.19 (t, 2H), 1.47 (m, 2H), 1.43 (m, 9H), 1.35 (m, 2H), 1.13 (m, 2H).

Example 49

Synthesis of 6-{tert-Butoxycarbonyl-[3-(4-cyano-benzyloxy)-5-formyl-2-methyl-pyridin-4-ylmethyl]-amino}-hexanoic acid (52)

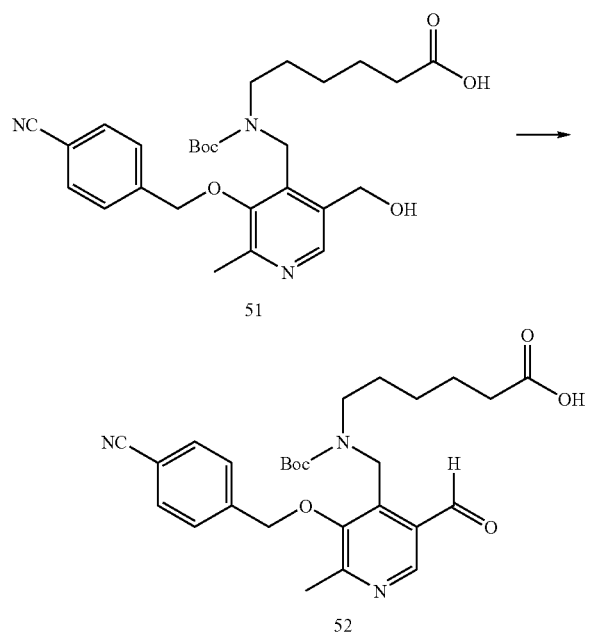

The oxidation of 6-{[3-(4-cyano-benzyloxy)-5-formyl-pyridin-4-ylmethyl]-ethoxycarbonyl-amino}-hexanoic acid (41) (1.0 g, 2.0 mmol) to 6-{tert-butoxycarbonyl-[3-(4-cyano-benzyloxy)-5-formyl-2-methyl-pyridin-4-ylmethyl]-amino}-hexanoic acid (52) (1.0 g, quantitative yield) was carried out as described in Example 20.

$^1$H-NMR (CDCl$_3$): δ 10.29 (s, 1H), 8.72 (s, 1H), 7.70 (d, 2H), 7.58 (d, 2H), 4.92 (s, 2H), 4.85 (s, 2H), 2.94 (t, 2H), 2.59 (s, 3H), 2.19 (t, 2H), 1.49 (m, 2H), 1.38 (m, 9H), 1.34 (m, 2H), 1.13 (m, 2H).

Example 50

Synthesis of 6-(tert-Butoxycarbonyl-{3-(4-cyano-benzyloxy)-5-[(4-cyano-phenylamino)-methyl]-2-methyl-pyridin-4-ylmethyl}-amino)-hexanoic acid (53)

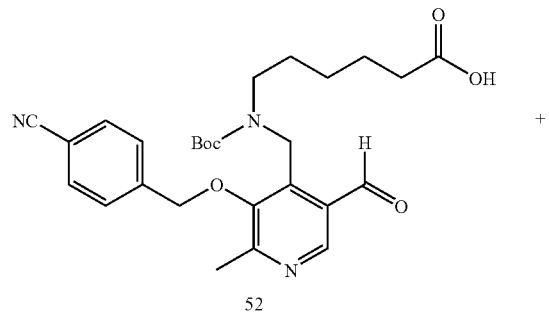

4-Aminobenzonitrile

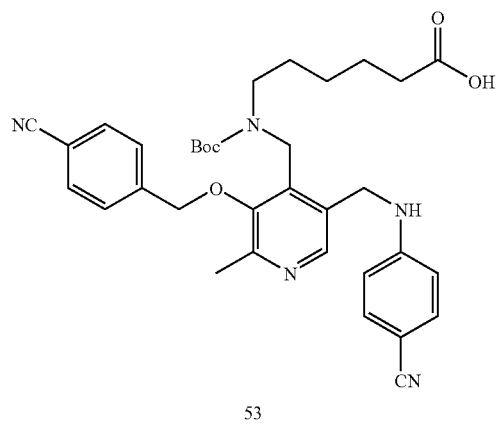

The reductive amination of 6-{tert-butoxycarbonyl-[3-(4-cyano-benzyloxy)-5-formyl-2-methyl-pyridin-4-ylmethyl]-amino}-hexanoic acid (52) (0.9 g, 0.2 mmol) and 4-aminobenzonitrile (1.6 g, 13.5 mmol), as described in Example 21, gave 6-(tert-butoxycarbonyl-{3-(4-cyano-benzyloxy)-5-[(4-cyano-phenylamino)-methyl]-2-methyl-pyridin-4-ylmethyl}-amino)-hexanoic acid (53) (0.9 g, 81% yield).

$^1$H-NMR (CDCl$_3$): δ 8.30 (s, 1H), 7.68 (d, 2H), 7.52 (d, 2H), 7.38 (d, 2H), 6.60 (d, 2H), 4.84 (s, 2H), 4.59 (s, 2H), 4.34 (d, 2H), 2.94 (t, 2H), 2.54 (s, 3H), 2.19 (t, 2H), 1.49 (m, 2H), 1.43 (m, 9H), 1.34 (m, 2H), 1.14 (m, 2H).

Example 51

Synthesis of 6-({3-(4-Carbamimidoyl-benzyloxy)-5-[(4-carbamimidoyl-phenylamino)-methyl]-2-methyl-pyridin-4-ylmethyl}-amino)-hexanoic acid (54)

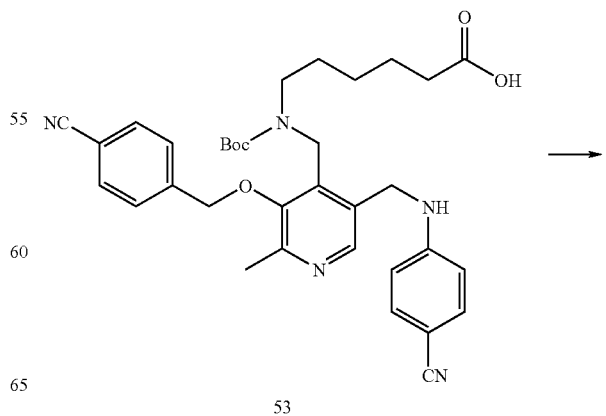

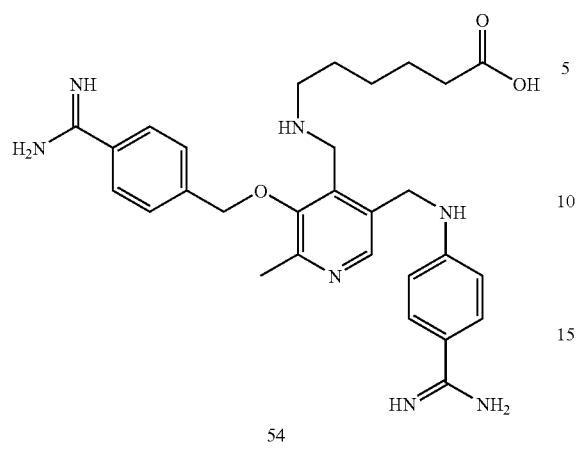

54

The conversion of bis-nitrile (53) to bis-amidine (54) was carried out as described in Example 36.

$^1$H-NMR (DMSO-d6): δ 7.87 (s, 1H), 7.80-7.72 (m, 4H), 7.57 (d, 2H), 6.87 (d, 2H), 4.97 (s, 2H), 4.47 (s, 2H), 4.39 (s, 2H), 3.04 (t, 2H), 2.49 (s, 3H), 2.22 (t, 2H), 1.72 (m, 2H), 1.57 (m, 9H), 1.37 (m, 2H).

Example 52

Synthesis of 6-(tert-Butoxycarbonyl-{3-(4-cyano-benzyloxy)-5-[(4'-cyano-biphenyl-4-ylamino)-methyl]-2-methyl-pyridin-4-ylmethyl}-amino)-hexanoic acid (55)

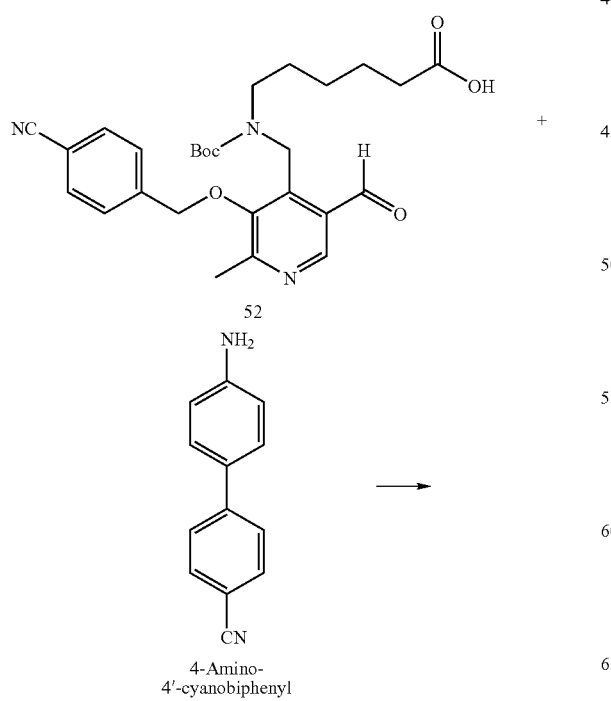

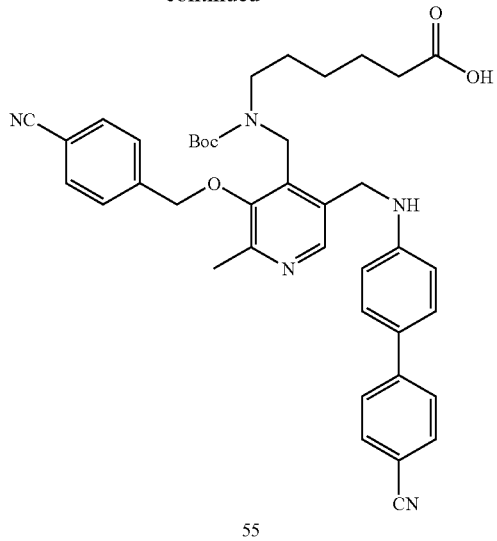

55

The reductive amination of 6-{tert-butoxycarbonyl-[3-(4-cyano-benzyloxy)-5-formyl-2-methyl-pyridin-4-ylmethyl]-amino}-hexanoic acid (52) (1.4 g, 2.8 mmol) and 4-amino-4'-cyanobiphenyl (2.1 g, 7.2 mmol), as described in Example 21, gave 6-(tert-butoxycarbonyl-{3-(4-cyano-benzyloxy)-5-[(4-cyano-biphenyl-4-ylamino)-methyl]-2-methyl-pyridin-4-ylmethyl}-amino)-hexanoic acid (55) (0.7 g, 36% yield).

$^1$H-NMR (CDCl$_3$): δ 8.36 (s, 1H), 7.71-7.47 (m, 10H), 6.69 (d, 2H), 4.84 (s, 2H), 4.61 (s, 2H), 4.36 (d, 2H), 2.94 (t, 2H), 2.53 (s, 3H), 2.20 (t, 2H), 1.48 (m, 2H), 1.40 (m, 9H), 1.32 (m, 2H), 1.14 (m, 2H).

Example 53

Synthesis of 6-({3-(4-Carbamimidoyl-benzyloxy)-5-[(4'-carbamimidoyl-biphenyl-4-ylamino)-methyl]-2-methyl-pyridin-4-ylmethyl}-amino) hexanoic acid (56)

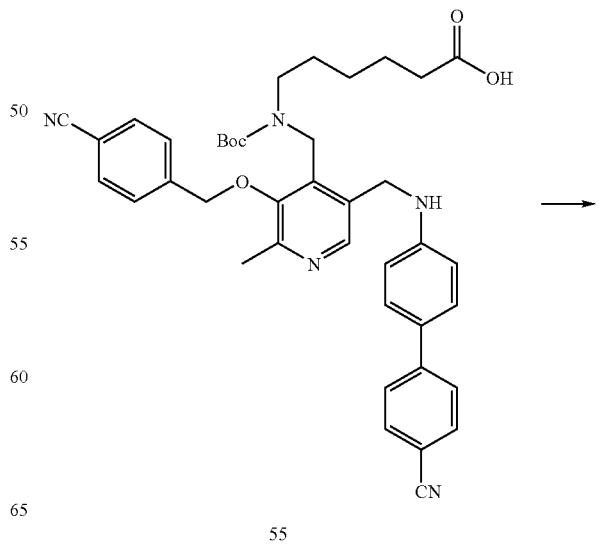

55

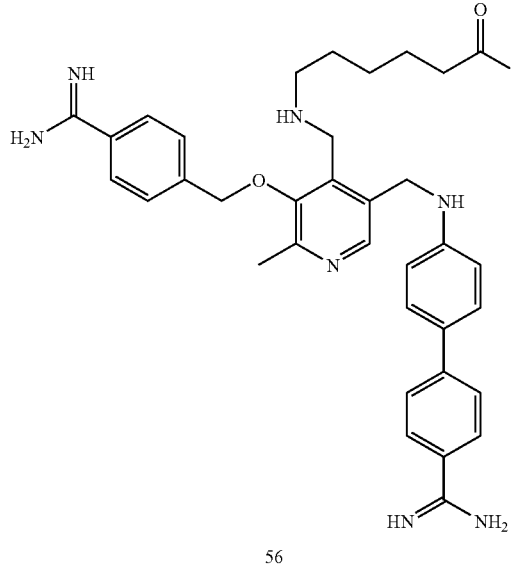

56

The conversion of bis-nitrile (55) to bis-amidine (56) was carried out as described in Example 36.

¹H-NMR (D₂O): δ 8.32 (s, 1H), 7.76-7.59 (m, 10H), 6.91 (d, 1H), 5.08 (s, 2H), 4.39 (s, 2H), 4.09 (s, 2H), 2.82 (t, 2H), 2.53 (s, 3H), 1.91 (t, 2H), 1.34 (m, 2H), 1.24 (m, 2H), 1.02 (m, 2H).

Example 54

Synthesis of 4-{6-[(5-Hydroxy-4-hydroxymethyl-6-methyl-pyridin-3-ylmethyl)-amino]pyridin-3-yl}-benzonitrile (58)

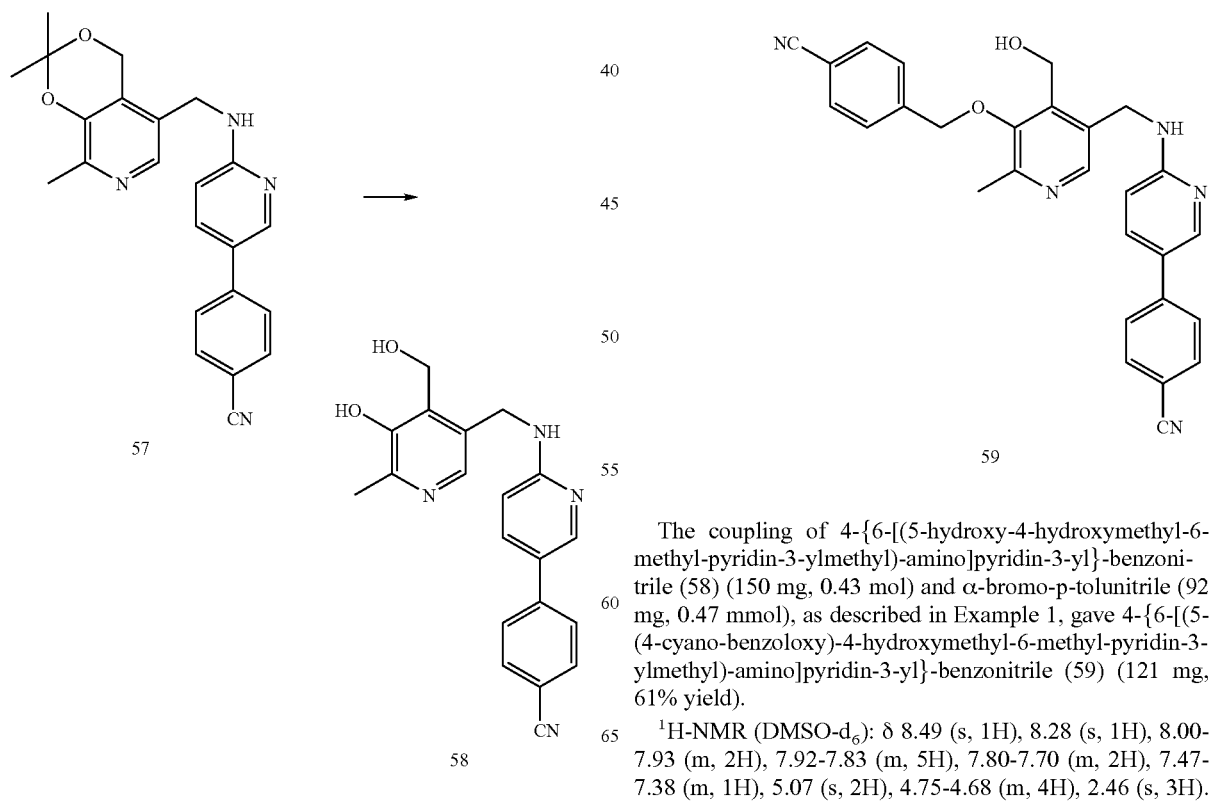

The hydrolysis of 4-{6-[(2,2,8-trimethyl-4H-[1,3]dioxino[,5-c]pyridin-5-ylmethyl)-amino]-pyridin-3-yl}-benzonitrile (57) (300 mg, 0.78 mmol), as described in Example 10, gave 4-{6-[(5-hydroxy-4-hydroxymethyl-6-methyl-pyridin-3-ylmethyl)-amino]pyridin-3-yl}-benzonitrile (58) (245 mg, 91% yield).

¹H-NMR (DMSO-d₆): δ 8.30 (s, 1H), 7.75 (s, 1H), 7.08 (s, 1H), 6.45 (s, 1H), 4.60 (s, 2H), 4.35 (d, 2H), 2.18 (s, 3H).

Example 55

Synthesis of 4-{6-[(5-(4-Cyano-benzoloxy)-4-hydroxymethyl-6-methyl-pyridin-3-ylmethyl)-amino]pyridin-3-yl}-benzonitrile (59)

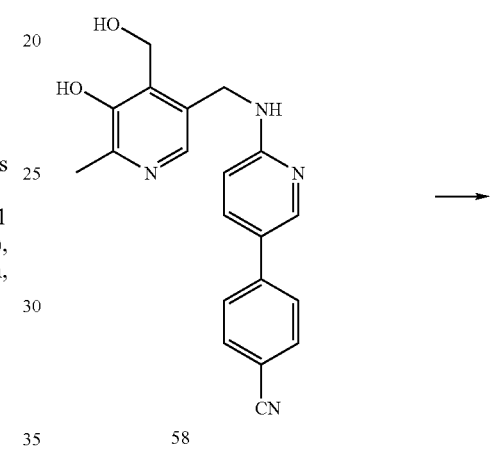

58

59

The coupling of 4-{6-[(5-hydroxy-4-hydroxymethyl-6-methyl-pyridin-3-ylmethyl)-amino]pyridin-3-yl}-benzonitrile (58) (150 mg, 0.43 mol) and α-bromo-p-tolunitrile (92 mg, 0.47 mmol), as described in Example 1, gave 4-{6-[(5-(4-cyano-benzoloxy)-4-hydroxymethyl-6-methyl-pyridin-3-ylmethyl)-amino]pyridin-3-yl}-benzonitrile (59) (121 mg, 61% yield).

¹H-NMR (DMSO-d₆): δ 8.49 (s, 1H), 8.28 (s, 1H), 8.00-7.93 (m, 2H), 7.92-7.83 (m, 5H), 7.80-7.70 (m, 2H), 7.47-7.38 (m, 1H), 5.07 (s, 2H), 4.75-4.68 (m, 4H), 2.46 (s, 3H).

Example 56

Synthesis of 4-(6-{[5-(4-Carbamimidoyl-benzyloxy)-4-hydroxymethyl-6-methyl-pyridin-3-ylmethyl]-amino}-pyridin-3-yl-benzamidine (60)

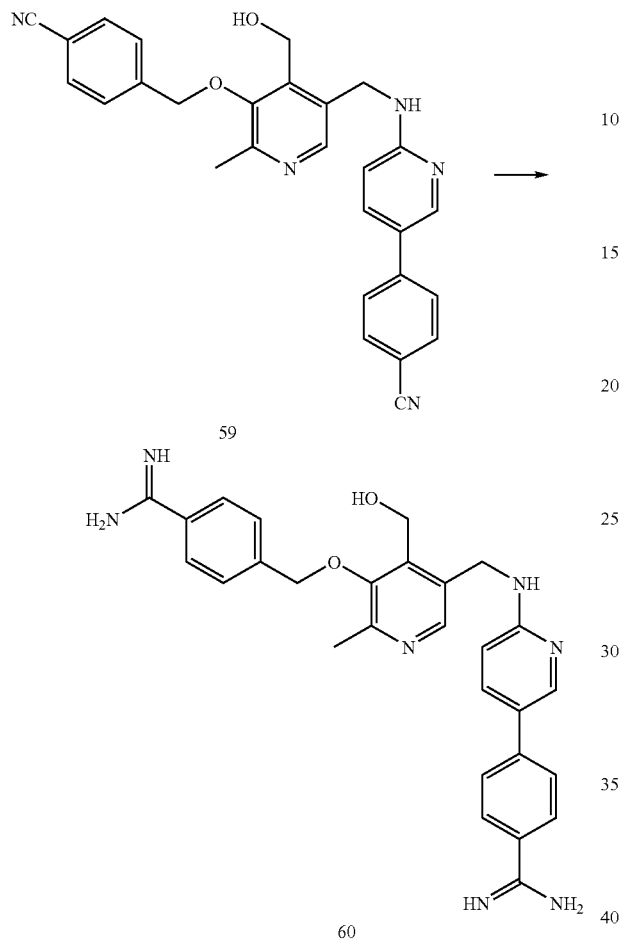

The conversion of bis-nitrile (59) to bis-amidine (60) was carried out as described in Example 2.

$^1$H-NMR (DMSO-d$_6$): δ 8.60 (s, 1H), 8.42 (s, 1H), 8.15-8.05 (m, 1H), 8.03 (m, 5H), 7.95-7.85 (m, 2H), 6.98-6.88 (m, 2H), 5.21 (s, 2H), 4.95-4.80 (m, 4H), 2.62 (s, 3H)

Example 57

Synthesis of 4'-{[5-(4-Cyano-benzyloxy)-4-hydroxymethyl-6-methyl-pyridin-3-ylmethyl]-amino}-3'-fluoro-biphenyl-4-carbonitrile (62)

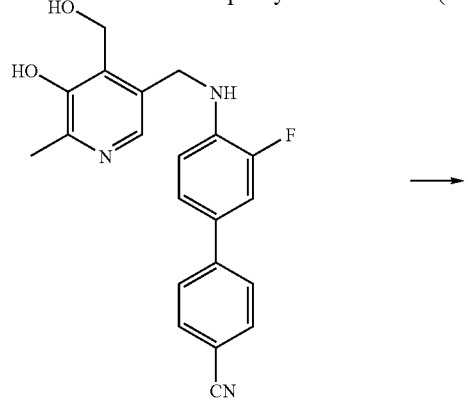

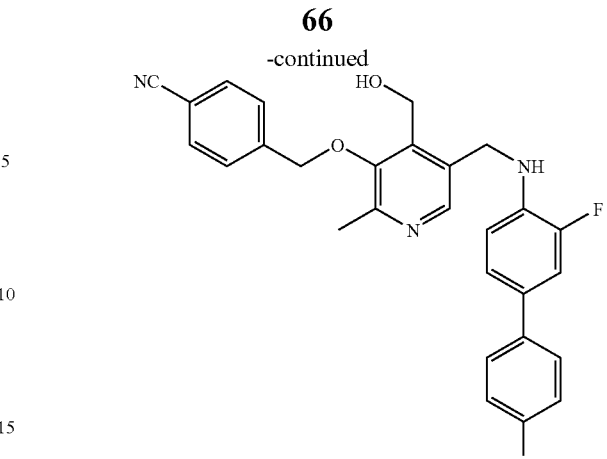

The coupling of 4'-[(5-hydroxy-4-hydroxymethyl-6-methyl-pyridine-3-ylmethyl)-amino]-3'-fluoro-biphenyl-4-carbonitrile (61) (250 mg, 0.69 mmol) and α-bromo-p-tolunitrile (149 mg, 0.76 mmol), as described in Example 1, gave 4'-{[5-(4-cyano-benzyloxy)-4-hydroxymethyl-6-methyl-pyridin-3-ylmethyl]-amino}-3'-fluoro-biphenyl-4-carbonitrile (62) (109 mg, 33% yield).

$^1$H-NMR (DMSO-d$_6$): δ 7.95 (s, 1H), 7.75-7.65 (m, 4H), 7.62-7.55 (m, 3H), 7.53-7.40 (m, 2H), 7.33-7.22 (m, 2H), 4.93 (s, 2H), 4.44-4.30 (m, 4H), 2.17 (s, 3H).

$^{19}$F-NMR (DMSO-d$_6$): δ-138.20 (s).

Example 58

Synthesis of 4'-{[5-(4-Carbamimidoyl-benzyloxy)-4-hydroxymethyl-6-methyl-pyridin-3-ylmethyl]-amino}-3'-fluoro-biphenyl-4-carboxamidine (63)

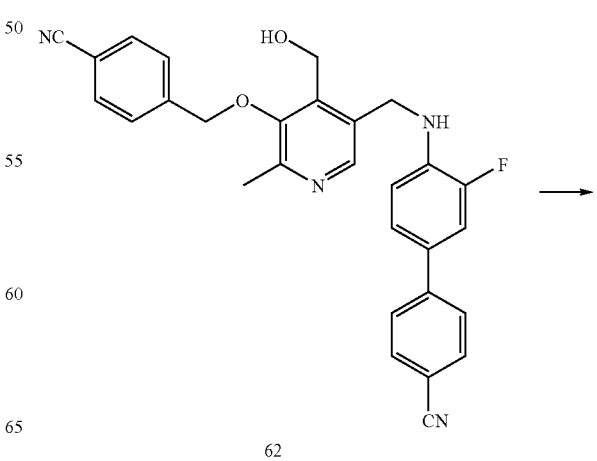

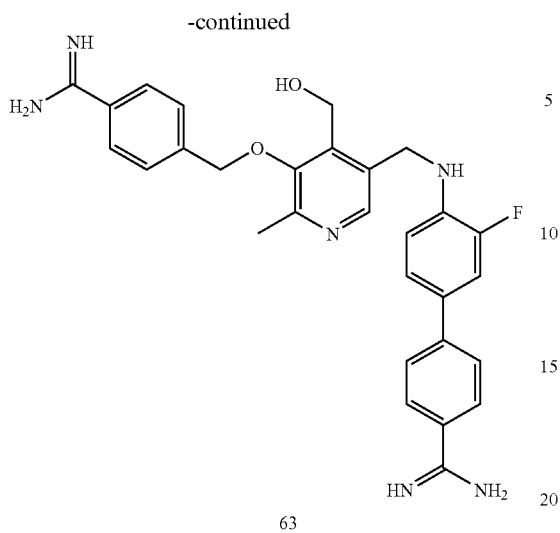

The conversion of bis-nitrile (62) to bis-amidine (63) was carried out as described in Example 2.

$^1$H-NMR (DMSO-$d_6$): δ 8.40 (s, 1H), 8.20-8.05 (m, 5H), 8.03-7.90 (m, 1H), 7.89-7.58 (m, 2H), 7.07-6.90 (m, 1H), 6.75 (s, 1H), 5.79 (s, 1H), 5.26 (s, 2H), 4.89 (d, 2H), 4.82 (d, 2H), (s, 3H).

$^{19}$F-NMR (DMSO-$d_6$): δ-138.29 (s).

Example 59

Synthesis of 4'-Cyano-biphenyl-4-carboxylic acid (5-(4-cyano-benzyloxy)-4-hydroxymethyl-6-methyl-pyridin-3-ylmethyl)-amide (65)

The coupling of 4'-cyano-biphenyl-4-carboxylic acid (5-hydroxy-4-hydroxymethyl-6-methyl-pyridin-3-ylmethyl)-amide (64) (650 mg, 1.7 mmol) and α-bromo-p-tolunitrile (375 mg, 1.9 mmol), as described in Example 3, gave 4'-cyano-biphenyl-4-carboxylic acid (5-(4-cyano-benzyloxy)-4-hydroxymethyl-6-methyl-pyridin-3-ylmethyl)-amide (65) (627 mg, 74% yield).

$^1$H-NMR (DMSO-$d_6$): δ 8.21 (s, 1H), 8.02-7.75 (m, 11H), 7.70 (s, 1H), 4.98 (s, 2H), 4.68-4.56 (m, 4H), 2.38 (s, 3H).

Example 60

Synthesis of 4'-Carbamimidoyl-biphenyl-4-carboxylic acid [5-(4-carbamimidoyl-benzyloxyl)-4-hydroxymethyl-6-methyl-pyridin-3-ylmethyl]-amide (68)

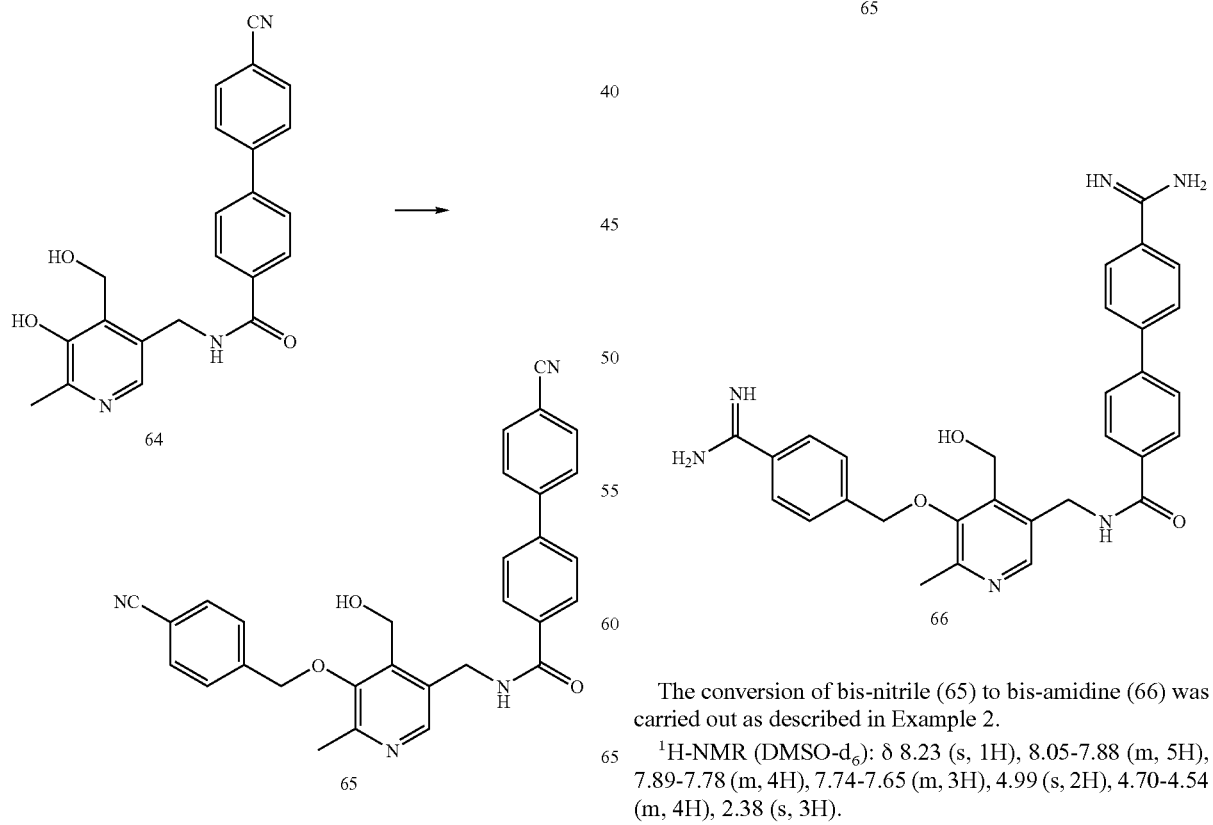

The conversion of bis-nitrile (65) to bis-amidine (66) was carried out as described in Example 2.

$^1$H-NMR (DMSO-$d_6$): δ 8.23 (s, 1H), 8.05-7.88 (m, 5H), 7.89-7.78 (m, 4H), 7.74-7.65 (m, 3H), 4.99 (s, 2H), 4.70-4.54 (m, 4H), 2.38 (s, 3H).

Example 61

Synthesis of 4-[4,6-Dimethyl-5-(4-cyano-benzyloxy)-pyridin-3-ylmethoxy]-benzonitrile (67)

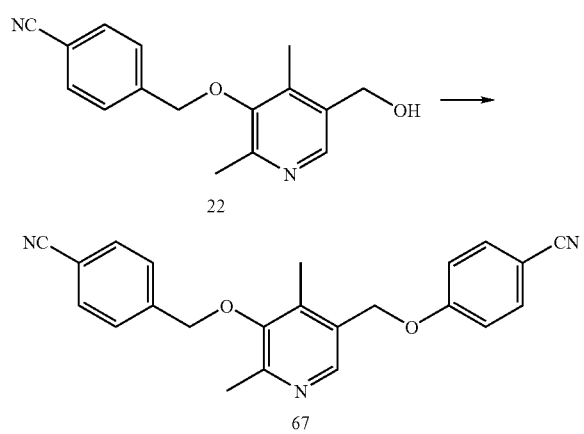

The coupling of 4-(5-hydroxymethyl-2,4-dimethyl-pyridin-3-yloxymethyl)-benzonitrile (22) (800 mg, 3.0 mmol) and 4-cyanophenol (715 mg, 6.0 mmol), as described in Example 9, gave 4-[4,6-dimethyl-5-(4-cyano-benzyloxy)-pyridin-3-ylmethoxy]-benzonitrile (67) (433 mg, 39% yield).

$^1$H-NMR (CDCl$_3$): δ 8.32 (s, 1H), 7.76-7.69 (m, 2H), 7.66-7.55 (m, 4H), 7.07-7.01 (m, 2H), 5.07 (s, 2H), 4.92 (s, 2H), 2.56 (s, 3H), 2.30 (s, 3H).

Example 62

Synthesis of 4-[4,6-Dimethyl-5-(4-carbamimidoyl-benzyloxyl)-pyridin-3-ylmethoxy]-benzamidine (68)

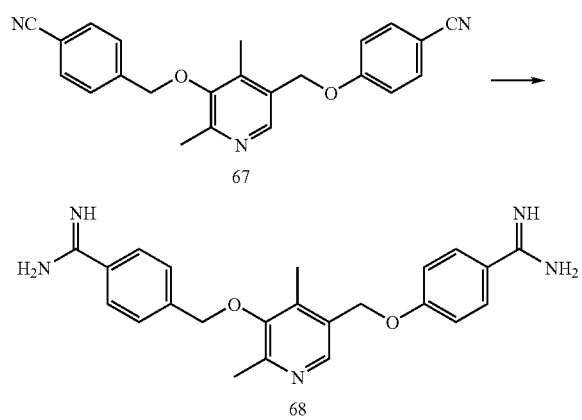

The conversion of bis-nitrile (67) to bis-amidine (68) was carried out as described in Example 2.

$^1$H-NMR (DMSO-d$_6$): δ 8.36 (s, 1H), 8.01-7.88 (m, 4H), 7.85-7.75 (m, 2H), 7.38-7.29 (m, 2H), 5.30 (s, 2H), 5.02 (s, 2H), 2.49 (s, 3H), 2.33 (s, 3H).

Example 63

Synthesis of 4-[4,6-Dimethyl-5-(3-cyano-benzyloxy)-pyridin-3-ylmethoxy]-benzonitrile (69)

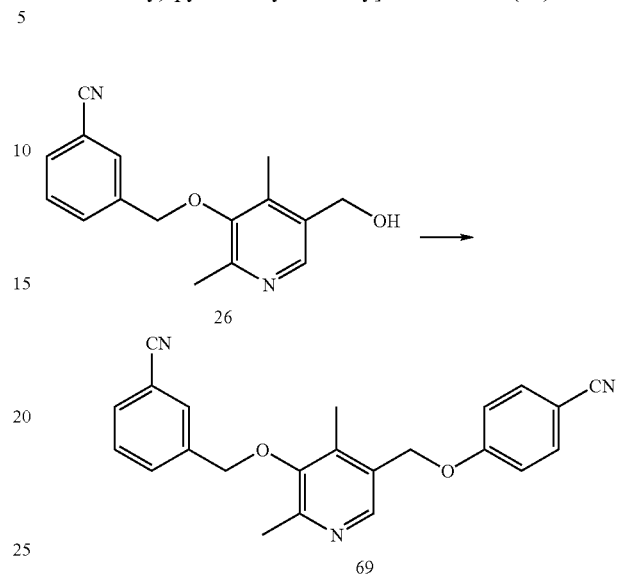

The coupling of 3-(5-hydroxymethyl-2,4-dimethyl-pyridin-3-yloxymethyl)-benzonitrile (26) (1.0 mg, 3.70 mmol) and 4-cyanophenol (885 mg, 7.40 mmol), as described in Example 9, gave 4-[4,6-dimethyl-5-(3-cyano-benzyloxy)-pyridin-3-ylmethoxy]-benzonitrile (69) (646 mg, 47% yield).

$^1$H-NMR (CD$_3$OD): δ 8.24 (s, 1H), 7.89-7.77 (m, 2H), 7.76-7.54 (m, 4H), 7.23-7.13 (m, 2H), 5.20 (s, 2H), 4.96 (s, 2H), 2.50 (s, 3H), 2.33 (s, 3H).

Example 64

Synthesis of 4-[4,6-Dimethyl-5-(3-carbamimidoyl-benzyloxyl)-pyridin-3-ylmethoxy]-benzamidine (70)

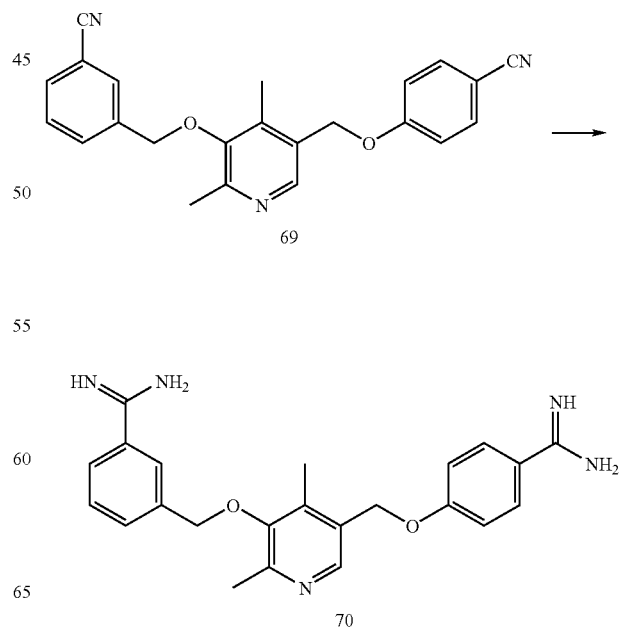

The conversion of bis-nitrile (69) to bis-amidine (70) was carried out as described in Example 2.

¹H-NMR (CD₃OD): δ 8.27 (s, 1H), 8.03-7.63 (m, 6H), 7.33-721 (m, 2H), 5.26 (s, 2H), 5.03 (s, 2H), 2.53 (s, 3H), 2.40 (s, 3H)

Example 65

Synthesis of 4-Cyano-N-[5-(4-cyano-benzyloxy)-4-hydroxymethyl-6-methyl-pyridin-3-ylmethyl]-benzamide (72)

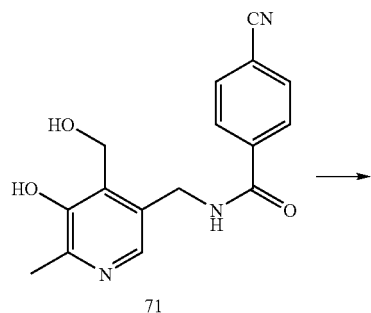

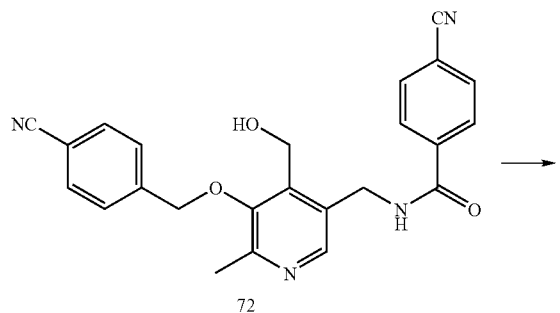

The coupling of 4-cyano-N-[5-hydroxy-4-hydroxymethyl-6-methyl-pyridin-3-ylmethyl]-benzamide (71) (580 mg, 3.0 mmol) and α-bromo-p-tolunitrile (580 mg, 3.0 mmol), as described in Example 3, gave 4-cyano-N-[5-(4-cyano-benzyloxy)-4-hydroxymethyl-6-methyl-pyridin-3-ylmethyl]-benzamide (72) (433 mg, 39% yield).

¹H-NMR (DMSO-d₆): δ 8.36 (s, 1H), 8.09-8.05 (m, 2H), 7.80-7.75 (m, 2H), 7.72-7.64 (m, 2H), 7.53-7.44 (m, 2H), 5.01 (s, 2H), 4.75-4.60 (m, 4H), 2.52 (s, 3H).

Example 66

Synthesis of 4-Carbamimidoyl-N-[5-(4-carbamimidoyl-benzyloxy)-4-hydroxymethyl-6-methyl-pyridin-3-ylmethyl]-benzamide (73)

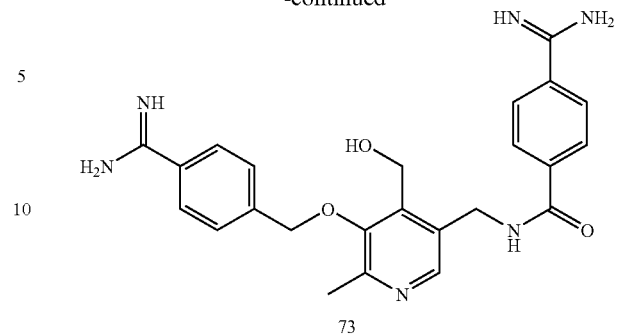

The conversion of bis-nitrile (72) to bis-amidine (73) was carried out as described in Example 2.

¹H-NMR (CD₃OD): δ 8.26 (s, 1H), 8.15-8.04 (m, 2H), 7.98-7.83 (m, 4H), 7.79-7.69 (m, 2H), 5.04 (s, 2H), 4.75 (m, 4H), 2.50 (s, 3H)

Example 67

Synthesis of 4-tert-Butyl-N-(2,2,8-trimethyl-4H-[1,3]dioxino[4,5-c]pyridin-5-yl-methyl)-benzamide (74)

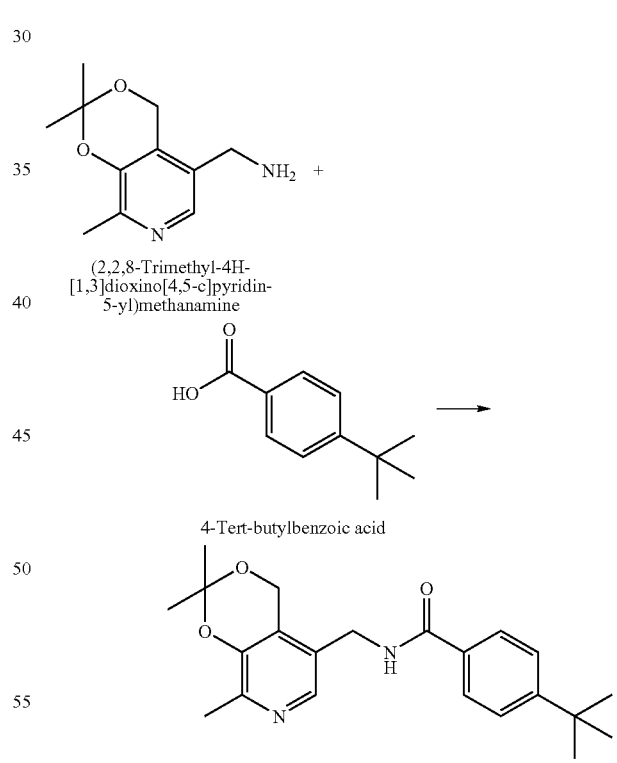

A mixture of C-(2,2,8-trimethyl-4H-[1,3]dioxino[4,5-c]pyridin-5-yl)-methylamine (1.77 g, 8.49 mmol), 4-tert-butylbenzoic acid (5.6 g, 31 mmol), EDC (5.7 g, 29 mmol), and DMAP (4.53 g, 35.6 mmol) was stirred in dichloromethane (200 mL) for 24 hours. Saturated aqueous sodium bicarbonate was added to the reaction mixture, and the dichloromethane layer was separated. The aqueous layer was then extracted with dichloromethane. The combined organic layer was dried over anhydrous magnesium sulfate, filtered and evaporated. The crude mixture was purified by column chromatography on silica gel using a gradient mixture of dichloromethane:acetone (1:0 to 7:3) as eluant to give 4-tert-butyl-N-(2,2,8-trimethyl-4H-[1,3]dioxino[4,5-c]pyridin-5-yl-methyl)-benzamide (74) (2.7 g, 85%) as a light yellow solid.

¹H-NMR (CDCl₃): δ 8.01 (s, 1H), 7.74-7.63 (m, 2H), 7.50-7.38 (m, 2H), 6.18 (t, 1H), 4.88 (s, 2H), 4.52 (d, 2H), 2.41 (s, 3H), 1.54 (s, 6H), 1.33 (s, 9H).

Example 68

Synthesis of 4-tert-Butyl-N-(5-hydroxy-4-hydroxymethyl-6-methyl-pyridin-3-yl-methyl)-benzamide (75)

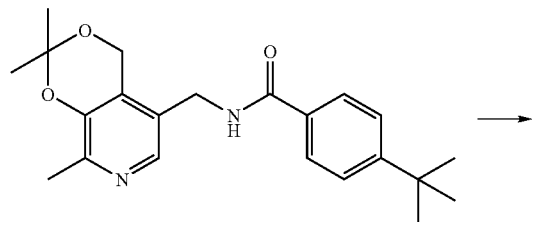

74

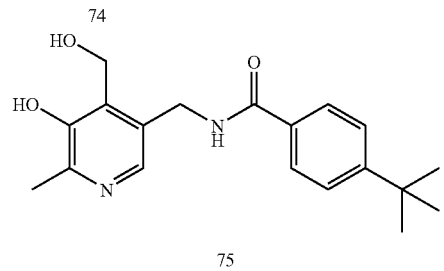

75

The hydrolysis of 4-tert-butyl-N-(2,2,8-trimethyl-4H-[1,3]dioxino[4,5-c]pyridin-5-yl-methyl)-benzamide (74) (2.6 g, 7.05 mmol), as described in Example 10, gave 4-tert-butyl-N-(5-hydroxy-4-hydroxymethyl-6-methyl-pyridin-3-yl-methyl)-benzamide (75) (1.4 g, 59% yield) as a colorless solid.

¹H-NMR (CD₃OD): δ 7.91 (s, 1H), 7.82-7.2 (m, 2H), 7.50-7.45 (m, 2H), 4.98 (s, 2H), 4.59 (s, 2H), 2.42 (s, 3H), 1.35 (s, 9H).

Example 69

Synthesis of 4-tert-Butyl-N-[5-(4-cyano-benzyloxy)-4-hydroxymethyl-6-methyl-pyridin-3-ylmethyl]-N-methyl-benzamide (76)

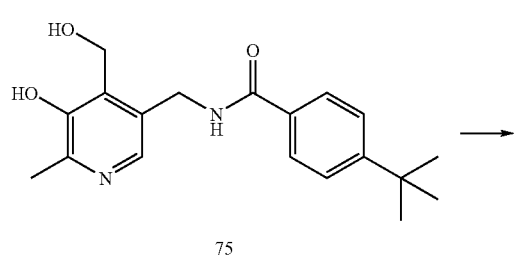

75

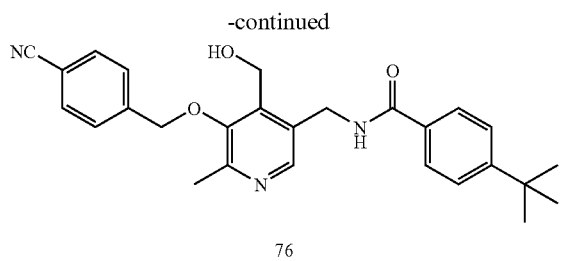

76

The coupling of 4-tert-butyl-N-(5-hydroxy-4-hydroxymethyl-6-methyl-pyridin-3-yl-methyl)-benzamide (75) (404 mg, 1.23 mmol) and α-bromo-p-tolunitrile (284 mg, 1.44 mmol), as described in Example 3, gave 4-tert-butyl-N-[5-(4-cyano-benzyloxy)-4-hydroxymethyl-6-methyl-pyridin-3-yl-methyl]-N-methyl-benzamide (76) (328 mg, 60% yield).

¹H-NMR CDCl₃: δ 8.33 (s, 1H), 7.70-7.65 (m, 4H), 7.64-7.55 (m, 2H), 7.48-7.37 (m, 2H), 7.05 (t, 1H), 5.04 (s, 2H), 4.84 (s, 2H), 4.70 (d, 2H), 4.36 (s br, 1H), 2.50 (s, 3H), 1.31 (s, 9H).

MS m/z (ES⁺): 444.49 (M+H⁺).

Example 70

Synthesis of 4-tert-Butyl-N-[5-(4-carbamimidoyl-benzyloxy)-4-hydroxymethyl-6-methyl-pyridin-3-ylmethyl]-benzamide (77)

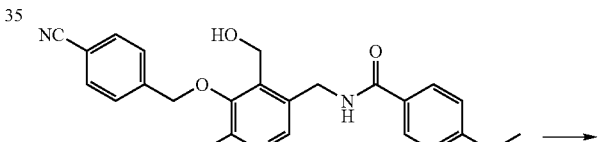

76

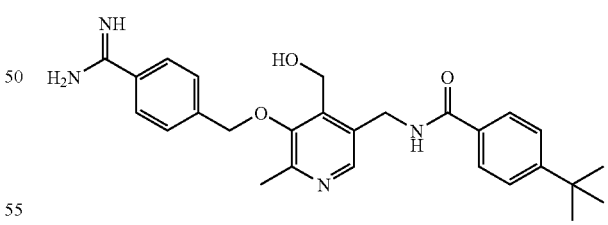

77

The conversion of nitrile (76) to amidine (77) was carried out as described in Example 2.

¹H-NMR (CD₃OD): δ 8.41 (s, 1H), 7.95-7.86 (m, 2H), 7.85-7.73 m, (4H), 7.60-7.49 (m, 2H), 5.23 (s, 2H), 4.94 (s, 2H), 2.66 (s, 3H), 1.36 (s, 9H).

MS m/z (ES⁺): 461.53 (M+H⁺).

Example 71

Synthesis of 2,2,8-Trimethyl-4H-[1,3]dioxino[4,5-c]pyridine-5-carboxylic acid amide (80)

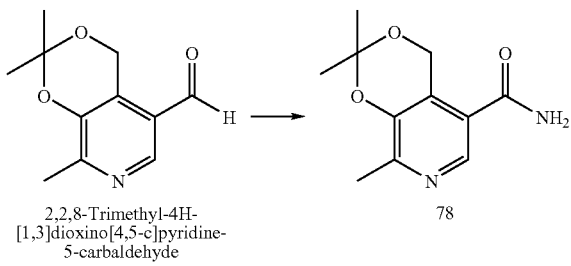

2,2,8-Trimethyl-4H-[1,3]dioxino[4,5-c]pyridine-5-carbaldehyde

78

Ammonia gas was bubbled into a solution of 2,2,8-trimethyl-4H-[1,3]dioxino[4,5-c]pyridine-5-carbaldehyde (31.3 g, 151 mmol) in isopropyl alcohol (2.4 L) at 0° C. for about 30 minutes. Manganese (IV) dioxide (210 g, 7.96 mmol) was added, and the solution was stirred for about 15 hours at room temperature. Excess manganese (IV) dioxide was filtered through a celite pad and washed with isopropyl alcohol. The filtrate was evaporated and washed with diethyl ether, water, and then with methyl alcohol to give 2,2,8-trimethyl-4H-[1,3]dioxino[4,5-c]pyridine-5-carboxylic acid amide (78) (23.1 g, 69% yield) as a light yellow solid.

$^1$H-NMR (CDCl$_3$): δ 8.27 (s, 1H), 5.13 (s, 2H), 2.45 (s, 3H), 1.57 (s, 6H).

Example 72

Synthesis of (2,2,8-Trimethyl-4H-[1,3]dioxino[4,5-c]pyridin-5-yl)-carbamic acid methyl ester (79) and 2,2,8-Trimethyl-4H-[1,3]dioxino[4,5-c]pyridin-5-ylamine (80)

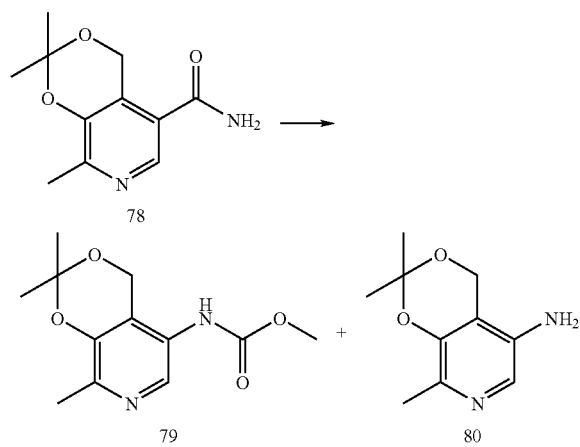

Commercial bleach (179 mL, 5.25%, 126 mmol) was added to a mixture of aqueous sodium hydroxide (0.1 N, 890 mL, 89 mmol) and a solution of 2,2,8-trimethyl-4H-[1,3]dioxino[4,5-c]pyridine-5-carboxylic acid amide (78) (22.5 g, 101 mmol) in methyl alcohol (2.1 L) at 50° C. The resulting mixture was stirred for 3 minutes, then slowly cooled down to room temperature and stirred for another 30 minutes. Methyl alcohol was evaporated, and the aqueous solution was extracted with ethyl acetate. The combined organic layer was dried over anhydrous magnesium sulfate, filtered and evaporated to give (2,2,8-trimethyl-4H-[1,3]dioxino[4,5-c]pyridin-5-yl)-carbamic acid methyl ester (79) (17.8 g, 70% yield) as a yellow powder.

$^1$H-NMR (CDCl$_3$): δ 8.03 (s, 1H, s), 6.73 (s br, 1H), 4.75 (s, 2H), 3.47 (s, 3H), 2.37 (s, 3H), 1.55 (s, 6H).

The aqueous solution was further extracted with CH$_2$Cl$_2$, the combined organic layer was dried over anhydrous magnesium sulfate, filtered and evaporated to give 2,2,8-trimethyl-4H-[1,3]dioxino[4,5-c]pyridin-5-ylamine (80) (3.4 g, 17% yield) as an off white powder.

$^1$H-NMR (CDCl$_3$): δ 7.53 (s, 1H), 4.66 (s, 2H), 2.31 (s, 3H), 1.55 (s, 6H).

Example 73

Synthesis of (4-Cyano-benzyl)-(2,2,8-trimethyl-4H-[1,3]dioxino[4,5-c]pyridin-5-yl)-carbamic acid methyl ester (81)

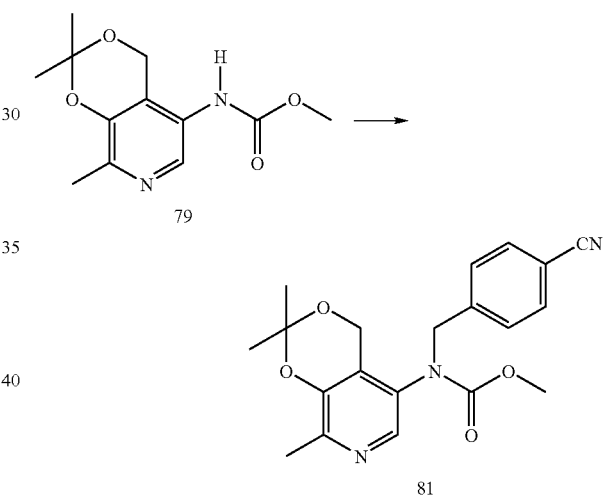

(2,2,8-Trimethyl-4H-[1,3]dioxino[4,5-c]pyridin-5-yl)-carbamic acid methyl ester (27) (5.3 g, 21 mmol) in dry THF (500 mL) was cannulated into a suspension of sodium hydride (860 mg, 60%, 21 mmol) in dry THF at −78° C. under nitrogen atmosphere. The resulting solution was slowly warmed to room temperature and stirred for about 15 minutes, then cooled to −78° C. To this solution was added a solution of α-bromo-p-tolunitrile (5.0 g, 25 mmol) in THF. The resulting mixture was slowly warmed to room temperature and stirred overnight. The reaction mixture was quenched with water, and extracted with ethyl acetate. The combined organic layer was dried over anhydrous magnesium sulfate, filtered and evaporated to give a crude product which was purified by column chromatography on silica gel using a gradient mixture of ethyl acetate:hexane (0:1 to 1:1) as eluant to give (4-cyano-benzyl)-(2,2,8-trimethyl-4H-[1,3]dioxino[4,5-c]pyridin-5-yl)-carbamic acid methyl ester (81) (5.3 g, 68%) as colorless foam.

¹H-NMR (CDCl₃): δ 7.72 (s br, 1H), 7.64-7.56 (m, 2H), 7.42-7.30 (m, 2H), 4.77 (s, 2H), 4.53 (d, 1H), 4.03 (d, 1H), 3.69 (s, 3H), 2.38 (s, 3H), 1.49 (s, 3H), 1.44 (s, 3H).

Example 74

Synthesis of 4-(5-Hydroxy-6-methyl-2-oxo-4H-pyrido[3,4-d][1,3]oxazin-1-ylmethyl)-benzonitrile (82)

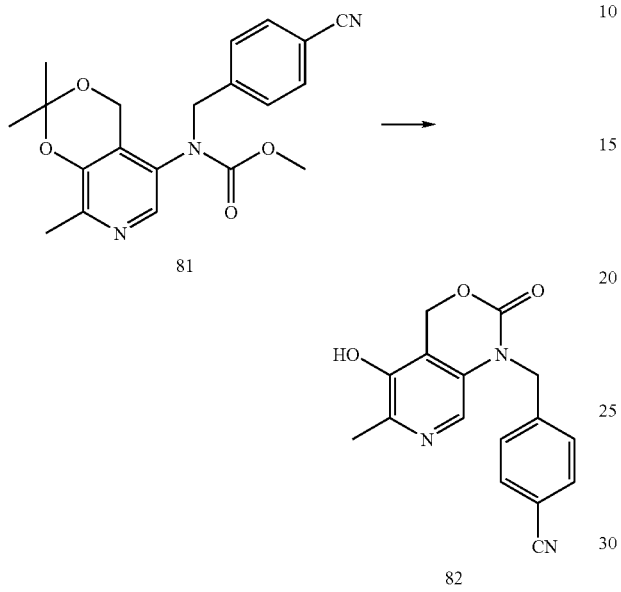

The hydrolysis of (4-cyano-benzyl)-(2,2,8-trimethyl-4H-[1,3]dioxino[4,5-c]pyridin-5-yl)-carbamic acid methyl ester (81) (5.1 g, 13.9 mmol) and subsequent cyclization was achieved by heating 81 in a 1:1 mixture of aqueous formic acid (20%) and ethyl alcohol at 80° C. for 2 hours. The evaporation of solvent, followed by the addition of water precipitated the product 4-(5-hydroxy-6-methyl-2-oxo-4H-pyrido[3,4-d][1,3]oxazin-1-ylmethyl)-benzonitrile (82) (2.8 g, 74% yield).

¹H-NMR (DMSO-d6): δ 9.56 (s, 1H), 7.85-7.78 (m, 2H), 7.58-7.53 (m, 2H), 7.51 (s, 1H), 5.44 (s, 2H), 5.21 (s, 2H), 2.59 (s, 3H).

MS m/z (ES⁺): 296.36 (M+H⁺).

Example 75

Synthesis of 4-[5-(4-Cyano-benzyloxy)-6-methyl-2-oxo-4H-pyrido[3,4-d][1,3]oxazin-1ylmethyl]-benzonitrile (83)

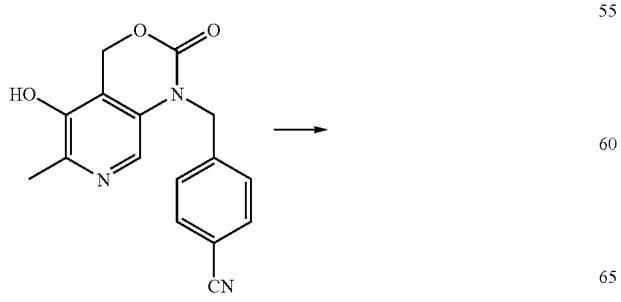

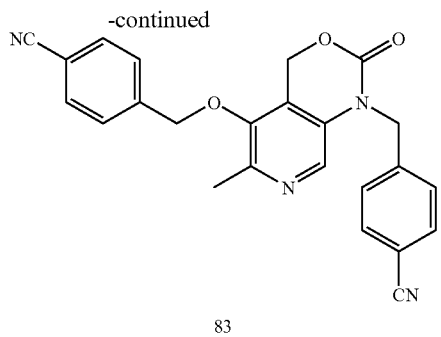

The coupling of 4-(5-hydroxy-6-methyl-2-oxo-4H-pyrido[3,4-d][1,3]oxazin-1-ylmethyl)-benzonitrile (82) (874 mg, 3.24 mmol) and α-bromo-p-tolunitrile (1.2 g, 6.17 mmol), as described in Example 1, gave 4-[5-(4-cyano-benzyloxy)-6-methyl-2-oxo-4H-pyrido[3,4-d][1,3]oxazin-1ylmethyl]-benzonitrile (83) (1.0 g, 84% yield) as a colorless solid.

¹H-NMR (CDCl₃): δ 7.81 (s, 1H), 7.77-7.70 (m, 2H), 7.69-7.62 (m, 2H), 7.57-7.49 (m, 2H), 7.44-7.37 (m, 2H), 5.26 (s, 2H), 5.19 (s, 2H), 4.96 (s, 2H), 2.50 (s, 3H).

MS m/z (ES⁺): 441.46 (M+H⁺).

Example 76

Synthesis of 4-[6-Methyl-5-(4-carbamimidoyl-benzyloxy)-2-oxo-4H-pyrido[3,4-d][1,3]oxazin-1-ylmethyl]-benzamidine (84)

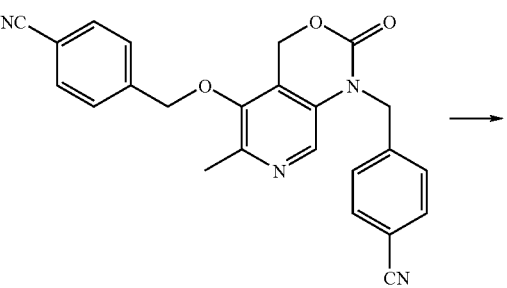

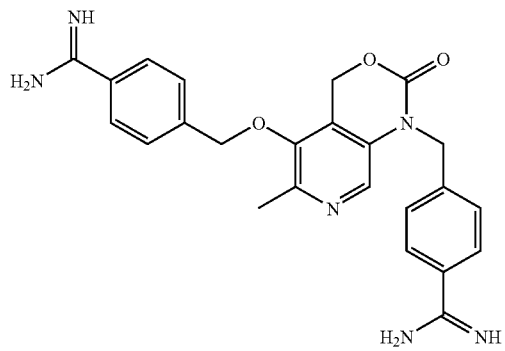

The conversion of bis-nitrile (83) to bis-amidine (84) was carried out as described in Example 2.

¹H-NMR (DMSO-d6): δ 9.40 and 9.2 (m, 4H), 9.20 and 9.05 (m, 4H), 7.91 (s, 1H), 7.90-7.84 (m, 2H), 7.83-7.73 (m, 4H), 7.63-7.54 (m, 2H), 5.53 (s, 2H), 5.29 (s, 2H), 5.06 (s, 2H), 2.38 (s, 3H).

MS m/z (ES+): 445.50 (M+H+).

Example 77

Synthesis of 4-[5-(3-Cyano-benzyloxy)-6-methyl-2-oxo-4H-pyrido[3,4-d][1,3]oxazin-1ylmethyl]-benzonitrile (85)

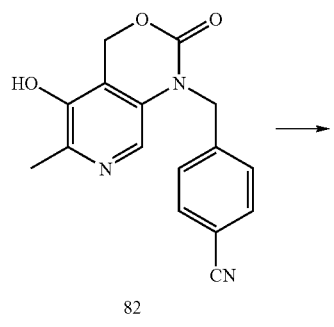

82

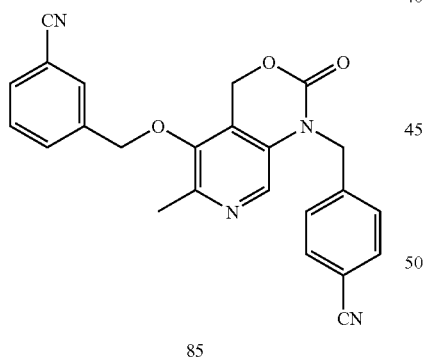

85

The coupling of 4-(5-hydroxy-6-methyl-2-oxo-4H-pyrido[3,4-d][1,3]oxazin-1-ylmethyl)-benzonitrile (82) (0.8 g, 2.8 mmol) and α-bromo-m-tolunitrile (5.9 g, 30 mmol), as described in Example 1, gave 4-[5-(3-cyano-benzyloxy)-6-methyl-2-oxo-4H-pyrido[3,4-d][1,3]oxazin-1ylmethyl]-benzonitrile (85) (322 mg, 28% yield) as.

¹H-NMR (DMSO-d6): δ 7.79 (s, 1H), 7.75-7.62 (m, 5H), 7.61-7.53 (m, 1H), 7.44-7.37 (m, 2H), 5.21 (s, 2H), 5.18 (s, 2H), 4.92 (s, 2H), 2.48 (s, 3H).

Example 78

Synthesis of 4-[6-Methyl-5-(3-carbamimidoyl-benzyloxy)-2-oxo-4H-pyrido[3,4-d][1,3]oxazin-1-ylmethyl]-benzamidine (86)

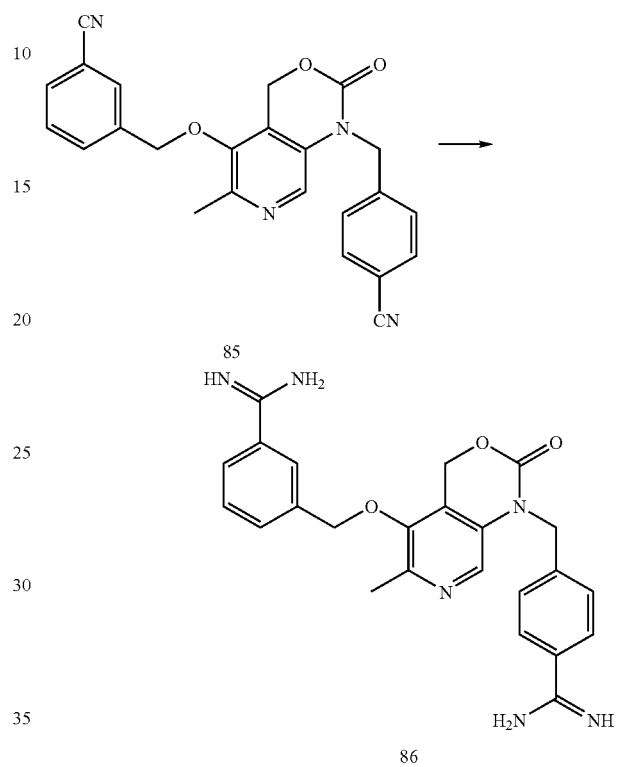

The conversion of bis-nitrile (85) to bis-amidine (86) was carried out as described in Example 2.

¹H-NMR (DMSO-d6): δ 9.45-9.20 (m, 4H), 9.20-9.05 (m, 4H), 7.98 (s, 1H), 7.92-7.76 (m, 5H), 7.76-7.67 (m, 1H), 7.63-7.54 (m, 2H), 5.52 (s, 2H), 5.29 (s, 2H), 5.01 (s, 2H), 2.42 (s, 3H).

MS m/z (ES+): 445.55 (M+H+).

Example 79

Synthesis of 4-{[4-Hydroxymethyl-6-methyl-5-(4-cyano-benzyloxy)-pyridin-3-ylamino]-methyl}-benzonitrile (87)

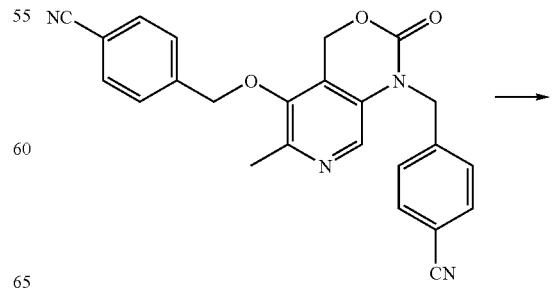

83

-continued

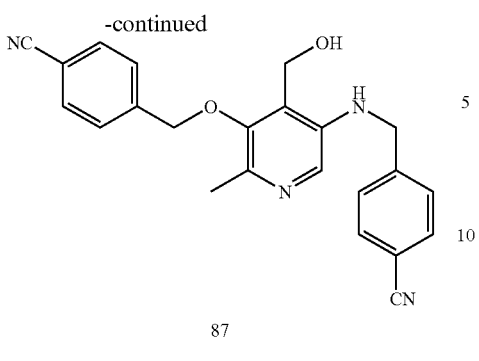

87

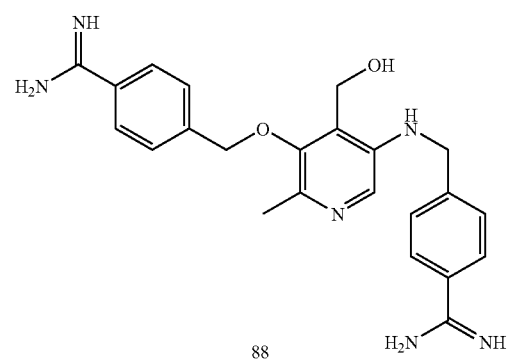

88

Sodium borohydride (2.6 g, 69 mmol) was added to a solution of 4-[5-(4-cyano-benzyloxy)-6-methyl-2-oxo-4H-pyrido[3,4-d][1,3]oxazin-1 ylmethyl]-benzonitrile (83) (587 mg, 1.4 mmol) in a mixture of methyl alcohol and dichloromethane (1:1, 20 mL) at 0° C. The resulting solution was warmed to room temperature and stirred for 24 hours. The solvent was evaporated, residue was diluted with water and the mixture was extracted with chloroform. The organic layer was dried over anhydrous magnesium sulfate, filtered and evaporated. The product was purified by column chromatography on silica gel using a gradient mixture of dichloromethane:methyl alcohol (1:0 to 40:1) as eluant to give 4-{[4-hydroxymethyl-6-methyl-5-(4-cyano-benzyloxy)-pyridin-3-ylamino]-methyl}-benzonitrile (87) (175 mg, 32% yield) as a colorless solid.

$^1$H-NMR (DMSO-d6): δ 7.96-7.89 (m, 2H), 7.85-7.78 (m, 2H), 7.74-7.67 (m, 2H), 7.62-7.59 (m, 2H), 7.49 (s, 1H), 6.07 (t, 1H), 5.33 (t, 1H), 4.95 (s, 2H), 4.61 (d, 2H), 4.54 (d, 2H), 2.37 (s, 3H).

MS m/z (ES$^+$): 385.36 (M+H$^+$).

Example 80

Synthesis of 4-{[4-Hydroxymethyl-6-methyl-5-(4-carbamimidoyl-benzyloxy)-pyridin-3-ylamino]-methyl}-N,N,N'-trimethyl-benzamidine (88)

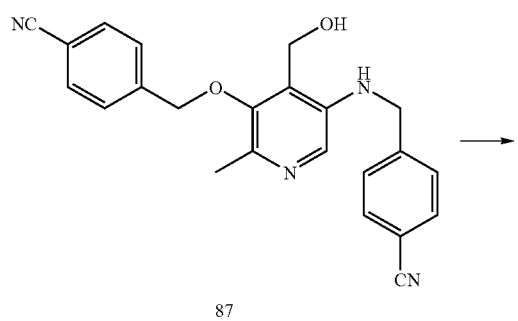

87

The conversion of bis-nitrile (87) to bis-amidine (88) was carried out as described in Example 2.

$^1$H-NMR (DMSO-d6): δ 9.45-9.12 (m, 6H), 7.91 (d, 1H), 7.81 (d, 1H), 7.76 (d, 1H), 7.63 (d, 1H), 7.62 (s, 1H), 5.08 (s, 2H), 4.74 (s, 2H), 4.65 (s, 2H), 2.42 (s, 3H).

MS m/z (ES$^+$): 419.15 (M+H$^+$).

Example 81

Synthesis of 4-(5-Hydroxymethyl-2,4-dimethyl-pyridin-3-yloxy)-benzonitrile (89)

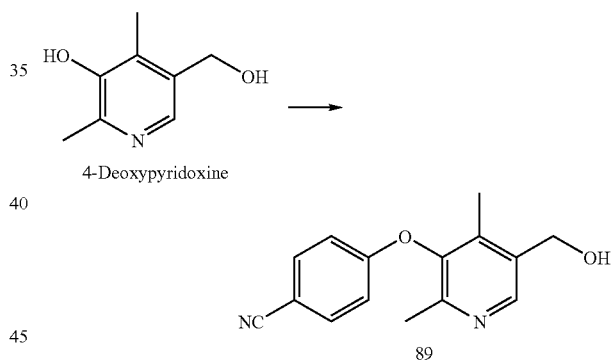

A mixture of 4-deoxypyridoxine hydrochloride (0.44 g, 2.8 mmol), copper (I) oxide (0.50 g, 3.5 mmol), dimethylglyoxime (0.15 g, 1.3 mmol), 4-iodobenzonitrile (1.08 g, 4.7 mmol), cesium carbonate (5.00 g, 15.3 mmol), and crushed molecular sieves 3° A (0.6 g) in anhydrous DMF (4 mL) were heated at 110° C. for 12 hours. The reaction mixture was evaporated to dryness, and the crude product purified by column chromatography on silica gel using a gradient of dichloromethane:methyl alcohol (1:0 to 9:1) as eluant to give 4-(5-hydroxymethyl-2,4-dimethyl-pyridin-3-yloxy)-benzonitrile (89) (50 mg, 7% yield).

$^1$H-NMR (CDCl$_3$): δ 8.70 (s, 1H), 7.30 (d, 2H), 6.95 (d, 2H), 4.80 (s, 2H), 2.52 (s, 3H), 2.16 (s, 3H).

Example 82

Synthesis of 4-(5-carboxy-2,4-dimethyl-pyridin-3-yloxy)-benzonitrile (90)

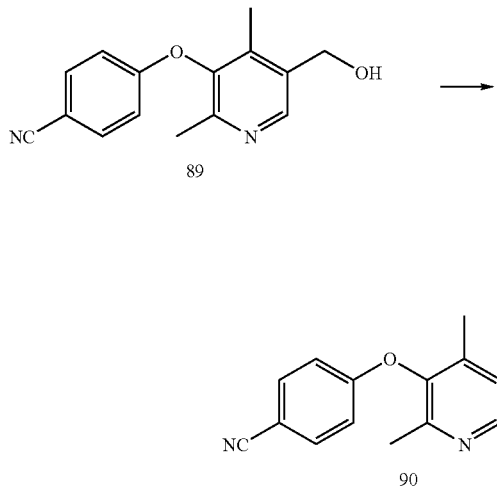

A solution of 4-(5-hydroxymethyl-2,4-dimethyl-pyridin-3-yloxy)-benzonitrile (500 mg, 2.0 mmol) and manganese (IV) dioxide (3.2 g, 36.8 mmol) in toluene (250 mL) was stirred at 90° C. for 30 minutes and then at room temperature for 12 hours. Excess manganese (IV) dioxide was filtered through a celite pad and washed with dichloromethane. The filtrate was evaporated to dryness and the crude product purified by column chromatography on silica gel using a gradient of dichloromethane:methyl alcohol (1:0 to 19:1) as eluant to give 4-(5-carboxy-2,4-dimethyl-pyridin-3-yloxy)-benzonitrile (90) (56 mg, 12% yield) as colorless solid.

$^1$H-NMR (CDCl$_3$): δ 10.40 (s, 1H), 8.93 (s, 1H), 7.75 (d, 2H), 6.96 (d, 2H), 4.53 (t, 1H), 2.59 (s, 3H), 2.56 (s, 3H).

Example 83

Synthesis of 4-{[3-(4-cyano-phenoxy)-2,4-dimethyl-pyridin-5-ylmethyl]-amino}benzonitrile (91)

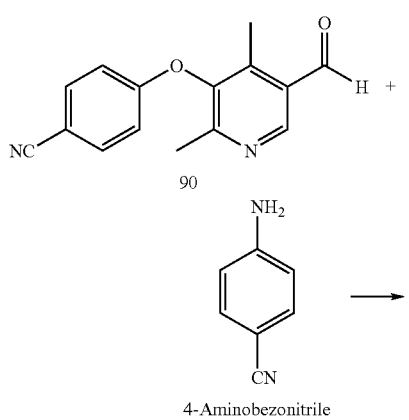

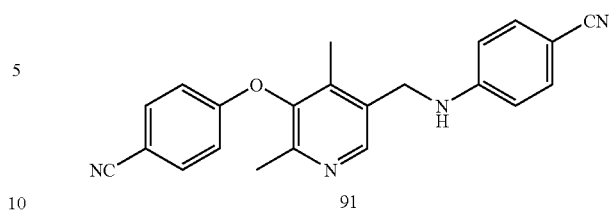

The reductive amination of 4-(5-carboxy-2,4-dimethyl-pyridin-3-yloxy)-benzonitrile (189 mg, 0.75 mmol) and 4-aminobenzonitrile (400 mg, 3.38 mmol), as described in Example 21, gave 4-{[3-(4-cyano-phenoxy)-2,4-dimethyl-pyridin-5-ylmethyl]-amino}-benzonitrile (91) (120 mg, 45% yield) as a brown oil.

$^1$H-NMR (CDCl$_3$): δ 8.37 (s, 1H), 7.61 (d, 2H), 7.46 (d, 2H), 6.85 (d, 2H), 6.65 (d, 2H), 4.53 (t, 1H), 4.37 (d, 2H), 2.35 (s, 3H), 2.16 (s, 3H).

Example 84

Synthesis of 4-{5-[(4-amidino-phenylamino)-methyl]-2,4-dimethyl-pyridin-3-yloxy}benzamidine (92)

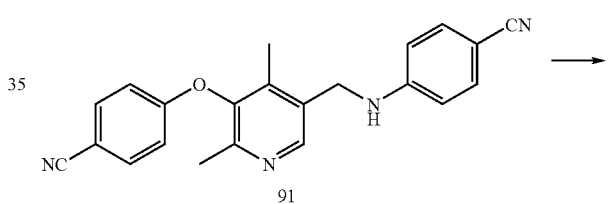

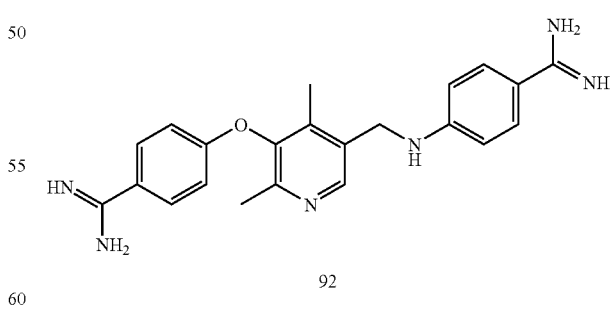

The conversion of bis-nitrile (91) to bis-amidine (92) was carried out as described in Example 2.

$^1$H-NMR (CD$_3$OD): δ 8.30 (s, 1H), 7.87 (d, 2H), 7.68 (d, 2H), 7.04 (d, 2H), 6.83 (d, 2H), 4.50 (d, 2H), 2.32 (s, 3H), 2.23 (s, 3H).

Example 85

Synthesis of 3-(5-Hydroxymethyl-2,4-dimethyl-pyridin-3-yloxy)-benzonitrile (93)

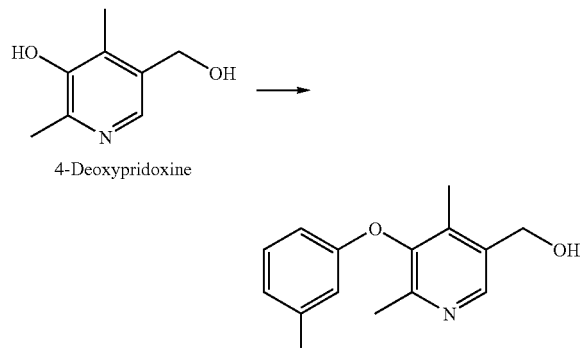

The coupling of 4-deoxypyridoxine hydrochloride (5.6 g, 29.5 mmol) and 3-iodobenzonitrile (10.0 g, 43.0 mmol), as described in Example 81, gave 3-(5-hydroxymethyl-2,4-dimethyl-pyridin-3-yloxy)-benzonitrile (93) (0.5 g, 7.5% yield).

$^1$H-NMR (CDCl$_3$): δ 7.40-7.27 (m, 3H), 7.05-7.97 (m, 2H), 6.95 (d, 2H), 4.74 (s, 2H), 2.32 (s, 3H), 2.14 (s, 3H).

Example 86

Synthesis of 3-(5-carboxy-2,4-dimethyl-pyridin-3-yloxy)-benzonitrile (94)

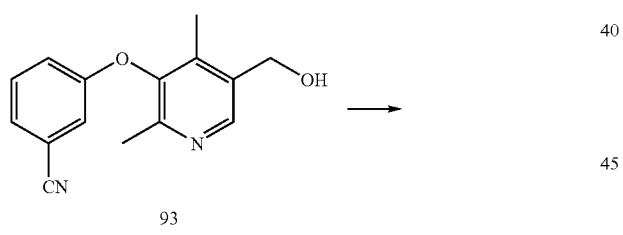

The oxidation of 3-(5-hydroxymethyl-2,4-dimethyl-pyridin-3-yloxy)-benzonitrile (93) (500 mg, 2.0 mmol) to 3-(5-carboxy-2,4-dimethyl-pyridin-3-yloxy)-benzonitrile (94) (252 mg, 12% yield) was carried out as described in Example 82.

$^1$H-NMR (CDCl$_3$): δ 10.19 (s, 1H), 8.71 (s, 1H), 7.40-7.26 (m, 2H), 6.99-6.92 (m, 2H), 4.53 (t, 1H), 2.38 (s, 3H), 2.35 (s, 3H).

Example 87

Synthesis of 4-{[3-(3-cyano-phenoxy)-2,4-dimethyl-pyridin-5-ylmethyl]-amino}benzonitrile (95)

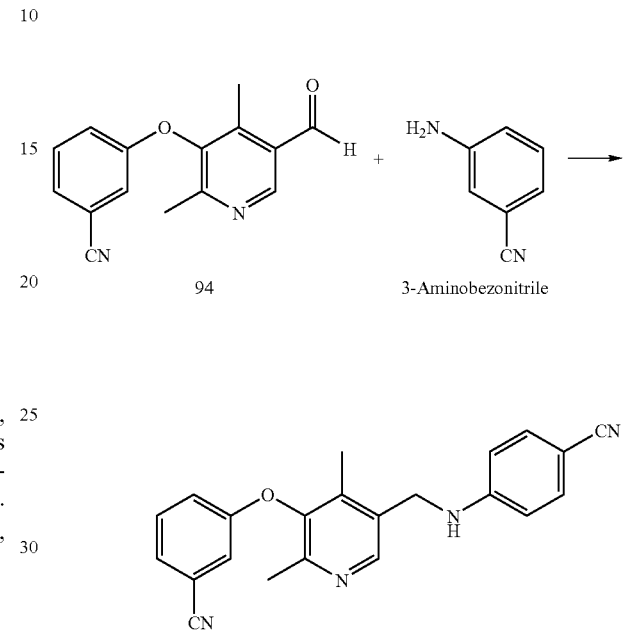

The reductive amination of 3-(5-carboxy-2,4-dimethyl-pyridin-3-yloxy)-benzonitrile (188 mg, 0.74 mmol) and 4-aminobenzonitrile (500 mg, 4.2 mmol), as described in Example 21, gave 4-{[3-(3-cyano-phenoxy)-2,4-dimethyl-pyridin-5-ylmethyl]-amino}-benzonitrile (95) (200 mg, 77% yield) as a brown oil.

$^1$H-NMR (CDCl$_3$): δ 8.33 (s, 1H), 7.44-7.39 (m, 3H), 7.34-7.31 (m, 1H), 7.07-7.03 (m, 1H), 6.96-6.95 (m, 1H), 6.64 (d, 2H), 4.81 (t, 1H), 4.36 (d, 2H), 2.32 (s, 3H), 2.02 (s, 3H).

Example 88

Synthesis of 4-{5-[(3-amidino-phenylamino)-methyl]-2,4-dimethyl-pyridin-3-yloxy}benzamidine (96)

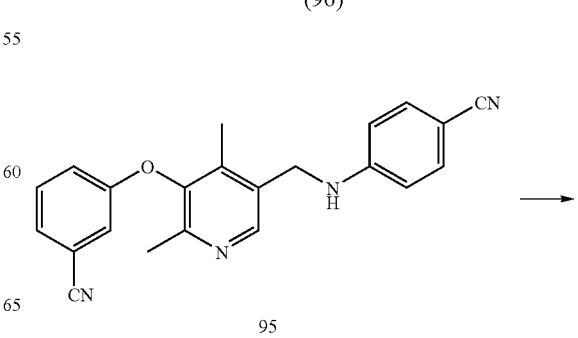

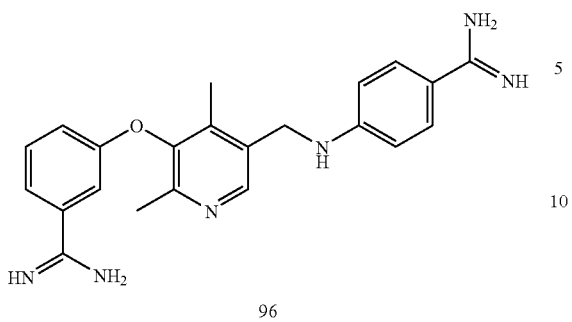

96

The conversion of bis-nitrile (95) to bis-amidine (96) was carried out as described in Example 2.

$^1$H-NMR (CD$_3$OD): δ 8.21 (s, 1H), 7.56 (d, 2H), 7.51-7.40 (m, 2H), 7.19 (t, 1H), 7.03 (dd, 1H), 6.76 (d, 2H), 4.43 (s, 2H), 2.24 (s, 3H), 2.14 (s, 3H).

Example 89

Synthesis of 3-Benzyloxy-2-methyl-1,3-dihydro-furo[4,5-c]pyridin-1-ol (97)

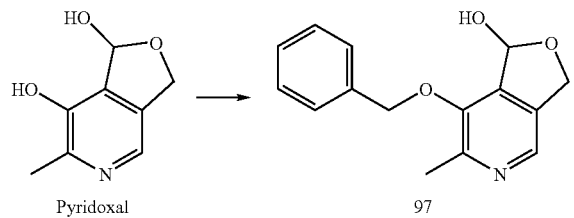

The coupling of pyridoxal hydrochloride (25 g, 0.12 mol) and benzyl bromide (51.6 g, 0.30 mol), as described in Example 1, gave 3-benzyloxy-2-methyl-1,3-dihydro-furo[4,5-c]pyridin-1-ol (97) (8.0 g, 25% yield).

$^1$H-NMR (DMSO-d6): δ 8.12 (s, 1H), 7.48-7.35 (m, 5H), 7.09 (d, 1H), 6.61 (dd, 1H), 5.26 (dd, 2H), 5.00 (dd, 2H), 2.41 (s, 3H).

Example 90

Synthesis of 3-Benzyloxy-2-methyl-1,3-dihydro-furo[4,5-c]pyridin-1-ol (98)

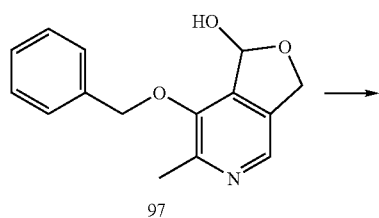

A mixture of 3-benzyloxy-2-methyl-1,3-dihydro-furo[4,5-c]pyridin-1-ol (97) (6.1 g, 23.7 mmol) and methyltriphenylphosphonium bromide (mixture with sodium amide) (10 g, 24 mmol) was stirred at room temperature for 12 hours then refluxed for 4 hours. The reaction mixture was evaporated to dryness, and the crude product purified by column chromatography on silica gel using a gradient of dichloromethane:methyl alcohol (1:0 to 9:1) as eluant to give of 3-benzyloxy-2-methyl-1,3-dihydro-furo[4,5-c]pyridin-1-ol (98) (1.2 g, 20% yield).

$^1$H-NMR (CDCl$_3$): δ 8.21 (s, 1H), 7.42-7.36 (m, 5H), 6.88 (dd, 1H), 6.02 (dd, 1H), 5.73 (dd, 1H), 4.79 (s, 2H), 4.69 (s, 2H), 2.46 (s, 3H).

Example 91

Synthesis of 4-Ethyl-5-hydroxymethyl-2-methyl-pyridin-3-ol (99)

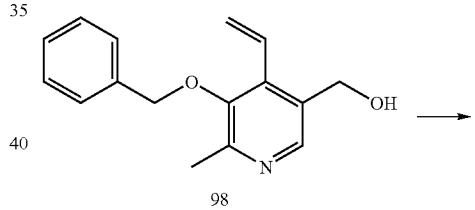

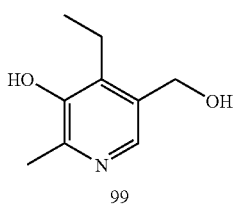

The hydrogenation of 3-benzyloxy-2-methyl-1,3-dihydro-furo[4,5-c]pyridin-1-ol (98)(1.2 g, 4.6 mmol) to 4-ethyl-5-hydroxymethyl-2-methyl-pyridin-3-ol (99) (780 mg, 96% yield) was carried out as described in Example 32.

$^1$H-NMR (CD$_3$OD): δ 7.99 (s, 1H), 4.70 (s, 2H), 2.82 (q, 3H), 2.53 (s, 3H), 1.93 (t, 3H)

Example 92

Synthesis of 3-(3-Amino-benzyloxy)-4-ethyl-2-methyl-pyridin-5-yl]-methanol (100)

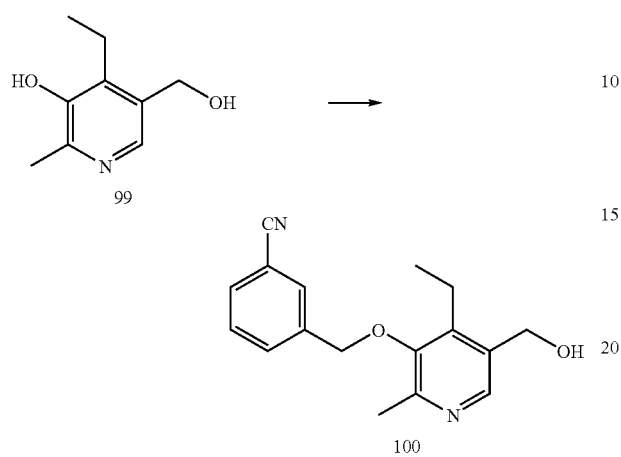

The coupling of 4-ethyl-5-hydroxymethyl-2-methyl-pyridin-3-ol (99) (0.9 g, 5.38 mmol) and α-bromo-m-tolunitrile (1.4 g, 7.14 mmol), as described in Example 3, gave [3-(3-amino-benzyloxy)-4-ethyl-2-methyl-pyridin-5-yl]-methanol (100) (1.08 g, 72% yield).

$^1$H-NMR (CDCl$_3$): δ 8.03 (s, 1H), 7.60 (s, 1H), 7.53-7.45 (m, 2H), 7.35 (t, 1H), 5.11 (s, 2H), 4.51 (s, 2H), 2.53 (q, 2H), 2.29 (s, 3H), 1.00 (t, 3H).

Example 93

Synthesis of 3-(3-Cyano-benzyloxy)-4-ethyl-2-methyl-pyridine-5-carbaldehyde (101)

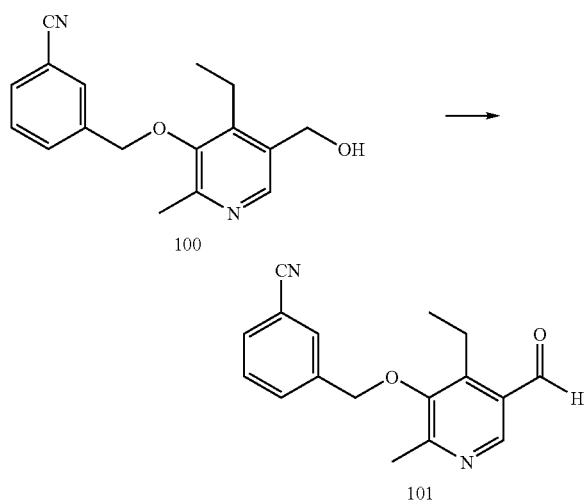

The oxidation of [3-(3-amino-benzyloxy)-4-ethyl-2-methyl-pyridin-5-yl]-methanol (100) (700 mg, 2.5 mmol) to 3-(3-cyano-benzyloxy)-4-ethyl-2-methyl-pyridine-5-carbaldehyde (101) (700 mg, quantitative) was carried out as described in Example 13.

$^1$H-NMR (CDCl$_3$): δ 10.17 (s, 1H) 8.64 (s, 1H), 7.77 (s, 1H), 7.66 (dd, 2H), 7.53 (t, 1H), 4.89 (s, 2H), 3.04 (q, 2H), 2.58 (s, 3H), 2.18 (t, 3H).

Example 94

Synthesis of 3-{5-[(4-Cyano-phenylamino)-methyl]-4-ethyl-2-methyl-pyridin-3-yloxymethyl}-benzonitrile (102)

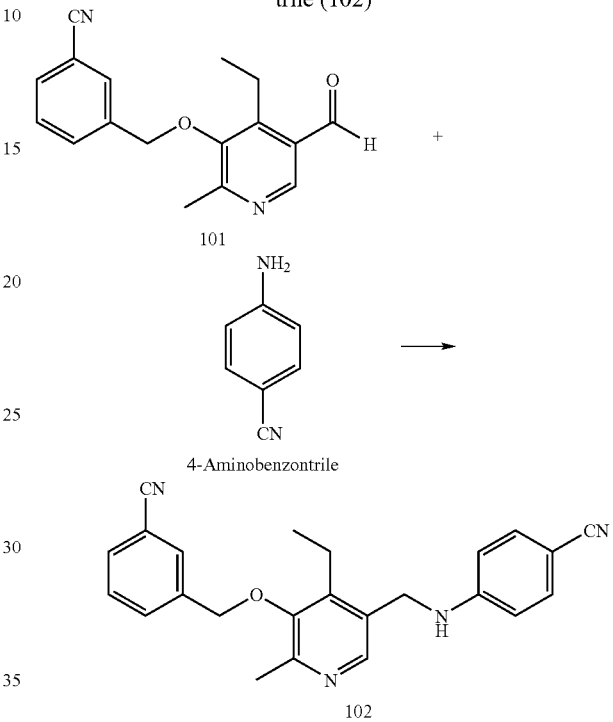

The reductive amination of 3-(3-cyano-benzyloxy)-4-ethyl-2-methyl-pyridine-5-carbaldehyde (101) (700 mg, 2.50 mmol) and 4-aminobenzonitrile (2.0 g, 16.9 mmol), as described in Example 21, gave 3-{5-[(4-cyano-phenylamino)-methyl]-4-ethyl-2-methyl-pyridin-3-yloxymethyl}-benzonitrile (102) (500 mg, 52% yield).

$^1$H-NMR (CDCl$_3$): δ 8.20 (s, 1H), 7.75 (s, 1H), 7.69 (d, 1H), 7.64-7.61 (m, 1H), 7.53 (t, 1H), 7.37 (dd, 1H), 6.61 (d, 2H), 6.26 (s, 2H), 4.88 (s, 2H), 4.32 (d, 2H), 2.69 (q, 2H), 2.48 (s, 3H), 1.89 (t, 3H).

Example 95

Synthesis of 3-{5-[(4-Amidino-phenylamino)-methyl]-4-ethyl-2-methyl-pyridin-3-yloxymethyl}-benzamidine (103)

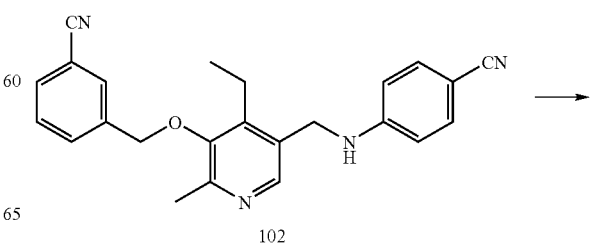

-continued

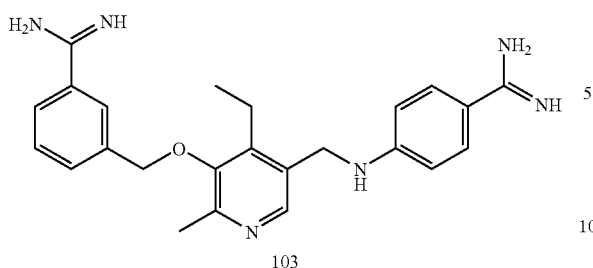

103

The conversion of bis-nitrile (102) to bis-amidine (103) was carried out as described in Example 2.

$^1$H-NMR (CD$_3$OD): δ 8.10 (s, 1H), 7.84-7.42 (m, 3H), 7.62 (t, 1H), 7.55 (d, 2H), 7.71 (d, 2H), 4.99 (s, 2H), 4.42 (s, 2H), 2.72 (t, 2H), 2.142 (s, 3H), 1.09 (t, 3H).

Example 96

Synthesis of (4-Cyano-phenyl)-(2,2,8-trimethyl-4H-[1,3]dioxino[4,5-c]pyridin-5-ylmethyl)-carbamic acid tert-butyl ester (104)

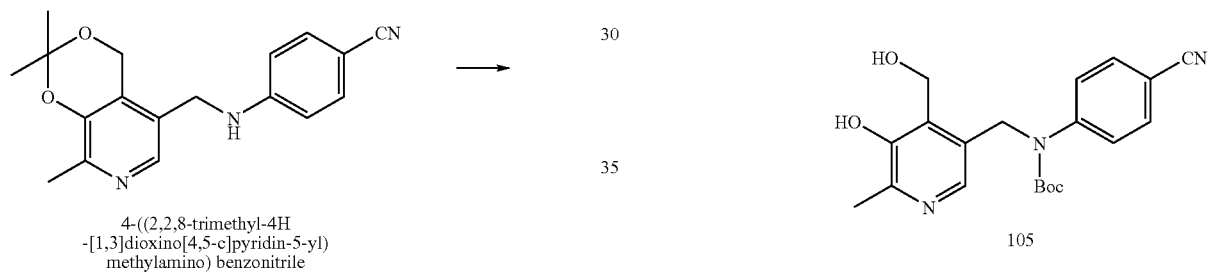

4-((2,2,8-trimethyl-4H-[1,3]dioxino[4,5-c]pyridin-5-yl)methylamino) benzonitrile

104

A solution mixture 4-((2,2,8-trimethyl-4H-[1,3]dioxino[4,5-c]pyridin-5-yl)methylamino) benzonitrile* (44.4 g, 0.143 mol), Boc anhydride (63.5 g, 0.29 mol) and DMAP (1.77 g, 0.14 mol) in dichloromethane was stirred at 47° C. overnight. The reaction mixture was evaporated to dryness, and diethyl ether (350 mL) was added to induce precipitation. The product was collected by filtration, washed with water and then with diethyl ether and dried under vacuum to give (4-cyanophenyl)-(2,2,8-trimethyl-4H-[1,3]dioxino[4,5-c]pyridin-5-ylmethyl)-carbamic acid tert-butyl ester (104) (52.4 g, 89% yield) as a light yellow solid.

$^1$H-NMR (CDCl$_3$): δ 7.78 (s, 1H), 7.56 (d, 2H), 7.25 (d, 2H), 4.75 (s, 2H), 4.74 (s, 2H), 2.36 (s, 3H), 1.51 (s, 6H), 1.44 (s, 9H).

MS m/s (ES$^+$): 410 (M+H$^+$).

Zhang et. al., *Bioorganic &Medicinal Chemistry Letters*. 2004, 14, 4747.

Example 97

Synthesis of (4-Cyano-phenyl)-(5-hydroxy-4-hydroxymethyl-6-methyl-pyridin-3-ylmethyl)-carbamic acid tert-butyl ester (105)

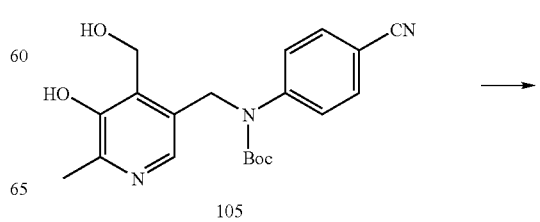

104

105

The hydrolysis of (4-cyano-phenyl)-(2,2,8-trimethyl-4H-[1,3]dioxino[4,5-c]pyridin-5-ylmethyl)-carbamic acid tert-butyl ester (104) (5.43 g, 13.0 mmol), as described in Example 10, gave (4-cyano-phenyl)-(5-hydroxy-4-hydroxymethyl-6-methyl-pyridin-3-ylmethyl)-carbamic acid tert-butyl ester (105) (3.7 g, 75% yield) as a colorless solid.

$^1$H-NMR (CDCl$_3$): δ 7.77 (d, 2H), 7.75 (s, 1H), 7.49 (d, 2H), 5.06 (s, 2H), 4.71 (s, 2H), 2.42 (s, 3H), 1.39 (s, 9H).

Example 98

Synthesis of [5-(3-Cyano-benzyloxy)-4-hydroxymethyl-6-methyl-pyridin-3-ylmethyl]-(4-cyano-phenyl)-carbamic acid tert-butyl ester (106)

105

-continued

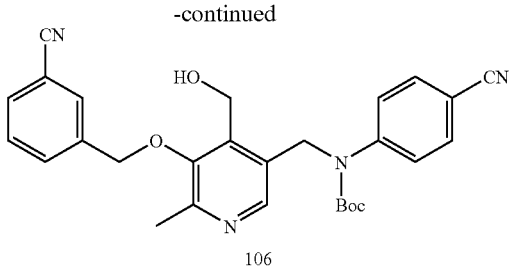
106

The coupling of (4-cyano-phenyl)-(5-hydroxy-4-hydroxymethyl-6-methyl-pyridin-3-ylmethyl)-carbamic acid tert-butyl ester (105) (8.7 g, 19.9 mmol) and α-bromo-m-tolunitrile (5.6 g, 28 mmol), as described in Example 1, gave [5-(3-cyano-benzyloxy)-4-hydroxymethyl-6-methyl-pyridin-3-ylmethyl]-(4-cyano-phenyl)-carbamic acid tert-butyl ester (106) (11.8 g, 68% yield).

$^1$H-NMR (CDCl$_3$): δ 7.91 (s, 1H), 7.80 (1H), 7.72 (d, 1H), 7.66 (d, 1H), 7.62 (d, 2H), 7.53 (dd, 1H), 7.29 (d, 2H), 5.01 (s, 2H), 5.00 (s, 2H), 4.76 (d, 2H), 3.49 (d, 1H), 2.49 (s, 3H), 1.39 (s, 9H).

MS m/s (ES$^+$): 485 (M+H$^+$).

Example 99

Synthesis of [5-(3-Cyano-benzyloxy)-4-fluoromethyl-6-methyl-pyridin-3-ylmethyl]-(4-cyano-phenyl)-carbamic acid tert-butyl ester (107)

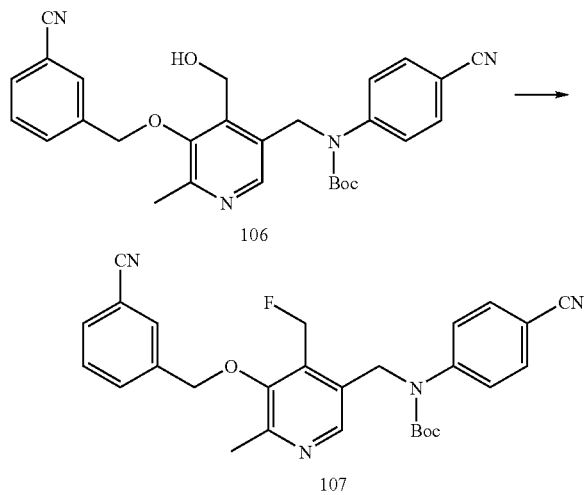

To a solution of [5-(3-cyano-benzyloxy)-4-hydroxymethyl-6-methyl-pyridin-3-ylmethyl]-(4-cyano-phenyl)-carbamic acid tert-butyl ester (106) (51.1 g, 0.10 mol) in dry dichloromethane (700 mL) was slowly added bis(2-methoxyethyl)aminosulfur trifluoride (39.7 g, 0.18 mol) at 0° C. under nitrogen atmosphere. The reaction was slowly warmed to room temperature and stirred for 2 hours. The reaction mixture was then poured into a cold solution of saturated aqueous sodium bicarbonate, and the crude product extracted with dichloromethane, dried over anhydrous magnesium sulfate. Evaporation of the solvent gave a crude residue, which was purified by column chromatography on silica gel using a gradient mixture of dichloromethane:acetone (1:0 to 18:1) as an eluant to give [5-(3-cyano-benzyloxy)-4-fluoromethyl-6-methyl-pyridin-3-ylmethyl]-(4-cyano-phenyl)-carbamic acid tert-butyl ester (107) (41.3 g, 80% yield) as a colorless solid.

$^1$H-NMR (CDCl$_3$): δ 8.16 (s, 1H), 7.77 (s, 1H), 7.72-7.63 (m, 2H), 7.58 (d, 2H), 7.54 (dd, 1H), 7.30 (d, 2H), 5.49 (d, 2H), 5.04 (s, 2H), 4.91 (s, 2H), 2.53 (s, 3H), 1.43 (s, 3H).

$^{19}$F-NMR (CDCl$_3$): δ-210.87 (t, 1F).

Example 100

Synthesis of 4-{[4-Fluoromethyl-5-(3-amidine-benzyloxy)-6-methyl-pyridin-3-ylmethyl]-amino}-benzamidine (108)

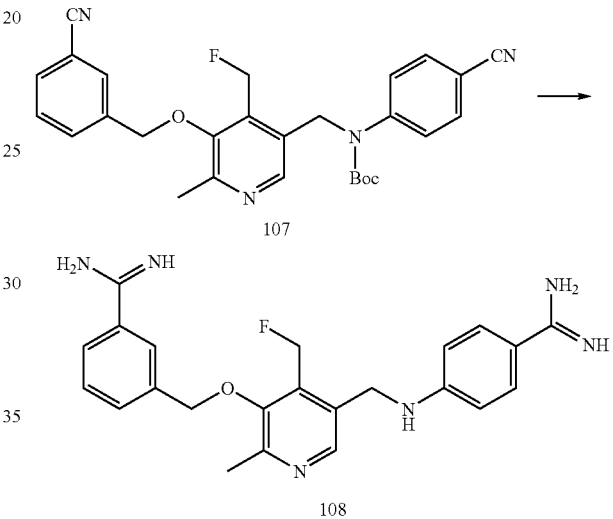

The conversion of bis-nitrile (107) to bis-amidine (108) was carried out as described in Example 2.

$^1$H-NMR (CD$_3$OD): δ 8.32 (s, 1H), 8.02 (s, 1H), 7.92 (d, 1H), 7.87 (d, 1H), 7.73 (dd, 1H), 7.68 (d, 2H), 6.81 (d, 2H), 5.71 (d, 2H), 5.10 (s, 2H), 4.64 (s, 2H), 2.58 (s, 3H).

MS m/s (ES$^+$): 421 (M+H$^+$).

Example 101

Synthesis of [5-(3-Cyano-benzyloxy)-4-formyl-6-methyl-pyridin-3-ylmethyl]-(4-cyano-phenyl)-carbamic acid tert-butyl ester (109)

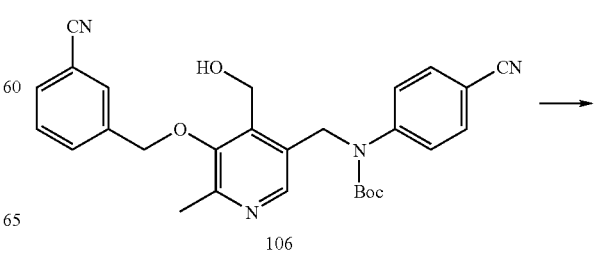
106

-continued

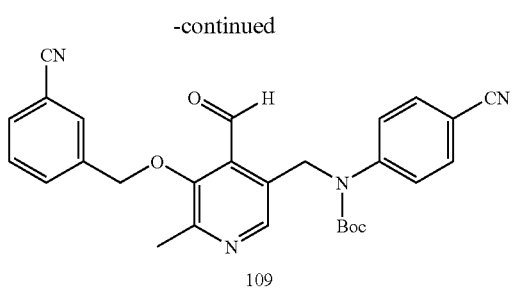
109

A mixture of Dess-Martin periodinone (5.0 g, 11.8 mmol) and [5-(3-cyano-benzyloxy)-4-hydroxymethyl-6-methyl-pyridin-3-ylmethyl]-(4-cyano-phenyl)-carbamic acid tert-butyl ester (106) (5.26 g, 10.8 mmol) in dichloromethane (200 mL) was stirred at room temperature for 30 minutes. The reaction mixture was then poured into a solution of saturated aqueous sodium bicarbonate, and the crude product extracted with dichloromethane, dried over anhydrous magnesium sulfate. Evaporation of the solvent gave a crude residue, which was purified by column chromatography on silica gel using a gradient mixture of ethyl acetate:hexane (0:1 to 2:3) as an eluant to give [5-(3-cyano-benzyloxy)-4-formyl-6-methyl-pyridin-3-ylmethyl]-(4-cyano-phenyl)-carbamic acid tert-butyl ester (109) (4.6 g, 88% yield) as a colorless solid.

$^1$H-NMR (CDCl$_3$): δ 10.42 (s, 1H), 8.42 (s, 1H), 7.73 (s, 1H), 7.69 (d, 1H), 7.64 (d, 1H), 7.57 (d, 2H), 7.54 (dd, 1H), 7.34 (d, 2H), 5.20 (s, 2H), 4.99 (s, 2H), 2.59 (s, 3H), 1.43 (s, 9H).

Example 102

[5-(3-Cyano-benzyloxy)-4-difluoromethyl-6-methyl-pyridin-3-ylmethyl]-(4cyano-phenyl)-carbamic acid tert-butyl ester (110)

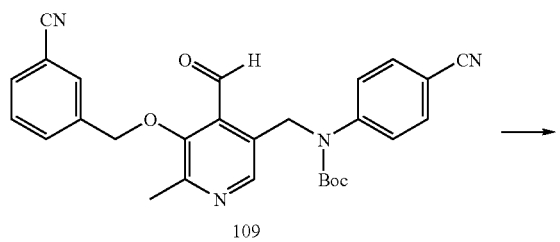
109

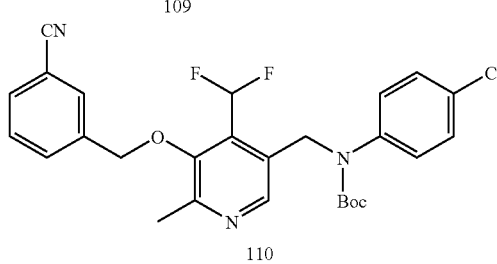
110

To a solution of 5-(3-cyano-benzyloxy)-4-formyl-6-methyl-pyridin-3-ylmethyl]-(4-cyano-phenyl)-carbamic acid tert-butyl ester (109) (126 mg, 0.261 mmol) in dry dichloromethane (10 mL) was slowly added bis(2-methoxyethyl)aminosulfur trifluoride (222 mg, 1.0 mmol) at 0° C. under nitrogen atmosphere. The reaction was slowly warmed to room temperature and stirred for 2 hours. The reaction mixture was then poured into a cold solution of saturated aqueous sodium bicarbonate, and the crude product extracted with dichloromethane, dried over anhydrous magnesium sulfate. Evaporation of the solvent gave a crude residue, which was purified by column chromatography on silica gel using a gradient mixture of ethyl acetate:hexane (0:1 to 1:1) as an eluant to give [5-(3-cyano-benzyloxy)-4-difluoromethyl-6-methyl-pyridin-3-ylmethyl]-(4cyano-phenyl)-carbamic acid tert-butyl ester (110) (114.5 mg, 88% yield) as a colorless foam.

$^1$H-NMR (CDCl$_3$): δ 8.33 (s, 1H), 7.74 (s, 1H), 7.69 (d, 1H), 7.64 (d, 1H), 7.58 (d, 2H), 7.55 (dd, 1H), 7.36 (d, 2H), 6.97 (t, 1H), 5.17 (s, 2H), 4.91 (s, 2H), 2.57 (s, 3H), 1.44 (s, 9H).

$^{19}$F-NMR (CDCl$_3$): δ-113.62 (d, 2F).

Example 103

4-{[4-Difluoromethyl-5-(3-amidine-benzyloxy)-6-methyl-pyridin-3-ylmethyl]-amino}-benzamidine (111)

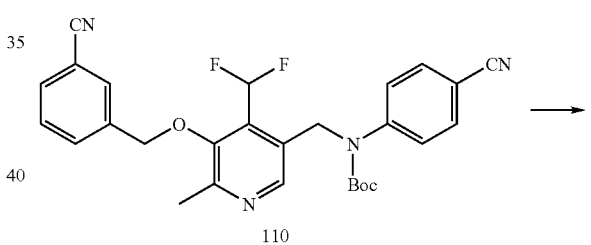
110

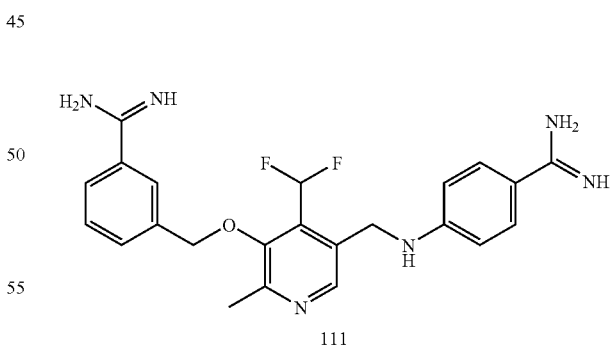
111

The conversion of bis-nitrile (110) to bis-amidine (111) was carried out as described in Example 2.

$^1$H-NMR (CD$_3$OD): δ 8.39 (s, 1H), 8.01 (s, 1H), 7.94-7.84 (m, 2H), 7.73 (dd, 1H), 7.66 (d, 2H), 7.26 (t, 1H), 6.77 (d, 2H), 5.14 (s, 2H), 4.72 (s, 2H), 2.61 (s, 2H).

$^{19}$F-NMR (CD$_3$OD): δ-115.14 (d, 2F).

MS m/s (ES$^+$): 439 (M+H$^+$).

Example 104

[5-(3-Cyano-benzyloxy)-4-(1-hydroxy-ethyl)-6-methyl-pyridin-3-ylmethyl]-(4-cyano-phenyl)-carbamic acid tert-butyl ester (112)

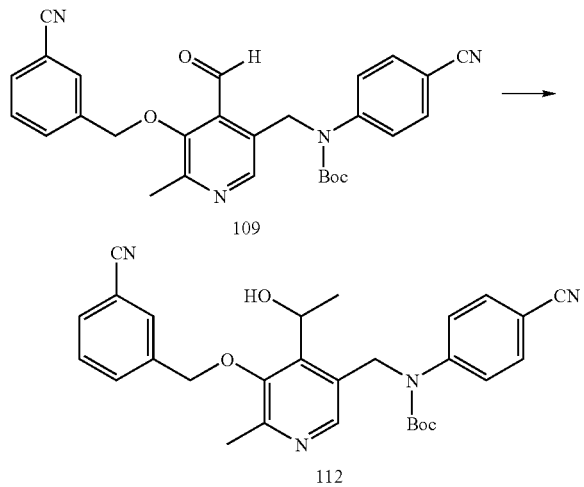

To a solution of 5-(3-cyano-benzyloxy)-4-formyl-6-methyl-pyridin-3-ylmethyl]-(4-cyano-phenyl)-carbamic acid tert-butyl ester (109) (1.4 g, 2.9 mmol) in anhydrous tetrahydrofuran (50 mL) was slowly added methyl magnesium bromide (4 mL, 1.0 M, 4.0 mmol) at −78° C. under nitrogen atmosphere and stirred for 30 minutes. The reaction mixture was quenched with a solution of saturated aqueous sodium bicarbonate, and the crude product extracted with ethyl acetate and dried over anhydrous magnesium sulfate. Evaporation of the solvent gave a crude residue, which was purified by column chromatography on silica gel using a gradient mixture of ethyl acetate:hexane (0:1 to 3:2) as an eluant to give [5-(3-cyano-benzyloxy)-4-(1-hydroxy-ethyl)-6-methyl-pyridin-3-ylmethyl]-(4-cyano-phenyl)-carbamic acid tert-butyl ester (112) (1.04 g, 72% yield).

$^1$H-NMR (CDCl$_3$): δ 8.08 (s, 1H), 7.78 (s, 1H), 7.72-7.64 (m, 2H), 7.59 (d, 2H), 7.54 (dd, 1H), 7.32 (d, 2H), 5.36 (dq, 1H), 5.20 (d, 1H), 5.12 (d, 1H), 4.98 (d, 1H), 4.89 (d, 1H), 2.98 (d, 1H), 2.51 (s, 3H), 1.52 (d, 3H), 1.44 (s, 9H).

Example 105

[5-(3-Cyano-benzyloxy)-4-(1-fluoro-ethyl)-6-methyl-pyridin-3-ylmethyl]-(4-cyano-phenyl)-carbamic acid tert-butyl ester (113) and 4-[3,5-Dimethyl-4-(3-cyano-benzyloxy)-7-oxo-5,9-dihydro-6-oxa-2,8-diaza-benzocyclohepten-8-yl]-benzonitrile (114)

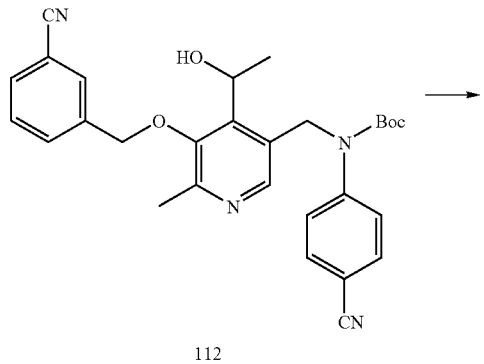

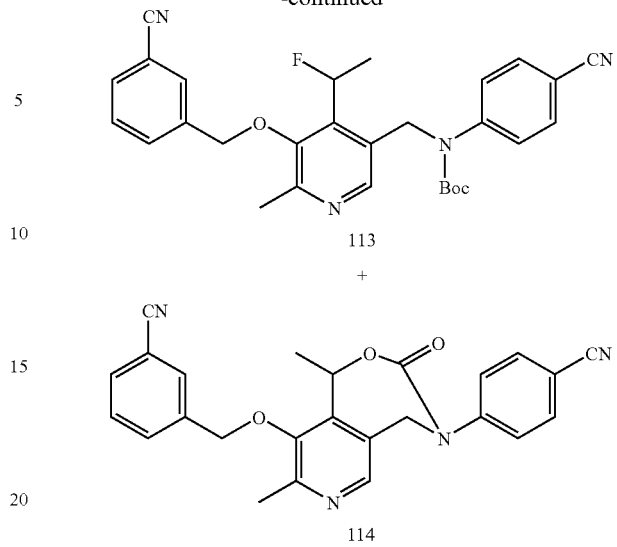

To a solution of [5-(3-cyano-benzyloxy)-4-(1-hydroxy-ethyl)-6-methyl-pyridin-3-ylmethyl]-(4-cyano-phenyl)-carbamic acid tert-butyl ester (112) (245 mg, 0.10 mol) in dry dichloromethane (7 mL) was slowly added bis(2-methoxyethyl)aminosulfur trifluoride (350 mg, 1.6 mol) at 0° C. under nitrogen atmosphere. The reaction was slowly warmed to room temperature and stirred for 30 minutes. The reaction mixture was then poured into a cold solution of saturated aqueous sodium bicarbonate, and the crude product extracted with dichloromethane, dried over anhydrous magnesium sulfate. Evaporation of the solvent gave a crude residue, which was purified by column chromatography on silica gel using a gradient mixture of ethyl acetate:hexane (0:1 to 1:1) as an eluant to give [5-(3-cyano-benzyloxy)-4-(1-fluoro-ethyl)-6-methyl-pyridin-3-ylmethyl]-(4-cyano-phenyl)-carbamic acid tert-butyl ester (113) (54 mg, 22% yield) and 4-[3,5-dimethyl-4-(3-cyano-benzyloxy)-7-oxo-5,9-dihydro-6-oxa-2,8-diaza-benzocyclohepten-8-yl]-benzonitrile (114) (90 mg, 43% yield).

[5-(3-Cyano-benzyloxy)-4-(1-fluoro-ethyl)-6-methyl-pyridin-3-ylmethyl]-(4-cyano-phenyl)-carbamic acid tert-butyl ester (113)

$^1$H-NMR (CDCl$_3$): δ 8.20 (s, 1H), 7.76 (s, 1H), 7.71-7.62 (m, 2H), 7.58 (d, 2H), 7.54 (dd, 1H), 7.33 (d, 2H), 6.01 (dq, 1H), 5.12 (d, 1H), 5.04 (d, 1H), 4.94 (d, 1H), 4.71 (d, 1H), 2.55 (s, 3H), 1.64 (dd, 1H), 1.43 (s, 9H).

$^{19}$F-NMR (CDCl$_3$): δ-176.91 (dq, 1F).

MS m/s (ES$^+$): 501 (M+H$^+$).

4-[3,5-Dimethyl-4-(3-cyano-benzyloxy)-7-oxo-5,9-dihydro-6-oxa-2,8-diaza-benzocyclohepten-8-yl]-benzonitrile (114)

$^1$H-NMR (CDCl$_3$): δ 8.25 (s, 1H), 7.71 (s, 1H), 7.70-7.60 (m, 2H), 7.66 (d, 2H), 7.54 (dd, 1H), 7.44 (d, 2H), 5.53 (q, 1H), 5.33 (d, 1H), 4.99 (d, 1H), 4.84 (d, 1H), 4.55 (d, 1H), 2.58 (s, 3H), 1.75 (d, 1H).

MS m/s (ES$^+$): 425 (M+H$^+$).

Example 106

4-{[4-(1-Fluoro-ethyl)-5-(3-amidine-benzyloxy)-6-methyl-pyridin-3-ylmethyl]-amino}-benzamidine (115)

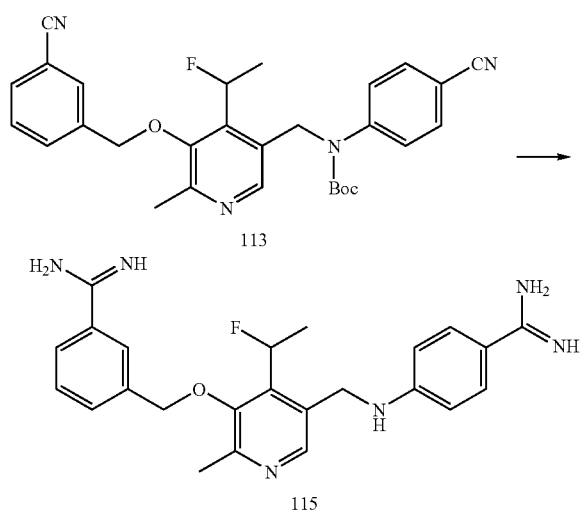

The conversion of bis-nitrile (113) to bis-amidine (115) was carried out as described in Example 2.

$^1$H-NMR (CD$_3$OD): δ 8.38 (s, 1H), 7.99 (s, 1H), 7.95 (d, 1H), 7.86 (d, 1H), 7.73 (dd, 1H), 7.67 (d, 2H), 6.80 (d, 2H), 6.21 (dq, 1H), 5.12 (s, 2H), 4.66 (s, 2H), 2.61 (s, 3H), 1.77 (dd, 3H).
$^{19}$F-NMR (CD$_3$OD): δ-178.43 (dq, 1F).
MS m/s (ES$^+$): 435.14 (M+H$^+$).

Example 107

4-{[4-(1-Hydroxy-ethyl)-5-(3-amidine-benzyloxy)-6-methyl-pyridin-3-ylmethyl]-amino}-benzamidine (116)

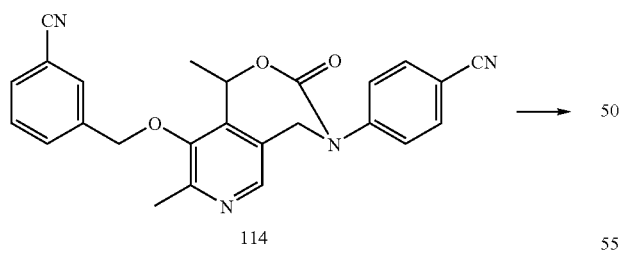

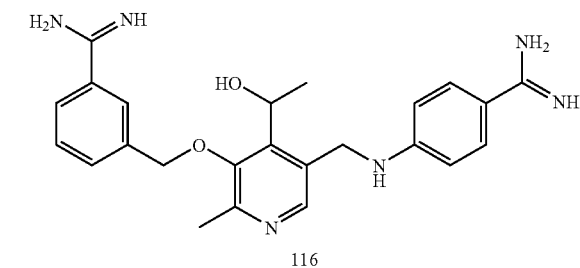

The conversion of bis-nitrile (114) to bis-amidine (116) was carried out as described in Example 2.

$^1$H-NMR (CD$_3$OD): δ 8.38 (s, 1H), 8.03 (s, 1H), 7.97 (d, 1H), 7.88 (d, 1H), 7.75 (dd, 1H), 7.68 (d, 2H), 6.82 (d, 2H), 5.61 (q, 1H), 5.28 (d, 1H), 5.19 (d, 1H), 5.10 (d, 1H), 4.80 (d, 1H), 2.74 (s, 3H), 1.63 (d, 3H).
MS m/s (ES$^+$): 433.12 (M+H$^+$).

Example 108

[5-(3-Cyano-benzyloxy)-4-(cyclopropyl-hydroxy-methyl)-6-methyl-pyridin-3-ylmethyl]-(4-cyano-phenyl)-carbamic acid tert-butyl ester (117)

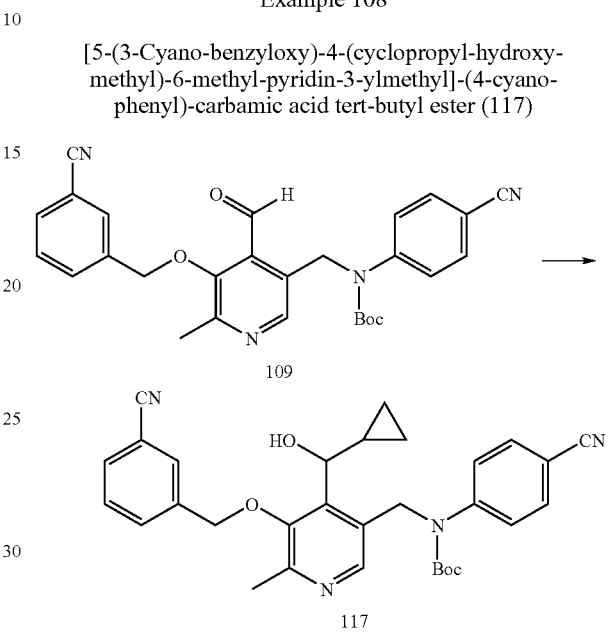

The addition of cyclopropyl magnesium bromide (2.8 mL, 0.5 M, 1.4 mmol) to 5-(3-cyano-benzyloxy)-4-formyl-6-methyl-pyridin-3-ylmethyl]-(4-cyano-phenyl)-carbamic acid tert-butyl ester (109) (474 mg, 0.9 mmol), was carried out as described in Example 104, gave [5-(3-cyano-benzyloxy)-4-(cyclopropyl-hydroxy-methyl)-6-methyl-pyridin-3-ylmethyl]-(4-cyano-phenyl)-carbamic acid tert-butyl ester (117) (293 mg, 57% yield).

$^1$H-NMR (CDCl$_3$): δ 8.01 (s, 1H), 7.76 (s, 1H), 7.70-7.63 (m, 2H), 7.59 (d, 2H), 7.53 (dd, 1H), 7.34 (d, 2H), 5.22 (d, 1H), 5.15 (d, 1H), 5.03 (d, 1H), 4.87 (d, 1H), 4.39 (dd, 1H), 2.73 (d, 1H), 2.55 (s, 3H), 1.50-1.32 (m, 1H), 1.42 (s, 9H), 0.72-0.60 (m, 1H), 0.56-0.40 (m, 2H), 0.40-0.28 (m, 1H).
MS m/s (ES$^+$): 525 (M+H$^+$).

Example 109

4-{[5-(3-Amidine-benzyloxy)-4-(cyclopropyl-hydroxy-methyl)-6-methyl-pyridin-3-ylmethyl]-amino}-benzamidine (118)

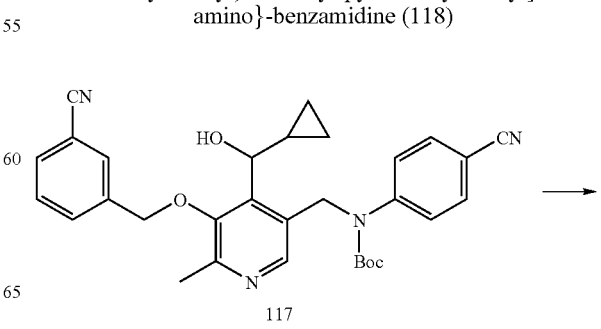

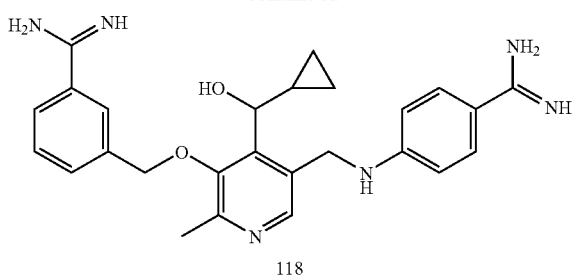

118

The conversion of bis-nitrile (117) to bis-amidine (118) was carried out as described in Example 2.

$^1$H-NMR (CD$_3$OD): δ 8.39 (s, 1H), 8.01 (s, 1H), 7.95 (d, 1H), 7.88 (d, 1H), 7.74 (dd, 1H), 7.68 (d, 2H), 6.83 (d, 2H), 5.28 (d, 1H), 5.13 (d, 1H), 5.08 (d, 1H), 4.80 (d, 1H), 4.65 (d, 1H), 2.72 (s, 3H), 1.59-1.41 (m, 1H), 0.81-0.63 (m, 1H), 0.63-0.45 (m, 1H), 0.45-0.32 (m, 1H).

MS m/s (ES$^+$): 459.18 (M+H$^+$).

Example 110

[5-(3-Cyano-benzyloxy)-4-(cyclopropyl-fluoro-methyl)-6-methyl-pyridin-3-ylmethyl]-(4-cyano-phenyl)-carbamic acid tert-butyl ester (119)

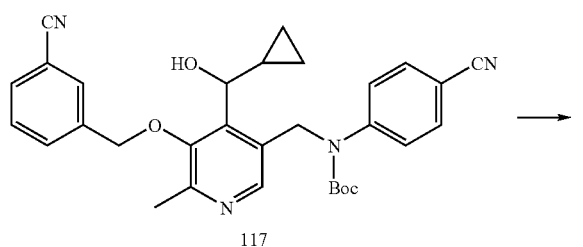

117

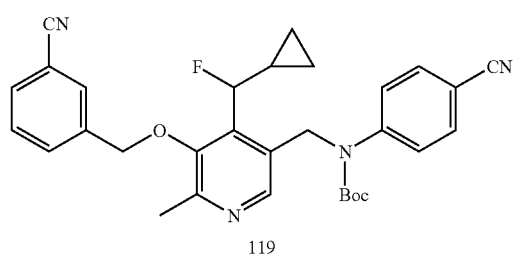

119

The fluorination of [5-(3-cyano-benzyloxy)-4-(cyclopropyl-hydroxy-methyl)-6-methyl-pyridin-3-ylmethyl]-(4-cyano-phenyl)-carbamic acid tert-butyl ester (117) (201.9 mg, 0.4 mmol), as described in Example 99, gave [5-(3-cyano-benzyloxy)-4-(cyclopropyl-fluoro-methyl)-6-methyl-pyridin-3-ylmethyl]-(4-cyano-phenyl)-carbamic acid tert-butyl ester (119) (117 mg, 57% yield).

$^1$H-NMR (CDCl$_3$): δ 8.17 (s, 1H), 7.75 (s, 1H), 7.68-7.60 (m, 2H), 7.56 (d, 2H), 7.51 (dd, 1H), 7.32 (d, 2H), 5.19 (dd, 1H), 5.01 (dd, 1H), 4.99 (d, 1H), 4.95 (d, 1H), 4.81 (d, 1H), 2.52 (s, 3H), 1.63-1.46 (m, 1H), 1.41 (s, 9H), 0.82-0.68 (m, 1H), 0.65-0.48 (m, 2H), 0.45-0.32 (m, 1H).

$^{19}$F-NMR (CDCl$_3$): δ-170.43 (d, 1F).

MS m/s (ES$^+$): 527.26 (M+H$^+$).

Example 111

(E)-3-[5-{[tert-Butoxycarbonyl-(4-cyano-phenyl)-amino]-methyl}-3-(3-cyano-benzyloxy)-2-methyl-pyridin-4-yl]-acrylic acid methyl ester (120)

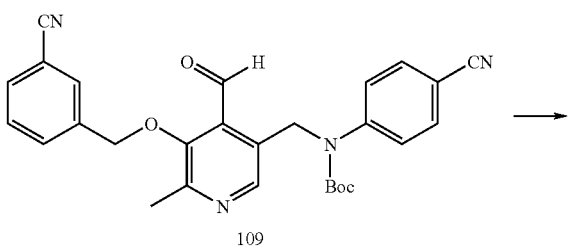

109

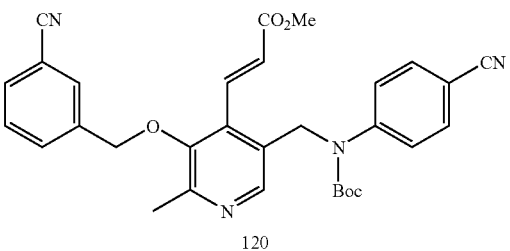

120

To a solution of sodium hydride (124 mg, 60% in oil, 3.1 mmol) in anhydrous tetrahydrofuran (10 mL) was added methyl diethyl phosphonoacetate (661 mg, 3.1 mmol) at −78° C. under nitrogen atmosphere and stirred for 15 minutes. To the reaction mixture was added 5-(3-cyano-benzyloxy)-4-formyl-6-methyl-pyridin-3-ylmethyl]-(4-cyano-phenyl)-carbamic acid tert-butyl ester (109) (523 mg, 1.1 mmol) and stirred for 15 minutes. The reaction mixture was then poured into a cold solution of saturated aqueous sodium bicarbonate, and the crude product extracted with dichloromethane, dried over anhydrous magnesium sulfate. Evaporation of the solvent gave a crude residue, which was purified by column chromatography on silica gel using a gradient mixture of ethyl acetate:hexane (0:1 to 1:1) as an eluant to give (E)-3-[5-{[tert-butoxycarbonyl-(4-cyano-phenyl)-amino]-methyl}-3-(3-cyano-benzyloxy)-2-methyl-pyridin-4-yl]-acrylic acid methyl ester (120) (428 mg, 738% yield) as a colorless oil.

$^1$H-NMR (CDCl$_3$): δ 8.25 (s, 1H), 7.72-7.63 (m, 2H), 7.61-7.52 (m, 1H), 7.57 (d, 1H), 7.55 (d, 2H), 7.50 (dd, 1H), 7.23 (d, 2H), 6.42 (d, 1H), 4.97 (s, 2H), 4.74 (s, 2H), 3.81 (s, 3H), 2.51 (s, 3H), 1.43 (s, 9H).

Example 112

3-(5-{[tert-Butoxycarbonyl-(4-cyano-phenyl)-amino]-methyl}-3-hydroxy-2-methyl-pyridin-4-yl)-propionic acid methyl ester (121)

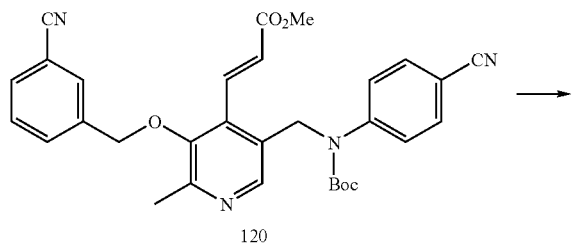

120

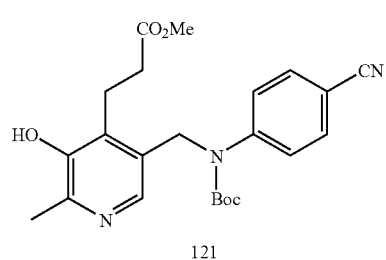

121

The hydrogenation of (E)-3-[5-{[tert-butoxycarbonyl-(4-cyano-phenyl)-amino]-methyl}-3-(3-cyano-benzyloxy)-2-methyl-pyridin-4-yl]-acrylic acid methyl ester (120) (226 mg, 0.4 mmol) to 3-(5-{[tert-butoxycarbonyl-(4-cyano-phenyl)-amino]-methyl}-3-hydroxy-2-methyl-pyridin-4-yl)-propionic acid methyl ester (121) was carried out as described in Example 32.

$^1$H-NMR (CDCl$_3$): δ 7.77 (s, 1H), 7.56 (d, 2H), 7.27 (d, 2H), 3.70 (s, 3H), 2.94 (t, 1H), 2.67 (t, 1H), 2.43 (s, 3H), 1.42 (s, 9H).

Example 113

3-[5-{[tert-Butoxycarbonyl-(4-cyano-phenyl)-amino]-methyl}-3-(3-cyano-benzyloxy)-2-methyl-pyridin-4-yl]-propionic acid methyl ester (122)

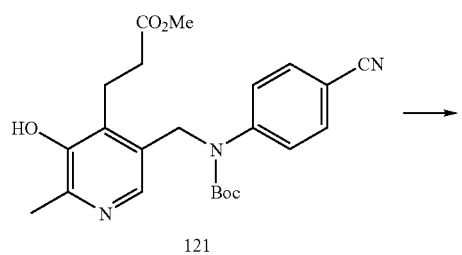

121

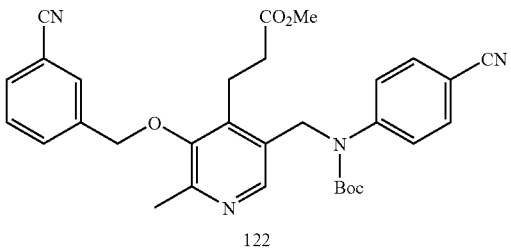

122

The coupling of 3-(5-{[tert-butoxycarbonyl-(4-cyano-phenyl)-amino]-methyl}-3-hydroxy-2-methyl-pyridin-4-yl)-propionic acid methyl ester (121) and α-bromo-m-tolunitrile (102 mg, 0.5 mmol), as described in Example 1, gave 3-[5-{[tert-butoxycarbonyl-(4-cyano-phenyl)-amino]-methyl}-3-(3-cyano-benzyloxy)-2-methyl-pyridin-4-yl]-propionic acid methyl ester (122) (162 mg, 68% yield for 2 steps).

$^1$H-NMR (CDCl$_3$): δ 8.10 (s, 1H), 7.78 (m, 1H), 7.70-7.63 (m, 2H), 7.58 (d, 2H), 7.54 (dd, 1H), 7.29 (d, 2H), 4.98 (s, 2H), 4.86 (s, 2H), 3.66 (s, 3H), 2.06 (t, 1H), 2.51 (s, 3H), 2.49 (t, 1H, t, J=7.5 Hz), 1.44 (s, 9H).

MS m/s (ES$^+$): 541 (M+H$^+$).

Example 114

3-[5-[(4-Carbamimidoyl-phenylamino)-methyl]-2-methyl-3-(3-amidine-benzyloxy)-pyridin-4-yl]-propionamide (123)

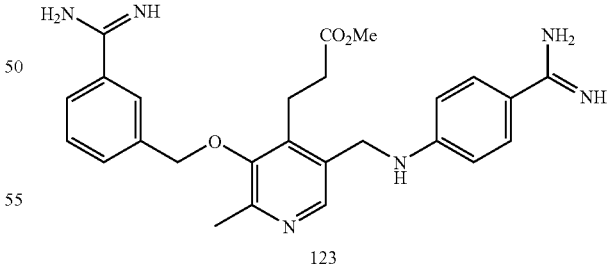

The conversion of bis-nitrile (122) to bis-amidine (123) was carried out as described in Example 2.

$^1$H-NMR (CD$_3$OD): δ 8.34 (s, 1H), 8.11 (s, 1H), 7.96 (d, 1H), 7.89 (d, 1H), 7.74 (dd, 1H), 7.70 (d, 2H), 6.85 (d, 2H), 5.25 (s, 2H), 4.74 (s, 2H), 3.26 (t, 2H), 2.79 (s, 3H, s), 2.66 (t, 2H).

MS m/s (ES$^+$): 460.16 (M+H$^+$).

Example 115

[5-(4-Cyano-benzyloxy)-4-hydroxymethyl-6-methyl-pyridin-3-ylmethyl]-(4-cyano-phenyl)-carbamic acid tert-butyl ester (124)

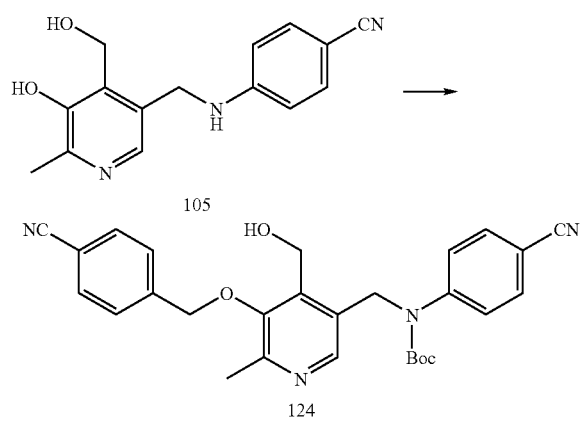

The coupling of (4-cyano-phenyl)-(5-hydroxy-4-hydroxymethyl-6-methyl-pyridin-3-ylmethyl)-carbamic acid tert-butyl ester (105) (137.0 g, 0.37 mole) and α-bromo-p-tolunitrile (72.7 g, 370 mmol), as described in Example 1, gave [5-(4-cyano-benzyloxy)-4-hydroxymethyl-6-methyl-pyridin-3-ylmethyl]-(4-cyano-phenyl)-carbamic acid tert-butyl ester (124) (126.0 g, 70% yield) as a colorless solid.

$^1$H-NMR (CDCl$_3$): δ 7.97 (s, 1H), 7.72-7.69 (m, 2H), 7.63-7.59 (m, 4H), 7.31-7.28 (m, 2H), 5.02 (s, 4H), 4.75 (m, 2H), 2.49 (s, 3H), 1.40 (s, 9H).

Example 116

[5-(4-Cyano-benzyloxy)-4-formyl-6-methyl-pyridin-3-ylmethyl]-(4-cyano-phenyl)-carbamic acid tert-butyl ester (125)

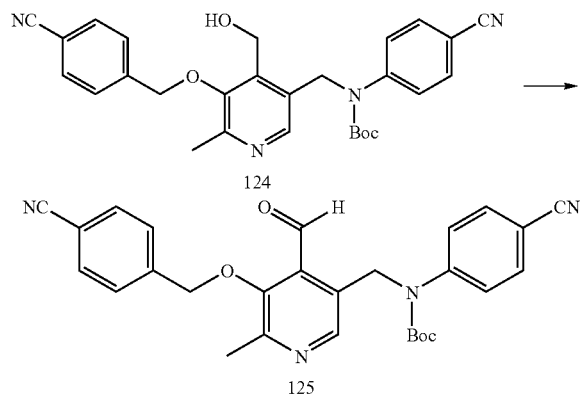

The oxidation of [5-(4-cyano-benzyloxy)-4-hydroxymethyl-6-methyl-pyridin-3-ylmethyl]-(4-cyano-phenyl)-carbamic acid tert-butyl ester (124) (5.8 g, 11.9 mmol) to give [5-(4-cyano-benzyloxy)-4-formyl-6-methyl-pyridin-3-ylmethyl]-(4-cyano-phenyl)-carbamic acid tert-butyl ester (125) (3.58 g, 62% yield) was carried out as described in Example 101.

$^1$H-NMR (CD$_3$OD): δ 10.42 (s, 1H), 8.40 (s, 1H), 7.70 (d, 2H), 7.56-7.51 (m, 4H), 7.33 (d, 2H), 5.19 (s, 2H), 5.02 (s, 2H), 2.57 (s, 2H), 1.42 (s, 9H).

Example 117

[5-(4-Cyano-benzyloxy)-4-difluoromethyl-6-methyl-pyridin-3-ylmethyl]-(4-cyano-phenyl)-carbamic acid tert-butyl ester (126)

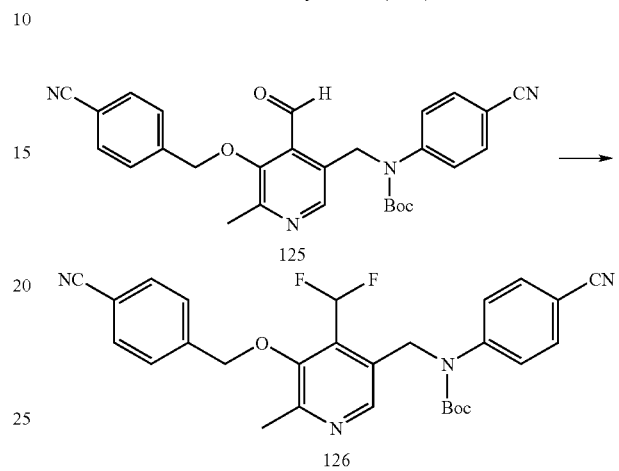

The fluorination of [5-(4-cyano-benzyloxy)-4-formyl-6-methyl-pyridin-3-ylmethyl]-(4-cyano-phenyl)-carbamic acid tert-butyl ester (125) (390 mg, 0.8 mmol), was carried out as described in Example 102, gave [5-(4-cyano-benzyloxy)-4-difluoromethyl-6-methyl-pyridin-3-ylmethyl]-(4-cyano-phenyl)-carbamic acid tert-butyl ester (126) (343 mg, 84% yield).

$^1$H-NMR (CDCl$_3$): δ 8.35 (s, 1H), 7.74 (d, 2H), 7.61-7.54 (m, 4H), 7.37 (d, 2H), 6.98 (t, 1H), 5.18 (s, 2H), 4.95 (s, 2H), 2.58 (s, 3H), 1.46 (s, 9H).

$^{19}$F-NMR (CDCl$_3$): δ-113.67 (d, 2F).

Example 118

4-{5-[(4-Carbamimidoyl-phenylamino)-methyl]-4-fluoromethyl-2-methyl-pyridin-3-yloxymethyl}-benzamidine (127)

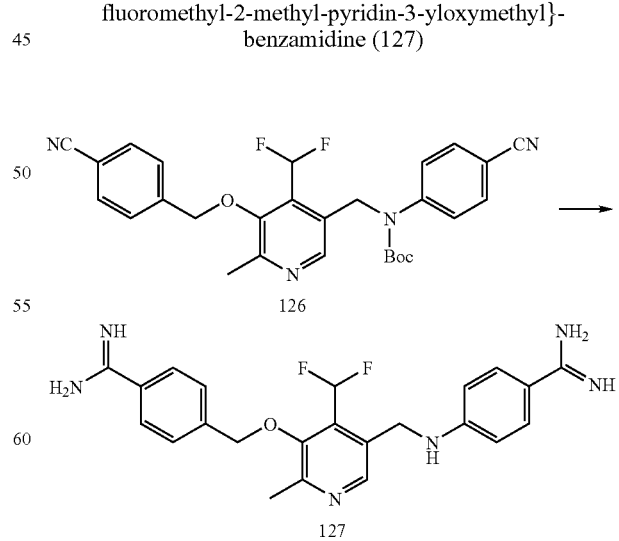

The conversion of bis-nitrile (126) to bis-amidine (127) was carried out as described in Example 2.

¹H-NMR (CD₃OD): δ 8.38 (s, 1H), 7.91 (d, 2H), 7.77 (d, 2H), 7.64 (d, 2H), 7.23 (t, 1H), 5.15 (s, 2H), 4.71 (s, 2H), 2.58 (s, 3H).
¹⁹F-NMR (CD₃OD): δ-115.36 (d, 2F).
MS m/s (ES⁺): 439.08 (M+H⁺).

Example 119

Synthesis of 4-((5-(3-cyanobenzyloxy)-4,6-dimethylpyridin-3-yl)methylamino-2,5-difluorobenzonitrile (128)

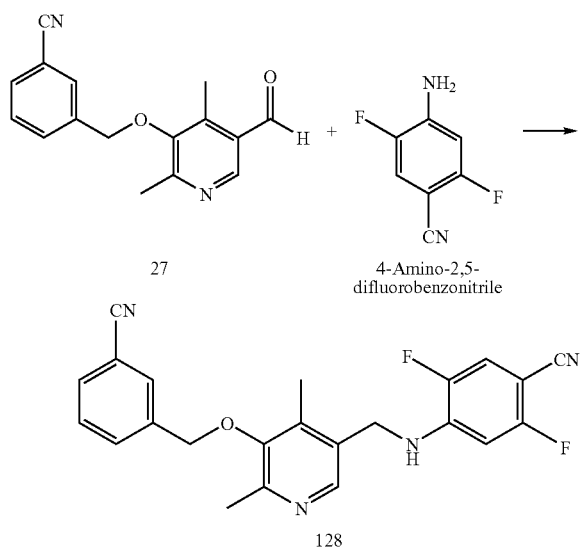

The reductive amination of 3-((5-formyl-2,4-dimethylpyridin-3-yloxy)methylbenzonitrile (27) (190 mg, 0.7 mmol) and 4-amino-2,5-difluorobenzonitrile (330 mg, 2.1 mmol), was carried out as described in Example 21, gave 4-((5-(3-cyanobenzyloxy)-4,6-dimethylpyridin-3-yl)methylamino-2, 5-difluorobenzonitrile a colorless solid (128) (97 mg, 34% yield).

¹H-NMR (DMSO-d6): δ 8.08 (s, 1H), 7.97 (s, 1H), 7.86 (d, 2H), 7.67-7.60 (m, 2H), 6.74 (q, 1H), 4.90 (s, 2H), 4.41 (d, 2H), 2.41 (s, 3H), 2.23 (s, 3H).
¹⁹F-NMR (DMSO-d6): δ-111.71 (d, 1F), -137.04 (d, 1F).

Example 120

Synthesis of 4-((5-(3-amidinebenzyloxy)-4,6-dimethylpyridin-3-yl)methylamino)-2,5-difluorobenzamidine (129)

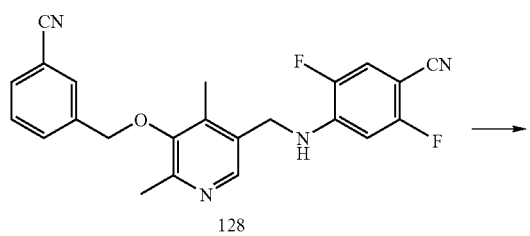

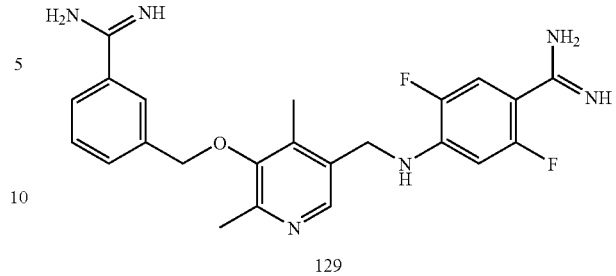

The conversion of bis-nitrile (128) to bis-amidine (129) was carried out as described in Example 2.
¹H-NMR (DMSO-d6): δ 8.08 (s, 1H), 7.99 (s, 1H), 7.89-7.85 (m, 4H), 6.71 (q, 1H), 4.91 (s, 2H), 4.44 (d, 2H), 2.43 (s, 3H), 2.32 (s, 3H).
¹⁹F-NMR (DMSO-d6): δ-114.03 (d, 1F), -138.38 (d, 1H).

Example 121

Synthesis of tert-butyl (5-(3-cyanobenzyloxy)-4,6-dimethylpyridin-3-yl)methyl-4-cyanophenylcarbamate (130)

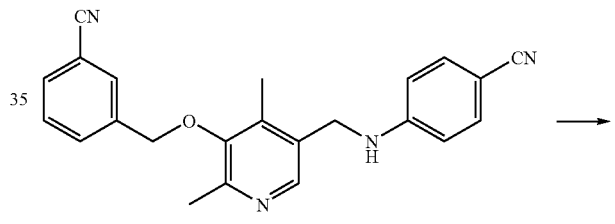

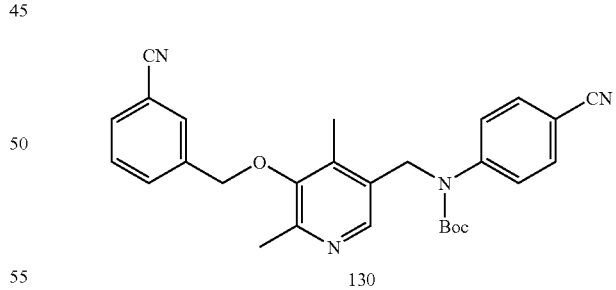

The amine 4-{[5-(3-cyano-benzyloxy)-4,6-dimethyl-pyridin-3-ylmethyl]-amino}-benzonitrile (32) (40.5 g, 109.93 mmol) on treatment with di-t-butyldicarbonate (47.9 g, 220 mmole), gave tert-butyl (5-(3-cyanobenzyloxy)-4,6-dimethylpyridin-3-yl)methyl-4-cyanophenylcarbamate (130) (49.7 g, 97% yield) as carried out in Example 96.

¹H-NMR (CDCl₃): δ 8.05 (s, 1H), 7.79 (s, 1H), 7.68 (d, 2H), 7.59-7.54 (m, 3H), 7.29 (d, 2H), 4.86 (d, 4H), 2.50 (s, 3H), 2.20 (s, 3H), 1.45 (s, 9H).

Example 122

Synthesis of [5-(3-cyano-benzyloxy)-4,6-dimethyl-1-oxy-pyridin-3-ylmethyl]-4(4-cyano-phenyl)-carbamic acid tert-butyl ester (131)

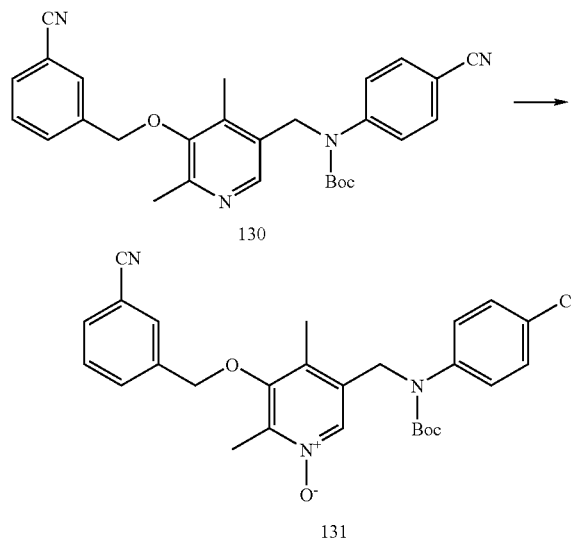

A solution of tert-butyl (5-(3-cyanobenzyloxy)-4,6-dimethylpyridin-3-yl)methyl-4-cyanophenycarbamate (130) (48.0 g, 102.44 mmol) and 3-chloroperoxybenzoic acid (22.8 g, 132 mmol) in anhydrous dichloromethane (500 mL) was stirred at room temperature overnight. The reaction mixture was poured into a solution of saturated aqueous sodium carbonate, and the crude product extracted with dichloromethane, and then dried over anhydrous magnesium sulfate. The solvent was evaporated to dryness, and diethyl ether was added to induce precipitation. The product was collected by filtration, washed with diethyl ether and dried under vacuum to give [5-(3-cyano-benzyloxy)-4,6-dimethyl-1-oxy-pyridin-3-ylmethyl]-4(4-cyano-phenyl)-carbamic acid tert-butyl ester (131) (44.6 g, 90% yield) as a colorless solid.

$^1$H-NMR (CDCl$_3$): δ 8.05 (s, 1H), 7.77 (s, 1H), 7.71-7.55 (m, 5H), 7.33 (d, 2H), 4.84 (d, 4H), 2.48 (s, 3H), 2.17 (s, 3H), 1.46 (s, 9H).

Example 123

Synthesis of 4-{[5-(3-amidine-benzyloxy)-4,6-dimethyl-1-oxy-pyridin-3-ylmethyl]-amino}-benzamidine (132)

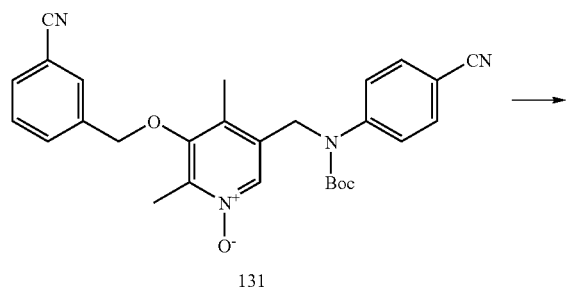

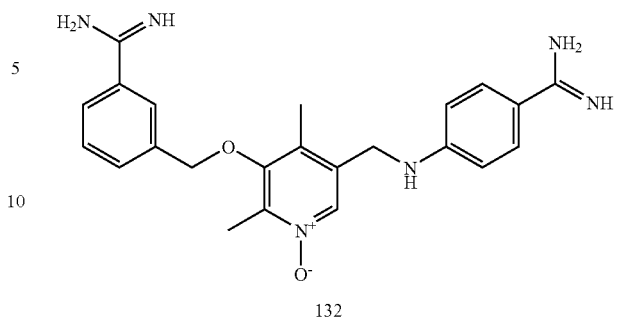

The conversion of bis-nitrile (131) to bis-amidine (132) was carried out as described in Example 2.

$^1$H-NMR (DMSO-d6): δ 8.07 (s, 1H), 8.00 (s, 1H), 7.92-7.84 (m, 2H), 7.74-7.65 (m, 3H) 6.78 (d, 2H), 5.07 (s, 2H), 4.51 (s, 2H), 2.47 (s, 3H), 2.42 (s, 3H).

Example 124

Synthesis of 3-((5-(hydroxymethyl)-2-methylpyridin-3-yloxy)benzonitrile (133)

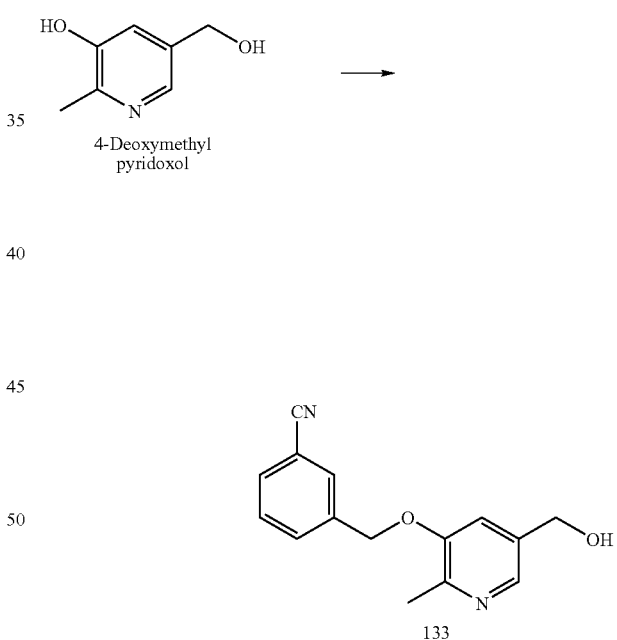

The coupling of 4-deoxymethylpyridoxol (600 mg, 4.3 mmol) and α-bromo-m-tolunitrile (2.5 g, 12.9 mmol), as described in Example 1, gave 3-((5-(hydroxymethyl)-2-methylpyridin-3-yloxy)benzonitrile (133) (489 mg, 44% yield) a light yellow solid.

$^1$H-NMR (CD$_3$OD): δ 8.00 (s, 1H), 7.87-7.81 (m, 2H), 7.73 (d, 1H), 7.61 (t, 1H), 7.45 (s, 1H), 5.24 (s, 2H), 4.63 (s, 2H), 2.49 (s, 3H).

Example 125

Synthesis of 3-((5-formyl-2-methylpyridin-3-yloxy)methyl)benzonitrile (134)

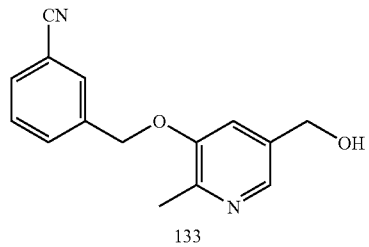
133

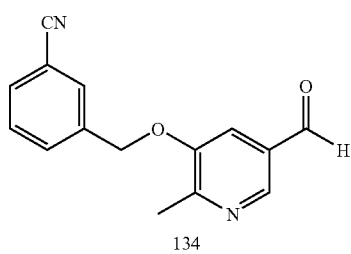
134

The oxidation of 3-((5-(hydroxymethyl)-2-methylpyridin-3-yloxy)benzonitrile (133) (490 mg, 1.9 mmol) to 3-((5-formyl-2-methylpyridin-3-yloxy)methyl)benzonitrile (134) (311 mg, 64% yield) as a light yellow solid was carried out as described in Example 13.

$^1$H-NMR (CD$_3$OD): δ 10.05 (s, 1H), 7.90-7.82 (m, 3H), 7.75-7.65 (m, 2H), 7.51 (s, 1H), 5.24 (s, 2H), 2.49 (s, 3H).

Example 126

Synthesis of 4-((5-(3-cyanobenzyloxy)-6-methylpyridin-3-yl)methylamino)benzonitrile (135)

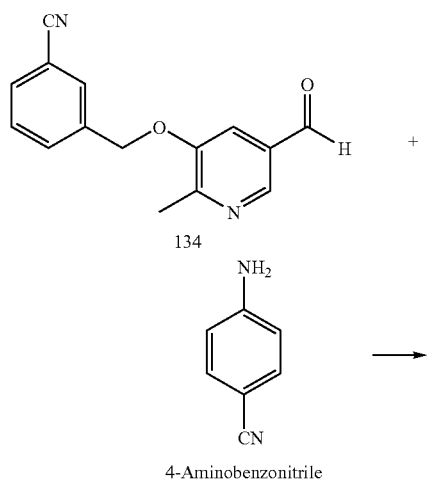

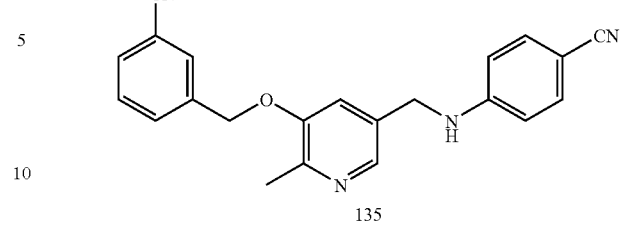
135

The reductive amination of 3-((5-formyl-2-methylpyridin-3-yloxy)methyl)benzonitrile (134) (300 mg, 1.2 mmol) and 4-aminobenzonitrile (422 mg, 3.6 mmol), as described in Example 21, gave 4-((5-(3-cyanobenzyloxy)-6-methylpyridin-3-yl)methylamino)benzonitrile (135) (95.24 mg, 22.58% yield).

$^1$H-NMR (CD$_3$OD): δ 8.00 (s, 1H), 7.74-7.64 (m, 3H), 7.55-7.50 (m, 1H), 7.36-7.33 (m, 3H), 6.61 (d, 2H), 5.18 (s, 2H), 4.38 (s, 2H), 2.46 (s, 3H).

Example 127

Synthesis of 4-((5-(3-amidinebenzyloxy)-6-methylpyridin-3-yl)methylamino)benzamidine

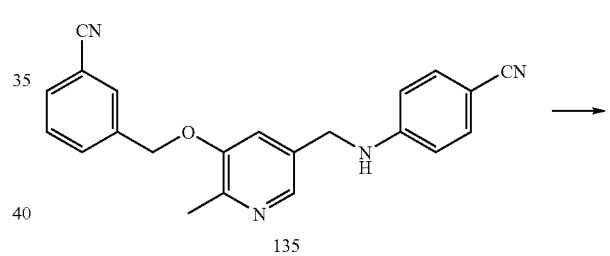
135

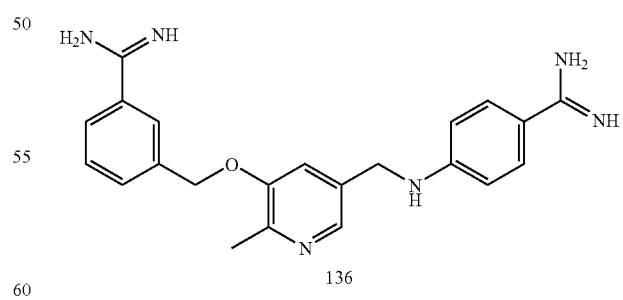
136

The conversion of bis-nitrile (135) to bis-amidine (136) was carried out as described in Example 2.

$^1$H-NMR (CD$_3$OD): δ 8.04 (s, 1H), 7.95 (s, 1H), 7.87 (d, 1H), 7.80 (d, 1H), 7.70-7.61 (m, 3H), 7.55 (s, 1H), 6.77 (d, 2H), 5.28 (s, 2H), 4.49 (s, 2H), 2.49 (s, 3H).

Example 128

Synthesis of [5-(3-cyano-benzyloxy)-6-hydroxymethyl-4-methyl-pyridin-3-ylmethyl]-(4-cyano-phenyl)-carbamic acid tert-butyl ester (137)

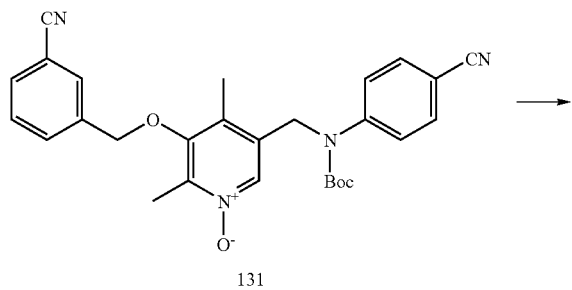
131

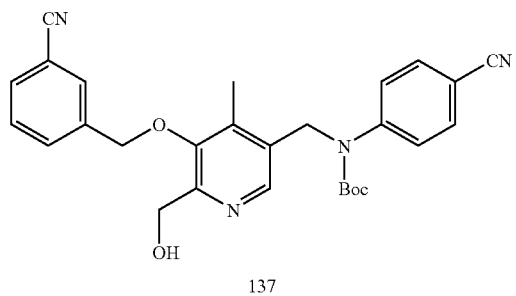
137

A mixture of [5-(3-cyano-benzyloxy)-4,6-dimethyl-1-oxy-pyridin-3-ylmethyl]-4(4-cyano-phenyl)-carbamic acid tert-butyl ester (131) (40.0 g, 82.5 mmol), trifluoroacetic anhydride (115 mL, 827 mmol) and anhydrous dichloromethane (1.0 L) was stirred at room temperature for 2 days. The reaction mixture was poured into a solution of aqueous sodium hydroxide (1 L, 1N), stirred for 15 minutes, and the crude product was extracted with dichloromethane, dried over anhydrous magnesium sulfate. The solvent was evaporated to dryness to give [5-(3-cyano-benzyloxy)-6-hydroxymethyl-4-methyl-pyridin-3-ylmethyl]-(4-cyano-phenyl)-carbamic acid tert-butyl ester (137) (23.9 g, 60% yield) as a colorless solid.

$^1$H-NMR (DMSO-d6): δ 8.01 (s, 1H), 7.96 (s, 1H), 7.87-7.82 (m, 2H), 7.76 (d, 2H), 7.65 (t, 1H), 7.49 (d, 2H), 5.0 (s, 2H), 4.93 (s, 2H), 4.50 (d, 2H), 2.19 (s, 3H), 1.40 (s, 9H).

Example 129

Synthesis of 4-{[5-(3-Amidine-benzyloxy)-6-hydroxymethyl-4-methyl-pyridin-3-ylmethyl]-amino}-benzamidine (138)

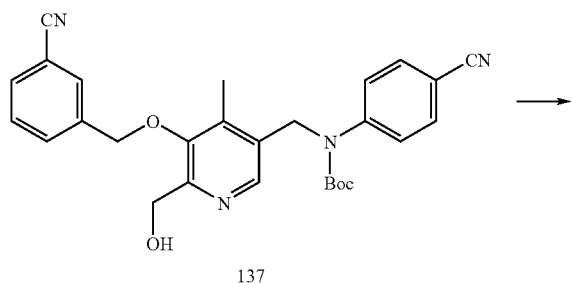
137

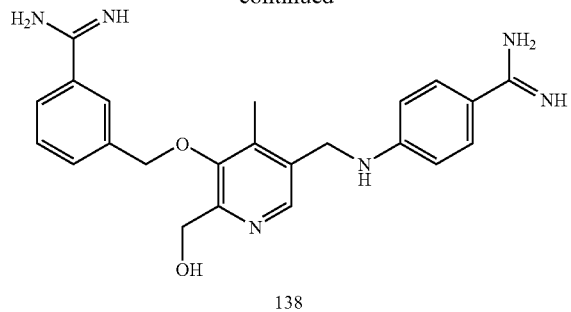
138

The conversion of bis-nitrile (137) to bis-amidine (138) was carried out as described in Example 2.

$^1$H-NMR (DMSO-d6): δ 9.40 and 9.25 (s, 3H), 8.82 and 8.59 (s, 3H), 8.24 (s, 1H), 7.97 (s, 1H), 7.92-7.80 (m, 2H), 7.71 (d, 1H), 7.66 (d, 2H), 6.77 (d, 2H), 5.03 (s, 2H), 4.71 (s, 2H), 4.48 (s, 2H), 2.40 (s, 3H).

Example 130

Synthesis of [5-(3-cyano-benzyloxy)-6-fluoromethyl-4-methyl-pyridin-3-ylmethyl]-(4-cyano-phenyl)-carbamic acid tert-butyl ester (139)

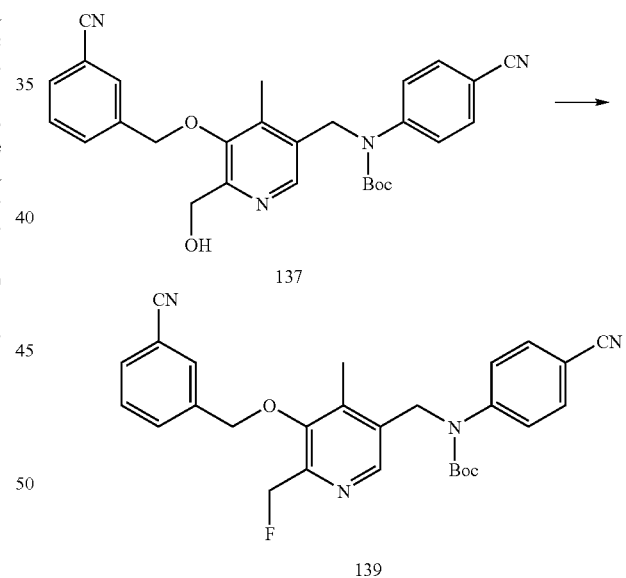

The fluorination of [5-(3-cyano-benzyloxy)-6-hydroxymethyl-4-methyl-pyridin-3-ylmethyl]-(4-cyano-phenyl)-carbamic acid tert-butyl ester (137) (17.0 g, 35.1 mmol), was carried out as described in Example 99, gave [5-(3-cyano-benzyloxy)-6-fluoromethyl-4-methyl-pyridin-3-ylmethyl]-(4-cyano-phenyl)-carbamic acid tert-butyl ester (139) (8.7 g, 51% yield).

$^1$H-NMR (DMSO-d6): δ 8.10 (s, 1H), 7.96 (s, 1H), 7.88-7.76 (m, 4H), 7.66 (t, 1H), 7.51 (d, 2H), 5.40 (d, 2H), 5.03 (s, 2H), 4.93 (s, 2H), 2.24 (s, 3H), 1.40 (s, 9H).

$^{19}$F-NMR (DMSO-d6): δ-209.97 (s, 1F).

Example 131

Synthesis of 4-{[5-(3-Amidine-benzyloxy)-6-fluoro-methyl-4-methyl-pyridin-3-ylmethyl]-amino}-benzamidine (140)

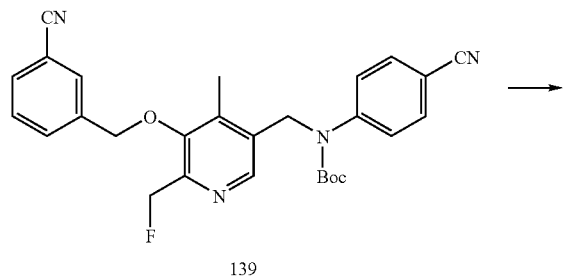

139

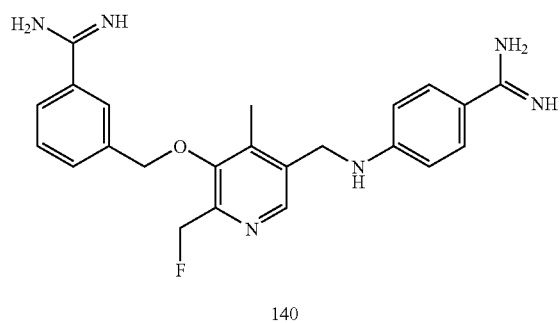

140

The conversion of bis-nitrile (139) to bis-amidine (140) was carried out as described in Example 2.

¹H-NMR (DMSO-d6): δ 9.50 and 9.28 (s, 4H), 8.89 and 8.65 (s, 4H), 8.30 (s, 1H), 8.00 (s, 1H), 7.90-7.82 (m, 2H), 7.71 (d, 1H), 7.69 (d, 2H), 7.43 (s, 2H), 7.36 (t, 1H), 7.27 (s, 2H), 7.10 (s, 2H), 6.77 (d, 2H), 5.48 (d, 2H), 4.99 (s, 2H), 4.45 (s, 2H), 2.37 (s, 3H).

¹⁹F-NMR (DMSO-d6): δ-208.89 (t, 1F).

Example 132

Synthesis of [5-(3-Cyano-benzyloxy)-6-formyl-4-methyl-pyridin-3-ylmethyl]-(4-cyano-phenyl)-carbamic acid tert-butyl ester (141)

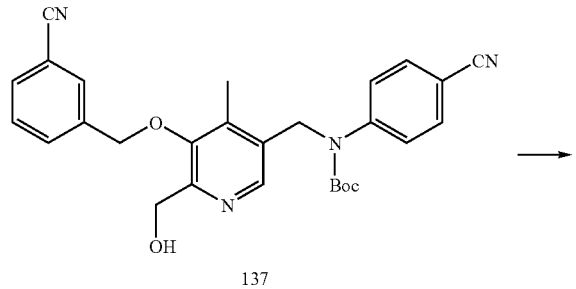

137

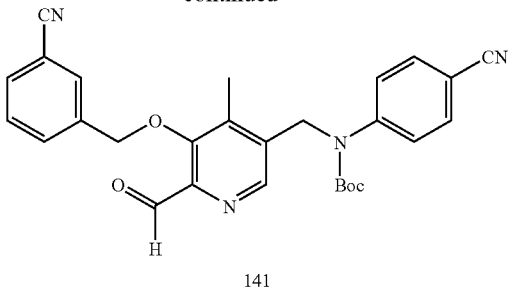

141

A solution of [5-(3-cyano-benzyloxy)-6-hydroxymethyl-4-methyl-pyridin-3-ylmethyl]-(4-cyano-phenyl)-carbamic acid tert-butyl ester (137) (235 mg, 0.484 mmol) and manganese (IV) dioxide (198 mg, 1.93 mmol) in methyl alcohol (5 mL) at room temperature for 2 hours. Excess manganese (IV) dioxide was filtered through a celite pad and washed with ethyl acetate. The filtrate was evaporated to give a crude residue, which was purified by column chromatography on silica gel using a gradient mixture of ethyl acetate:hexane (0:1 to 1:0) as eluant to give [5-(3-cyano-benzyloxy)-6-formyl-4-methyl-pyridin-3-ylmethyl]-(4-cyano-phenyl)-carbamic acid tert-butyl ester (141) (154 mg, 66% yield) as a colorless solid.

¹H-NMR (CDCl₃): δ 10.12 (s, 1H), 8.39 (s, 1H), 7.84 (s, 1H), 7.78 (d, 1H), 7.68 (d, 1H), 7.61 (d, 2H), 7.54 (dd, 1H), 7.32 (d, 2H), 4.99 (s, 2H), 4.96 (s, 2H), 2.24 (s, 3H), 1.44 (s, 9H).

Example 133

Synthesis of 4-{[5-(3-Amidine-benzyloxy)-6-formyl-4-methyl-pyridin-3-ylmethyl]-amino}-benzamidine (142)

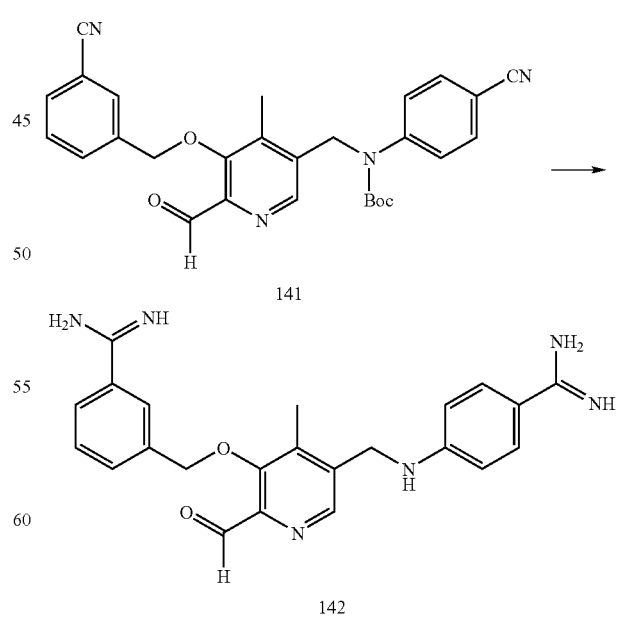

The conversion of bis-nitrile (141) to bis-amidine (142) was carried out as described in Example 2.

¹H-NMR (DMSO-d6): δ 10.1 (s, 1H), 9.39 and 9.21 (s, 4H), 8.82 and 8.56 (s, 4H), 8.45 (s, 1H), 7.98 (s, 1H), 7.93-7.88 (m, 1H), 7.86-7.80 (m, 1H), 7.71 (d, 1H), 7.65 (d, 2H), 6.76 (d, 2H), 5.07 (s, 2H), 4.52 (s, 2H), 2.35 (s, 3H).

Example 134

Synthesis of 5-{[tert-Butoxycarbonyl-(4-cyano-phenyl)-amino]-methyl}-3-(3-cyano-benzyloxy)-4-methyl-pyridine-2-carboxylic acid methyl ester (143)

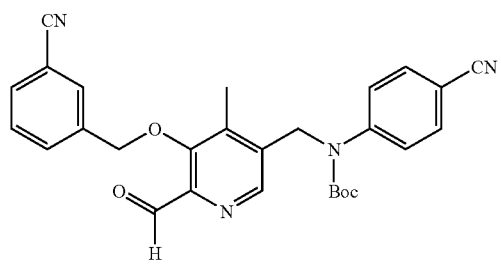

A mixture of [5-(3-cyano-benzyloxy)-6-formyl-4-methyl-pyridin-3-ylmethyl]-(4-cyano-phenyl)-carbamic acid tert-butyl ester (141) (140 mg, 0.3 mmol), sodium cyanide (272 mg, 5.5 mmol), manganese (IV) dioxide (422 mg, 85%, 0.29 mmol), acetic acid (256 mg, 4.2 mmol) in methyl alcohol (40 mL) was stirred at room temperature for 12 hours. The solid was filtered through a celite pad and washed several times with methanol. The filtrate was evaporated to give a crude residue, which was purified by column chromatography on silica gel using a gradient mixture of ethyl acetate:hexane (0:1 to 1:0) as eluant to give 5-{[tert-butoxycarbonyl-(4-cyano-phenyl)-amino]-methyl}-3-(3-cyano-benzyloxy)-4-methyl-pyridine-2-carboxylic acid methyl ester (143) (142 mg, 96% yield) as a light yellow oil.

¹H-NMR (CDCl₃): δ 8.28 (s, 1H), 7.83 (s, 1H), 7.74 (ddd, 1H), 7.67 (ddd, 1H), 7.59 (dd, 1H), 7.58 (dd, 1H), 7.53 (dd, 1H), 7.30 (dd, 1H), 7.29 (dd, 1H), 5.01 (s, 2H), 4.95 (s, 2H), 3.96 (s, 3H), 1.44 (s, 9H).

MS m/s (ES⁺): 513.1 (M+H⁺).

Example 135

Synthesis of 3-(3-Carbamimidoyl-benzyloxy)-5-[(4-carbamimidoyl-phenylamino)-methyl]-4-methyl-pyridine-2-carboxylic acid amide (144)

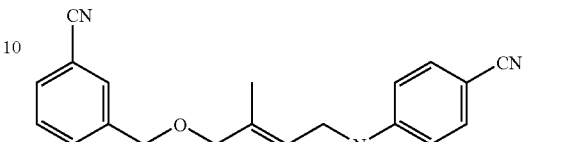

The conversion of bis-nitrile (143) to bis-amidine (144) was carried out as described in Example 2.

¹H-NMR (DMSO-d6): δ 9.37 (s, 2H), 9.22 (s, 2H), 8.81 (s, 2H), 8.58 (s, 2H), 8.23 (s, 1H), 7.98-7.86 (m, 2H), 7.79 (d, 1H), 7.67 (d, 1H), 7.49 (d, 2H), 6.76 (d, 2H), 5.08 (s, 2H), 4.46 (s, 2H), 2.33 (s, 3H).

MS m/s (ES⁺): 432 (M+H⁺).

Example 136

Synthesis of 5-(3-Cyano-benzyloxy)-4-hydroxymethyl-6-methyl-1-oxy-pyridin-3-ylmethyl]-(4-cyano-phenyl)-carbamic acid tert-butyl ester (145)

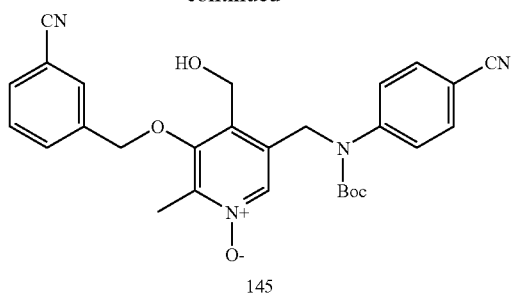

145

The oxidation of [5-(3-cyano-benzyloxy)-4-hydroxymethyl-6-methyl-pyridin-3-ylmethyl]-(4-cyano-phenyl)-carbamic acid tert-butyl ester (106) (2.0 g, 4.1 mmol), was carried out as described in Example 122, gave 5-(3-cyano-benzyloxy)-4-hydroxymethyl-6-methyl-1-oxy-pyridin-3-ylmethyl]-(4-cyano-phenyl)-carbamic acid tert-butyl ester (145) (1.7 g, 82% yield).

$^1$H-NMR (CDCl$_3$): δ 7.98 (s, 1H), 7.79 (s, 1H), 7.73-7.65 (m, 2H), 7.66 (d, 2H), 7.55 (dd, 1H), 7.35 (d, 2H), 5.03 (s, 2H), 4.98 (s, 2H), 4.72 (s, 2H), 2.47 (s, 3H), 1.41 (s, 9H).

Example 137

Synthesis of [5-(3-Cyano-benzyloxy)-4,6-bis-hydroxymethyl-pyridin-3-ylmethyl]-(4-cyano-phenyl)-carbamic acid tert-butyl ester (146)

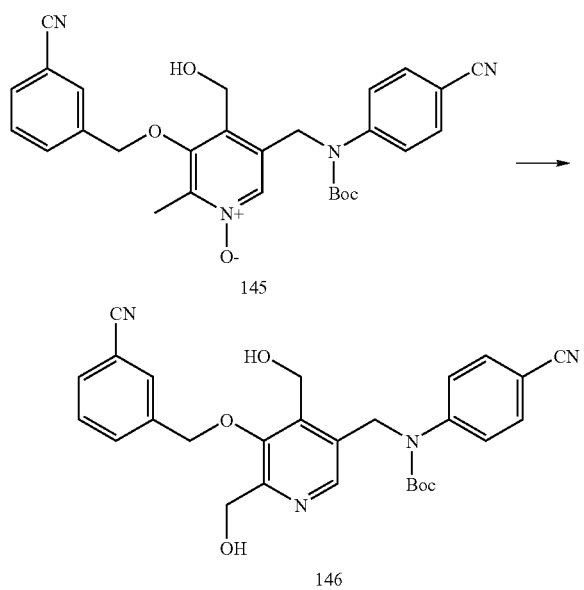

The conversion of 5-(3-cyano-benzyloxy)-4-hydroxymethyl-6-methyl-1-oxy-pyridin-3-ylmethyl]-(4-cyano-phenyl)-carbamic acid tert-butyl ester (145) (1.7 g, 3.4 mmol) to [5-(3-cyano-benzyloxy)-4,6-bis-hydroxymethyl-pyridin-3-ylmethyl]-(4-cyano-phenyl)-carbamic acid tert-butyl ester (146) (740 mg, 44% yield) as a light yellow solid was carried out as described in Example 128.

$^1$H-NMR (CDCl$_3$): δ 8.03 (s, 1H), 7.77 (s, 1H), 7.70 (d, 1H), 7.67 (d, 1H), 7.64 (d, 2H), 7.54 (dd, 1H), 7.31 (d, 2H), 5.05 (s, 2H), 5.04 (s, 2H), 4.79 (s, 2H), 4.72 (s, 2H), 1.40 (s, 9H).

MS m/s (ES$^+$): 501 (M+H$^+$).

Example 138

Synthesis of [5-(3-Cyano-benzyloxy)-4,6-bis-fluoromethyl-pyridin-3-ylmethyl]-(4-cyano-phenyl)-carbamic acid tert-butyl ester (147)

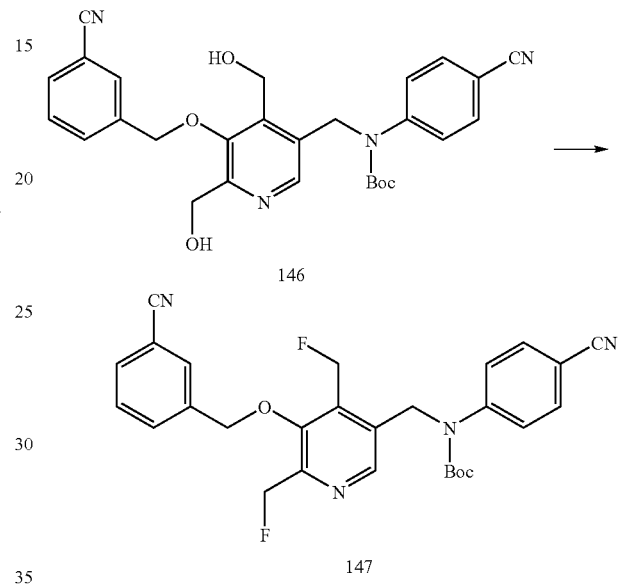

The fluorination of [5-(3-cyano-benzyloxy)-4,6-bis-hydroxymethyl-pyridin-3-ylmethyl]-(4-cyano-phenyl)-carbamic acid tert-butyl ester (146) (551 mg, 1.1 mmol), was carried out as described in Example 102, gave [5-(3-cyano-benzyloxy)-4,6-bis-fluoromethyl-pyridin-3-ylmethyl]-(4-cyano-phenyl)-carbamic acid tert-butyl ester (147) (320 mg, 57% yield) as a colorless foam.

$^1$H-NMR (CDCl$_3$): δ 8.35 (s, 1H), 7.79 (s, 1H), 7.73-7.64 (m, 2H), 7.60 (d, 2H), 7.55 (dd, 1H), 7.32 (d, 2H), 5.53 (d, 2H), 5.50 (d, 2H), 5.09 (s, 2H), 5.02 (s, 2H), 1.43 (s, 9H).

$^{19}$F-NMR (CDCl$_3$) δ-211.08 (t, 1F), -211.60 (t, 1F).

Example 139

Synthesis of 4-{[4,6-Bis-fluoromethyl-5-(3-amidine-benzyloxy)-pyridin-3-ylmethyl]-amino}-benzamidine (148)

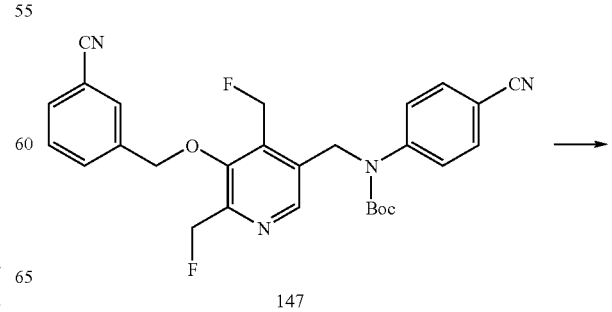

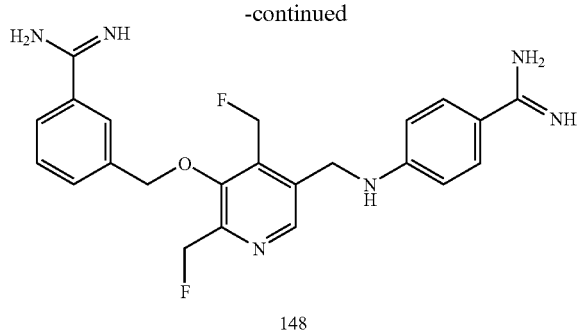

148

The conversion of bis-nitrile (147) to bis-amidine (148) was carried out as described in Example 2.

$^1$H-NMR (CD$_3$OD): δ 8.49 (s, 1H), 8.02 (s, 1H), 7.93 (d, 1H), 7.88 (d, 1H), 7.74 (dd, 1H), 7.68 (d, 2H), 6.82 (d, 2H), 5.85 (d, 2H), 5.57 (d, 2H), 5.18 (s, 2H), 4.72 (s, 2H).

$^{19}$F-NMR (CD$_3$OD): δ -213.65 (t, 1F), -215.03 (t, 1F).

MS m/s (ES$^+$): 439 (M+H$^+$).

Example 140

Synthesis of [5-(4-Cyano-benzyloxy)-1-hydroxy-4-hydroxymethyl-6-methyl-pyridin-3-ylmethyl]-(4-cyano-phenyl)-carbamic acid tert-butyl ester (149)

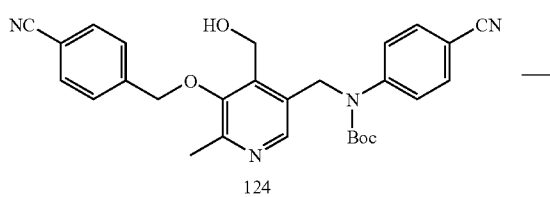

124

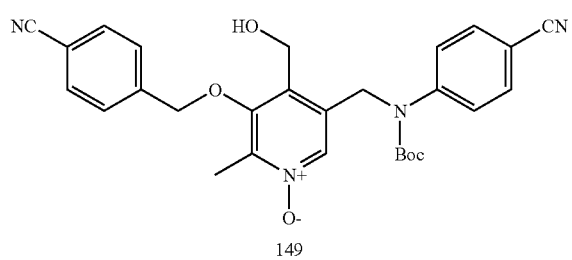

149

The oxidation of [5-(4-cyano-benzyloxy)-4-hydroxymethyl-6-methyl-pyridin-3-ylmethyl]-(4-cyano-phenyl)-carbamic acid tert-butyl ester (124) (5.00 g, 10.3 mmole), was carried out as described in Example 122, gave [5-(4-cyano-benzyloxy)-1-hydroxy-4-hydroxymethyl-6-methyl-pyridin-3-ylmethyl]-(4-cyano-phenyl)-carbamic acid tert-butyl ester [5-(4-cyano-benzyloxy)-1-hydroxy-4-hydroxymethyl-6-methyl-pyridin-3-ylmethyl]-(4-cyano-phenyl)-carbamic acid tert-butyl ester (149) (4.8 g, 93% yield).

$^1$H-NMR (CDCl$_3$): δ 7.98 (s, 1H), 7.72 (d, 2H), 7.63 (d, 2H), 7.58 (d, 2H), 7.36 (d, 2H), 5.04 (s, 2H), 5.00 (s, 2H), 4.69 (s, 2H), 2.45 (s, 3H), 1.42 (s, 9H).

Example 141

Synthesis of [5-(4-Cyano-benzyloxy)-4,6-bis-hydroxymethyl-pyridin-3-ylmethyl]-(4-cyano-phenyl)-carbamic acid tert-butyl ester (150)

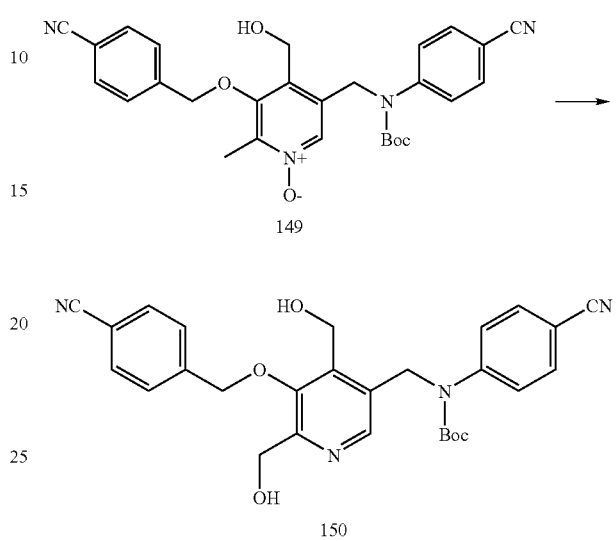

149

150

The conversion of [5-(4-cyano-benzyloxy)-1-hydroxy-4-hydroxymethyl-6-methyl-pyridin-3-ylmethyl]-(4-cyano-phenyl)-carbamic acid tert-butyl ester (149) (4.73 g, 9.4 mmol) to [5-(4-cyano-benzyloxy)-4,6-bis-hydroxymethyl-pyridin-3-ylmethyl]-(4-cyano-phenyl)-carbamic acid tert-butyl ester (150) (3.0 g, 63% yield) was carried out as described in Example 128.

$^1$H-NMR (CDCl$_3$): δ 8.07 (s, 1H), 7.66 (d, 2H), 7.60-7.54 (m, 4H), 7.36 (d, 2H), 5.07 (s, 2H), 5.03 (s, 2H), 4.74 (s, 2H), 4.69 (s, 2H), 2.00 (s, 3H), 1.38 (s, 9H).

Example 142

Synthesis of 4-{5-[(4-Carbamimidoyl-phenylamino)-methyl]-2,4-bis-hydroxymethyl-pyridin-3-yloxymethyl}-benzamidine (151)

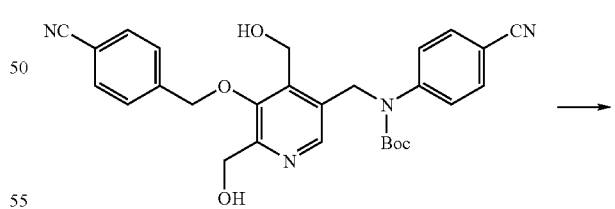

150

151

The conversion of bis-nitrile (147) to bis-amidine (148) was carried out as described in Example 2.

¹H-NMR (CD₃OD): δ 8.35 (s, 1H), 7.92 (d, 2H), 7.81 (d, 2H), 7.67 (d, 2H), 5.27 (s, 2H), 4.93-4.90 (m, 4H), 4.83 (s, 2H).

MS m/z (ES⁺): 435.07 (M+H⁺).

Example 143

Synthesis of [5-(4-Cyano-benzyloxy)-4,6-bis-fluoromethyl-pyridin-3-ylmethyl]-(4-cyano-phenyl)-carbamic acid tert-butylester (152)

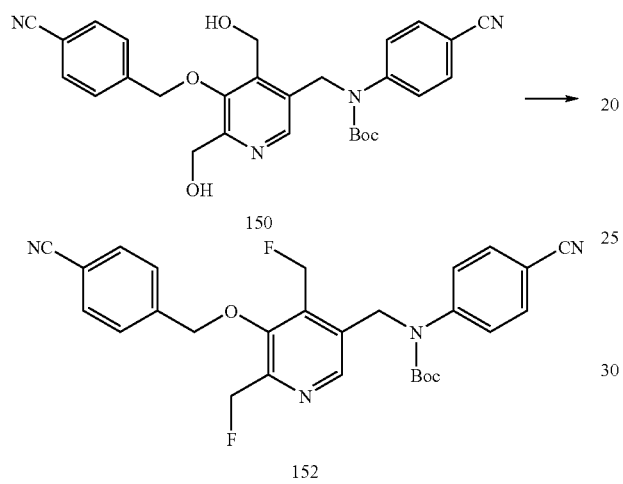

The fluorination [5-(4-cyano-benzyloxy)-4,6-bis-hydroxymethyl-pyridin-3-ylmethyl]-(4-cyano-phenyl)-carbamic acid tert-butyl ester (150) (912 mg, 1.8 mmol), was carried out as described in Example 102, gave [5-(4-cyano-benzyloxy)-4,6-bis-fluoromethyl-pyridin-3-ylmethyl]-(4-cyano-phenyl)-carbamic acid tert-butylester (152) (453 mg, 49% yield).

¹H-NMR (CDCl₃): δ 8.36 (s, 1H), 7.75-7.73 (m, 2H), 7.62-7.58 (m, 4H), 7.35-7.32 (m, 2H), 5.61 (d, 1H), 5.59 (d, 1H), 5.45 (d, 1H), 5.43 (d, 1H), 5.10 (s, 2H), 5.06 (s, 2H), 1.44 (s, 9H).

¹⁹F-NMR (CDCl₃): δ-211.13 (t, 1F), -211.68 (t, 1F).

Example 144

Synthesis of 4-{5-[(4-Carbamimidoyl-phenylamino)-methyl]-2,4-bis-fluoromethyl-pyridin-3-yloxymethyl}-benzamidine (153)

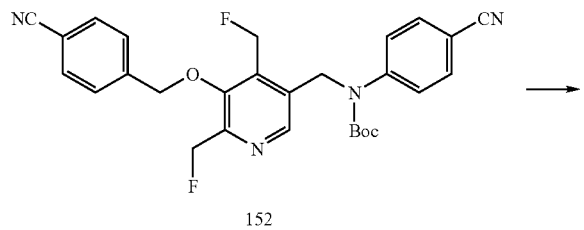

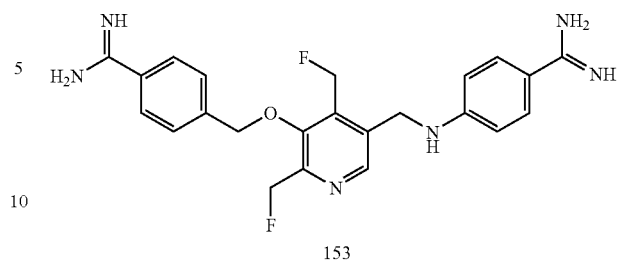

The conversion of bis-nitrile (152) to bis-amidine (153) was carried out as described in Example 2.

¹H-NMR (CD₃OD): δ 8.47 (s, 1H), 7.90 (d, 2H), 7.78 (d, 2H), 7.65 (d, 2H), 6.79 (d, 2H), 5.72 (d, 2H), 5.31 (d, 2H), 5.17 (s, 2H), 4.69 (s, 2H),

¹⁹F-NMR (CD₃OD): δ-213.88 (t, 1F), -215.14 (t, 1F).

MS m/z (ES⁺): 439.09 (M+H⁺).

Example 145

Synthesis of [5-(3-Cyano-benzyloxy)-4-(1-hydroxy-ethyl)-6-methyl-1-oxy-pyridin-3-ylmethyl]-(4-cyano-phenyl)-carbamic acid tert-butyl ester (154)

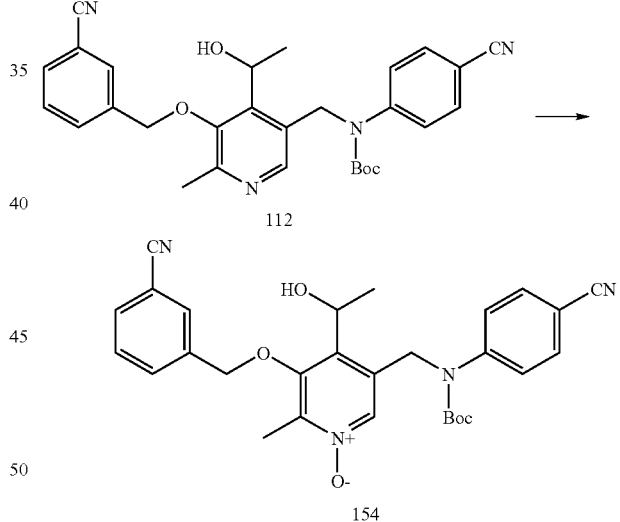

The oxidation of [5-(3-cyano-benzyloxy)-4-(1-hydroxy-ethyl)-6-methyl-pyridin-3-ylmethyl]-(4-cyano-phenyl)-carbamic acid tert-butyl ester (112) (769 mg, 1.5), was carried out as described in Example 122, gave [5-(3-cyano-benzyloxy)-4-(1-hydroxy-ethyl)-6-methyl-1-oxy-pyridin-3-ylmethyl]-(4-cyano-phenyl)-carbamic acid tert-butyl ester (154) (794 g, 100% yield).

¹H-NMR (CDCl₃): δ 8.09 (s, 1H), 7.76 (s, 1H), 7.73-7.64 (m, 2H), 7.60 (d, 2H), 7.56 (dd, 1H), 7.38 (d, 2H), 5.34 (q, 1H), 5.25 (d, 1H), 5.09 (d, 1H), 4.98 (d, 1H), 4.91 (d, 1H), 2.48 (s, 3H), 1.51 (d, 1H), 1.44 (s, 9H).

MS m/s (ES⁺): 515 (M+H⁺).

Example 146

Synthesis of [5-(3-Cyano-benzyloxy)-4-(1-hydroxy-ethyl)-6-hydroxymethyl-pyridin-3-ylmethyl]-(4-cyano-phenyl)-carbamic acid tert-butyl ester (155)

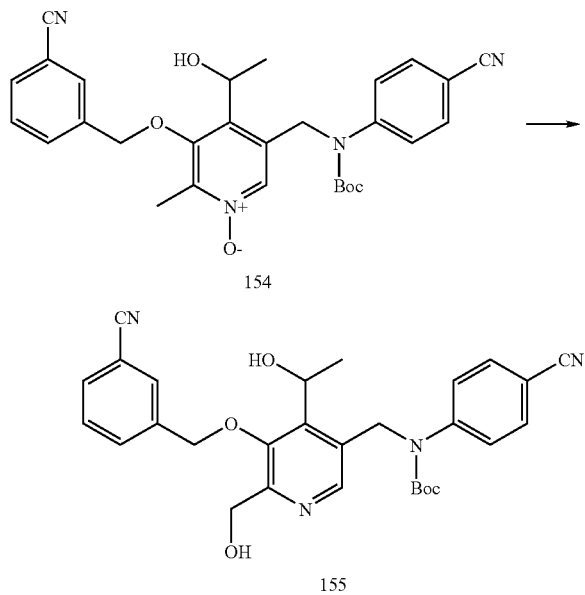

The conversion of [5-(3-cyano-benzyloxy)-4-(1-hydroxy-ethyl)-6-methyl-1-oxy-pyridin-3-ylmethyl]-(4-cyano-phenyl)-carbamic acid tert-butyl ester (154) (794 mg, 1.5 mmol) to [5-(3-cyano-benzyloxy)-4-(1-hydroxy-ethyl)-6-hydroxymethyl-pyridin-3-ylmethyl]-(4-cyano-phenyl)-carbamic acid tert-butyl ester (155) (172 mg, 22% yield) was carried out as described in Example 128.

$^1$H-NMR (CDCl$_3$): δ 8.16 (s, 1H), 7.72 (s, 1H), 7.70-7.62 (m, 2H), 7.57 (d, 2H), 7.53 (dd, 1H), 7.34 (d, 2H), 5.39 (q, 1H), 5.27 (d, 1H), 5.18 (d, 1H), 4.99 (d, 1H), 4.89 (d, 1H), 4.70 (s, 2H), 1.51 (d, 3H), 1.44 (s, 9H).

Example 147

Synthesis of [5-(3-Cyano-benzyloxy)-4-(1-fluoro-ethyl)-6-fluoromethyl-pyridin-3-ylmethyl]-(4-cyano-phenyl)-carbamic acid tert-butyl ester (156)

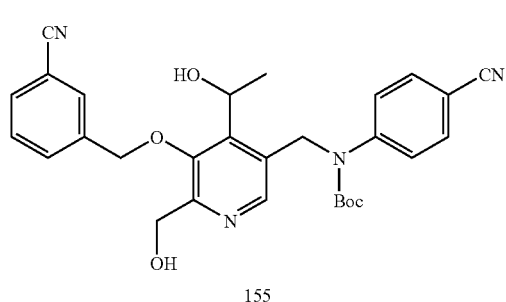

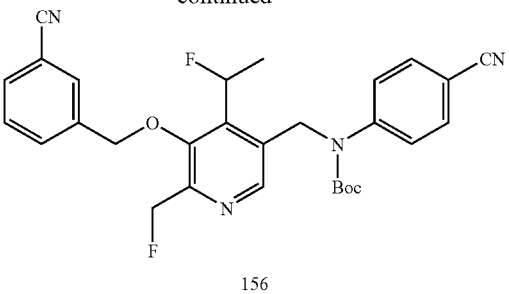

The fluorination of [5-(3-cyano-benzyloxy)-4-(1-hydroxy-ethyl)-6-hydroxymethyl-pyridin-3-ylmethyl]-(4-cyano-phenyl)-carbamic acid tert-butyl ester (155) (170 mg, 0.3 mmol), was carried out as described in Example 102, gave [5-(3-cyano-benzyloxy)-4-(1-fluoro-ethyl)-6-fluoromethyl-pyridin-3-ylmethyl]-(4-cyano-phenyl)-carbamic acid tert-butyl ester (156) (55 mg, 32% yield).

$^1$H-NMR (CDCl$_3$): δ 8.38 (s, 1H), 7.77 (s, 1H), 7.72-7.64 (m, 2H), 7.59 (d, 2H), 7.54 (dd, 1H), 7.35 (d, 2H), 6.05 (dq, 1H), 5.48 (d, 1H), 5.19 (d, 1H), 5.09 (d, 1H), 5.07 (d, 1H), 4.99 (d, 1H), 1.67 (dd, 3H), 1.44 (s, 9H).

$^{19}$F-NMR (CDCl$_3$): δ-177.18 (dq, 1F), −210.05 (t, 1F).

MS m/s (ES$^+$): 519 (M+H$^+$).

Example 148

Synthesis of 4-{[4-(1-Fluoro-ethyl)-6-fluoromethyl-5-(3-amidine-benzyloxy)-pyridin-3-ylmethyl]-amino}-benzamidine (157)

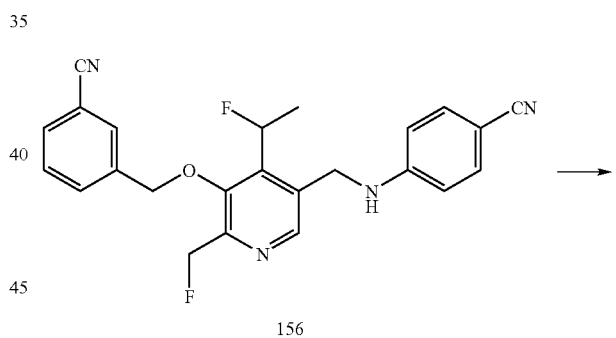

The conversion of bis-nitrile (156) to bis-amidine (157) was carried out as described in Example 2.

$^1$H-NMR (CD$_3$OD): δ 8.50 (s, 1H), 8.00 (s, 1H), 7.94 (d, 1H), 7.87 (d, 1H), 7.74 (dd, 1H), 7.68 (d, 2H), 6.80 (d, 2H), 6.24 (dq, 1H), 5.60 (dd, 1H), 5.55 (dd, 1H), 5.22 (d, 1H), 5.17 (d, 1H), 4.72 (s, 2H), 3.74-3.48 (m, 1H), 1.79 (dd, 3H).

$^{19}$F-NMR (CD$_3$OD): δ-178.21 (dq, 1F), -213.61 (dd, 1F).

MS m/s (ES$^+$): 543.14 (M+H$^+$).

Example 149

Synthesis of (E)-3-[5-{[tert-Butoxycarbonyl-(4-cyano-phenyl)-amino]-methyl}-3-(3-cyano-benzyloxy)-4-methyl-pyridin-2-yl]-acrylic acid methyl ester (158)

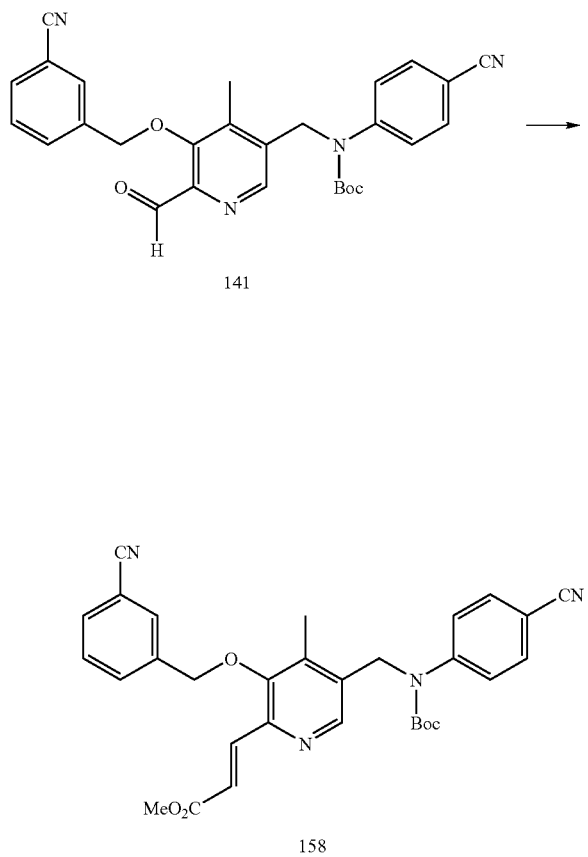

The Wittig-reaction of methyl diethyl phosphonoacetate (125 mg, 0.6 mmol) to 3[5-(3-cyano-benzyloxy)-6-formyl-4-methyl-pyridin-3-ylmethyl]-(4-cyano-phenyl)-carbamic acid tert-butyl ester (141) (110 mg, 0.2 mmol), as described in Example 111, (E)-3-[5-{[tert-Butoxycarbonyl-(4-cyano-phenyl)-amino]-methyl}-3-(3-cyano-benzyloxy)-4-methyl-pyridin-2-yl]-acrylic acid methyl ester (158) (103 mg, 84% yield).

$^1$H-NMR (CDCl$_3$): δ 8.21 (s, 1H), 7.87 (d, 1H), 7.72 (s, 1H), 7.72-7.63 (m, 2H), 7.59 (d, 2H), 7.54 (dd, 1H), 7.30 (d, 2H), 6.99 (d, 1H), 4.92 (s, 2H), 4.84 (s, 2H), 3.79 (s, 3H), 2.21 (s, 3H), 1.44 (s, 9H).

Example 150

Synthesis of (E)-3-[5-[(4-Carbamimidoyl-phenylamino)-methyl]-4-methyl-3-(3-amidine-benzyloxy)-pyridin-2-yl]-acrylamide (159) and 3-Amino-3-[5-[(4-carbamimidoyl-phenylamino)-methyl]-4-methyl-3-(3-amidine-benzyloxy)-pyridin-2-yl]-propionamide (160)

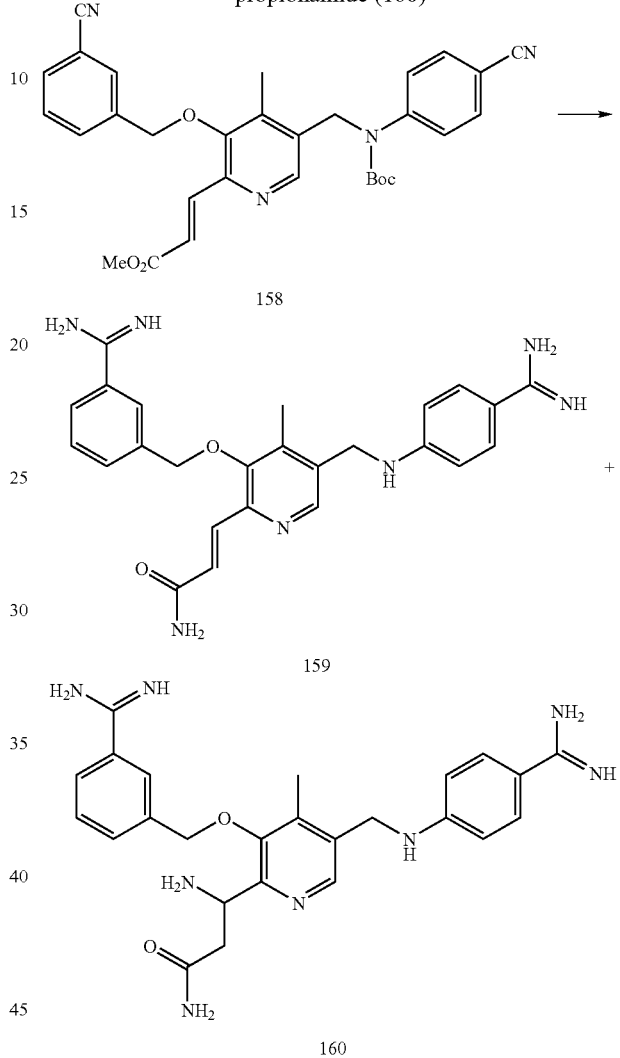

Hydrogen chloride gas was bubbled into a suspension of (E)-3-[5-{[tert-butoxycarbonyl-(4-cyano-phenyl)-amino]-methyl}-3-(3-cyano-benzyloxy)-4-methyl-pyridin-2-yl]-acrylic acid methyl ester (158) (106 mg, 0.20 mmol) in absolute ethyl alcohol (20 mL) at 0° C. for 15 minutes. The flask was sealed with a rubber septum and the reaction mixture was stirred at room temperature overnight. The reaction mixture was purged with nitrogen gas for 1 hour to remove the excess hydrogen chloride gas and the solvent evaporated to give the crude imino ester. Ammonia in methyl alcohol (20 mL, 7M, 140 mmol) was then added to the crude ester and stirred overnight at room temperature. The solvent was evaporated and the product purified by HPLC on C18 column using a gradient mixture of water with 0.1% trifluoro acetic acid: methyl alcohol (98:2 to 0:1) as eluant to give (E)-3-[5-[(4-carbamimidoyl-phenylamino)-methyl]-4-methyl-3-(3-amidine-benzyloxy)-pyridin-2-yl]-acrylamide (159) (51 mg, 38% yield) and 3-amino-3-[5-[(4-carbamimidoyl-phenylamino)-methyl]-4-methyl-3-(3-amidine-benzyloxy)-pyridin-2-yl]-propionamide (160) (9 mg, 6% yield)

(E)-3-[5-[(4-Carbamimidoyl-phenylamino)-methyl]-4-methyl-3-(3-amidine-benzyloxy)-pyridin-2-yl]-acrylamide (159)

$^1$H-NMR (CD$_3$OD): δ 8.34 (s, 1H), 8.07 (s, 1H), 7.87 (d, 1H), 7.86 (d, 1H), 7.85 (d, 1H), 7.69 (d, 2H), 7.69 (dd, 1H), 7.08 (d, 1H), 6.82 (d, 2H), 5.07 (s, 2H), 4.56 (s, 2H), 2.51 (s, 3H).

MS m/s (ES$^+$): 458.21 (M+H$^+$).

3-Amino-3-[5-[(4-carbamimidoyl-phenylamino)-methyl]-4-methyl-3-(3-amidine-benzyloxy)-pyridin-2-yl]-propionamide (160)

$^1$H-NMR (CD$_3$OD): δ 8.40 (s, 1H), 8.09 (s, 1H), 7.92 (d, 1H), 7.86 (d, 1H), 7.71 (dd, 1H), 7.68 (d, 2H), 6.82 (d, 2H), 5.18 (d, 2H), 5.11 (dd, 2H), 5.09 (d, 2H), 4.53 (s, 2H), 2.94 (dd, 2H), 2.80 (dd, 2H), 2.49 (s, 3H).

MS m/s (ES$^+$): 475.22 (M+H$^+$).

Example 151

Synthesis of 3-[4-(3-Cyano-benzyloxy)-5-hydroxymethyl-2-methyl-pyridin-3-yloxymethyl]-benzonitrile (161)

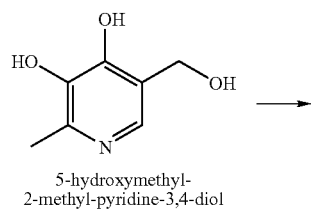

5-hydroxymethyl-2-methyl-pyridine-3,4-diol

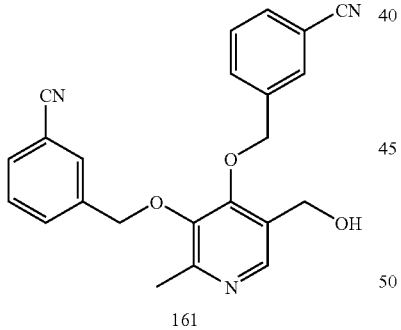

161

A mixture of 5-hydroxymethyl-2-methyl-pyridine-3,4-diol (4.0 g, 35.8 mmol), α-bromo-m-tolunitrile (8.8 g, 44.8 mmol) and cesium carbonate (15.6 g, 47.8 mmol) was stirred in DMF (20 mL) for 150 minutes. The reaction mixture was evaporated to dryness, and the crude product purified by column chromatography on silica gel using a gradient of dichloromethane:methyl alcohol (1:0 to 19:1) as eluant to give product 3-[4-(3-cyano-benzyloxy)-5-hydroxymethyl-2-methyl-pyridin-3-yloxymethyl]-benzonitrile (161) (2 g, 20% yield).

$^1$H-NMR (DMSO-d6): δ 7.91 (s, 1H), 7.81-7.73 (m, 4H), 7.62-7.52 (m, 3H), 7.29 (d, 1H), 5.33 (s, 2H), 5.01 (s, 2H), 4.38 (d, 2H), 2.01 (s, 3H).

Example 152

Synthesis of 3-[4-(3-Amidino-benzyloxy)-5-hydroxymethyl-2-methyl-pyridin-3-yloxymethyl]-benzamidine (162)

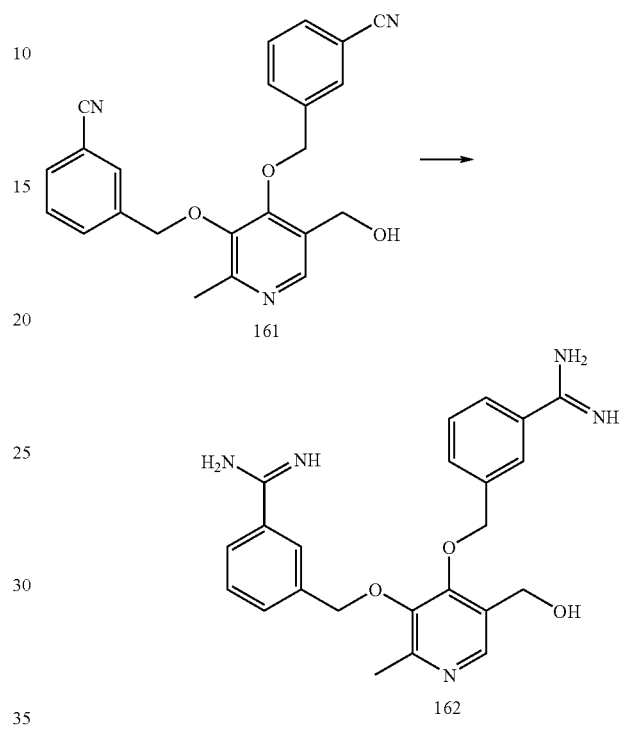

The conversion of bis-nitrile (161) to bis-amidine (162) was carried out as described in Example 2.

$^1$H-NMR (CD$_3$OD): δ 7.66 (s, 1H), 7.52 (t, 1H), 7.45-7.34 (m, 3H), 7.28 (t, 1H), 7.19 (t, 1H), 7.14 (s, 1H), 6.98 (d, 2H), 5.06 (s, 2H), 4.78 (s, 2H), 4.28 (s, 2H), 1.68 (s, 2H).

Example 153

Synthesis of 2-(Cyclopropanecarbonyl-amino)-propionic acid ethyl ester (163)

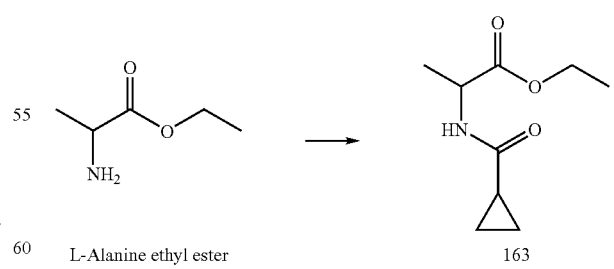

L-Alanine ethyl ester                163

To a solution of L-alanine ethyl ester hydrochloride (50 g, 325 mmol) in anhydrous dichloromethane (800 mL) added triethylamine (65.8 g, 650 mmol) and stirred at room temperature for 30 minutes. To the reaction mixture cyclopropanecarbonyl chloride (50.96 g, 0.487 mole) was slowly added and stirred at room temperature for overnight. The reaction mixture was then poured into a cold solution of saturated aqueous sodium bicarbonate, and the crude product extracted with dichloromethane, dried over anhydrous magnesium sulfate. Evaporation of the solvent gave a crude residue, which was purified by column chromatography on silica gel using a mixture of ethyl acetate:hexane (1:1) as eluant to give 2-(cyclopropanecarbonyl-amino)-propionic acid ethyl ester (163) (58.0 g, 96% yield).

$^1$H-NMR (CDCl$_3$): δ 6.5 (s, 1H), 4.58-4.48 (m, 1H), 4.17-4.10 (m, 2H), 1.35-1.33 (m, 3H), 1.24-1.19 (m, 3H), 0.92-0.87 (m, 3H), 0.72-0.65 (m, 2H).

Example 154

Synthesis of 4-Cyclopropyl-5-ethoxy-2-methyl-oxazole (164)

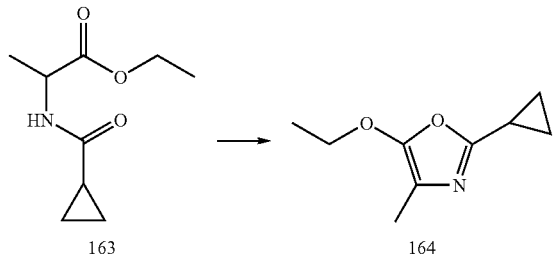

A solution of 2-(cyclopropanecarbonyl-amino)-propionic acid ethyl ester (163) (50.0 g, 269 mmol) in chloroform anhydrous was cannulated into a solution of P$_2$O$_5$ (153 g, 539 mmol) in anhydrous chloroform (1000 mL) at room temperature. The reaction mixture was then poured into a cold solution of 20% aqueous solution of potassium hydroxide (800 mL), stirred at room temperature for 4 hours and the crude product was extracted with chloroform, dried over anhydrous magnesium sulfate. Evaporation of the solvent to dryness gave 4-cyclopropyl-5-ethoxy-2-methyl-oxazole (164) (41.2 g, 91% yield) as a light brown oil $^1$H-NMR (CDCl$_3$): δ 4.03-3.96 (m, 2H), 1.89 (s, 3H), 1.80 (m, 1H), 1.26-1.22 (m, 3H), 0.89-0.82 (m, 4H).

Example 155

Synthesis of 2-Cyclopropyl-5-hydroxy-6-methyl-pyridine-3,4-dicarboxylic acid dimethyl ester (165)

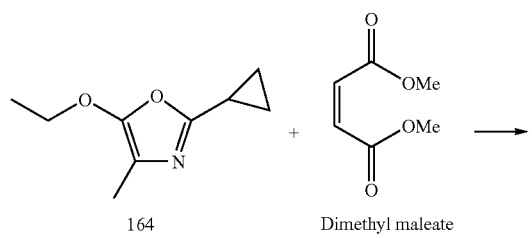

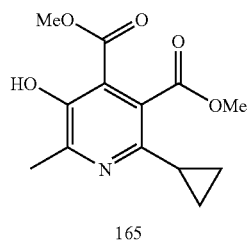

2-Cyclopropyl-5-ethoxy-4-methyl-oxazole (164) (33.8 g, 0202 mmol) in neat dimethyl maleate (115.8 g, 807 mmol) was refluxed for 4 hours. The reaction was cooled to 0° C., added anhydrous methyl alcohol (500 mL) and bubbled hydrogen chloride gas into the suspension for 15 minutes. The reaction flask was sealed with a rubber septum and kept in a fridge for overnight. The solid was filtered off and washed with methanol and diethyl ether. The filtrate was evaporated to give 2-cyclopropyl-5-hydroxy-6-methyl-pyridine-3,4-dicarboxylic acid dimethyl ester (165) (35.2 g, 66% yield) as a colorless solids.

$^1$H-NMR (CDCl$_3$): δ 10.20-10.14 (m, 2H), 3.78 (s, 6H), 2.38 (s, 3H), 1.15-1.08 (m, 1H), 0.89-0.84 (m, 4H).

Example 156

Synthesis of 6-Cyclopropyl-4,5-bis-hydroxymethyl-2-methyl-pyridin-3-ol (166)

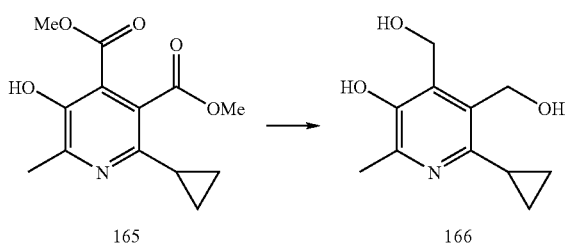

A solution of 2-cyclopropyl-5-hydroxy-6-methyl-pyridine-3,4-dicarboxylic acid dimethyl ester (165) (30 g, 113 mmol) in anhydrous tetrahydrofuran (400 mL) was slowly cannulated into a suspension of LiAlH$_4$ in anhydrous tetrahydrofuran (400 mL) at 0° C. The reaction mixture was heated at 60° C. for 3 hours, cooled in an ice bath and slowly quenched with water. The colorless gel formed was filtered off through a celite pad and washed with methyl alcohol. The filtrate was evaporated to dryness to give 6-cyclopropyl-4,5-bis-hydroxymethyl-2-methyl-pyridin-3-ol (166) (15.0 g, 63% yield) as a colorless solids.

$^1$H-NMR (CDCl$_3$): δ 4.39 (s, 2H), 4.22 (s, 2H), 1.85 (s, 3H), 1.81-1.74 (m, 1H), 0.49-0.33 (m, 4H).

Example 157

Synthesis of (6-Cyclopropyl-2,2,8-trimethyl-4H-[1,3]dioxino[4,5-c]pyridin-5-yl)-methanol (167)

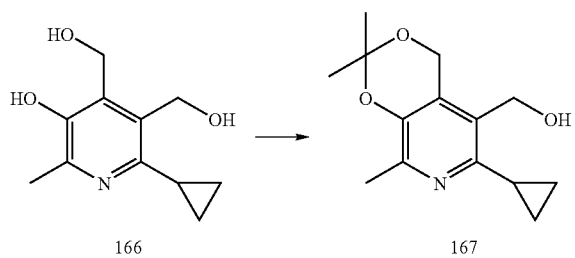

Sulfuric acid (18.71 g, 0.1908 mole, 10 ml) was added to a solution of 6-cyclopropyl-4,5-bis-hydroxymethyl-2-methyl-pyridin-3-ol (166) (10.0 g, 47.7 mmol) in anhydrous acetone (60 mL) at 0° C. The reaction mixture was slowly warmed to room temperature and stirred overnight, poured into a cold solution of aqueous sodium hydroxide (excess) and the crude product was extracted with chloroform and dried over anhydrous magnesium sulfate. Evaporation of the solvent gave a crude residue, which was purified on a silica gel column using a mixture of ethyl acetate hexane (2:8) as eluant to give (6-cyclopropyl-2,2,8-trimethyl-4H-[1,3]dioxino[4,5-c]pyridin-5-yl)-methanol (167) (5.2 g, 44% yield) as a brown liquid.

$^1$H-NMR (CDCl$_3$): δ 4.92 (s, 2H), 4.70 (s, 2H), 2.30 (s, 3H), 2.13-2.05 (m, 1H), 1.51 (s, 6H), 0.99-0.96 (m, 2H), 0.87-0.83 (m, 2H).

Example 158

Synthesis of 6-Cyclopropyl-2,2,8-trimethyl-4H-[1,3]dioxino[4,5-c]pyridine-5-carbaldehyde (168)

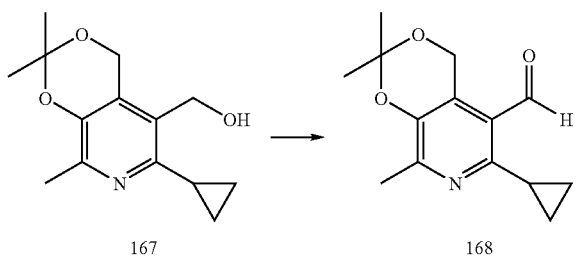

The oxidation of (6-cyclopropyl-2,2,8-trimethyl-4H-[1,3]dioxino[4,5-c]pyridin-5-yl)-methanol (167) (4.89 g, 19.2 mmol) to 6-cyclopropyl-2,2,8-trimethyl-4H-[1,3]dioxino[4,5-c]pyridine-5-carbaldehyde (168) (3.1 g, 65% yield) was carried out as described in Example 13.

$^1$H-NMR (CDCl$_3$): δ 10.71 (s, 1H), 5.10 (s, 2H), 2.49-2.43 (m, 1H), 2.37 (s, 3H), 1.51 (s, 6H), 1.19-1.14 (m, 2H), 1.01-0.95 (m, 2H).

Example 159

Synthesis of 4-[(6-Cyclopropyl-2,2,8-trimethyl-4H-[1,3]dioxino[4,5-c]pyridin-5-ylmethyl)-amino]-benzonitrile (169)

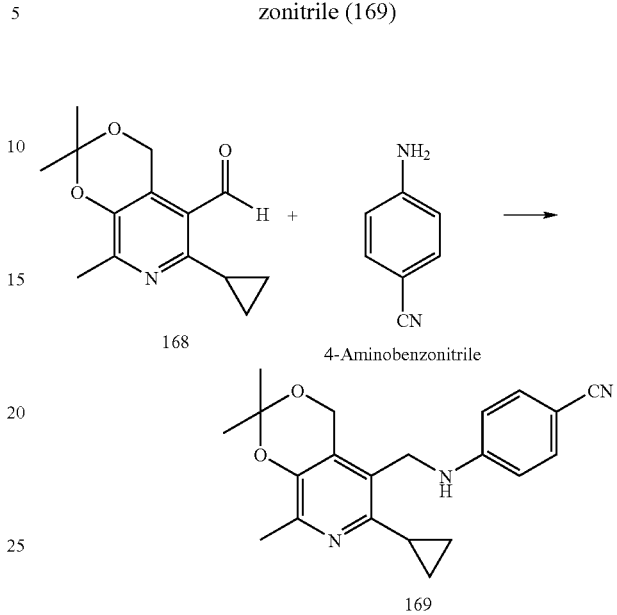

The reductive amination of 6-cyclopropyl-2,2,8-trimethyl-4H-[1,3]dioxino[4,5-c]pyridine-5-carbaldehyde (168) (5.11 g, 20.6 mmol) and 4-aminobenzonitrile (2.9 g, 24.7 mmol), as described in Example 21, gave give 4-[(6-cyclopropyl-2,2,8-trimethyl-4H-[1,3]dioxino[4,5-c]pyridin-5-ylmethyl)-amino]-benzonitrile (169) (3.7 g, 51% yield).

$^1$H-NMR (CDCl$_3$): δ 7.49-7.46 (d, 2H), 6.67-6.64 (d, 2H), 4.86 (s, 2H), 4.25-4.16 (s, 2H), 2.35 (s, 3H), 2.02-1.94 (m, 1H), 1.53 (s, 6H), 1.05-1.02 (m, 2H), 0.89-0.84 (m, 2H).

Example 160

Synthesis of 4-[(2-Cyclopropyl-5-hydroxy-4-hydroxymethyl-6-methyl-pyridin-3-ylmethyl)-amino]-benzonitrile (170)

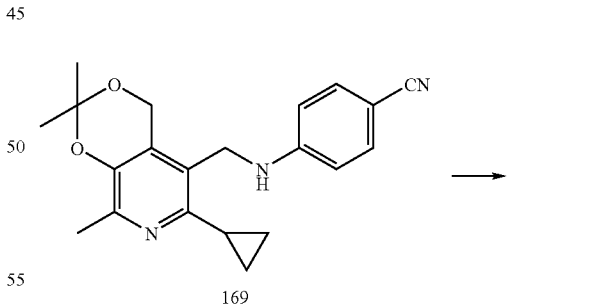

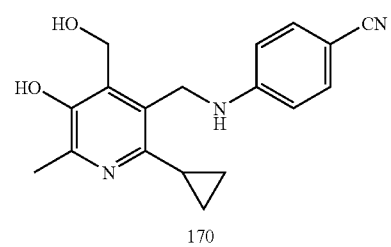

The hydrolysis of 4-[(6-cyclopropyl-2,2,8-trimethyl-4H-[1,3]dioxino[4,5-c]pyridin-5-ylmethyl)-amino]-benzonitrile (169) (3.7 g, 10.59 mmol), as described in Example 10, gave 4-[(2-cyclopropyl-5-hydroxy-4-hydroxymethyl-6-methyl-pyridin-3-ylmethyl)-amino]-benzonitrile (170) (1.98 g, 61% yield).

$^1$H-NMR (DMSO-d6): δ 8.95 (s, 1H), 7.49-7.46 (d, 2H), 6.78-6.75 (d, 2H), 6.65-6.62 (m, 1H), 5.60-5.57 (m, 1H), 4.66-4.64 (d, 2H), 4.34-4.33 (d, 2H), 2.30 (s, 3H), 2.05-2.00 (m, 1H), 0.88-0.83 (m, 2H), 0.79-0.73 (m, 2H).

Example 161

Synthesis of 3-((5-((4-aminophenylcyano)methyl)-6-cyclopropyl-4-(hydroxymethyl)-2-methylpyridin-3-yloxy)methyl)benzonitrile (171)

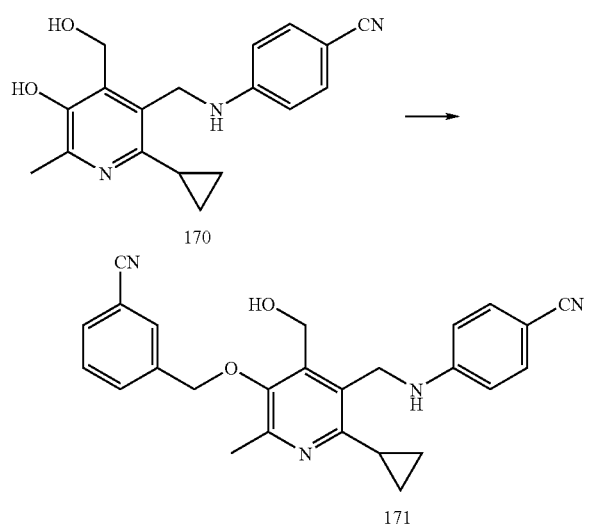

The coupling of 4-[(2-cyclopropyl-5-hydroxy-4-hydroxymethyl-6-methyl-pyridin-3-ylmethyl)-amino]-benzonitrile (170) (754 mg, 2.4 mmol) and α-bromo-m-tolunitrile (526 mg, 2.7 mmol), as described in Example 1, gave 3-((5-((4-aminophenylcyano)methyl)-6-cyclopropyl-4-(hydroxymethyl)-2-methylpyridin-3-yloxy)methyl)benzonitrile (171) (550 mg, 54% yield).

$^1$H-NMR (DMSO-d6): δ 7.98 (s, 1H), 7.89-7.84 (m, 2H), 7.68-7.62 (m, 1H), 7.50-7.47 (m, 2H), 6.81-6.75 (m, 3H), 4.95 (s, 2H), 4.55 (s, 2H), 4.46-4.45 (m, 2H), 2.37 (s, 3H), 2.13-2.08 (m, 1H), 0.95-0.79 (m, 4H).

Example 162

Synthesis of 3-{5-[(4-Carbamimidoyl-phenylamino)-methyl]-6-cyclopropyl-4-hydroxymethyl-2-methyl-pyridin-3-yloxymethyl}-benzamidine (172)

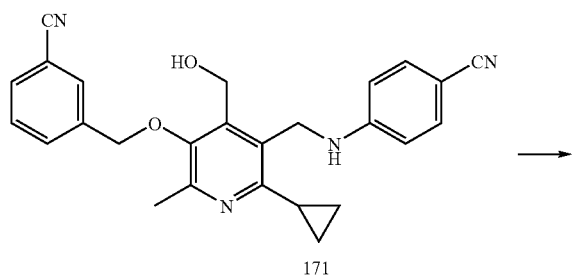

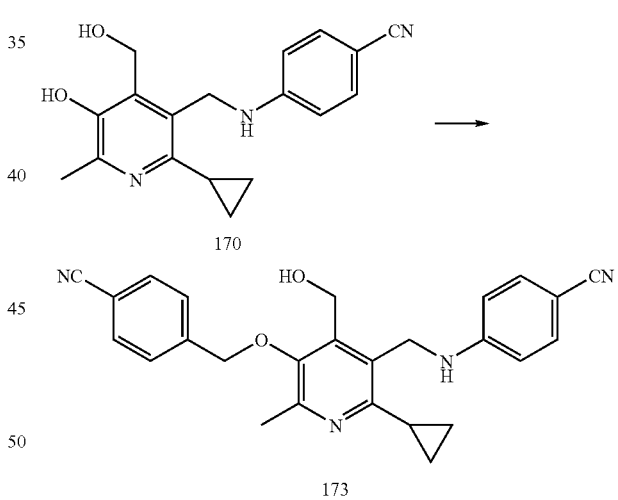

The conversion of bis-nitrile (171) to bis-amidine (172) was carried out as described in Example 2.

$^1$H-NMR (DMSO-d6): δ 9.39 (s, 2H), 9.28 (s, 2H), 8.81 (s, 2H), 8.59 (s, 2H), 7.95-7.82 (m, 3H), 7.71-7.66 (m, 3H), 6.83-6.82 (m, 2H), 4.98 (s, 2H), 4.60 (s, 2H), 4.53 (s, 2H), 2.43 (s, 3H), 2.15-2.08 (m, 1H), 0.98-0.93 (m, 2H), 0.88-0.82 (m, 2H)

MS m/z (ES$^+$): 459.60 (M+H$^+$).

Example 163

Synthesis of 4-((5-((4-Aminophenylcyano)methyl)-6-cyclopropyl-4-(hydroxymethyl)-2-methylpyridin-3-yloxy)methyl)benzonitrile (173)

The coupling of 4-[(2-cyclopropyl-5-hydroxy-4-hydroxymethyl-6-methyl-pyridin-3-ylmethyl)-amino]-benzonitrile (170) (743 mg, 2.4 mmol) and α-bromo-p-tolunitrile (517 mg, 2.6 mmol), as described in Example 1, gave 4-((5-((4-aminophenylcyano)methyl)-6-cyclopropyl-4-(hydroxymethyl)-2-methylpyridin-3-yloxy)methyl)benzonitrile (173) (742 mg, 73% yield).

$^1$H-NMR (DMSO-d6): δ 7.91-7.88 (d, 2H), 7.73-7.70 (d, 2H), 7.49-7.47 (d, 2H), 6.81-6.76 (d, 2H), 6.72 (s, 1H), 5.33 (s, 1H), 4.99 (s, 2H), 4.55 (s, 2H), 4.46-4.45 (m, 2H), 2.37 (s, 3H), 2.14-2.06 (m, 1H), 0.94-0.91 (m, 2H), 0.86-0.81 (m, 2H).

Example 164

Synthesis of 4-{5-[(4-Carbamimidoyl-phenylamino)-methyl]-6-cyclopropyl-4-hydroxymethyl-2-methyl-pyridin-3-yloxymethyl}-benzamidine (174)

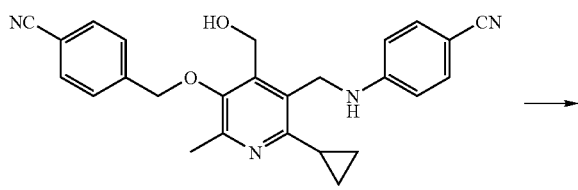

173

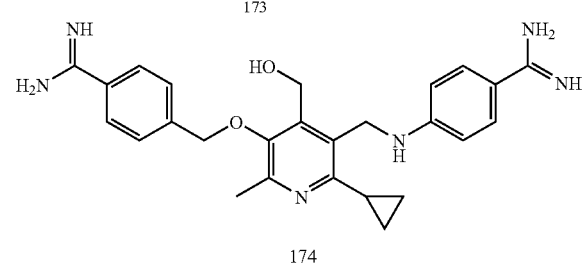

174

The conversion of bis-nitrile (173) to bis-amidine (174) was carried out as described in Example 2.

$^1$H-NMR (D$_2$O): δ 7.74-7.71 (m, 2H), 7.63-7.60 (m, 4H), 6.81-6.79 (m, 2H), 5.13 (s, 2H), 4.99 (s, 2H), 2.64 (s, 3H), 2.33-2.31 (m, 1H), 1.20-1.15 (m, 2H), 1.04-1.00 (m, 2H).

MS m/z (ES$^+$): 459.60 (M+H$^+$).

Example 165

Synthesis of Acetic acid 4-carboxyoxymethyl-6-cyclopropyl-5-hydroxymethyl-2-methyl-pyridin-3-yl ester (175)

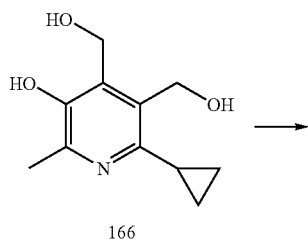

166

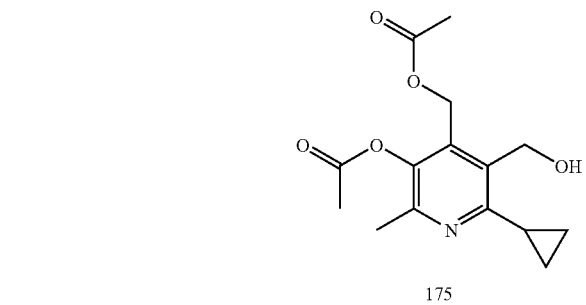

175

To a solution of 6-cyclopropyl-4,5-bis-hydroxymethyl-2-methyl-pyridin-3-ol (166) (10.2 g, 48.8 mmol) in water (100 mL) was added hydrochloric acid (60 mL, 1N), followed by acetic anhydride (12.5 mL) and stirred at room temperature for one hour. The crude product extracted with ethyl acetate, dried over anhydrous magnesium sulfate. The solvent was evaporated to give acetic acid 4-carboxyoxymethyl-6-cyclopropyl-5-hydroxymethyl-2-methyl-pyridin-3-yl ester (175) (10.6 g, 74% yield).

$^1$H-NMR (CDCl$_3$): δ 5.24 (s, 2H), 4.91 (s, 2H), 2.34 (s, 3H), 2.29 (s, 3H), 2.01 (s, 3H), 1.10-1.06 (m, 2H), 0.98-0.93 (m, 2H).

Example 166

Synthesis of Acetic acid 5-hydroxymethyl-2,4-dimethyl-6-propyl-pyridin-3-yl ester (176)

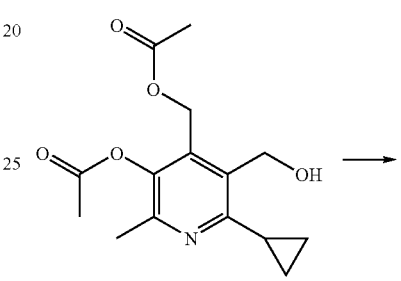

175

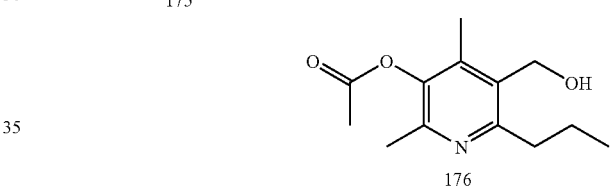

176

The acetic acid 4-carboxyoxymethyl-6-cyclopropyl-5-hydroxymethyl-2-methyl-pyridin-3-yl ester (175) (10.6 g, 35.9 mmol) in methyl alcohol:water (1:1, 100 mL) was hydrogenated in the presence of 10% palladium on carbon (3.8 g) at room temperature for overnight. The product was filtered through a celite pad and evaporated to give acetic acid 5-hydroxymethyl-2,4-dimethyl-6-propyl-pyridin-3-yl ester (176) (7.2 g, 89% yield).

$^1$H-NMR (CDCl$_3$): δ 4.70 (s, 2H), 2.81-2.76 (m, 2H), 2.36 (s, 3H), 2.32 (s, 3H), 2.20 (s, 3H), 1.70-1.63 (m, 2H), 0.99 (t, 3H).

Example 167

Synthesis of 5-Hydroxymethyl-2,4-dimethyl-6-propyl-pyridin-3-ol (177)

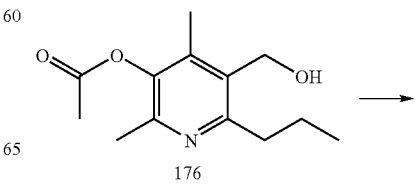

176

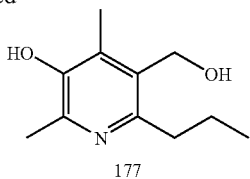

A solution of acetic acid 5-hydroxymethyl-2,4-dimethyl-6-propyl-pyridin-3-yl ester (176) (7.8 g, 32.9 mmol) in hydrochloric acid (100 mL, 1N) was refluxed for 90 minutes. The reaction mixture was evaporated to give 5-hydroxymethyl-2,4-dimethyl-6-propyl-pyridin-3-ol (177) (6.8 g, 97% yield).

$^1$H-NMR (DMSO-d6): δ 4.53 (s, 2H), 3.04-2.99 (m, 2H), 2.65 (s, 3H), 2.44 (s, 3H), 1.67-1.57 (m, 2H), 0.94 (t, 3H).

Example 168

Synthesis of 3-(5-Hydroxymethyl-2,4-dimethyl-6-propyl-pyridin-3-yloxymethyl)-benzonitrile (178)

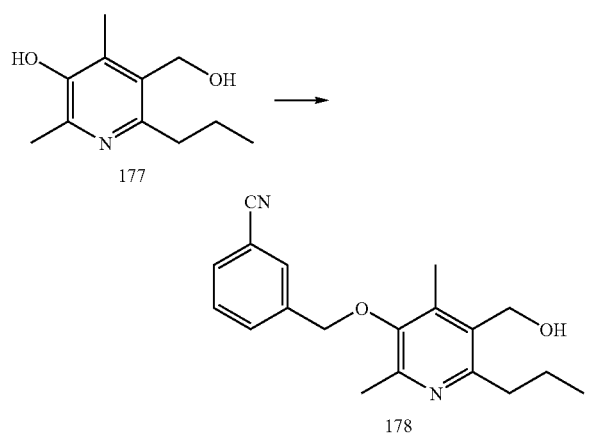

The coupling of 5-hydroxymethyl-2,4-dimethyl-6-propyl-pyridin-3-ol (177) (6.8 g, 29.3 mmol) and α-bromo-m-tolunitrile (5.74 g, 29.3 mol), as described in Example 1, gave 4-((5-((4-aminophenylcyano)methyl)-6-cyclopropyl-4-(hydroxymethyl)-2-methylpyridin-3-yloxy)methyl)benzonitrile (173) (742 mg, 73% yield).

$^1$H-NMR (DMSO-d6): δ 7.95 (1H, s), 7.87-7.83 (m, 2), 7.64 (t, 1H), 4.8 (s, 2H), 4.48 (d, 2H), 2.75-2.70 (m, 2H), 2.37 (s, 3H), 2.29 (s, 3H), 1.66-1.59 (m, 2H), 0.933 (t, 3H).

Example 169

Synthesis of 3-(5-Formyl-2,4-dimethyl-6-propyl-pyridin-3-yloxymethyl)-benzonitrile (179)

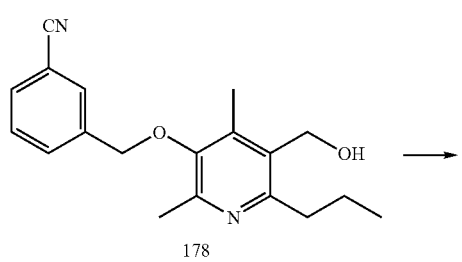

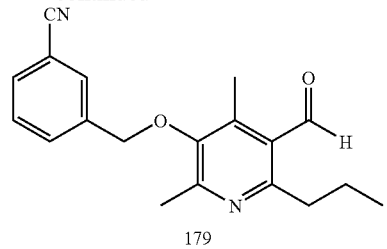

The oxidation of 3-(5-hydroxymethyl-2,4-dimethyl-6-propyl-pyridin-3-yloxymethyl)-benzonitrile (178) (5.0 g, 16.1 mmol) to 3-(5-formyl-2,4-dimethyl-6-propyl-pyridin-3-yloxymethyl)-benzonitrile (179) (750 mg, 15% yield) was carried out as described in Example 13.

$^1$H-NMR (CD$_3$OD): δ 8.83 (1H, s), 7.75 (d, 1H), 7.62 (t, 1H), 7.34 (d, 2H), 4.96 (s, 2H), 3.01-2.96 (m, 2H), 2.53 (s, 3H), 2.52 (s, 3H), 1.74-1.66 (m, 2H), 0.98 (t, 3H).

Example 170

Synthesis of 4-{[5-(3-Cyano-benzyloxy)-4,6-dimethyl-2-propyl-pyridin-3-ylmethyl]-amino}-benzonitrile; compound with ethane (180)

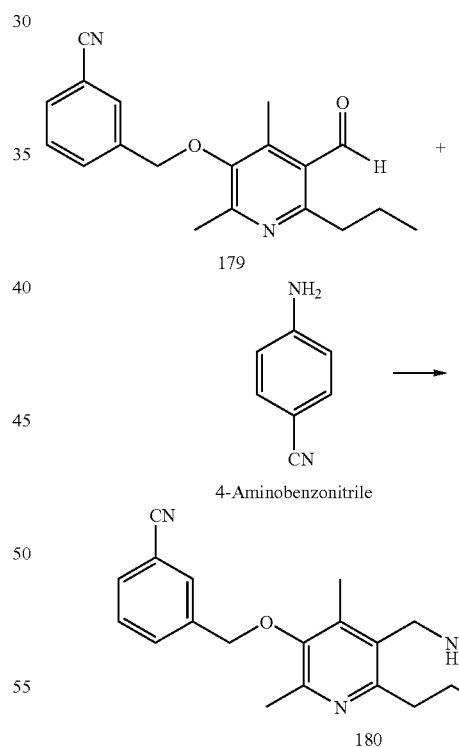

The reductive amination of 3-(5-formyl-2,4-dimethyl-6-propyl-pyridin-3-yloxymethyl)-benzonitrile (179) (675 mg, 2.18 mmol) and 4-aminobenzonitrile (516 mg, 4.4 mmol), was carried out as described in Example 21, gave 4-{[5-(3-cyano-benzyloxy)-4,6-dimethyl-2-propyl-pyridin-3-ylmethyl]-amino}-benzonitrile (180) (324 mg, 36% yield).

$^1$H-NMR (CD$_3$OD): δ 7.86 (1H, s), 7.82 (d, 1H), 7.73 (d, 1H), 7.60 (t, 1H), 7.47-7.43 (m, 2H), 6.76 (d, 2H), 4.91 (s,

2H), 4.84 (s, 2H), 2.8-2.74 (m, 2H), 2.46 (s, 3H), 2.33 (s, 3H), 1.75-1.62 (m, 2H), 0.976 (t, 3).

Example 171

Synthesis of 3-{5-[(4-Carbamimidoyl-phenylamino)-methyl]-2,4-dimethyl-6-propyl-pyridin-3-yloxymethyl}-benzamide (181)

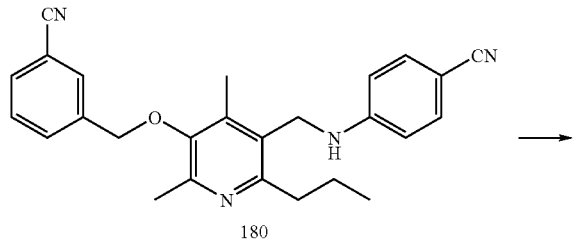

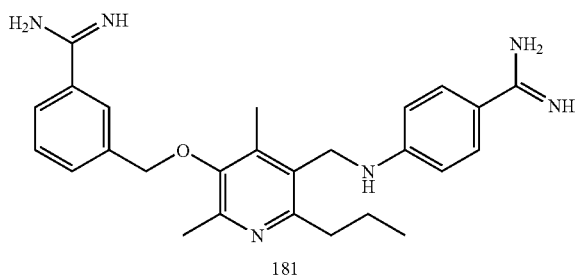

The conversion of bis-nitrile (180) to bis-amidine (181) was carried out as described in Example 2.

$^1$H-NMR (D$_2$O): δ 8.01 (1H, s), 7.92 (d, 1H), 7.86 (d, 1H), 7.75-7.69 (m, 3H), 6.90 (d, 2H), 5.12 (s, 2H), 4.48 (s, 2H), 3.02-2.97 (m, 2), 2.71 (s, 3H), 2.59 (s, 3H), 1.81-1.73 (m, 2H), 1.03 (t, 3H).

MS m/z (ES$^+$): 445.17 (M+H$^+$).

Example 172

Synthesis of 6-Cyclopropyl-3-hydroxy-2-methyl-isonicotinic acid methyl ester (182) and 2-Cyclopropyl-5-hydroxy-6-methyl-nicotinic acid methyl ester (183)

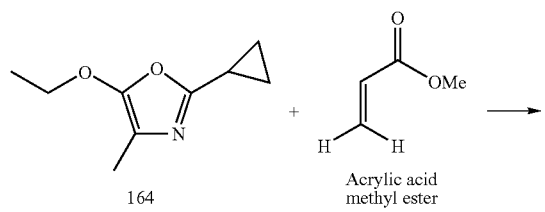

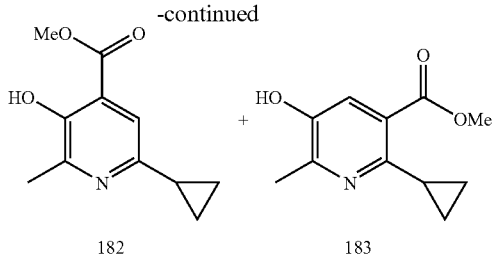

2-Cyclopropyl-5-ethoxy-4-methyl-oxazole (164) (10.0 g, 60.0 mmol) in neat acrylic acid methyl ester (20.6 g, 239 mmol) was refluxed for 4 hours. The reaction was cooled to 0° C., added anhydrous methyl alcohol and bubbled hydrogen chloride gas into the suspension for 15 minutes. The reaction flask with a rubber septum was kept in a fridge for overnight. The solid was filtered off and washed with methanol and diethyl ether. The filtrate was evaporated to give a crude residue, which was purified by column chromatography on silica gel using a gradient mixture of ethyl acetate:hexane (0:1 to 1:4) as eluant to give 6-cyclopropyl-3-hydroxy-2-methyl-isonicotinic acid methyl ester (182) (3.71 g, 30% yield), and 2-cyclopropyl-5-hydroxy-6-methyl-nicotinic acid methyl ester (183) (1.34 g, 10% yield).

6-Cyclopropyl-3-hydroxy-2-methyl-isonicotinic acid methyl ester (182)

$^1$H-NMR (DMSO-d6): δ 9.97 (s, 1H), 3.91 (s, 3H), 2.35 (s, 3H), 2.09-2.00 (m, 1H), 0.86-0.77 (m, 4H).

2-Cyclopropyl-5-hydroxy-6-methyl-nicotinic acid methyl ester (183)

$^1$H-NMR (DMSO-d6): δ 7.92 (s, 1H), 3.87 (s, 3H), 2.72-2.63 (m, 1H), 2.45 (s, 3H), 0.99-0.96 (m, 4H).

Example 173

Synthesis of 5-(3-Cyano-benzyloxy)-2-cyclopropyl-6-methyl-nicotinic acid methyl ester (184)

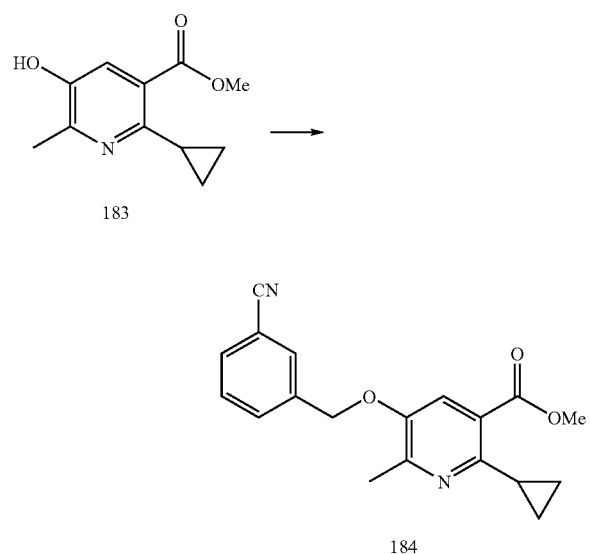

The coupling of 2-cyclopropyl-5-hydroxy-6-methyl-nicotinic acid methyl ester (183) (605 mg, 2.9 mmol) and α-bromo-m-tolunitrile (629 mg, 3.2 mmol), as described in Example 1, gave 5-(3-cyano-benzyloxy)-2-cyclopropyl-6-methyl-nicotinic acid methyl ester (184) (680 mg, 72% yield).

¹H-NMR (CDCl₃): δ 7.75 (s, 1H), 7.69-7.63 (m, 2H), 7.57-7.53 (m, 2H), 5.10 (s, 2H), 2.99-2.92 (m, 1H), 1.12-1.08 (m, 2H), 0.95-0.88 (m, 2H).

Example 174

Synthesis of 5-(3-Cyano-benzyloxy)-2-cyclopropyl-6-methyl-nicotinic acid (185)

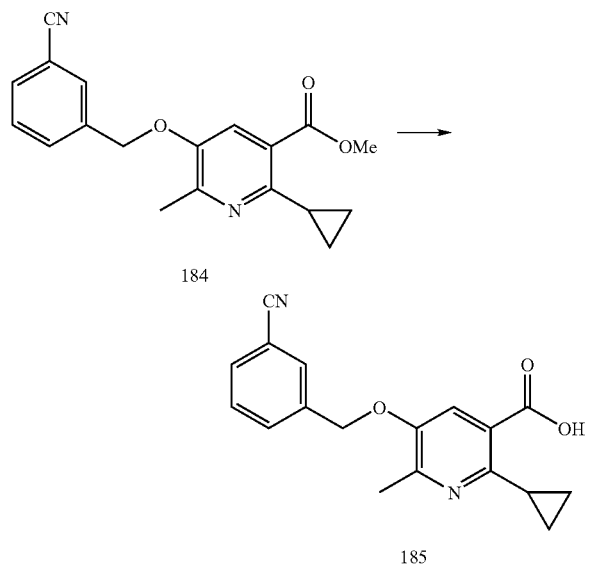

To a solution of 5-(3-cyano-benzyloxy)-2-cyclopropyl-6-methyl-nicotinic acid methyl ester (184) (500 mg, 1.55 mmol) in methanol (10 mL), added aqueous sodium hydroxide (10 mL, 1N) and stirred at room temperature for 3 days. Hydrochloric acid (5 mL, 12N) was added to the reaction mixture and methyl alcohol was evaporated. The precipitate was collected by filtration to give 5-(3-cyano-benzyloxy)-2-cyclopropyl-6-methyl-nicotinic acid (185) (300 mg, 63% yield).

¹H-NMR (DMSO-d6): δ 7.92 (s, 1H), 7.83-7.80 (m, 2H), 7.70-7.63 (m, 2H), 5.22 (s, 2H), 2.99-2.92 (m, 1H), 2.40 (s, 3H), 0.97-0.85 (m, 4H).

Example 175

Synthesis of 5-(3-Cyano-benzyloxy)-N-(4-cyano-phenyl)-2-cyclopropyl-6-methyl-nicotinamide (186)

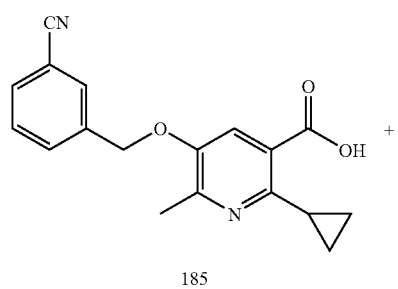

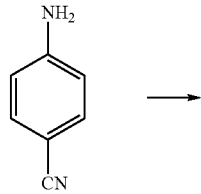

4-Aminobenzonitrile

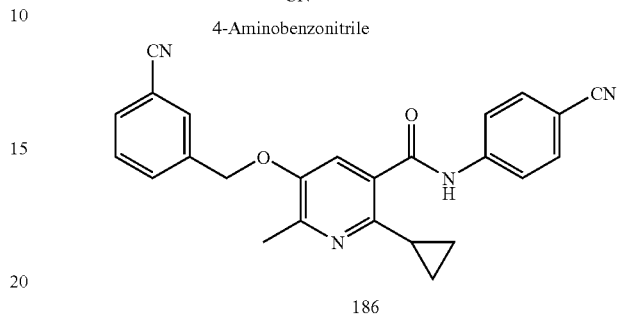

The amide coupling of 5-(3-cyano-benzyloxy)-2-cyclopropyl-6-methyl-nicotinic acid (185) (230 mg, 0.7 mmol) and 4-amino-benzonitrile (106 mg, 0.9 mmol), as described in Example 67, gave 5-(3-cyano-benzyloxy)-N-(4-cyano-phenyl)-2-cyclopropyl-6-methyl-nicotinamide (186) (95 mg, 27% yield).

¹H-NMR (CDCl₃): δ 8.67 (s, 1H), 7.87-7.82 (m, 2H), 7.73-7.70 (m, 1H), 7.68-7.64 (m, 2H), 7.59-7.44 (m, 3H), 5.09 (s, 2H), 2.47-2.46 (m, 3H), 2.31-2.25 (m, 1H), 1.21-1.18 (m, 2H), 1.00-0.96 (m, 2H).

Example 176

Synthesis of 5-(3-Carbamimidoyl-benzyloxy)-N-(4-carbamimidoyl-phenyl)-2-cyclopropyl-6-methyl-nicotinamide (187)

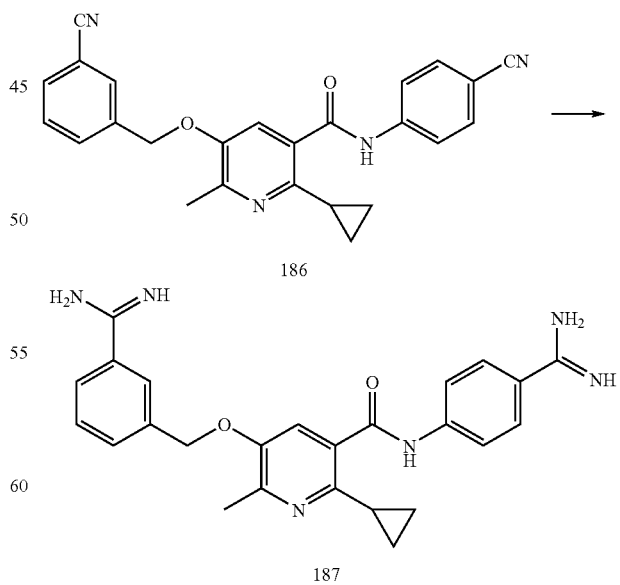

The conversion of bis-nitrile (188) to bis-amidine (187) was carried out as described in Example 2.

¹H-NMR (D₂O): δ 8.00 (s, 1H), 7.88-7.85 (m, 2H), 7.82-7.76 (m, 4H), 7.72-7.70 (m, 2H), 7.55 (t, 1H), 5.32 (s, 2H), 2.62 (s, 3H), 2.36-2.27 (m, 1H), 1.13-1.06 (m, 2H), 0.92-0.87 (m, 2H).

MS m/z (ES⁺): 443 (M+H⁺).

Example 177

Synthesis of 3-(3-Cyano-benzyloxy)-6-cyclopropyl-2-methyl-isonicotinic acid methyl ester (188)

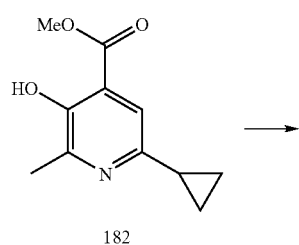

182

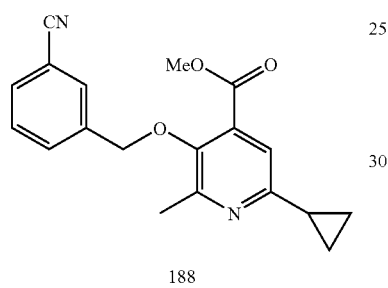

188

The coupling of 6-cyclopropyl-3-hydroxy-2-methyl-isonicotinic acid methyl ester (182) (614 mg, 2.9 mmol) and α-bromo-m-tolunitrile (638 mg, 3.26 mmol), as described in Example 1, gave 3-(3-cyano-benzyloxy)-6-cyclopropyl-2-methyl-isonicotinic acid methyl ester (188) (600 mg, 63% yield).

¹H-NMR (CDCl₃): δ 7.82 (s, 1H), 7.74-7.71 (m, 1H), 7.66-7.63 (m, 1H), 7.55-7.49 (m, 1H), 4.96 (s, 2H), 2.5 (s, 3H), 2.09-2.00 (m, 1H), 1.00-0.97 (m, 4H).

Example 178

Synthesis of 3-(3-Cyano-benzyloxy)-6-cyclopropyl-2-methyl-isonicotinic acid (189)

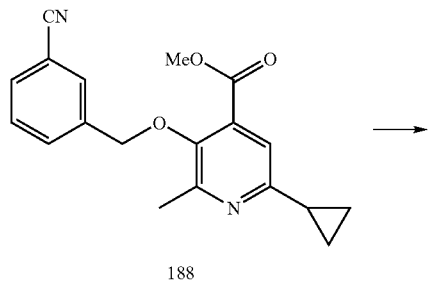

188

-continued

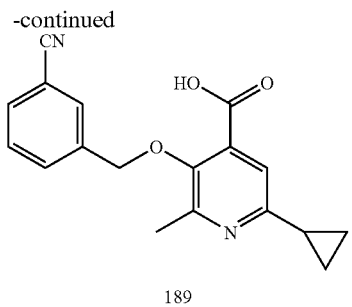

189

The hydrolysis of 3-(3-cyano-benzyloxy)-6-cyclopropyl-2-methyl-isonicotinic acid methyl ester (188) (400 mg, 1.2 mmol), as described in Example 174, gave 3-(3-cyano-benzyloxy)-6-cyclopropyl-2-methyl-isonicotinic acid (189) (248 mg, 65% yield).

¹H-NMR (DMSO-d6): δ 7.91 (s, 1H), 7.84-7.80 (m, 2H), 7.65-7.60 (m, 1H), 7.34 (s, 1H), 4.97 (s, 2H), 2.40 (s, 3H), 2.16-2.07 (m, 1H), 0.95-0.82 (m, 4H).

Example 179

Synthesis of 3-(3-Cyano-benzyloxy)-N-(4-cyano-phenyl)-6-cyclopropyl-2-methyl-isonicotinamide (190)

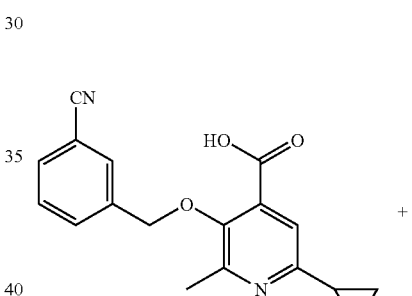

189

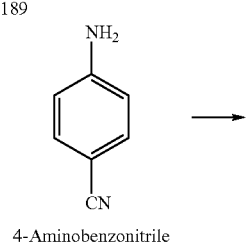

4-Aminobenzonitrile

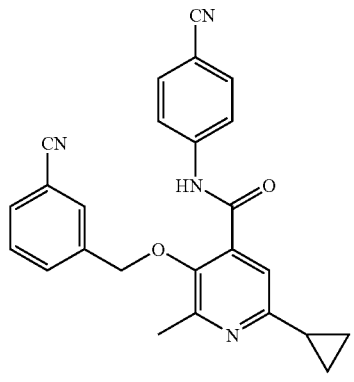

190

147

The amide coupling of 3-(3-cyano-benzyloxy)-6-cyclopropyl-2-methyl-isonicotinic acid (189) (112 mg, 0.4 mmol) and 4-amino-benzonitrile (51 mg, 0.4 mmol), as described in Example 67, gave 3-(3-cyano-benzyloxy)-N-(4-cyano-phenyl)-6-cyclopropyl-2-methyl-isonicotinamide (190) (90.0 mg, 61% yield).

¹H-NMR (DMSO-d6): δ 8.23-8.20 (m, 4H), 7.85-7.84 (m, 2H), 7.76-7.73 (m, 1H), 5.01 (s, 2H), 2.58 (s, 3H), 1.79-1.72 (m, 1H), 1.16-1.01 (m, 4H).

Example 180

Synthesis of 3-(3-Carbamimidoyl-benzyloxy)-N-(4-carbamimidoyl-phenyl)-6-cyclopropyl-2-methyl-isonicotinamide (191)

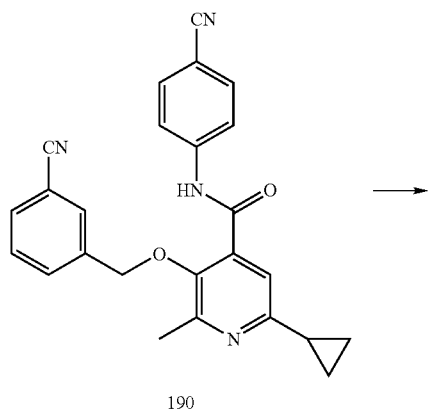

190

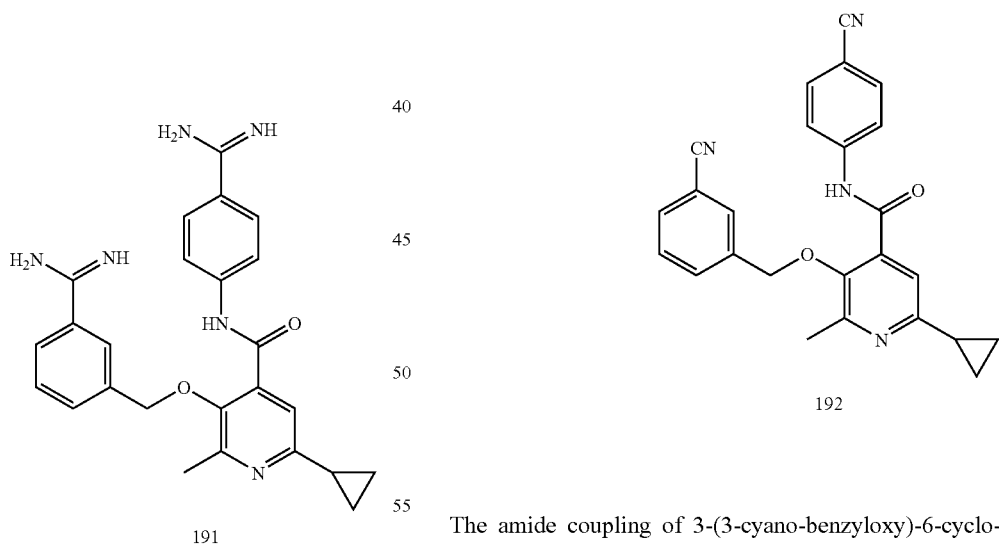

191

The conversion of bis-nitrile (190) to bis-amidine (191) was carried out as described in Example 2.

¹H-NMR (D₂O): δ 7.75-7.72 (m, 2H), 7.65 (s, 1H), 7.55-7.50 (m, 4H), 7.42-7.36 (m, 2H), 5.15 (s, 2H), 2.77 (s, 3H), 2.29-2.26 (m, 1H), 1.37-1.34 (m, 2H), 1.07-1.06 (m, 2H).

MS m/z (ES⁺): 443 (M+H⁺).

148

Example 181

Synthesis of 3-(3-Cyano-benzyloxy)-N-(3-cyano-phenyl)-6-cyclopropyl-2-methyl-isonicotinamide (192)

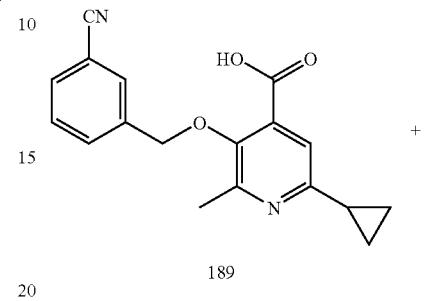

189

+

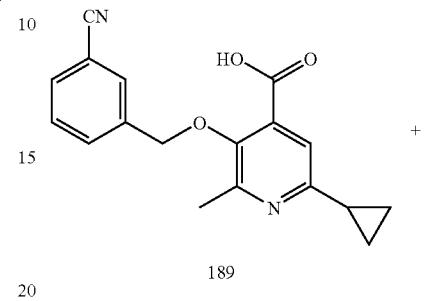

4-Aminobenzonitrile

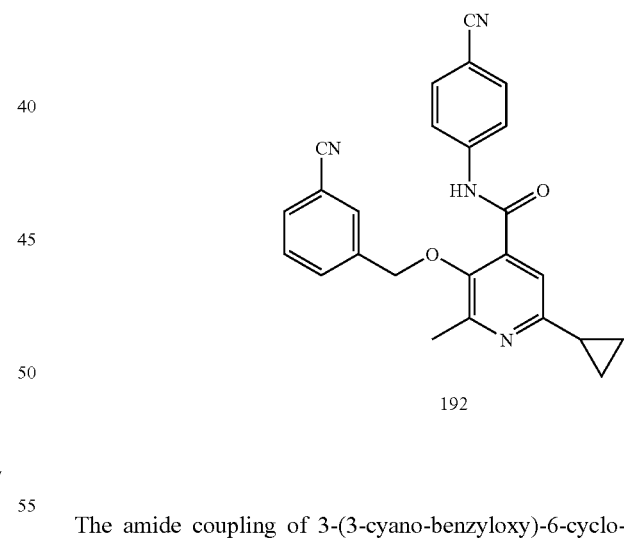

192

The amide coupling of 3-(3-cyano-benzyloxy)-6-cyclopropyl-2-methyl-isonicotinic acid (189) (128 mg, 0.4 mmol) and 3-aminobenzonitrile (59 mg, 0.4 mol), as described in Example 67, gave 3-(3-cyano-benzyloxy)-N-(3-cyano-phenyl)-6-cyclopropyl-2-methyl-isonicotinamide (192) (39.4 mg, 23% yield).

¹H-NMR (CDCl₃): δ 9.3 (s, 1H), 7.78-7.77 (m, 1H), 7.71-7.66 (m, 2H), 7.61-7.56 (m, 1H), 7.54-7.40 (m, 3H), 7.42 (m, 1H), 4.96 (s, 2H), 2.62 (s, 3H), 2.16-2.10 (m, 1H), 1.06-1.01 (m, 4H).

Example 182

Synthesis of 3-(3-Carbamimidoyl-benzyloxy)-N-(3-carbamimidoyl-phenyl)-6-cyclopropyl-2-methyl-isonicotinamide (193)

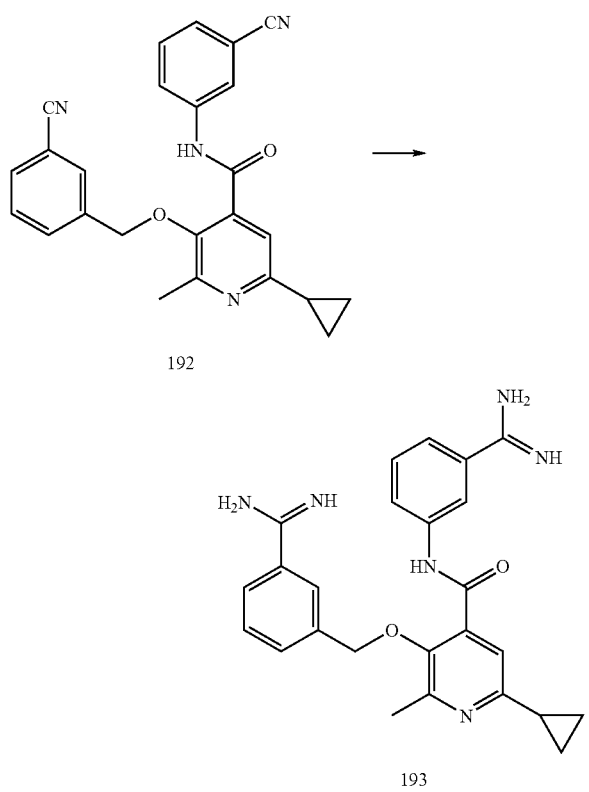

The conversion of bis-nitrile (192) to bis-amidine (193) was carried out as described in Example 2.

$^1$H-NMR (D$_2$O): δ 7.74-7.72 (m, 1H), 7.66-7.65 (m, 1H), 7.57-7.53 (m, 4H), 7.40-7.36 (m, 2H), 5.15 (s, 2H), 2.77 (s, 3H), 2.30-2.24 (m, 1H), 1.39-1.32 (m, 2H), 1.09-1.03 (m, 2H).

MS m/z (ES$^+$): 326 (M+H$^+$).

Example 183

Synthesis of 4-{[4,6-Dimethyl-5-(3-hydroxyamidine-benzyloxy)-pyridin-3-ylmethyl]-amino}-N-hydroxy-benzamidine (194)

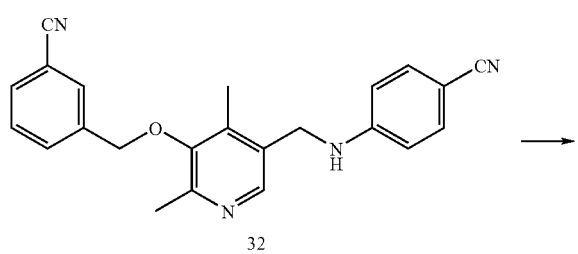

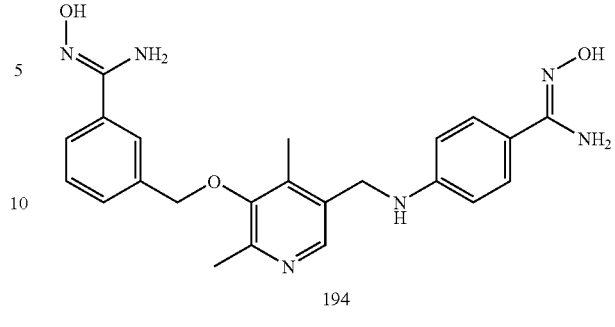

To a mixture of hydroxylamine hydrochloride (2.2 g, 33 mmol) and diisopropylethylamine (0.42 g, 33 mmol) in methyl alcohol (100 mL), was added 4-{[5-(3-cyano-benzyloxy)-4,6-dimethyl-pyridin-3-ylmethyl]-amino-benzonitrile 32 (3 g, 8.1 mmol) and the reaction was stirred at room temperature overnight. The solvent was evaporated to give crude product 4-{[4,6-dimethyl-5-(3-hydroxyamidine-benzyloxy)-pyridin-3-ylmethyl]-amino}-N-hydroxy-benzamidine (194) (2.8 g), which was used in the next step without further purification.

Example 184

Synthesis of 4-{[5(3-Methoxyamidine-benzyloxy)-4,6-dimethyl-pyridin-3-ylmethyl]-amino}-N-methoxy-benzamidine hydrochloride (195)

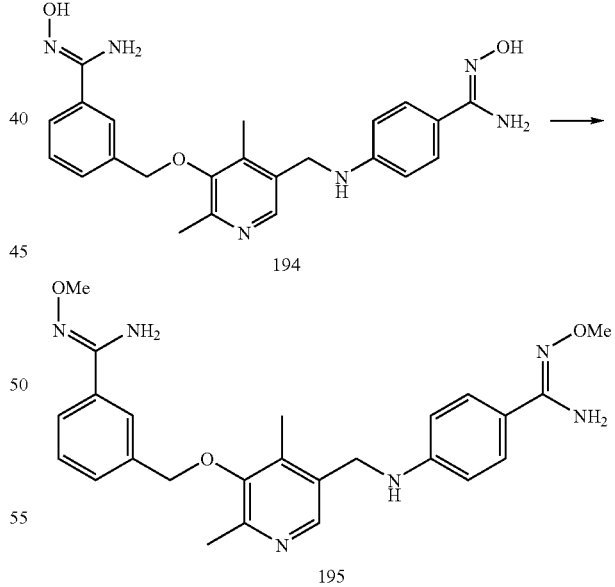

A solution of aqueous sodium hydroxide (23 mL, 2 N, 46 mmol) was added to a solution of 4-{[4,6-dimethyl-5-(3-hydroxyamidine-benzyloxy)-pyridin-3-ylmethyl]-amino}-N-hydroxy-benzamidine (194) (1.0 g) in 1,4-dioxane (20 mL) at 0° C., followed by the addition of methyl iodide (1.29 g, 9.2 mmol) in 1,4-dioxine (0.5 mL). The ice bath was removed and the reaction mixture was stirred at room temperature overnight. The layer was evaporated, water added and the product was extracted with ethyl acetate. The organic solution was dried over anhydrous magnesium sulfate. Evaporation of the solvent gave a crude residue, which was purified by column chromatography on silica gel using dichloromethane:methyl alcohol (49:1) as an eluant to give 4-{[5-(3-methoxyamidine-benzyloxy)-4,6-dimethyl-pyridin-3-ylmethyl]-amino}-N-methoxybenzamidine hydrochloride (195) (85 mg, 6% yield for two steps) as a colorless solid.

$^1$H-NMR (CD$_3$OD): δ 8.10 (s, 1H), 7.76 (s, 1H), 7.64 (d, 1H), 7.56 (d, 1H), 7.48-7.41 (m, 3H), 6.62 (d, 2H), 4.90 (s, 2H), 4.32 (s, 2H), 3.85 (s, 3H), 3.79 (s, 3H), 2.66 (s, 3H), 2.47 (s, 3H), 2.31 (s, 3H).

Example 185

Synthesis of 4-{[5(3-Ethoxy-amidine-benzyloxy)-4,6-dimethyl-pyridin-3-ylmethyl]-amino}-N-ethoxy-benzamidine hydrochloride (196)

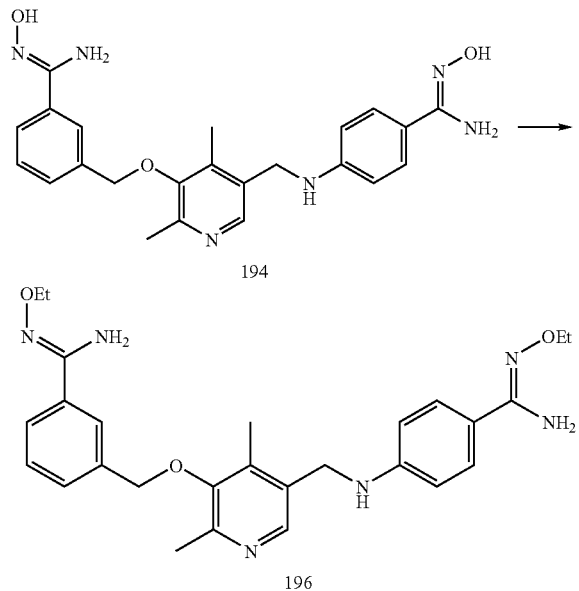

The alkylation of 4-{[4,6-dimethyl-5-(3-hydroxyamidine-benzyloxy)-pyridin-3-ylmethyl]-amino}-N-hydroxy-benzamidine (194) (1 g) with ethyl bromide (0.99 g, 9.2 mmol), as described in Example 184, gave 4-{[5(3-ethoxy-amidine-benzyloxy)-4,6-dimethyl-pyridin-3-ylmethyl]-amino}-N-ethoxybenzamidine hydrochloride (196) (84 mg, 6% yield for two steps).

$^1$H-NMR (CD$_3$OD): δ 8.11 (s, 1H), 7.76 (s, 1H), 7.65 (d, 1H), 7.56 (d, 1H), 7.48-7.41 (m, 3H), 6.63 (d, 2H), 4.92 (s, 2H), 4.33 (s, 2H), 4.12-3.99 (m, 4H), 2.47 (s, 3H), 2.32 (s, 3H), 1.33-1.28 (m, 6H).

Example 186

Inhibition of Platelet Aggregation

Platelet rich plasma (PRP) was obtained by drawing whole blood from normal human donors (not on any medication) into sodium citrate tubes (3.2%), and centrifuging at 160×g for about 10 minutes. Platelet poor plasma (PPP) was obtained by centrifuging the remainder of the sample after the platelets were removed at 800×g for about 10 minutes. The PRP was adjusted to a count of 280×10$^9$/L using a mixture of PRP and PPP. The platelets (200 μL) were incubated with the test compounds (25 μL) adjusted to various concentrations (5, 10, 20, 30, 50, and 100 μM) for about 30 minutes at room temperature (approximate final platelet count in the incubation mixture of 250×10$^9$/L). The samples were incubated for about 3 minutes at about 37° C., and then transferred to the mixing wells of a Chrono-log 4 channel aggregometer (Chrono-log Corp., Havertown, Pa.). After baselines were established, agonist (25 μL of 40 μM ADP (Sigma, St. Louis, Mo.) or 25 μL of 50 μg/mL and 10 μg/mL collagen (Helena Laboratories, Beaumont, Tex.) or 25 μL of 120 μM thrombin receptor activating peptide (TRAP) (Sigma)) was then added. Aggregation was monitored for 5 minutes at 37° C. with stirring (1000 rpm). The amplitude and slope of each tracing were calculated to determine the amount of aggregation. Control samples were performed using only solvent. The % reduction in aggregation was calculated for each sample compared to the proper solvent control. See Table 1.

TABLE 1

| | | Platelet inhibition | | | |
|---|---|---|---|---|---|
| | | % Reduction in Aggregation | | | |
| Compound | Concentration (μM) | Collagen (5 μg/mL) | Collagen (1 μg/mL) | ADP (4 μM) | TRAP (12 μM) |
| 46 | 100 | 19 | 35 | 46 | 29 |
| 3 | 50 | 0 | 20 | 27 | 81 |
| 33 | 50 | | 81 | 84 | 79 |
| 6 | 30 | 44 | 100 | 89 | 86 |
| 25 | 30 | 52 | 96 | 93 | 95 |
| 60 | 30 | 26 | 47 | 87 | 89 |
| 29 | 30 | 15 | 32 | 52 | 32 |
| 63 | 30 | 41 | 95 | 95 | 94 |
| 9 | 30 | 0 | 16 | 39 | 78 |
| 54 | 30 | 13 | 15 | 23 | 53 |
| 38 | 20 | | 94 | 81 | 84 |
| 31 | 10 | | 83 | 80 | 84 |
| 56 | 5 | 63 | 91 | 96 | 90 |

Example 187

Activity of Various Compounds of the Invention

A. Determination of Anti-Factor Xa (Fxa) Activity

The test compounds (40 μL) adjusted to various concentrations (0.25 to 100 μM) were incubated with 5 nM Human FXa (Calbiochem, San Diego, Calif.) enzyme in 125 mM Tris [Tris(hydroxymethyl)aminomethane] buffer (pH 7.5) containing 375 mM sodium chloride and 0.25% polyethylene glycol (MW 8000) (80 μL) at room temperature for about 30 minutes. 80 μL of synthetic substrate Pefachrome® Xa (Pentapharm, Basel, Switzerland), adjusted to various concentrations from 125 μM to 1.25 mM, was added. The activity was measured at 37° C. by monitoring absorbance at 405 nM for 15 minutes using a FLUOstar OPTIMA™ (BMG Labtech GmbH, Offenburg, Germany) microplate reader. Control sample was the solvent alone. Each test compound was analyzed twice using 4 concentrations of compound plus control (in duplicate) with 5 concentrations of substrate (50, 100, 200, 300 and 500 μM). The specific activity (ΔA$_{405}$/min/nM enzyme) was determined for each data point. The Ki for competitive inhibition was then determined for each test compound using the Enzyme Kinetics module of Sigmaplot 8.0 (SPSS Inc., Chicago, Ill.). The results (Ki) are shown in Table 2.

TABLE 2

Anticoagulant Properties

| Compounds | Ki Value (μM) | | |
|---|---|---|---|
| | Thrombin | Factor Xa | Trypsin |
| 148 | 0.009 | 0.473 | — |
| 153 | 0.012 | 0.665 | — |
| 140 | 0.017 | 0.423 | 0.210 |
| 108 | 0.022 | 0.378 | 0.199 |
| 11 | 0.022 | 1.05 | 0.467 |
| 33 | 0.031 | 0.284 | 0.264 |
| 174 | 0.037 | 1.080 | 0.814 |
| 138 | 0.039 | 0.412 | 0.531 |
| 172 | 0.041 | 0.380 | 1.070 |
| 103 | 0.047 | 0.961 | 0.793 |
| 96 | 0.053 | 1.000 | — |
| 31 | 0.062 | 1.34 | 0.778 |
| 38 | 0.146 | 16.000 | 1.000 |
| 142 | 0.186 | 0.589 | — |
| 136 | 0.333 | 0.503 | — |
| 21 | 0.510 | 19.000 | 1.170 |
| 9 | 0.65 | 5.800 | 0.997 |
| 70 | 0.700 | 9.000 | 0.420 |
| 73 | 0.720 | 3.500 | 1.210 |
| 56 | 0.848 | 6.200 | 5.030 |
| 15 | 1.650 | 11.000 | 0.730 |
| 88 | 3.500 | 20.000 | 3.300 |
| 25 | 3.770 | 0.320 | 0.068 |
| 29 | 4.600 | 0.140 | 0.390 |
| 6 | 10.300 | 2.300 | 0.880 |
| 60 | 11.000 | 25.000 | 2.200 |

B. Determination of Anti-Thrombin (Factor IIa) Activity

The test compounds (40 μL) adjusted to various concentrations (0.25 to 100 μM) were incubated with Human Thrombin (Calbiochem) enzyme (5 nM) in 31 mM Tris buffer (pH 8.3) containing 81 mM sodium chloride and 0.63% bovine serum albumin (fraction V)(80 μL) at room temperature for about 30 minutes. 80 μL of Pefachrome® Thr (Pentapharm) was adjusted to various concentrations, from 62.5 μM to 1.25 mM. The activity was measured at about 37° C. by monitoring absorbance at 405 nM for about 15 minutes using a FLUOstar OPTIMA™. Control sample was the solvent alone. Each test compound was analyzed twice using 4 concentrations of compound plus control (in duplicate) with 5 concentrations of substrate (50, 100, 200, 300 and 500 μM). The specific activity ($\Delta A_{405}$/min/nM enzyme) was determined for each data point. The Ki for competitive inhibition was then determined for each test compound using the Enzyme Kinetics module of Sigmaplot 8.0 (SPSS). The results (Ki) are shown in Table 2.

C. Determination of Anti-Trypsin Activity

The test compounds (40 μL), adjusted to various concentrations (0.25 to 100 μM) were incubated with Human Trypsin (Calbiochem) enzyme (5 nM) in 125 mM Tris buffer (pH 7.5) containing 75 mM sodium chloride and 0.5% bovine serum albumin (fraction V) (80 μL) at room temperature for about 30 minutes. 80 μL of Pefachrome® Try (Pentapharm), adjusted to various concentrations from 125 μM to 1.25 mM, was added. The activity was measured at about 37° C. by monitoring absorbance at 405 nM for about 15 minutes using a FLUOstar Optima. Control sample was the solvent alone. Each test compound was analyzed twice using 4 concentrations of compound plus control (in duplicate) with 5 concentrations of substrate (50, 100, 200, 300 and 500 μM. The specific activity ($\Delta A_{405}$/min/nM enzyme) was determined for each data point. The Ki for competitive inhibition was then determined for each test compound using the Enzyme Kinetics module of Sigmaplot 8.0 (SPSS). The results (Ki±standard error) are shown in Table 2.

The invention claimed is:
1. A compound of the formula:

I wherein
$R^1$ is —$(CR^7R^8)_m$OH, where m is an integer from 0 to 8, where $R^7$ is H, halo, alkyl, cycloalkyl, hydroxyl, O-alkyl, or O-alkyl, or O-alkyl-aryl-$R^6$, where $R^6$ is —$NO_2$, —$NH_2$, amidine, alkyl, cycloalkyl, —CN, where $R^9$ is H, OH, or O-alkyl, and where $R^8$ is H, halo, alkyl, cycloalkyl, hydroxyl, O-alkyl, or O-alkyl-aryl-$R^6$, where $R^6$ is as defined above;
—$(CR^7R^8)_m$O-alkyl, wherein m, $R^7$, and $R^8$ are as defined above;
—$(CR^7R^8)_m$O-aryl-$R^6$, where m, $R^6$, $R^7$, and $R^8$ are as defined above;
—$(CR^7R^8)_m$O-alkyl-aryl-$R^6$, where m and $R^6$ are as defined above;
—$(CR^7R^8)_n$—NH-aryl-$R^6$, where n is an integer from 0 to 8, and where $R^6$, $R^7$ and $R^8$ are as defined above;
—$(CR^7R^8)_n$—NH—CO-aryl-$R^6$, where n, $R^6$, $R^7$ and $R^8$ are as defined above;
—$(CR^7R^8)_n$—NH-aryl-aryl-$R^6$, where n, $R^6$, $R^7$ and $R^8$ are as defined above;
—$(CR^7R^8)_n$—NH—CO-aryl-aryl-$R^6$ where n, $R^6$, $R^7$ and $R^8$ are as defined above;
—NH-aryl-$R^6$, where $R^6$ is as defined above;
—$(CR^7R^8)_n$—CO—NH-aryl-$R^6$, where n, $R^6$, $R^7$ and $R^8$ are as defined above; or
—$(CR^7R^8)_n$—CO—NH-aryl-aryl-$R^6$, where n, $R^6$, $R^7$ and $R^8$ are as defined above;
$R^2$ is hydroxyl;
halo;
alkyl;
—$(CR^7R^8)_m$—X, where m, $R^7$ and $R^8$ are as defined above, where X is OH, F, Cl or Br;
—$(CH_2)_n$COOH, where n is as defined above;
—$(CR^7R^8)_m$COO$(CR^7R^8)_n$CH$_3$, where m, n, $R^7$ and $R^8$ are as defined above;
—$(CR^7R^8)_m$NH$(CR^7R^8)_n$COOH, where m, n, $R^7$ and $R^8$ are as defined above;
—$(CR^7R^8)_n$-aryl-$R^6$, where n, $R^6$, $R^7$ and $R^8$ are as defined above;
—$(CR^7R^8)_n$-aryl-aryl-$R^6$, where n, $R^6$, $R^7$ and $R^8$ are as defined above;

—(CR$^7$R$^8$)$_m$—CHF$_2$, where m, R$^7$ and R$^8$ are defined as above;
—(CR$^7$R$^8$)$_n$—NH-aryl-R$^6$, where n, R$^6$, R$^7$ and R$^8$ are as defined above;
—(CR$^7$R$^8$)$_n$—NH—CO-aryl-R$^6$, where n, R$^6$, R$^7$ and R$^8$ are as defined above;
—(CR$^7$R$^8$)$_n$—NH-aryl-aryl-R$^6$, where n, R$^6$, R$^7$ and R$^8$ are as defined above;
—(CR$^7$R$^8$)$_n$—NH—CO-aryl-aryl-R$^6$ where n, R$^6$, R$^7$ and R$^8$ are as defined above;
NH-aryl-R$^6$, where R$^6$ is as defined above;
—(CR$^7$R$^8$)$_n$—CO—NH-aryl-R$^6$, where n, R$^6$, R$^7$ and R$^8$ are as defined above; or
—(CR$^7$R$^8$)$_n$—CO—NH-aryl-aryl-R$^6$, where n, R$^6$, R$^7$ and R$^8$ are as defined above;
R$^3$ is —(CR$^7$R$^8$)$_m$OH, where m, R$^7$, and R$^8$ are as defined above;
—(CR$^7$R$^8$)$_m$O-alkyl, where m, R$^7$, and R$^8$ are as defined above;
—(CR$^7$R$^8$)$_m$O-aryl-R$^6$, where m, R$^6$, R$^7$, and R$^8$ are as defined above;
—(CR$^7$R$^8$)$_m$O-alkyl-aryl-R$^6$, where m and R$^6$ is as defined above;
—(CR$^7$R$^8$)$_n$OH, where n, R$^6$, R$^7$, and R$^8$ are as defined above;
—(CR$^7$R$^8$)$_n$—NH-aryl-R$^6$, where n, R$^6$, R$^7$ and R$^8$ are as defined above;
—(CR$^7$R$^8$)$_n$—NH—CO-aryl-R$^6$, where n, R$^6$, R$^7$ and R$^8$ are as defined above;
—(CR$^7$R$^8$)$_n$—NH-aryl-aryl-R$^9$, where n, R$^6$, R$^7$ and R$^8$ are as defined above;
—(CR$^7$R$^8$)$_n$—NH—CO-aryl-aryl-R$^6$, where n, R$^6$, R$^7$ and R$^8$ are as defined above;
—NH-aryl-R$^6$, where R$^6$ is as defined above;
—(CR$^7$R$^8$)$_n$—CO—NH-aryl-R$^6$, where n, R$^6$, R$^7$ and R$^8$ are as defined above; or
—(CR$^7$R$^8$)$_n$—CO—NH-aryl-aryl-R$^6$, where n, R$^6$, R$^7$ and R$^8$ are as defined above;
R$^4$ is H, aryl, cycloalkyl, arylalkyl, CHF$_2$, CHO, or R$^2$;
R$^5$ is H, aryl, cycloalkyl, arylalkyl, CHF$_2$, CHO, or R$^2$;
wherein aryl is phenyl or naphthyl; and
at least two of R$^1$, R$^2$, R$^3$, R$^4$, and R$^5$ have amidine groups;
or a pharmaceutically acceptable salt thereof.

2. A pharmaceutical composition comprising a therapeutically effective amount of at least one compound of claim 1 and a pharmaceutically acceptable carrier.

3. A compound of the formula

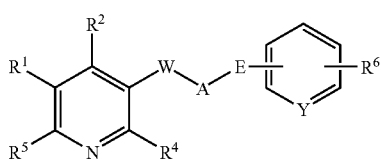

III wherein
R$^1$ is hydroxyl; O-alkyl; or

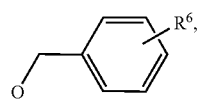

where R$^6$ is —NO$_2$, —NH$_2$, amidine, alkyl, cycloalkyl, —CN,

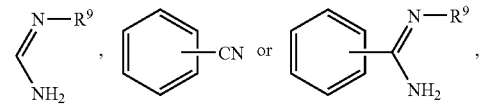

where R$^9$ is H, OH, or O-alkyl;
R$_2$ is CH$_2$OH;
CH$_2$OCH$_3$;
COOZ, where Z is OH, OCH$_3$, OCH$_2$CH$_3$, or

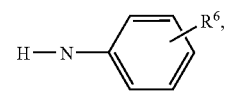

where R$^6$ is defined above;
CH$_2$OBn;
CH$_3$;
CH$_2$F;
CHF$_2$;
CH$_2$—NH—(CH$_2$)$_{m'}$—CO$_2$Z, where m'=0, 1, 2, 3, 4, or 5, and where Z is as defined above; or
(CH$_2$)$_{n'}$—CO$_2$Z, where n'=1, 2 or 3, and where Z is as defined above;
A is O or NH;
W is C=O or (CH$_2$)$_{n'}$, where n' is as defined above;
E is C=O; (CH$_2$)$_{n'}$, where n' is as defined above; or CHR$^{10}$, where R$^{10}$ is CH$_2$COZ, where Z is as defined above;
Y is C—H, C—F, C—OCH$_3$, C—OCF$_3$, or C—CF$_3$;
R$^4$ is H;
halo;
aryl;
cycloalkyl;
arylalkyl;
CHF$_2$;
CHO;
alkyl;
—(CR$^7$R$^8$)$_m$—X, where m is an integer from 0 to 8, where R$^7$ is H, F, alkyl, cycloalkyl, hydroxyl, O-alkyl, or O-alkyl-aryl-R$^6$, where R$^8$ is H, F, alkyl, cycloalkyl, hydroxyl, O-alkyl, or O-alkyl-aryl-R$^6$, where R$^6$ is as defined above, and where X is OH, F, or Br;
—(CH$_2$)$_n$COOH, where n is an integer from 0 to 8;
—(CR$^7$R$^8$)$_m$COO(CR$^7$R$^8$)$_n$CH$_3$, where m, n, R$^7$, and R$^8$ are as defined above;
—(CR$^7$R$^8$)$_m$NH(CR$^7$R$^8$)$_n$COOH, where m, n, R$^7$, and R$^8$ are as defined above;
—(CR$^7$R$^8$)$_n$-aryl-R$^6$, where n, R$^6$, R$^7$, and R$^8$ are as defined above;
—(CR$^7$R$^8$)$_n$-aryl-aryl-R$^6$, where n, R$^6$, R$^7$, and R$^8$ are as defined above;
—(CR$^7$R$^8$)$_n$—CHF$_2$, where n, R$^7$ and R$^8$ are defined as above;
—(CR$^7$R$^8$)$_n$—NH-aryl-R$^6$, where n, R$^6$, R$^7$, and R$^8$ are as defined above;
—(CR$^7$R$^8$)$_n$—NH—CO-aryl-R$^6$, where n, R$^6$, R$^7$, and R$^8$ are as defined above;
—(CR$^7$R$^8$)$_n$—NH-aryl-aryl-R$^6$, where n, R$^6$, R$^7$ and R$^8$ are as defined above;

—(CR⁷R⁸)ₙ—NH—CO-aryl-aryl-R⁶, where n, R⁶, R⁷, and R⁸ are as defined above;
NH-aryl-R⁶ where R⁶ is as defined above;
—(CR⁷R⁸)ₙ—CO—NH-aryl-R⁶, where n, R⁶, R⁷, and R⁸ are as defined above; or
—(CR⁷R⁸)ₙ—CO—NH-aryl-R⁶, where n, R⁶, R⁷, and R⁸ are as defined above;
R⁵ is H, aryl, cycloalkyl, arylalkyl, CHF₂, CHO, or R⁴, where R⁴ is as defined above; and
at least two of R¹, R⁴, R⁵, and R⁶ have amidine groups;
or a pharmaceutically acceptable salt thereof.

4. The compound of claim 3, wherein the compound is 4-{4-fluoromethyl-2-methyl-5-[(4-carbamimidoyl-benzyloxy)-methyl]-pyridin-3-yloxymethyl}-benzamidine.

5. The compound of claim 3, wherein the compound is 4-{[5-(4-carbamimidoyl-benzyloxy)-4,6-dimethyl-pyridin-3-ylmethyl]-amino}-benzamidine.

6. The compound of claim 3, wherein the compound is 4-{[5-(3-carbamimidoyl-benzyloxy)-4,6-dimethyl-pyridin-3-ylmethyl]-amino}-benzamidine.

7. The compound of claim 3, wherein the compound is 3-[3-(4-carbamimidoyl-benzyloxy)-5-(4-carbamimidoyl-phenoxymethyl)-2-methyl-pyridin-4-yl]-propionic acid ethyl ester.

8. The compound of claim 3, wherein the compound is 6-({3-(4-carbamimidoyl-benzyloxy)-5-[(4-carbamimidoyl-phenylamino)-methyl]-2-methyl-pyridin-4-ylmethyl}-amino)-hexanoic acid.

9. The compound of claim 3, wherein the compound is 6-({3-(4-carbamimidoyl-benzyloxy)-5-[(4'-carbamimidoyl-biphenyl-4-ylamino)-methyl]-2-methyl-pyridin-4-ylmethyl}-amino) hexanoic acid.

10. The compound of claim 3, wherein the compound is 4-{[4,6-Bis-fluoromethyl-5-(3-amidine-benzyloxy)-pyridin-3-ylmethyl]-amino}-benzamidine.

11. The compound of claim 3, wherein the compound is 4-{5-[(4-Carbamimidoyl-phenylamino)-methyl]-2,4-bis-fluoromethyl-pyridin-3-yloxymethyl}-benzamidine.

12. The compound of claim 3, wherein the compound is 4-{[5-(3-Amidine-benzyloxy)-6-fluoro-methyl-4-methyl-pyridin-3-ylmethyl]-amino}-benzamidine.

13. The compound of claim 3, wherein the compound is 4-{[4-Fluoromethyl-5-(3-amidine-benzyloxy)-6-methyl-pyridin-3-ylmethyl]-amino}-benzamidine.

14. The compound of claim 3, wherein the compound is 4-{5-[(4-Carbamimidoyl-phenylamino)-methyl]-6-cyclopropyl-4-hydroxymethyl-2-methyl-pyridin-3-yloxymethyl}-benzamidine.

15. The compound of claim 3, wherein the compound is 4-{[5-(3-Amidine-benzyloxy)-6-hydroxymethyl-4-methyl-pyridin-3-ylmethyl]-amino}-benzamidine.

16. The compound of claim 3, wherein the compound is 3-{5-[(4-Carbamimidoyl-phenylamino)-methyl]-6-cyclopropyl-4-hydroxymethyl-2-methyl-pyridin-3-yloxymethyl}-benzamidine.

17. The compound of claim 3, wherein the compound is 3-{5-[(4-Amidino-phenylamino)-methyl]-4-ethyl-2-methyl-pyridin-3-yloxymethyl}-benzamidine.

18. The compound of claim 3, wherein the compound is 4-{5-[(3-amidino-phenylamino)-methyl]-2,4-dimethyl-pyridin-3-yloxy}benzamidine.

19. The compound of claim 3, wherein the compound is 4-{[5-(3-Amidine-benzyloxy)-6-formyl-4-methyl-pyridin-3-ylmethyl]-amino}-benzamidine.

20. The compound of claim 3, wherein the compound is 4-{[4,6-Dimethyl-5-(3-hydroxyamidine-benzyloxy)-pyridin-3-ylmethyl]-amino-}-N-hydroxybenzamidine.

21. The compound of claim 3, wherein the compound is 4-{[5(3-Methoxyamidine-benzyloxy)-4,6-dimethyl-pyridin-3-ylmethyl]-amino}-N-methoxybenzamidine hydrochloride.

22. The compound of claim 3, wherein the compound is 4-{[5(3-Ethoxy-amidine-benzyloxy)-4,6-dimethyl-pyridin-3-ylmethyl]-amino}-N-ethoxybenzamidine hydrochloride.

* * * * *

UNITED STATES PATENT AND TRADEMARK OFFICE
CERTIFICATE OF CORRECTION

PATENT NO.       : 7,812,037 B2
APPLICATION NO.  : 11/262509
DATED            : October 12, 2010
INVENTOR(S)      : Haque et al.

It is certified that error appears in the above-identified patent and that said Letters Patent is hereby corrected as shown below:

IN THE SPECIFICATIONS:

Col. 2, line 51: "$(CR^7R^8)_n$-NH-CO-aryl-aryl-$R^6$" should read --$(CR^7R^8)_n$-CO-NH-aryl-$R^6$--

Col. 3, line 15: "$(CR^7R^8)_n$-NH-CO-aryl-aryl-$R^6$" should read --$(CR^7R^8)_n$-CO-NH-aryl-$R^6$--

Col. 3, line 17: "$(CR^7R^8)_n$-NH-CO-aryl-aryl-$R^6$" should read --$(CR^7R^8)_n$-CO-NH-aryl-aryl-$R^6$--

Col. 3, lines 30-31: "-$(CR^7R^8)_n$-NH-aryl-$R^6$, where n, $R^6$, $R^7$, and $R^8$ as defined above" should be deleted as a duplicate of col. 3, lines 32-33

Col. 3, lines 16-18: "or -$(CR^7R^8)_n$-NH-CO-aryl-aryl-$R^6$, where n, $R^6$, $R^7$, and $R^8$ are as defined above" should be -- -$(CR^7R^8)_n$-NH-CO-aryl-$R^6$, where n, $R^6$, $R^7$, and $R^8$ are as defined above; -$(CR^7R^8)_n$-NH-aryl-aryl-$R^6$, where n, $R^6$, $R^7$, and $R^8$ are as defined above; -NH-aryl-$R^6$, where $R^6$ is as defined above; -$(CR^7R^8)_n$-CO-NH-aryl-$R^6$, where n, $R^6$, $R^7$, and $R^8$ are as defined above; or -$(CR^7R^8)_n$-CO-NH-aryl-aryl-$R^6$, where n, $R^6$, $R^7$, and $R^8$ are as defined above--

Col. 3, line 60: 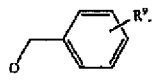 should be 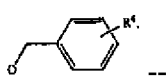 --

Col. 4, line 1: "where $R^9$ is" should be --where $R^6$ is--

Col. 4, line 2: "-CN" should be -- -CN,--

Col. 4, lines 3-13: 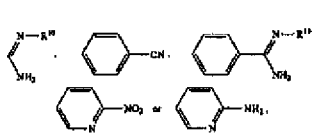 should be 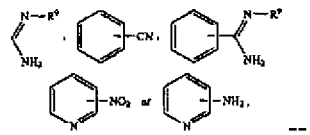 --

Col. 4, line 14: "where $R^{10}$ is" should be --where $R^9$ is--

Signed and Sealed this
Twenty-sixth Day of April, 2011

David J. Kappos
*Director of the United States Patent and Trademark Office*

CERTIFICATE OF CORRECTION (continued)

Col. 4, lines 45-46: "-(CR$^7$R$^8$)$_n$-NH-aryl-R$^6$, where n, R$^6$, R$^7$, and R$^8$ as defined above" should be deleted as a duplicate of col. 4, lines 43-44

Col. 4, line 49: "NH-CO-aryl-R$^6$" should be --NH-aryl-aryl-R$^6$--

Col. 4, line 55: "NH-CO-aryl-aryl-R$^6$" should be --CO-NH-aryl-R$^6$--

Col. 4, line 57: "NH-CO-aryl-aryl-R$^6$" should be --CO-NH-aryl-aryl-R$^6$--

Col. 4, line 58: "or R$^8$" should be --and R$^8$--

Col. 5, line 49: "NH-CO-aryl-aryl-R$^6$" should be --CO-NH-aryl-R$^6$--

Col. 5, line 51: "NH-CO-aryl-aryl-R$^6$" should be --CO-NH-aryl-aryl-R$^6$--

Col. 6, line 12: "NH-CO-aryl-aryl-R$^6$" should be --CO-NH-aryl-R$^6$--

Col. 6, line 14: "NH-CO-aryl-aryl-R$^6$" should be --CO-NH-aryl-aryl-R$^6$--

Col. 6, line 36: "NH-CO-aryl-aryl-R$^6$" should be --CO-NH-aryl-R$^6$--

Col. 6, line 38: "NH-CO-aryl-aryl-R$^6$" should be --CO-NH-aryl-aryl-R$^6$--

Col. 6, lines 60-65: " 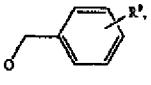 " should be -- 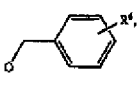 --

Col. 7, line 1: "where R$^9$ is" should be --where R$^6$ is--

Col. 7, lines 3-13: " 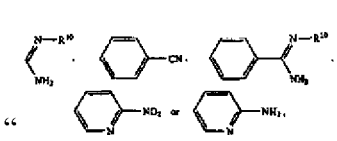 " should be -- 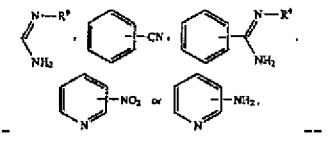 --

Col. 7, line 54: "NH-CO-aryl-aryl-R$^6$" should be --CO-NH-aryl-R$^6$--

Col. 7, line 56: "NH-aryl-R$^6$, where R$^6$ is as defined above" should be -- -(CR$^7$R$^8$)-CO-NH-aryl-aryl-R$^6$, where n, R$^6$, R$^7$ and R$^8$ are as defined above--

Col. 8, lines 38-45: "where Z is H, CH$_3$, CH$_2$CH$_3$, or 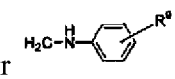 ," should be -- where Z is OH, OCH$_3$, OCH$_2$CH$_3$, or 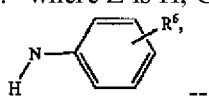 --

Col. 8, line 47: "where R$^9$ is" should be --where R$^6$ is--

Col. 9, line 34: "-NH-CO-aryl-aryl-R$^6$," should be -- -CO-NH-aryl-R$^6$--

Col. 10, line 48: "-NH-aryl-aryl-R$^6$," should be -- -NH-aryl-R$^6$--

CERTIFICATE OF CORRECTION (continued)
U.S. Pat. No. 7,812,037 B2

Col. 10, line 50: "-NH-CH-aryl-$R^6$," should be -- -NH-CO-aryl-$R^6$--

Col. 10, line 55: "-NH-CO-NH-aryl-$R^6$," should be -- -NH-CO-aryl-aryl-$R^6$--

Col. 10, line 59: "-CO-NH-aryl-aryl-$R^6$," should be -- -CO-NH-aryl-$R^6$--